United States Patent
Torino et al.

(10) Patent No.: US 11,597,702 B2
(45) Date of Patent: Mar. 7, 2023

(54) SUBSTITUTED PYRAZOLES FFA4/GPR120 RECEPTOR AGONISTS

(71) Applicant: AXXAM S.P.A., Bresso (IT)

(72) Inventors: Domenica Torino, Bresso (IT); Francesco Piscitelli, Bresso (IT); Valentina Cusano, Bresso (IT); Rocco Vitalone, Bresso (IT); Andrew Griffin, Bresso (IT); Russell Thomas, Bresso (IT); Paolo Pevarello, Bresso (IT); Ali Munaim Yousif, Bresso (IT)

(73) Assignee: GOLGI NEUROSCIENCES S.R.L., Milan (IT)

( * ) Notice: Subject to any disclaimer, the term of this patent is extended or adjusted under 35 U.S.C. 154(b) by 0 days.

(21) Appl. No.: 16/977,401

(22) PCT Filed: Mar. 12, 2019

(86) PCT No.: PCT/EP2019/056131
§ 371 (c)(1),
(2) Date: Sep. 1, 2020

(87) PCT Pub. No.: WO2019/175152
PCT Pub. Date: Sep. 19, 2019

(65) Prior Publication Data
US 2021/0087148 A1    Mar. 25, 2021

(30) Foreign Application Priority Data
Mar. 15, 2018    (EP) .................................... 18162003

(51) Int. Cl.
C07D 231/14    (2006.01)
(52) U.S. Cl.
CPC .................. C07D 231/14 (2013.01)
(58) Field of Classification Search
CPC .................................................. C07D 231/14
See application file for complete search history.

(56) References Cited

U.S. PATENT DOCUMENTS

| 8,912,227 | B1 | 12/2014 | Sui et al. |
| 2008/0300260 | A1 | 12/2008 | Geneste et al. |
| 2013/0137865 | A1 | 5/2013 | Nakamura et al. |
| 2014/0275172 | A1 | 9/2014 | Sui et al. |
| 2014/0275173 | A1 | 9/2014 | Zhang et al. |
| 2014/0275179 | A1 | 9/2014 | Sui et al. |
| 2014/0275182 | A1 | 9/2014 | Sui et al. |

FOREIGN PATENT DOCUMENTS

| EP | 3 190 111 | 7/2017 |
| JP | 2010-83763 A | 4/2010 |
| JP | 2014-214118 | 11/2014 |
| WO | 2010/048207 | 4/2010 |
| WO | 2013/111796 | 8/2013 |
| WO | 2013/139341 | 9/2013 |
| WO | 2013/185766 | 12/2013 |
| WO | 2014/059232 | 4/2014 |
| WO | 2014/069963 | 5/2014 |
| WO | 2014/151247 | 9/2014 |
| WO | 2014/159794 | 10/2014 |
| WO | 2014/159802 | 10/2014 |
| WO | 2014/209034 | 12/2014 |
| WO | 2015/125085 | 8/2015 |
| WO | 2015/134038 | 9/2015 |
| WO | 2015/134039 | 9/2015 |
| WO | 2016/012965 | 1/2016 |
| WO | 2016/038540 | 3/2016 |
| WO | 2016/040222 | 3/2016 |
| WO | 2016/040223 | 3/2016 |
| WO | 2016/040225 | 3/2016 |
| WO | 2016/125182 | 8/2016 |
| WO | 2016/184312 | 11/2016 |
| WO | 2017/205193 | 11/2017 |

OTHER PUBLICATIONS

Wu, et al. Document No. 166:28318, retrieved from STN; Nov. 24, 2016.*
WO2016184312 A1 (Wu, et al.) Nov. 24, 2016 (abstract) STN [database online], CAPLUS [retrieved on Aug. 25, 2021], Accession No. 2016:1910731.*
Cancer and Metastasis Reviews (1998), 17(1), 91-106.*
Science (1999), vol. 286, 531-537.*
Cancer [online], [retrieved on Jul. 6, 2007], Retrieved from the internet, URL http://www.nlm.nih.gov/medlineplus/cancer.html>.*
International Search Report for PCT/EP2019/056131 dated May 15, 2019, 7 pages.

(Continued)

*Primary Examiner* — Shawquia Jackson
(74) *Attorney, Agent, or Firm* — Nixon & Vanderhye

(57) ABSTRACT

Disclosed are compounds of formula (I) or a pharmaceutically acceptable salt thereof:

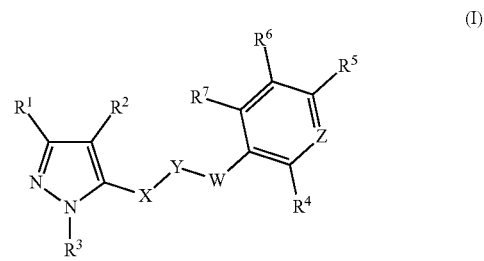

These compounds have FFA4/GPR120 receptor (FFA4) agonistic properties. Also disclosed are pharmaceutical compositions including these compounds, chemical processes for preparing them and their use in the treatment or prophylaxis of diseases associated with FFA4 receptor activity in animals, in particular humans.

9 Claims, No Drawings

(56) References Cited

OTHER PUBLICATIONS

Written Opinion of the ISA for PCT/EP2019/056131 dated May 15, 2019, 7 pages.
Halder et al., "The therapeutic potential of GPR120: a patent review", Expert Opinion on Therapeutic Patents, 2013, vol. 23, No. 12, pp. 1581-1590.
Deshayes et al., "Synthesis of some 4H,10H[1]Benzoxepino[3,4-c]pyrazol-4-one Derivatives", Journal of Heterocyclic Chemistry, 1984, vol. 21, No. 2, pp. 301-304.
Mukherjee et al., "On the regiospecificity of 3,5-disubstituted pyrazoles derived from C-acylated-beta-enaminonitriles and esters", Indian Journal of Chemistry, 2005, vol. 44B, No. 11, pp. 2333-2337.
Chew et al., "Effect of Omega-3 Fatty Acids, Lutein/Zeaxanthin, or Other Nutrient Supplementation on Cognitive Function: The AREDS2 Randomized Clinical Trial," JAMA, Aug. 25, 2015, vol. 314, No. 8, pp. 791-801.
Connor and Neuringer, "The Effects of n-3 Fatty Acid Deficiency and Repletion Upon the Fatty Acid Composition and Function of the Brain and Retina," Biological Membranes: Aberrations in Membrane Structure and Function, 1988 Alan R. Liss, Inc. pp. 275-294.
Connor et al., "Increased dietary intake of Omega-3-polyunsaturated fatty acids reduces pathological retinal angiogenesis," Nature Medicine, Jul. 2007, pp. 868-873.
Datilo et al., "Omega-3 from Flaxseed Oil Protects Obese Mice Against Diabetic Retinopathy Through GPR120 Receptor," Scientific Reports, 2018, pp. 1-13.
Dragano et al., "Polyunsaturated fatty acid receptors, GPR40 and GPR120, are expressed in the hypothalamus and control energy homeostasis and inflammation," Journal of Neuroinflammation, 2017, pp. 1-16.
Dragano et al., "Figure S1. Testing the specificity of the antibodies against GPR120 and GPR40" and "Figure S2. Specific activation of GPR120 and GPR40," additional file, 2017, 3 pages.
Ichimura et al., "Dysfunction of lipid sensor GPR120 leads to obesity in both mouse and human," Nature, Mar. 15, 2012, vol. 483, pp. 350-354.
Ichimura et al., "Dysfunction of lipid sensor GPR120 leads to obesity in both mouse and human," Nature, Supplementary Information, 2012, 17 pages.
Kalogerou et al., "Omega-3 fatty acids protect retinal neurons in the DBA/2J hereditary glaucoma mouse model," Experimental Eye Research, 2018, pp. 128-139.
Kimura et al., "Free Fatty Acid Receptors in Health and Disease," Physiological Reviews, 2020, pp. 171-210.
Moniri, "Free-fatty acid receptor-4 (GPR120): Cellular and molecular function and its role in metabolic disorders," Biochemical Pharmacology, 2016, pp. 1-15.
Mukhtar and Ambati, "The value of nutritional supplements in treating Age-Related Macular Degeneration: a review of the literature," International Ophthalmology, 2019, vol. 39, pp. 2975-2983.
Oh et al., "GPR120 Is an Omega-3 Fatty Acid Receptor Mediating Potent Anti-inflammatory and Insulin-Sensitizing Effects," Cell, Sep. 3, 2010, pp. 687-698.
Oh et al., "A Gpr120-selective agonist improves insulin resistance and chronic inflammation in obese mice," Nature Medicine, Jul. 6, 2014, pp. 1-8.
Oh et al., "A Gpr120-selective agonist improves insulin resistance and chronic inflammation in obese mice," Nature Medicine, Supplementary Information, 2014, 12 pages.
Prokopiou et al., "Therapeutic potential of omega-3 fatty acids supplementation in a mouse model of dry macular degeneration," BMJ Open Ophthalmology, 2017, pp. 1-13.
Sala-Vila et al., "Dietary Marine ω-3 Fatty Acids and Incident Sight-Threatening Retinopathy in Middle-Aged and Older Individuals With Type 2 Diabetes," JAMA Ophthalmology, Oct. 2016, vol. 134, No. 10, pp. 1142-1149.
Secor et al., "Free Fatty Acid Receptors as Mediators and Therapeutic Targets in Liver Disease," Frontiers in Physiology, Apr. 2021, vol. 12, pp. 1-9.
Tikhonenko et al., "N-3 Polyunsaturated Fatty Acids Prevent Diabetic Retinopathy by Inhibition of Retinal Vascular Damage and Enhanced Endothelial Progenitor Cell Reparative Function," PLOS ONE, Jan. 2013, vol. 8, No. 1, pp. 1-10.
Tomita et al., "Free fatty acid receptor 4 activation protects against choroidal neovascularization in mice," Angiogenesis, 2020, vol. 23, pp. 385-394.
Ulven and Christiansen, "Dietary Fatty Acids and Their Potential for Controlling Metabolic Diseases Through Activation of FFA4/GPR120," Annual Review of Nutrition, 2015, pp. 239-263.
Office Action issued in European Patent Application No. 19 715 396.8 dated Nov. 14, 2022.
Chowdhury et al., "A short and expeditious regiospecific synthesis of novel pyrazoles", J. Chem. Research (S), 2003, pp. 746-748.

* cited by examiner

SUBSTITUTED PYRAZOLES FFA4/GPR120 RECEPTOR AGONISTS

This application is the U.S. national phase of International Application No. PCT/EP2019/056131 filed Mar. 12, 2019 which designated the U.S. and claims priority to EP Patent Application No. 18162003.0 filed Mar. 15, 2018, the entire contents of each of which are hereby incorporated by reference.

The present invention relates to novel substituted pyrazole compounds of formula (I) having FFA4/GPR120 receptor (FFA4) agonistic properties, pharmaceutical compositions comprising these compounds, chemical processes for preparing these compounds and their use in the treatment or prophylaxis of diseases associated with FFA4 receptor activity in animals, in particular humans.

TECHNOLOGICAL BACKGROUND

Free fatty acids (FFAs) are essential dietary nutrients which act in various metabolic and cellular processes. FFAs exert their function via influence on lipid membrane composition and diverse receptors and pathways including nuclear peroxisome proliferator-activated receptors (PPARs) and a subfamily of transmembrane G protein-coupled receptors (GPCRs), the FFA receptor family. The receptors FFA2 and FFA3 are activated by short chain fatty acids while receptors FFA1 and FFA4 have been shown to bind poly-unsaturated (long-chain) fatty acids (PUFA) with a C16 to C22 backbone such as α-linolenic acid, linoleic acid and palmitoleic acid. In humans, FFA4 is expressed in the intestinal tract (ileum, cecum, enteroendocrine L cells of the colon, rectum), but also in the thymus, lung, spleen, adrenal gland, pancreas and taste buds. Activation of FFA4 present on endoenterocrine cells triggers a rise in intracellular $Ca^{++}$ causing secretion of GLP-1 (a potent incretin hormone that enhances the secretion of insulin from pancreatic β cells) in vitro and in vivo which leads to a subsequent increase in circulating insulin. A role for FFA4 in adipogenesis has been described as well. FFA4 mRNA is highly expressed in four different adipose tissues (subcutaneous, perirenal, mesenteric, epididymal) and the amount of mRNA is elevated in adipose tissues of mice fed a high fat diet. The level of FFA4 mRNA increased during adipocyte differentiation of 3T3-L1 cells used as an in vitro model system for adipogenesis. Similar results were observed in human adipose tissue, human preadipocytes, and cultured adipocytes. It has been also shown that dysfunction of the lipid sensor FFA4 leads to obesity in both mouse and human where the non-synonymous mutation p.R270H (that inhibits FFA4 signalling) increases the risk of obesity in Europeans populations.

Interestingly, the potent anti-inflammatory role of omega-3 fatty acids has been recognized for a long time and it was demonstrated that FFA4 expressed on macrophages plays a central role thereby repressing the release of inflammatory cytokines. In particular, FFA4-induced anti-inflammatory effects were demonstrated to be mediated by β-arrestin signaling. Recently, it was shown that a selective high-affinity, orally available, small-molecule FFA4 agonist exerted potent anti-inflammatory effects on macrophages in vitro and in obese mice in vivo. FFA4 agonist treatment of high-fat diet-fed obese mice caused improved glucose tolerance, decreased hyperinsulinemia, increased insulin sensitivity and decreased hepatic steatosis. Recently, FFA4 has also been linked to neuroinflammation since these receptors are expressed in the hypothalamus and control energy homeostasis and inflammation.

In addition to its involvement in metabolic diseases and inflammatory processes, FFA4 has also recently been linked to cancer. However, it remains unclear what role FFA4 plays in cancer and what possible effects receptor modulators might have as one study showed a role of FFA4 in suppression of cell proliferation in prostate cancer while another group found FFA4 to be tumor-promoting in colorectal cancer.

Based on these findings, the identification of FFA4 selective agonists would open new treatment opportunities for hepatic diseases, diabetes, obesity and inflammatory diseases.

FFA4 agonists are described in in various patent applications (Formicola et al. Pharmaceutical Patent Analyst 2015, 4(6), 62-66), such as:

US2014/0275172 discloses benzo-fused heterocyclic derivatives with FFA4 agonistic properties;

US2014/0275179 deals with isothiazole and thiophene derivatives FFA4 agonists;

Bicyclic-pyrrole derivatives are described and tested in US2014/0275182 and U.S. Pat. No. 8,912,227;

WO2014059232 discloses azaspiro- and oxaazaspiro-piperidinyl compounds as FFA4 modulators for the treatment and/or preventing diabetes, obesity, hyperlipidemia, inflammation and related disorders;

WO2014069963 discloses biaryl derivatives as FFA4 agonists;

WO2014209034 claims thioaryl derivatives as FFA4 agonists;

WO2013139341A1 and WO2013185766A1 disclose substituted fluorophenyl-methoxy-benzene-carboxylic acid compounds as FFA4 modulators;

US20140275173 and WO2014151247 claim oxabicyclo[2.2.2]acid derivatives for FFA4 agonism;

WO2014159794 reports bicyclo[2.2.1]heptane and WO2014159802 bicyclo[2.2.1]octane derivatives as FFA4 agonists.

Isothiazole derivatives as GPR120 agonists for the treatment of type II diabetes are disclosed in WO 2015134039.

Bicyclic pyrrole derivatives as GPR120 agonists are disclosed in WO 2015134038.

Thiazole and thiophene derivatives containing carbon-carbon linker as gpr120 agonists for disease therapy are claimed in WO 2016125182, WO 2016038540, WO 2016012965, and WO 2015125085

Cyclopropanecarboxylic acid and cyclobutanecarboxylic acid gpr120 modulators are described in WO 2016040222 and WO 2016040223;

Phenyl-(aza)cycloalkyl carboxylic acid gpr120 modulators are claimed in WO 2016040225.

Compounds containing carbon-carbon linker as gpr120 agonists are disclosed in WO 2016125182.

Finally, tetrahydroisoquinoline compounds useful as GPR120 agonists are disclosed in WO 2017205193.

All the compounds in the prior art cited above are characterized by the presence of a carboxylic acid moiety that is detrimental, in general, for the cell permeability of the compounds and in particular for the penetration of the compounds into tissue compartments such as the Central Nervous System (CNS) which is key to a possible medical treatment of neuroinflammation and the underlying pathological condition, thus hampering the use of these compounds in certain therapeutic areas (Formicola et al. Pharmaceutical Patent Analyst 2015, 4(6), 62-66).

Consequently, there is still an unmet need for compounds which are able to efficiently agonize FFA4 and that can be delivered to the different target organs which are sites of a FFA4-mediated pathology, in particular to the brain. Such compounds are provided herein.

Various embodiments of the invention are presented hereafter;

DISCLOSURE OF THE INVENTION

The present invention relates to pyrazole compounds of the following formula (I) or a pharmaceutically acceptable salt thereof:

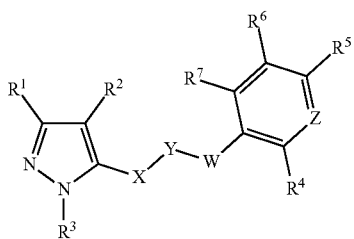

(I)

including any stereochemically isomeric form thereof, wherein:

X is a $C_1$-$C_6$ alkanediyl group, unsubstituted or substituted by a methyl group or one or more halogen atoms;

Y is selected from: —O—; —$NR^8$—, wherein $R^8$ is an hydrogen or $C_1$-$C_6$ alkyl; —S—; —SO— and —$SO_2$—;

W is —$(CH_2)_n$—, wherein n is an integer between 0 and 6;

Z is selected from —$CR^9$—, wherein $R^9$ is hydrogen, halogen, $C_1$-$C_6$ alkyl, $C_1$-$C_4$ hydroxyalkyl and —N—;

$R^1$ is selected from hydrogen; $C_1$-$C_6$ alkyl and $C_3$-$C_{10}$ cycloalkyl;

$R^2$ is selected from hydrogen; CN; trifluoromethyl; $SO_2R^{10}$, wherein $R^{10}$ is $C_1$-$C_4$ alkyl; COOH and $CONR^{10}R^{11}$, wherein each of $R^{10}$ and $R^{11}$ is independently hydrogen or $C_1$-$C_4$ alkyl;

$R^3$ is aryl; hetaryl; benzyl; $C_1$-$C_4$ alkyl or $C_3$-$C_{10}$ cycloalkyl; which can be unsubstituted or substituted by one or more substituents selected from halogen, $C_1$-$C_4$ alkyl (unsubstituted or substituted by halogen), $C_1$-$C_4$ alkyloxy (unsubstituted or substituted by halogens), CN and $R^{12}SO_2$—, wherein $R^{12}$ is a $C_1$-$C_6$ alkyl or cycloalkyl;

each of $R^4$, $R^6$ and $R^7$ is independently selected from the group consisting of hydrogen; halogen; CN; $C_1$-$C_6$ alkyl (unsubstituted or substituted by halogen or hydroxyl); $C_1$-$C_4$ alkyloxy (unsubstituted or substituted by halogen or hydroxyl); —$CONH_2$; —$NHCOCH_3$ and —$NO_2$;

$R^5$ is selected from: hydrogen; halogen; $C_1$-$C_6$ alkyl (unsubstituted or substituted by halogen, hydroxyl, methyl or methoxy group); $C_1$-$C_4$ alkyloxy (unsubstituted or substituted by one or more halogens); —$(CH_2)$ CN, wherein n is between 0 and 6; —$(CHR^{13})(CH_2)_n$—$NHR^{14}$, wherein n is between 0 and 6, $R^{13}$ is hydrogen or hydroxyl and $R^{14}$ is hydrogen, $CH_3CO$—, PhCO—, $CH_3SO_2$—, $PhSO_2$—, $PhCH_2CO$—; —$(CH_2)_nOR^{15}$, wherein n is between 0 and 6 and $R^{15}$ is $C_1$-$C_4$ alkyl unsubstituted or substituted by —$OC_1$-$C_4$ alkyl; —$(CH_2)_nCONR^{16}R^{17}$, wherein n is between 0 and 6, $R^{16}$ is hydrogen or methyl and $R^{17}$ is hydrogen, —$CH_2CH_2OH$, or —$CH_2CF_3$; —$(CH_2)_nCOR^{18}$ wherein n is between 0 and 6, $R^{18}$ is hydroxyl, $C_1$-$C_6$ alkyl, $C_1$-$C_4$ alkyloxy or $CH_2COCF_3$; —$(CH_2)_n$-Het, wherein n is between 0 and 6, and Het is an 5 or 6 member heterocycle unsubstituted or substituted by —$NH_2$, $C_1$-$C_4$ hydroxyalkyl or one or more halogen atoms; or $R^5$ and $R^6$, taken together with the aromatic ring to which they are bound, form a group:

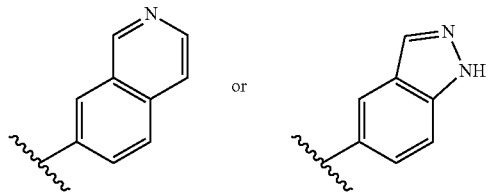 [SMILES: *c1ccc2ccncc2c1 ; *c1ccc2[nH]ncc2c1]

or $R^6$ and $R^7$, taken together with the aromatic ring to which they are bound, form a group:

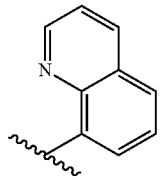 [SMILES: *c1cccc2cccnc12]

with the proviso that the compound of formula (I) is not:
5-[(4-cyanophenoxy)methyl]-3-methyl-1-phenyl-pyrazole-4-carbonitrile,
5-[[2-chloro-4-(hydroxymethyl)phenoxy]methyl]-3-methyl-1-phenyl-pyrazole-4-carbonitrile;
5-[(2-chloro-4-cyano-phenoxy)methyl]-3-methyl-1-phenyl-pyrazole-4-carbonitrile; and
3-methyl-5-(phenoxymethyl)-1-phenyl-pyrazole-4-carbonitrile.

As used in the foregoing definitions:

The terms "halo", "halogen" and "halide", which may be used interchangeably, refer to a substituent fluoro, chloro, bromo, or iodo.

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration.

Stereochemically isomeric forms of the compounds of formula (I) are obviously intended to be embraced within the scope of this invention.

The absolute stereochemical configuration of the compounds of formula (I) and of the intermediates used in their preparation may easily be determined by those skilled in the art while using well-known methods such as, for example, X-ray diffraction.

Furthermore, some compounds of formula (I) and some of the intermediates used in their preparation may exhibit polymorphism. It is to be understood that the present invention encompasses any polymorphic forms possessing properties useful in the treatment of the conditions noted hereinabove.

The pharmaceutically acceptable salts as mentioned hereinabove are meant to comprise the therapeutically active non-toxic acid addition salt forms that the compounds of formula (I) are able to form. These pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, trifluoromethanesulfonic, ethanesulfonic, benzenesulfonic, p-toluenesulfonic, cyclamic, salicylic, p-aminosalicylic, pamoic and the like acids.

Conversely, said salt forms can be converted by treatment with an appropriate base into the free base form.

The compounds of formula (I) may exist in both unsolvated and solvated forms. The term 'solvate' is used herein to describe a molecular association comprising a compound of the invention and one or more pharmaceutically acceptable solvent molecules, e.g. water or ethanol. The term 'hydrate' is used when said solvent is water.

The term $C_1$-$C_6$ alkanediyl group means a —$(CH_2)_n$— chain wherein n is an integer from 1 to 6. Preferably n is 1, 2 or 3.

In the present specification the term "$C_1$-$C_6$ alkyl group" means a monovalent unsubstituted saturated straight-chain or branched-chain hydrocarbon radical having from 1 to 8 carbon atoms and includes methyl, ethyl, propyl, iso-propyl, butyl, iso-butyl, sec-butyl, t-butyl, pentyl, hexyl, heptyl, octyl, and the like. Likewise, the term "$C_1$-$C_4$ alkyl" means a monovalent unsubstituted saturated straight-chain or branched-chain hydrocarbon radical having from 1 to 4 carbon atoms and includes methyl, ethyl, propyl, iso-propyl, butyl, iso-butyl, sec-butyl, and t-butyl.

The term "$C_1$-$C_4$ alkyloxy" means a monovalent unsubstituted saturated straight-chain or branched-chain hydrocarbon radical having from 1 to 4 carbon atoms linked to the point of substitution by an O atom, and includes methoxy, ethoxy, propoxy, iso-propoxy, butoxy, iso-butoxy, sec-butoxy, and t-butoxy.

The term "$C_3$-$C_{10}$ cycloalkyl" means a monovalent unsubstituted saturated cyclic hydrocarbon radical having from 3 to 10 carbon atoms and includes cyclopropane, cyclobutane, cyclopentane, cyclohexane, cycloheptanemethyl, and the like.

As used herein, the term "aryl" means a monovalent monocyclic or bicyclic aromatic hydrocarbon radical of 6 to 10 ring atoms. More specifically the term aryl includes, but is not limited to, phenyl, 1-naphthyl, 2-naphthyl, and derivatives thereof.

In the context of the present invention, the term "hetaryl" (also referred to as heteroaryl) refers to heteroaromatic mono- or polycyclic radicals, comprising, in addition to ring carbon atoms, 1, 2, 3, 4 or more than 4 heteroatoms as ring members. The heteroatoms are preferably selected from oxygen, nitrogen, and sulphur.

A preferred embodiment relates to a compound of Formula (I) or a pharmaceutically acceptable salt thereof wherein:

X is a $C_1$-$C_4$ alkanediyl group, unsubstituted or substituted by a methyl group or one or more halogen atoms selected from F and Cl;

Y is selected from: —O—; —$NR^8$—, wherein $R^8$ is an hydrogen or $C_1$-$C_4$ alkyl; —S—; —SO— and —$SO_2$—;

W is —$(CH_2)_n$—, wherein n is 0 or 1;

Z is selected from —$CR^9$—, wherein $R^9$ is hydrogen, halogen selected from Cl or F, $C_1$-$C_4$ alkyl, $C_1$-$C_4$ hydroxyalkyl and —N—;

$R^1$ is selected from hydrogen; $C_1$-$C_4$ alkyl and $C_3$-$C_6$ cycloalkyl;

$R^2$ is selected from hydrogen; CN; trifluoromethyl; COOH and $CONR^{10}R^{11}$, wherein each of $R^{10}$ and $R^{11}$ is independently hydrogen or $C_1$-$C_4$ alkyl;

$R^3$ is phenyl unsubstituted or substituted by one or more substituents selected from Br, Cl, F or $C_1$-$C_4$ alkyl (unsubstituted or substituted by F, Cl or Br), $C_1$-$C_4$ alkyloxy (unsubstituted or substituted by F, Cl or Br), CN, and $R^{12}SO_2$—, wherein $R^{12}$ is a $C_1$-$C_4$ alkyl; hetaryl unsubstituted or substituted by one or more substituents selected from Br, Cl, F, $C_1$-$C_4$ alkyl or $C_1$-$C_4$ alkyloxy; benzyl unsubstituted or substituted by $C_1$-$C_4$ alkyl, $C_1$-$C_4$ alkyloxy, $C_3$-$C_6$ cycloalkyl; each of $R^4$, $R^6$ and $R^7$ is independently selected from the group consisting of hydrogen; halogen selected from F, Cl or Br; CN; $C_1$-$C_4$ alkyl (unsubstituted or substituted by F, Cl, Br or hydroxyl); $C_1$-$C_4$ alkyloxy (unsubstituted or substituted by hydroxyl); —$CONH_2$; and —$NHCOCH_3$;

$R^5$ is selected from: hydrogen; F, Cl, Br; $C_1$-$C_4$ alkyl (unsubstituted or substituted hydroxyl, F, Cl or Br, $C_1$-$C_4$ alkyl); $C_1$-$C_4$ alkyloxy, (unsubstituted or substituted F, Cl, Br; —$(CH_2)_n$CN, wherein n is an integer between 0 and 2; —$(CHR^{13})(CH_2)_n$—$NHR^{14}$, wherein n is 1, $R^{13}$ is hydrogen or hydroxyl, and $R^{14}$ is hydrogen, $CH_3CO$—, PhCO—, $CH_3SO_2$—, $PhSO_2$—, $PhCH_2CO$—; —$(CH_2)_nOR^{15}$, wherein n is an integer between 1 and 3, $R^{15}$ is $C_1$-$C_4$ alkyl, or $CH_2CH_2OCH(CH_3)CH_3$; —$(CH_2)_nCONR^{16}R^{17}$, wherein n is 0 or 1, $R^{16}$ is hydrogen or $C_1$-$C_4$ alkyl and $R^{17}$ is hydrogen, $C_1$-$C_4$ alkyl unsubstituted or substituted hydroxyl or F, Cl or Br; —$(CH_2)_nCOR^{18}$, wherein n is an integer between 0 and 2, $R^{18}$ is hydroxyl, $C_1$-$C_4$ alkyl, $C_1$-$C_4$ alkyloxy, $CH_2COCF_3$; —$(CH_2)_n$-Het, wherein n is an integer between 0 and 2, and Het is piperidinyl, triazolyl, thiazolyl, oxodiazolyl unsubstituted or substituted by one or more halogen atoms or hydroxymethyl;

or $R^5$ and $R^6$, taken together with the aromatic ring to which they are bound, form a group:

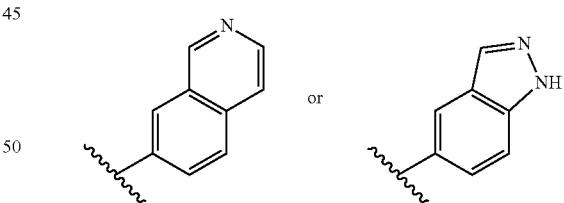

or $R^6$ and $R^7$, taken together with the aromatic ring to which they are bound, form a group:

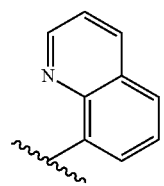 [SMILES: *c1cccc2cccnc12]

with the proviso that the compound of formula (I) is not:

5-[(4-cyanophenoxy)methyl]-3-methyl-1-phenyl-pyrazole-4-carbonitrile,

5-[[2-chloro-4-(hydroxymethyl)phenoxy]methyl]-3-methyl-1-phenyl-pyrazole-4-carbonitrile;

5-[(2-chloro-4-cyano-phenoxy)methyl]-3-methyl-1-phenyl-pyrazole-4-carbonitrile; and 3-methyl-5-(phenoxymethyl)-1-phenyl-pyrazole-4-carbonitrile.

Another preferred embodiment relates to a compound of Formula (I) or a salt thereof wherein:

X is —$CH_2$—, or —$CH_2$—$CH_2$— unsubstituted or substituted by a methyl group or F;

Y is selected from: —O—; —$NR^8$—, wherein $R^8$ is an H or methyl or ethyl; —S—; —SO— or —$SO_2$—;

W is —$(CH_2)_n$—, wherein n is 0 or 1;

Z is selected from: $CR^9$, wherein $R^9$ is an H, Cl or F; methyl, ethyl; hydroxymethyl, hydroxyethyl; or —N—;

$R^1$ is selected from: hydrogen, methyl, ethyl, cyclopropyl;

$R^2$ is selected from hydrogen, CN, trifluoromethyl, $CONR^{10}R^{11}$ wherein $R^{10}$ and $R^{11}$ independently are hydrogen, methyl, ethyl, n-propyl, isopropyl, t-butyl; COOH;

$R^3$ is selected from the group consisting of phenyl unsubstituted or substituted by Cl, F, methyl (unsubstituted or substituted by F), ethyl (unsubstituted or substituted by F), methoxy (unsubstituted or substituted by F), cyano, $R^{12}SO_2$—, wherein $R^{12}$ is methyl); pyridine (unsubstituted or substituted by Br, Cl, F, methyl or methoxy); pyrimidine; pyrazine (unsubstituted or substituted by Cl); benzyl (unsubstituted or substituted by methoxy); isopropyl; t-butyl; cyclopentyl (unsubstituted or substituted by F); cyclohexyl (unsubstituted or substituted by F);

each of $R^4$, $R^6$ and $R^7$ is independently selected from the group consisting of hydrogen; Cl; F; CN; methyl (unsubstituted or substituted by hydroxyl or F); ethyl (unsubstituted or substituted by hydroxyl); $C_1$-$C_4$ alkyloxy, selected from methoxy and ethoxy unsubstituted or substituted by hydroxyl; —$CONH_2$; and —$NHCOCH_3$;

$R^5$ is selected from: hydrogen; F; methyl (unsubstituted or substituted by F or hydroxyl); ethyl (unsubstituted or substituted by hydroxyl); propyl (unsubstituted or substituted by hydroxyl or methyl); isopropyl (unsubstituted or substituted by hydroxyl); butyl (unsubstituted or substituted by hydroxyl, methyl or F); methoxy (unsubstituted or substituted by F); —$(CH_2)_n$ CN, wherein n is an integer between 0 and 2; —$(CHR^{13})(CH_2)$—$NHR^{14}$, wherein n is 1, $R^{13}$ is hydrogen or hydroxyl, and $R^{14}$ is hydrogen, $CH_3CO$—, PhCO—, $CH_3SO_2$—, $PhSO_2$—, $PhCH_2CO$—; —$(CH_2)_nOR^1$, wherein n is an integer between 1 and 3, $R^{15}$ is methyl or $CH_2CH_2OCH(CH_3)CH_3$; —$(CH_2)_nCONR^{16}R^{17}$, wherein n is 0 or 1, $R^{16}$ is hydrogen or methyl, and $R^{17}$ is hydrogen, ethyl (unsubstituted or substituted by hydroxyl or F); —$(CH_2)$ $COR^{18}$, wherein n is an integer between 0 and 2, $R^{18}$ is hydroxyl, ethyl, methoxy, $CH_2COCF_3$; —$(CH_2)_n$-Het, wherein n is an integer between 0 and 2, and Het is piperidinyl, triazolyl, thiazolyl or oxodiazolyl, unsubstituted or substituted by one or more halogen atoms or hydroxymethyl;

or $R^5$ and $R^6$ taken together with the aromatic ring to which they are bound form a group:

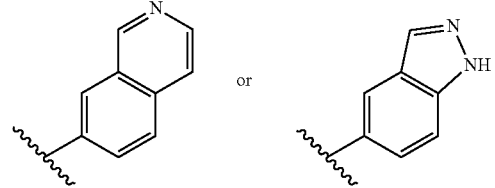 [SMILES: *c1ccc2ccncc2c1 ; *c1ccc2[nH]ncc2c1]

or $R^6$ and $R^7$ taken together with the aromatic ring to which they are bound form a

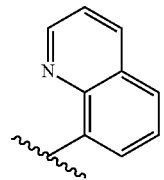 [SMILES: *c1cccc2cccnc12]

with the proviso that the compound of formula (I) is not:
5-[(4-cyanophenoxy)methyl]-3-methyl-1-phenyl-pyrazole-4-carbonitrile,
5-[[2-chloro-4-(hydroxymethyl)phenoxy]methyl]-3-methyl-1-phenyl-pyrazole-4-carbonitrile;
5-[(2-chloro-4-cyano-phenoxy)methyl]-3-methyl-1-phenyl-pyrazole-4-carbonitrile; and
3-methyl-5-(phenoxymethyl)-1-phenyl-pyrazole-4-carbonitrile.

Another preferred embodiment relates to a compound of Formula (I) wherein:

X is selected from —$CH_2$—, —$CH(CH_3)$—, or —$CF_2$—;
Y is selected from: —O—, —NH—, —$NCH_3$—, —S—, —SO—, or —$SO_2$—;
W represents —$(CH_2)_n$—, wherein n is 0 or 1;
Z is selected from $CR^9$, wherein $R^9$ is an H, Cl or F, methyl, hydroxymethyl or hydroxyethyl; or —N—;
$R^1$ is selected from hydrogen or methyl;
$R^2$ is selected from hydrogen, —CN, —$CONH_2$, —$CONHC(CH_3)_3$, or —COOH;
$R^3$ is selected from the group consisting of: phenyl, 2-methylphenyl, 3-methylphenyl, 4-methylphenyl, 2-ethylphenyl, 3-ethylphenyl 4-ethylphenyl, 2-chlorophenyl, 3-chlorophenyl, 4-chlorophenyl, 2,6-dichlorophenyl, 2-fluorophenyl, 3-fluorophenyl, 4-fluorophenyl, 2,4-difluorophenyl, 2,6-difluorophenyl, 2-methoxyphenyl, 3-methoxyphenyl, 4-methoxyphenyl, 2-trifluoromethylphenyl, 3-trifluoromethylphenyl, 4-trifluoromethylphenyl, 2-trifluoromethoxyphenyl 3-trifluoromethoxyphenyl, 4-trifluoromethoxyphenyl, 2-cyanophenyl 3-cyanophenyl, 4-cyanophenyl, 4-methanesulfonylphenyl, pyridine-2-yl, 6-bromopyridin-2-yl, 5-fluoropyridin-2-yl, 5-methylpyridin-2-yl, 5-chloropyridin-2-yl, 5-methoxypyridin-2-yl, pyridin-3-yl, pyridin-4-yl, pyrimidin-2-yl, pyrazine-3-yl, 6-chloropyrazin-3-yl, benzyl, 4-methoxybenzyl, cyclopentyl, cyclohexyl, 4,4'-difluorocyclohexyl, tert-butyl or isopropyl;

each of $R^4$, $R^6$ and $R^7$ is independently selected from the group consisting of hydrogen, F, Cl, methyl, ethyl, trifluoromethyl, hydroxymethyl, 2-hydroxyethyl, 2-hydroxyethyloxy, methoxy, ethoxy, —CONH$_2$, —NHCOCH$_3$, or CN;

R$^5$ is selected from: H, CH$_3$, CH$_2$CH$_3$, CH$_2$H, —CH(CH$_3$)OH, —C(CH$_3$)$_2$OH, —CH$_2$CH$_2$OH, —CH$_2$CH$_2$CH$_2$OH, —CH$_2$CH$_2$CH(CH$_3$)OH, —CH$_2$CH(CH$_3$)CH$_2$OH, —CH(OH)CH$_2$CH$_3$, —CH(OH)CH$_2$CH(CF$_3$)OH, F, CF$_3$, CN, —CH$_2$CN, —CH$_2$CH$_2$CN, —OCH$_3$, —OCF$_3$, —CH$_2$OCH$_3$, —CH$_2$CH$_2$OCH$_3$, —CH$_2$CH$_2$CH$_2$OCH$_3$, —CH$_2$COOH, —CH$_2$CH$_2$COOH, —COOCH$_3$, —CONH$_2$, —COCH$_2$CH$_3$, —COCH$_2$COCF$_3$, —CH$_2$OCH$_2$CH$_2$OCH(CH$_3$)CH$_3$, —CON(CH$_3$)CH$_2$CH$_2$OH, —CONHCH$_2$CF$_3$, —CH$_2$CONHCH$_2$CH$_2$OH, —CH$_2$CH$_2$NH$_2$, —CH(OH)CH$_2$NH$_2$, —CH$_2$CH$_2$NHCOCH$_3$, —CH$_2$CH$_2$NHCOPh, —CH$_2$CH$_2$NHSO$_2$CH$_3$, —CH$_2$CH$_2$NHSO$_2$Ph, —CH$_2$CH$_2$NHCOCH$_2$Ph, or a (CH$_2$)$_n$-Het wherein n is an integer between 0 and 2 and Het is an heterocycle group selected from:

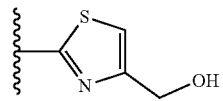 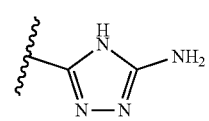

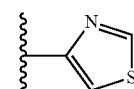

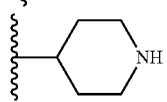

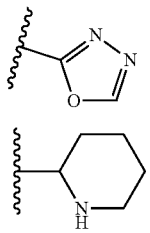

or R$^5$ and R$^6$ taken together with the aromatic ring to which they are bound form a group:

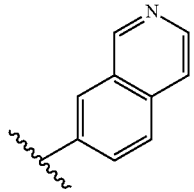 or 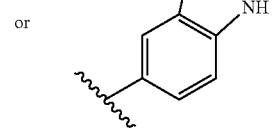

or R$^6$ and R$^7$, taken together with the aromatic ring to which they are bound, form a group:

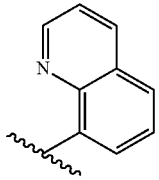

with the proviso that the compound of formula (I) is not:
5-[(4-cyanophenoxy)methyl]-3-methyl-1-phenyl-pyrazole-4-carbonitrile,
5-[[2-chloro-4-(hydroxymethyl)phenoxy]methyl]-3-methyl-1-phenyl-pyrazole-4-carbonitrile;
5-[(2-chloro-4-cyano-phenoxy)methyl]-3-methyl-1-phenyl-pyrazole-4-carbonitrile; and
3-methyl-5-(phenoxymethyl)-1-phenyl-pyrazole-4-carbonitrile.

Most preferably, a compound of formula (I) according to this invention is selected from the group consisting of:

| Example | Chemical Name |
|---|---|
| 3 | 5-[(4-methoxyphenoxy)methyl]-3-methyl-1-phenyl-pyrazole-4-carbonitrile |
| 4 | 3-methyl-5-[(4-methylphenoxy)methyl]-1-phenyl-pyrazole-4-carbonitrile |
| 5 | 5-[[4-(hydroxymethyl)phenoxy]methyl]-3-methyl-1-phenyl-pyrazole-4-carbonitrile |
| 6 | 5-[[4-(2-hydroxyethyl)phenoxy]methyl]-3-methyl-1-phenyl-pyrazole-4-carbonitrile |
| 9 | 5-[(4-cyano-2,6-difluoro-phenoxy)methyl]-3-methyl-1-phenyl-pyrazole-4-carbonitrile |
| 10 | 5-[(4-cyano-2-fluoro-phenoxy)methyl]-3-methyl-1-phenyl-pyrazole-4-carbonitrile |
| 11 | 5-[(4-cyano-2-methyl-phenoxy)methyl]-3-methyl-1-phenyl-pyrazole-4-carbonitrile |
| 12 | 5-[(4-cyano-2,6-dimethyl-phenoxy)methyl]-3-methyl-1-phenyl-pyrazole-4-carbonitrile |
| 13 | 5-[(4-cyano-2,3-difluoro-phenoxy)methyl]-3-methyl-1-phenyl-pyrazole-4-carbonitrile |
| 14 | 5-[[2,3-difluoro-4-(hydroxymethyl)phenoxy]methyl]-3-methyl-1-phenyl-pyrazole-4-carbonitrile |
| 15 | 5-[(4-cyano-2,3-dimethyl-phenoxy)methyl]-3-methyl-1-phenyl-pyrazole-4-carbonitrile |
| 16 | 5-[[4-(hydroxymethyl)-2-methyl-phenoxy]methyl]-3-methyl-1-phenyl-pyrazole-4-carbonitrile |
| 17 | 5-[[4-(hydroxymethyl)-2,6-dimethyl-phenoxy]methyl]-3-methyl-1-phenyl-pyrazole-4-carbonitrile |
| 18 | 5-[(4-fluorophenoxy)methyl]-3-methyl-1-phenyl-pyrazole-4-carbonitrile |
| 19 | 5-[(4-ethylphenoxy)methyl]-3-methyl-1-phenyl-pyrazole-4-carbonitrile |
| 20 | 5-[[2-fluoro-4-(hydroxymethyl)phenoxy]methyl]-3-methyl-1-phenyl-pyrazole-4-carbonitrile |
| 21 | 5-[[2,6-difluoro-4-(hydroxymethyl)phenoxy]methyl]-3-methyl-1-phenyl-pyrazole-4-carbonitrile |
| 22 | 5-[(3,5-dimethylphenoxy)methyl]-3-methyl-1-phenyl-pyrazole-4-carbonitrile |
| 23 | 5-[[2-(hydroxymethyl)phenoxy]methyl]-3-methyl-1-phenyl-pyrazole-4-carbonitrile |

-continued

| Example | Chemical Name |
|---|---|
| 24 | 5-[[3-(hydroxymethyl)phenoxy]methyl]-3-methyl-1-phenyl-pyrazole-4-carbonitrile |
| 25 | 5-[(2,6-dimethylphenoxy)methyl]-3-methyl-1-phenyl-pyrazole-4-carbonitrile |
| 26 | 3-methyl-5-[(2-methylphenoxy)methyl]-1-phenyl-pyrazole-4-carbonitrile |
| 27 | 5-[(2,5-dimethylphenoxy)methyl]-3-methyl-1-phenyl-pyrazole-4-carbonitrile |
| 28 | 3-methyl-5-[(3-methylphenoxy)methyl]-1-phenyl-pyrazole-4-carbonitrile |
| 29 | 5-[[4-(cyanomethyl)phenoxy]methyl]-3-methyl-1-phenyl-pyrazole-4-carbonitrile |
| 30 | 5-[(2,3-dimethylphenoxy)methyl]-3-methyl-1-phenyl-pyrazole-4-carbonitrile |
| 31 | 5-[[4-(2-cyanoethyl)phenoxy]methyl]-3-methyl-1-phenyl-pyrazole-4-carbonitrile |
| 32 | 5-[[2,6-difluoro-4-(3-hydroxypropyl)phenoxy]methyl]-3-methyl-1-phenyl-pyrazole-4-carbonitrile |
| 33 | 5-[[2-fluoro-4-(2-hydroxyethyl)phenoxy]methyl]-3-methyl-1-phenyl-pyrazole-4-carbonitrile |
| 34 | 3-methyl-1-phenyl-5-[(2,3,4-trimethylphenoxy)methyl]pyrazole-4-carbonitrile |
| 35 | 5-[[4-(3-hydroxypropyl)phenoxy]methyl]-3-methyl-1-phenyl-pyrazole-4-carbonitrile |
| 36 | 5-[[2-(2-hydroxyethoxy)phenoxy]methyl]-3-methyl-1-phenyl-pyrazole-4-carbonitrile |
| 37 | N-[2-[(4-cyano-5-methyl-2-phenyl-pyrazol-3-yl)methoxy]phenyl]acetamide |
| 38 | 5-[[3-(2-hydroxyethyl)phenoxy]methyl]-3-methyl-1-phenyl-pyrazole-4-carbonitrile |
| 39 | 5-[(2-ethylphenoxy)methyl]-3-methyl-1-phenyl-pyrazole-4-carbonitrile |
| 40 | 5-[(3-fluorophenoxy)methyl]-3-methyl-1-phenyl-pyrazole-4-carbonitrile |
| 41 | 5-[(3-chlorophenoxy)methyl]-3-methyl-1-phenyl-pyrazole-4-carbonitrile |
| 42 | 5-[[2-fluoro-4-(3-hydroxypropyl)phenoxy]methyl]-3-methyl-1-phenyl-pyrazole-4-carbonitrile |
| 43 | 5-[[2,6-difluoro-4-(3-hydroxy-2-methyl-propyl)phenoxy]methyl]-3-methyl-1-phenyl-pyrazole-4-carbonitrile |
| 43A | (+)-5-[[2,6-difluoro-4-(3-hydroxy-2-methyl-propyl)phenoxy]methyl]-3-methyl-1-phenyl-pyrazole-4-carbonitrile |
| 43B | (+)-5-[[2,6-difluoro-4-(3-hydroxy-2-methyl-propyl)phenoxy]methyl]-3-methyl-1-phenyl-pyrazole-4-carbonitrile |
| 44 | 3-methyl-1-phenyl-5-[[4-(trifluoromethyl)phenoxy]methyl]pyrazole-4-carbonitrile |
| 45 | 4-[(4-cyano-5-methyl-2-phenyl-pyrazol-3-yl)methoxy]-~{N}-(2-hydroxyethyl)-~{N}-methyl-benzamide |
| 46 | 4-[(4-cyano-5-methyl-2-phenyl-pyrazol-3-yl)methoxy]-~{N}-(2,2,2-trifluoroethyl)benzamide |
| 47 | 5-[[4-(3-hydroxybutyl)phenoxy]methyl]-3-methyl-1-phenyl-pyrazole-4-carbonitrile |
| 47A | (+)-5-[[4-(3-hydroxybutyl)phenoxy]methyl]-3-methyl-1-phenyl-pyrazole-4-carbonitrile |
| 47B | (−)-5-[[4-(3-hydroxybutyl)phenoxy]methyl]-3-methyl-1-phenyl-pyrazole-4-carbonitrile |
| 48 | 3-methyl-1-phenyl-5-[(4-thiazol-4-ylphenoxy)methyl]pyrazole-4-carbonitrile |
| 49 | 2-[4-[(4-cyano-5-methyl-2-phenyl-pyrazol-3-yl)methoxy]phenyl]-~{N}-(2-hydroxyethyl)acetamide |
| 50 | 5-[[4-(1-hydroxypropyl)phenoxy]methyl]-3-methyl-1-phenyl-pyrazole-4-carbonitrile |
| 51 | 5-[[4-(1-hydroxy-1-methyl-ethyl)phenoxy]methyl]-3-methyl-1-phenyl-pyrazole-4-carbonitrile |
| 52 | 5-[[4-(2-isopropoxyethoxymethyl)phenoxy]methyl]-3-methyl-1-phenyl-pyrazole-4-carbonitrile |
| 53 | 5-[[4-(3-hydroxypropyl)-2-methoxy-phenoxy]methyl]-3-methyl-1-phenyl-pyrazole-4-carbonitrile |
| 54 | 5-[[4-(1-hydroxyethyl)phenoxy]methyl]-3-methyl-1-phenyl-pyrazole-4-carbonitrile |
| 55 | 5-[[4-(methoxymethyl)phenoxy]methyl]-3-methyl-1-phenyl-pyrazole-4-carbonitrile |
| 56 | 5-[[4-(2-methoxyethyl)phenoxy]methyl]-3-methyl-1-phenyl-pyrazole-4-carbonitrile |
| 57 | 5-[[4-(2-hydroxyethyl)anilino]methyl]-3-methyl-1-phenyl-pyrazole-4-carbonitrile |
| 58 | 5-[[4-(2-hydroxyethyl)-~{N}-methyl-anilino]methyl]-3-methyl-1-phenyl-pyrazole-4-carbonitrile |
| 59 | 5-[[4-(2-hydroxyethyl)phenyl]sulfanylmethyl]-3-methyl-1-phenyl-pyrazole-4-carbonitrile |
| 60 | 5-[(4-cyano-5-methyl-2-phenyl-pyrazol-3-yl)methoxy]pyridine-2-carbonitrile |
| 61 | 5-(2~{H}-indazol-5-yloxymethyl)-3-methyl-1-phenyl-pyrazole-4-carbonitrile |

-continued

| Example | Chemical Name |
|---|---|
| 62 | 5-(7-isoquinolyloxymethyl)-3-methyl-1-phenyl-pyrazole-4-carbonitrile |
| 63 | 3-methyl-1-phenyl-5-(8-quinolyloxymethyl)pyrazole-4-carbonitrile |
| 64 | 3-[(4-cyano-5-methyl-2-phenyl-pyrazol-3-yl)methoxy]pyridine-2-carbonitrile |
| 65 | 5-[(2-fluoro-3-pyridyl)oxymethyl]-3-methyl-1-phenyl-pyrazole-4-carbonitrile |
| 66 | 5-[(5-fluoro-3-pyridyl)oxymethyl]-3-methyl-1-phenyl-pyrazole-4-carbonitrile |
| 67 | 5-[[6-(hydroxymethyl)-3-pyridyl]oxymethyl]-3-methyl-1-phenyl-pyrazole-4-carbonitrile |
| 68 | 3-methyl-5-[(4-methyl-3-pyridyl)oxymethyl]-1-phenyl-pyrazole-4-carbonitrile |
| 69 | 3-methyl-5-[(6-methyl-3-pyridyl)oxymethyl]-1-phenyl-pyrazole-4-carbonitrile |
| 70 | 5-[(2,4-dimethyl-3-pyridyl)oxymethyl]-3-methyl-1-phenyl-pyrazole-4-carbonitrile |
| 71 | 5-[(2,6-difluoro-3-pyridyl)oxymethyl]-3-methyl-1-phenyl-pyrazole-4-carbonitrile |
| 72 | 5-[[4-(2-hydroxyethyl)phenoxy]methyl]-3-methyl-1-(o-tolyl)pyrazole-4-carbonitrile |
| 73 | 5-[[4-(2-hydroxyethyl)phenoxy]methyl]-3-methyl-1-(m-tolyl)pyrazole-4-carbonitrile |
| 74 | 5-[[4-(2-hydroxyethyl)phenoxy]methyl]-3-methyl-1-(p-tolyl)pyrazole-4-carbonitrile |
| 75 | 1-(3-chlorophenyl)-5-[[4-(2-hydroxyethyl)phenoxy]methyl]-3-methyl-pyrazole-4-carbonitrile |
| 76 | 1-(4-chlorophenyl)-5-[[4-(2-hydroxyethyl)phenoxy]methyl]-3-methyl-pyrazole-4-carbonitrile |
| 77 | 5-[[4-(2-hydroxyethyl)phenoxy]methyl]-3-methyl-1-[3-(trifluoromethyl)phenyl]pyrazole-4-carbonitrile |
| 78 | 1-(4-ethylphenyl)-5-[[4-(2-hydroxyethyl)phenoxy]methyl]-3-methyl-pyrazole-4-carbonitrile |
| 79 | 5-[[4-(2-hydroxyethyl)phenoxy]methyl]-1-(3-methoxyphenyl)-3-methyl-pyrazole-4-carbonitrile |
| 80 | 5-[[4-(2-hydroxyethyl)phenoxy]methyl]-1-(4-methoxyphenyl)-3-methyl-pyrazole-4-carbonitrile |
| 81 | 5-[[4-(2-hydroxyethyl)phenoxy]methyl]-3-methyl-1-[3-(trifluoromethoxy)phenyl]pyrazole-4-carbonitrile |
| 82 | 1-(2-fluorophenyl)-5-[[4-(2-hydroxyethyl)phenoxy]methyl]-3-methyl-pyrazole-4-carbonitrile |
| 83 | 1-(4-fluorophenyl)-3-methyl-5-(phenoxymethyl)pyrazole-4-carbonitrile |
| 84 | 1-(4-fluorophenyl)-5-[[4-(2-hydroxyethyl)phenoxy]methyl]-3-methyl-pyrazole-4-carbonitrile |
| 85 | 5-[(3-fluorophenoxy)methyl]-1-(4-fluorophenyl)-3-methyl-pyrazole-4-carbonitrile |
| 86 | 1-(4-fluorophenyl)-3-methyl-5-[(2-methylphenoxy)methyl]pyrazole-4-carbonitrile |
| 87 | 1-(4-fluorophenyl)-5-[[4-(3-hydroxypropyl)phenoxy]methyl]-3-methyl-pyrazole-4-carbonitrile |
| 88 | 1-benzyl-5-[[4-(2-hydroxyethyl)phenoxy]methyl]-3-methyl-pyrazole-4-carbonitrile |
| 89 | 1-benzyl-5-[[4-(3-hydroxypropyl)phenoxy]methyl]-3-methyl-pyrazole-4-carbonitrile |
| 90 | 1-benzyl-5-[[2,6-difluoro-4-(3-hydroxypropyl)phenoxy]methyl]-3-methyl-pyrazole-4-carbonitrile |
| 91 | 5-[[4-(2-hydroxyethyl)phenoxy]methyl]-1-[(4-methoxyphenyl)methyl]-3-methyl-pyrazole-4-carbonitrile |
| 92 | 5-[1-[4-(2-hydroxyethyl)phenoxy]ethyl]-3-methyl-1-phenyl-pyrazole-4-carbonitrile |
| 93 | 5-[1-[2,6-difluoro-4-(3-hydroxypropyl)phenoxy]ethyl]-3-methyl-1-phenyl-pyrazole-4-carbonitrile |
| 94 | 5-[difluoro-[4-(2-hydroxyethyl)phenoxy]methyl]-3-methyl-1-phenyl-pyrazole-4-carbonitrile |
| 95 | 5-[difluoro-[4-(3-hydroxypropyl)phenoxy]methyl]-3-methyl-1-phenyl-pyrazole-4-carbonitrile |
| 96 | 5-[[2,6-difluoro-4-(3-hydroxypropyl)phenoxy]-difluoro-methyl]-3-methyl-1-phenyl-pyrazole-4-carbonitrile |
| 97 | 5-[(4-cyanophenyl)methoxymethyl]-3-methyl-1-phenyl-pyrazole-4-carbonitrile |
| 98 | 5-(benzyloxymethyl)-1-(4-fluorophenyl)-3-methyl-pyrazole-4-carbonitrile |
| 99 | 1-(2-ethylphenyl)-5-[[4-(2-hydroxyethyl)phenoxy]methyl]-3-methyl-pyrazole-4-carbonitrile |
| 100 | 5-[[4-(2-hydroxyethyl)phenoxy]methyl]-3-methyl-1-(4-methylsulfonylphenyl)pyrazole-4-carbonitrile |
| 101 | 1-(3-fluorophenyl)-5-[[4-(2-hydroxyethyl)phenoxy]methyl]-3-methyl-pyrazole-4-carbonitrile |

-continued

| Example | Chemical Name |
|---|---|
| 102 | 5-[[4-(2-hydroxyethyl)phenoxy]methyl]-3-methyl-1-(2-pyridyl)pyrazole-4-carbonitrile |
| 103 | 5-[[4-(2-hydroxyethyl)phenoxy]methyl]-3-methyl-1-(3-pyridyl)pyrazole-4-carbonitrile |
| 104 | 5-[[4-(2-hydroxyethyl)phenoxy]methyl]-3-methyl-1-(4-pyridyl)pyrazole-4-carbonitrile |
| 105 | 5-[[4-(2-hydroxyethyl)phenoxy]methyl]-3-methyl-1-pyrimidin-2-yl-pyrazole-4-carbonitrile |
| 106 | 5-[[4-(2-hydroxyethyl)phenoxy]methyl]-3-methyl-1-pyridazin-3-yl-pyrazole-4-carbonitrile |
| 107 | 1-(4-cyanophenyl)-5-[[4-(2-hydroxyethyl)phenoxy]methyl]-3-methyl-pyrazole-4-carbonitrile |
| 108 | 1-(3-cyanophenyl)-5-[[4-(2-hydroxyethyl)phenoxy]methyl]-3-methyl-pyrazole-4-carbonitrile |
| 109 | 5-[[4-(2-hydroxyethyl)phenoxy]methyl]-3-methyl-1-[4-(trifluoromethyl)phenyl]pyrazole-4-carbonitrile |
| 110 | 1-(3-bromo-2-pyridyl)-5-[[4-(2-hydroxyethyl)phenoxy]methyl]-3-methyl-pyrazole-4-carbonitrile |
| 111 | 1-(2,6-dichlorophenyl)-5-[[4-(2-hydroxyethyl)phenoxy]methyl]-3-methyl-pyrazole-4-carbonitrile |
| 112 | 1-(2,6-difluorophenyl)-5-[[4-(2-hydroxyethyl)phenoxy]methyl]-3-methyl-pyrazole-4-carbonitrile |
| 113 | 1-(2-chlorophenyl)-5-[[4-(2-hydroxyethyl)phenoxy]methyl]-3-methyl-pyrazole-4-carbonitrile |
| 114 | 1-(2,4-difluorophenyl)-5-[[4-(2-hydroxyethyl)phenoxy]methyl]-3-methyl-pyrazole-4-carbonitrile |
| 115 | 5-[[4-(2-hydroxyethyl)phenoxy]methyl]-3-methyl-1-[4-(trifluoromethoxy)phenyl]pyrazole-4-carbonitrile |
| 116 | 1-(6-chloropyridazin-3-yl)-5-[[4-(2-hydroxyethyl)phenoxy]methyl]-3-methyl-pyrazole-4-carbonitrile |
| 117 | 1-cyclopentyl-5-[[4-(2-hydroxyethyl)phenoxy]methyl]-3-methyl-pyrazole-4-carbonitrile |
| 118 | 1-cyclohexyl-5-[[4-(2-hydroxyethyl)phenoxy]methyl]-3-methyl-pyrazole-4-carbonitrile |
| 119 | 1-(4,4-difluorocyclohexyl)-5-[[4-(2-hydroxyethyl)phenoxy]methyl]-3-methyl-pyrazole-4-carbonitrile |
| 120 | 5-[[2,6-difluoro-4-(3-hydroxypropyl)phenoxy]methyl]-3-methyl-1-phenyl-pyrazole-4-carboxamide |
| 121A | 5-[[2-fluoro-4-(2-hydroxyethyl)phenoxy]methyl]-3-methyl-1-phenyl-pyrazole-4-carboxamide |
| 121B | 5-[[2-fluoro-4-(2-hydroxyethyl)phenoxy]methyl]-3-methyl-1-phenyl-pyrazole-4-carboxylic acid |
| 122 | 2-[4-[(2-phenylpyrazol-3-yl)methoxy]phenyl]ethanol |
| 123 | [3-fluoro-4-[(2-phenylpyrazol-3-yl)methoxy]phenyl]methanol |
| 124 | [3,5-difluoro-4-[(2-phenylpyrazol-3-yl)methoxy]phenyl]methanol |
| 125 | [3-fluoro-4-[(5-methyl-2-phenyl-pyrazol-3-yl)methoxy]phenyl]methanol |
| 126 | 2-[4-[(5-methyl-2-phenyl-pyrazol-3-yl)methoxy]phenyl]ethanol |
| 127 | [3,5-difluoro-4-[(5-methyl-2-phenyl-pyrazol-3-yl)methoxy]phenyl]methanol |
| 128 | N-tert-butyl-5-[[4-(2-hydroxyethyl)phenoxy]methyl]-1-phenyl-pyrazole-4-carboxamide |
| 129 | 5-[[4-(2-hydroxyethyl)phenoxy]methyl]-1-phenyl-pyrazole-4-carbonitrile |
| 130 | 5-[[4-(3-hydroxypropyl)phenoxy]methyl]-1-phenyl-pyrazole-4-carbonitrile |
| 131 | 5-[[4-(2-hydroxyethyl)phenyl]sulfinylmethyl]-3-methyl-1-phenyl-pyrazole-4-carbonitrile |
| 132 | 5-[[4-(2-hydroxyethyl)phenyl]sulfonylmethyl]-3-methyl-1-phenyl-pyrazole-4-carbonitrile |
| 133 | 3-[4-[(4-cyano-5-methyl-2-phenyl-pyrazol-3-yl)methoxy]-3,5-difluoro-phenyl]propanoic acid |
| 134 | 2-[4-[(4-cyano-5-methyl-2-phenyl-pyrazol-3-yl)methoxy]phenyl]acetic acid |
| 135 | 5-[[4-(3-methoxypropyl)phenoxy]methyl]-3-methyl-1-phenyl-pyrazole-4-carbonitrile |
| 136 | 3-methyl-1-phenyl-5-[[4-[2-(4-piperidyl)ethyl]phenoxy]methyl]pyrazole-4-carbonitrile |
| 137 | 5-[[4-(2-amino-1-hydroxy-ethyl)phenoxy]methyl]-3-methyl-1-phenyl-pyrazole-4-carbonitrile |
| 138 | 3-methyl-1-phenyl-5-[[4-[2-(2-piperidyl)ethyl]phenoxy]methyl]pyrazole-4-carbonitrile |
| 139 | 5-[[4-(5-amino-4~{H}-1,2,4-triazol-3-yl)phenoxy]methyl]-3-methyl-1-phenyl-pyrazole-4-carbonitrile |
| 140 | 54[4-(2-aminoethyl)phenoxy]methyl]-3-methyl-1-phenyl-pyrazole-4-carbonitrile |
| 141 | N-[2-[4-[(4-cyano-5-methyl-2-phenyl-pyrazol-3-yl)methoxy]phenyl]ethyl]acetamide |
| 142 | N-[2-[4-[(4-cyano-5-methyl-2-phenyl-pyrazol-3-yl)methoxy]phenyl]ethyl]benzamide |

-continued

| Example | Chemical Name |
|---|---|
| 143 | N-[2-[4-[(4-cyano-5-methyl-2-phenyl-pyrazol-3-yl)methoxy]phenyl]ethyl]methanesulfonamide |
| 144 | N-[2-[4-[(4-cyano-5-methyl-2-phenyl-pyrazol-3-yl)methoxy]phenyl]ethyl]benzenesulfonamide |
| 145 | N-[2-[4-[(4-cyano-5-methyl-2-phenyl-pyrazol-3-yl)methoxy]phenyl]ethyl]-2-phenyl-acetamide |
| 146 | 5-[[4-[4-(hydroxymethyl)thiazol-2-yl]phenoxy]methyl]-3-methyl-1-phenyl-pyrazole-4-carbonitrile |
| 147 | 5-[[4-(hydroxymethyl)-2-(trifluoromethyl)phenoxy]methyl]-3-methyl-1-phenyl-pyrazole-4-carbonitrile |
| 148 | 3-methyl-1-phenyl-5-[[4-(4,4,4-trifluoro-1,3-dihydroxy-butyl)phenoxy]methyl]pyrazole-4-carbonitrile |
| 149 | 5-[[4-(3-hydroxypropyl)phenoxy]methyl]-3-methyl-1-(2-pyridyl)pyrazole-4-carbonitrile |
| 150 | 5-[[4-(3-hydroxypropyl)phenoxy]methyl]-3-methyl-1-(p-tolyl)pyrazole-4-carbonitrile |
| 151 | 1-(4-ethylphenyl)-5-[[4-(3-hydroxypropyl)phenoxy]methyl]-3-methyl-pyrazole-4-carbonitrile |
| 152 | 1-(4-chlorophenyl)-5-[[4-(3-hydroxypropyl)phenoxy]methyl]-3-methyl-pyrazole-4-carbonitrile |
| 153 | 1-cyclopentyl-5-[[4-(3-hydroxypropyl)phenoxy]methyl]-3-methyl-pyrazole-4-carbonitrile |
| 154 | 1-(5-fluoro-2-pyridyl)-5-[[4-(3-hydroxypropyl)phenoxy]methyl]-3-methyl-pyrazole-4-carbonitrile |
| 155 | 1-(5-chloro-2-pyridyl)-5-[[4-(3-hydroxypropyl)phenoxy]methyl]-3-methyl-pyrazole-4-carbonitrile |
| 156 | 5-[[4-(3-hydroxypropyl)phenoxy]methyl]-3-methyl-1-(5-methyl-2-pyridyl)pyrazole-4-carbonitrile |
| 157 | 5-[[4-(3-hydroxypropyl)phenoxy]methyl]-1-(5-methoxy-2-pyridyl)-3-methyl-pyrazole-4-carbonitrile |
| 158 | 5-[[2,6-difluoro-4-(3-hydroxypropyl)phenoxy]methyl]-3-methyl-1-(2-pyridyl)pyrazole-4-carbonitrile |
| 159 | 5-[[2,6-difluoro-4-(3-hydroxypropyl)phenoxy]methyl]-3-methyl-1-(p-tolyl)pyrazole-4-carbonitrile |
| 160 | 5-[[2,6-difluoro-4-(3-hydroxypropyl)phenoxy]methyl]-1-(4-ethylphenyl)-3-methyl-pyrazole-4-carbonitrile |
| 161 | 5-[[2,6-difluoro-4-(3-hydroxypropyl)phenoxy]methyl]-1-(4-methoxyphenyl)-3-methyl-pyrazole-4-carbonitrile |
| 162 | 1-(4-chlorophenyl)-5-[[2,6-difluoro-4-(3-hydroxypropyl)phenoxy]methyl]-3-methyl-pyrazole-4-carbonitrile |
| 163 | 1-cyclopentyl-5-[[2,6-difluoro-4-(3-hydroxypropyl)phenoxy]methyl]-3-methyl-pyrazole-4-carbonitrile |
| 164 | 5-[[2,6-difluoro-4-(3-hydroxypropyl)phenoxy]methyl]-1-(5-fluoro-2-pyridyl)-3-methyl-pyrazole-4-carbonitrile |
| 165 | 5-[[2,6-difluoro-4-(3-hydroxypropyl)phenoxy]methyl]-3-methyl-1-(5-methyl-2-pyridyl)pyrazole-4-carbonitrile |
| 166 | 1-(5-chloro-2-pyridyl)-5-[[2,6-difluoro-4-(3-hydroxypropyl)phenoxy]methyl]-3-methyl-pyrazole-4-carbonitrile |
| 167 | 5-[[2,6-difluoro-4-(3-hydroxypropyl)phenoxy]methyl]-1-(5-methoxy-2-pyridyl)-3-methyl-pyrazole-4-carbonitrile |

Compounds of formula (I) can be prepared:
a) by reacting a compound of formula (II):

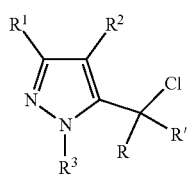

wherein the meanings of $R^1$, $R^2$ and $R^3$ are as defined above, R and R' are independently selected from hydrogen, methyl group or F, with a compound of formula (III)

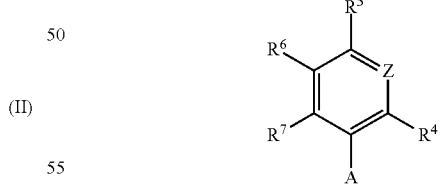

wherein the meanings of $R^4$, $R^5$, $R^6$, $R^7$ and Z are defined above, and A is an hydroxyl, thiol, amino, methylamino, or hydroxymethylene group The reaction of a compound of formula (II) with a compound of formula (III) may be carried out in a reaction-inert solvent such as acetonitrile or DMF and in the presence of a suitable base such as cesium carbonate, potassium carbonate or sodium hydride. The reaction may conveniently be carried out at a temperatures between room temperature and the reflux temperature of the reaction mixture and optionally converting the obtained compound of formula (I) into an addition salt thereof, and/or preparing stereochemically isomeric forms thereof.

Compounds of formula (III) are known in the art or can be prepared following the processes reported in the examples.

Compounds of formula (II) are commercially available, or can be prepared according to the following scheme:

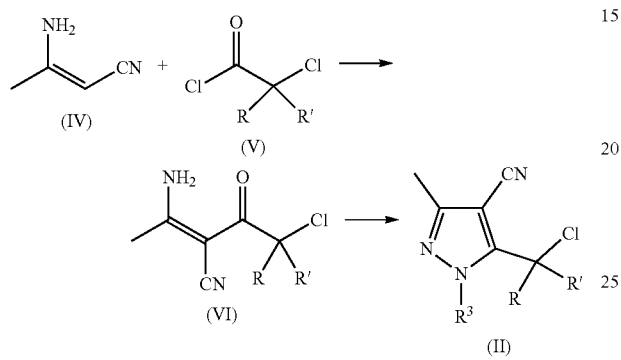

wherein the meanings of $R^3$, R and R' are defined above.

Compounds of formula (II) can be obtained by reaction of compound of formula (VI) with the appropriate substituted hydrazine in acetonitrile, and in the presence of sodium acetate at room temperature. Compounds of formula (VI) are known in the art, or can be synthesized by reaction of compounds of formula (V) with a compound of formula (IV) in toluene, in the presence of pyridine at a temperature ranging between −10° C. and room temperature.

b) by reacting a compound of formula (VII) or its salt:

wherein the meanings of $R^3$ are defined above
with compounds of formula (VIII) or its salt:

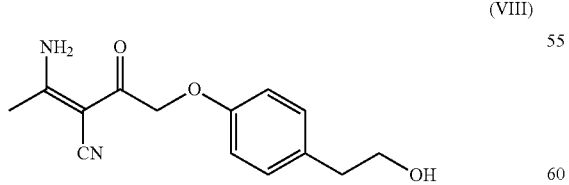

The reaction can be carried out in the presence of sodium acetate heating the reaction mixture using microwave irradiation at the temperature indicated in the reported example, or using potassium acetate as base, in acetic acid and water at 90° C.

Compound of formula (VII) are known in the art, while compound of formula (VIII) can be synthesized from compound of formula (VI), wherein R and R' are hydrogens, and 4-(2-hydroxyethyl)phenol in the presence of an appropriate base such as potassium carbonate in a suitable solvent like acetonitrile.

c) by reacting a compound of formula (IX):

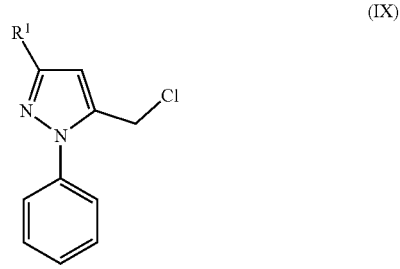

wherein the meanings of $R^1$ are defined above
with a compound of formula (X)

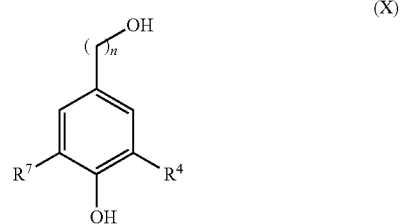

wherein n is between 0 and 1 and the meanings of $R^4$ and $R^7$ are as defined above The reaction of a compound of formula (IX) with a compound of formula (X) may be carried out in a reaction-inert solvent such as acetonitrile and in the presence of a suitable base such as potassium carbonate. The reaction may conveniently be carried out at a temperatures between room temperature and the reflux temperature of the reaction mixture Compound of formula (IX) and (X) are known in the art d) by reacting a compound of formula (XI):

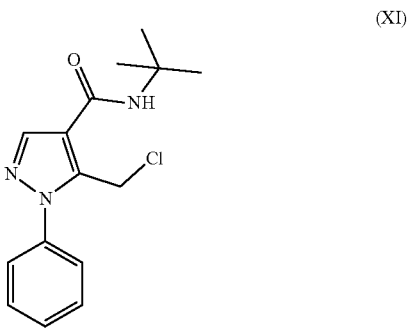 [SMILES: CC(C)(C)NC(=O)c1cnn(-c2ccccc2)c1CCl]

with a compound of formula (XII)

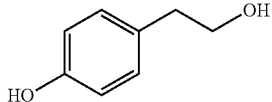

Compound of formula (XI) can be synthesized as reported in the specific example.

Compound of formula (XII) is commercially available.

The reaction of a compound of formula (IX) with a compound of formula (X) may be carried out in a reaction-inert solvent such as acetonitrile and in the presence of a suitable base such as potassium carbonate. The reaction may conveniently be carried out at the reflux temperature of the reaction mixture e) by reacting a compound of formula (XIII):

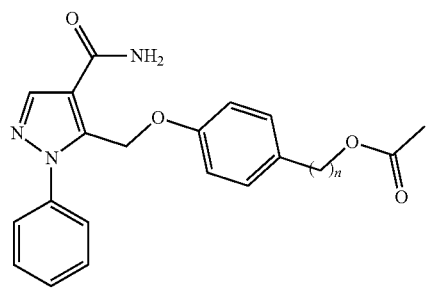

wherein n is between 1 and 3
with $Tf_2O$ and then hydrolyzed with NaOH.

Compound of formula (XIII) can be synthesized as reported in the specific example.

The reaction can be carried out in dry $CH_2C2$ at room temperature after adding $Tf_2O$ at 0° C.

f) by reacting a compound of formula (XIV):

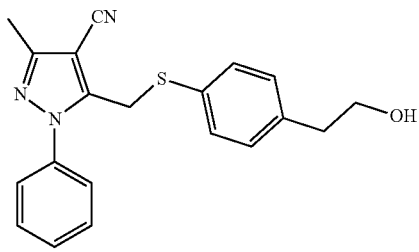

with mCPBA

Compound of formula (XIV) can be prepared from compound of formula (II) and 2-(4-sulfanylphenyl)ethanol in the presence of an appropriate base such as potassium carbonate in a suitable solvent like acetonitrile.

g) by reacting a compound of formula (XV):

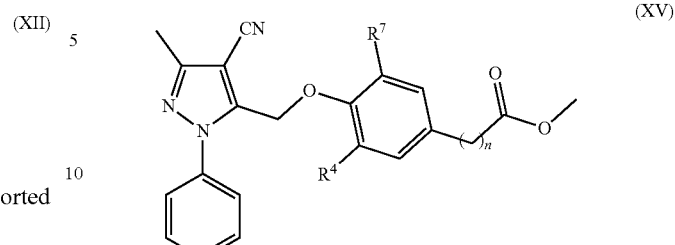

wherein n is between 1 and 2 and the meanings of $R^4$ and $R^7$ are as defining above with NaOH or LioH Compound of formula (XV) can be prepared from compound of formula (II) and the appropriate phenol in the presence of an appropriate base such as potassium carbonate in a suitable solvent like acetonitrile.

h) by reacting a compound of formula (XVI):

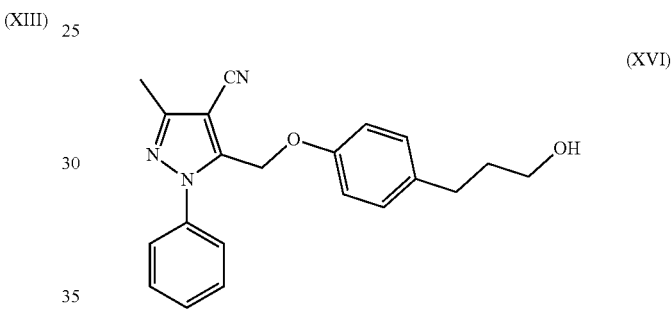

with MeI in the presence of NaH

Compound of formula (XVI) can be prepared from compound of formula (II) and 4-(3-hydroxypropyl)phenol in the presence of an appropriate base such as potassium carbonate in a suitable solvent like acetonitrile.

i) by reacting a compound of formula (XVII):
ii)

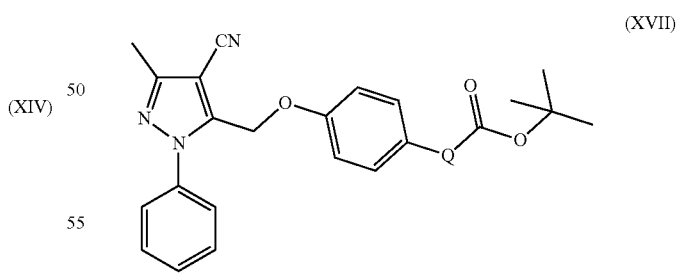

wherein the meanings of Q is a 4-ethylpiperidine, 2-ethylpiperidine, 2-aminoethanol, 4H-1,2,4-triazol-3-amine or 2-aminoethyl with TFA.

Compound of formula (XVII) can be prepared as reported in the specific example.

The reaction may be carried out in a solvent such as dichloromethane at room temperature.

1) by reacting a compound of formula (XVIII):

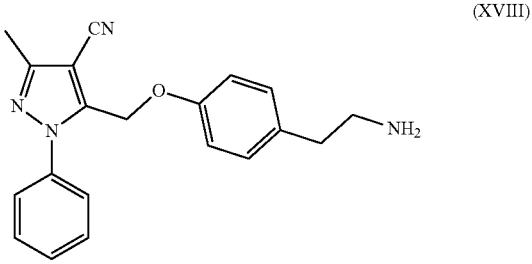 [SMILES: Cc1nn(-c2ccccc2)c(COc2ccc(CCN)cc2)c1C#N]

with a compound of formula (XIX)

wherein the meanings of L is a methyl, a phenyl or a benzyl group and M is a carbonyl group or L is a phenyl or a methyl and M is a sulfonyl group.

Compounds of formula (XIX) are known in the art while compound of formula (XVIII) can be prepared from compound of formula (II) as reported in the specific example.

The reaction of a compound of formula (XVIII) with a compound of formula (XIX) may be carried out in a solvent such as dichloromethane and in the presence of a suitable base such as trimethylamine at room temperature.

m) by reacting a compound of formula (XX):

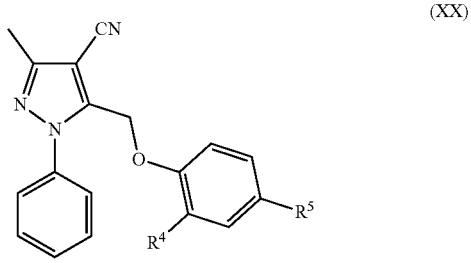

wherein the meanings of $R^4$ and $R^5$ are as reported above with $NaBH_4$

The reaction can be carried out in methanol at room temperature after adding $NaBH_4$ at 0° C.

Compound of formula (XX) can be synthesized from compound of formula (II) and the appropriate phenols in the presence of an appropriate base such as potassium carbonate in a suitable solvent like acetonitrile.

The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of formula (1) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the pharmaceutically acceptable salts and stereoisomeric forms thereof possess GPR120 receptor modulating properties as demonstrated in the Pharmacological Examples. Other examples of art-known group transformation reactions to convert compounds of formula (I) into other compounds of formula (I) are hydrolysis of carboxylic esters to the corresponding carboxylic acid or alcohol; hydrolysis of amides to the corresponding carboxylic acids or amines; alcohols may be converted into esters and ethers; primary amines may be converted into secondary or tertiary amines; double bonds may be hydrogenated to the corresponding single bond. The starting materials and some of the intermediates are known compounds and are commercially available or may be prepared according to conventional reaction procedures generally known in the art. The compounds of formula (I) as prepared in the hereinabove described processes may be synthesized in the form of racemic mixtures of enantiomers which can be separated from one another following art-known resolution procedures. Those compounds of formula (I) that are obtained in racemic form may be converted into the corresponding diastereomeric salt forms by reaction with a suitable chiral acid. Said diastereomeric salt forms are subsequently separated, for example, by selective or fractional crystallization and the enantiomers are liberated there from by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials. In the preparation of the compounds of formula I and the starting materials and/or intermediates described herein it may be useful to protect certain groups which are sensitive to the reaction conditions. The evaluation of the usefulness of the optional protection, as well as the selection of the suitable protecting agent, according to the reaction carried out in the preparation of the compounds of the invention and the functional group to be protected, are within the common knowledge of the skilled person. The removal of the optional protective groups is carried out according to conventional techniques. For a general reference to the use of protective groups in organic chemistry, see Theodora W. Greene and Peter G. M. Wuts "Protective groups in organic synthesis", John Wiley & Sons, Inc., II Ed., 1991.

The preparation of the salts of the compounds of formula I is carried out according to known methods.

The present compounds of formula (I) are useful as a medicine especially in the treatment of a condition or disease mediated by the FFA4 receptor, in particular FFA4 receptor agonistic activity. Subsequently the present compounds may be used for the manufacture of a medicine for treatment of a condition or a disease mediated by FFA4 receptor activity, in particular FFA4 receptor agonistic activity.

The present invention also provides the use of a compound of formula (I) or a pharmaceutically acceptable salt thereof for the manufacture of a medicament for the treatment of conditions or diseases selected from FFA4 receptor mediated conditions or diseases.

The compounds of the invention inhibit inflammatory processes affecting all body systems. Therefore are useful in the treatment of inflammatory processes of the muscular-skeletal system of which the following is a list of examples but it is not comprehensive of all target disorders: arthritic conditions such as ankylosing spondylitis, cervical arthritis, fibromyalgia, gout, juvenile rheumatoid arthritis, lumbosacral arthritis, osteoarthritis, osteoporosis, psoriatic arthritis, rheumatic disease; disorders affecting skin and related tissues: eczema, psoriasis, dermatitis and inflammatory conditions such as sunburn; disorders of the respiratory system: asthma, allergic rhinitis and respiratory distress syndrome, lung disorders in which inflammation is involved such as asthma and bronchitis; chronic obstructive pulmonary disease; disorders of the immune and endocrine systems: periarthritis nodosa, thyroiditis, aplastic anaemia, scleroderma, myasthenia gravis, multiple sclerosis and other demyelinating disorders, encephalomyelitis, sarcoidosis, nephritic syndrome, Bechet's syndrome, polymyositis, gingivitis.

Compounds of the invention are also useful in the treatment of gastrointestinal (GI) tract disorders such as inflammatory bowel disorders including but not limited to ulcerative colitis, Crohn's disease, ileitis, proctitis, celiac disease, enteropathies, microscopic or collagenous colitis, eosinophilic gastroenteritis, or pouchitis resulting after proctocolectomy and post ileonatal anastomosis, and irritable bowel syndrome including any disorders associated with abdominal pain and/or abdominal discomfort such as pylorospasm, nervous indigestion, spastic colon, spastic colitis, spastic bowel, intestinal neurosis, functional colitis, mucous colitis, laxative colitis and functional dyspepsia; but also for treatment of atrophic gastritis, gastritis varioliforme, ulcerative colitis, peptic ulceration, pyrosis, and other damages to the GI tract, for example, by *Helicobacter pylori*, gastroesophageal reflux disease, gastroparesis, such as diabetic gastroparesis; and other functional bowel disorders, such as non-ulcerative dyspepsia (NUD); emesis, diarrhoea, and visceral inflammation.

Compounds of the invention are also useful in the treatment of disorders of the genito-urinary tract such as overactive bladder, prostatitis (chronic bacterial and chronic non-bacterial prostatitis), prostadynia, interstitial cystitis, urinary incontinence and benign prostatic hyperplasia, annexities, pelvic inflammation, bartholinities and vaginitis. In particular, overactive bladder and urinary incontinence.

The compounds of the invention are also useful in the treatment of ophthalmic diseases such as retinitis, retinopathies, uveitis and acute injury to the eye tissue, age-related macular degeneration or glaucoma, conjunctivitis.

The compounds of the invention are also useful in the treatment of eating disorders such as anorexia nervosa including the subtypes restricting type and binge-eating/purging type; bulimia nervosa including the subtypes purging type and non-purging type; obesity; compulsive eating disorders; binge eating disorder; and eating disorder not otherwise specified.

The compounds of the invention are also useful in the treatment of prevention or treatment of neuro-inflammatory disorders.

The compounds of the invention are also useful in the treatment of allergic dermatitis, hyper-responsiveness of the airway, chronic obstructive pulmonary disease (COPD), bronchitis, septic shock, Sjögren's syndrome, glomerulonephritis, atherosclerosis, growth and metastases of malignant cells, myeloblastic leukaemia, diabetes, meningitis, osteoporosis, burn injury, ischaemic heart disease, stroke, peripheral vascular disease, varicose veins, glaucoma.

The term "treating" and "treatment', as used herein, refers to curative, palliative and prophylactic treatment, including reversing, alleviating, inhibiting the progress of, or preventing the disease, disorder or condition to which such term applies, or one or more symptoms of such disease, disorder or condition.

Additionally the present invention provides pharmaceutical compositions comprising at least one pharmaceutically acceptable carrier and a therapeutically effective amount of a compound of formula (I).

In order to prepare the pharmaceutical compositions of this invention, an effective amount of the particular compound, in base or acid addition salt form, as the active ingredient is combined in intimate admixture with at least one pharmaceutically acceptable carrier, which carrier may take a wide variety of forms depending on the form of preparation desired for administration. These pharmaceutical compositions are desirably in unitary dosage form suitable, preferably, for oral administration, rectal administration, percutaneous administration or parenteral injection.

For example in preparing the compositions in oral dosage form, any of the usual liquid pharmaceutical carriers may be employed, such as for instance water, glycols, oils, alcohols and the like in the case of oral liquid preparations such as suspensions, syrups, elixirs and solutions; or solid pharmaceutical carriers such as starches, sugars, kaolin, lubricants, binders, disintegrating agents and the like in the case of powders, pills, capsules and tablets. Because of their easy administration, tablets and capsules represent the most advantageous oral dosage unit form, in which case solid pharmaceutical carriers are obviously employed. For parenteral injection compositions, the pharmaceutical carrier will mainly comprise sterile water, although other ingredients may be included in order to improve solubility of the active ingredient.

Injectable solutions may be prepared for instance by using a pharmaceutical carrier comprising a saline solution, a glucose solution or a mixture of both. Injectable suspensions may also be prepared by using appropriate liquid carriers, suspending agents and the like. In compositions suitable for percutaneous administration, the pharmaceutical carrier may optionally comprise a penetration enhancing agent and/or a suitable wetting agent, optionally combined with minor proportions of suitable additives which do not cause a significant deleterious effect to the skin. Said additives may be selected in order to facilitate administration of the active ingredient to the skin and/or be helpful for preparing the desired compositions. These topical compositions may be administered in various ways, e.g., as a transdermal patch, a spot-on or an ointment. Addition salts of the compounds of formula (1), due to their increased water solubility over the corresponding base form, are obviously more suitable in the preparation of aqueous compositions.

It is especially advantageous to formulate the pharmaceutical compositions of the invention in dosage unit form for ease of administration and uniformity of dosage.

"Dosage unit form" as used herein refers to physically discrete units suitable as unitary dosages, each unit containing a predetermined amount of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions of the present invention may take the form of solid dose forms, for example, tablets (both swallowable and chewable forms), capsules or gelcaps, prepared by conventional means with pharmaceutically acceptable excipients and carriers such as binding agents (e.g. pregelatinised maize starch, polyvinylpyrrolidone, hydroxypropylmethylcellulose and the like), fillers (e.g. lactose, microcrystalline cellulose, calcium phosphate and the like), lubricants (e.g. magnesium stearate, talc, silica and the like), disintegrating agents (e.g. potato starch, sodium starch glycollate and the like), wetting agents (e.g. sodium lauryl sulphate) and the like. Such tablets may also be coated by methods well known in the art.

Liquid preparations for oral administration may take the form of e.g. solutions, syrups or suspensions, or they may be formulated as a dry product for admixture with water and/or another suitable liquid carrier before use. Such liquid preparations may be prepared by conventional means, optionally with other pharmaceutically acceptable additives such as suspending agents (e.g. sorbitol syrup, methylcellulose, hydroxypropylmethylcellulose or hydrogenated edible fats), emulsifying agents (e.g. lecithin or acacia), non-aqueous carriers (e.g. almond oil, oily esters or ethyl alcohol), sweeteners, flavours, masking agents and preservatives (e.g. methyl or propyl p-hydroxybenzoates or sorbic acid).

Pharmaceutically acceptable sweeteners useful in the pharmaceutical compositions of the invention comprise preferably at least one intense sweetener such as aspartame, acesulfame potassium, sodium cyclamate, alitame, dihydrochalcone sweetener, monellin, stevioside sucralose (4,1',6'-trichloro-4,1',6'-trideoxygalactosucrose) or, preferably, saccharin, sodium or calcium saccharin, and optionally at least one bulk sweetener such as sorbitol, mannitol, fructose, sucrose, maltose, isomalt, glucose, hydrogenated glucose syrup, xylitol, caramel or honey. Intense sweeteners are conveniently used in low concentrations. For example, in the case of sodium saccharin, the said concentration may range from about 0.04% to 0.1% (weight/volume) of the final formulation. The bulk sweetener can effectively be used in larger concentrations ranging from about 10% to about 35%, preferably from about 10% to 15% (weight/volume). The pharmaceutically acceptable flavours which can mask the bitter tasting ingredients in the low-dosage formulations comprise preferably fruit flavours such as cherry, raspberry, black currant or strawberry flavour. A combination of two flavours may yield very good results. In the high-dosage formulations, stronger pharmaceutically acceptable flavours may be required such as Caramel Chocolate, Mint Cool, Fantasy and the like.

Each flavour may be present in the final composition in a concentration ranging from about 0.05% to 1% (weight/volume). Combinations of said strong flavours are advantageously used. Preferably a flavour is used that does not undergo any change or loss of taste and/or color under the circumstances of the formulation.

The compounds of formula (I) may be formulated for parenteral administration by injection, conveniently intravenous, intra-muscular or subcutaneous injection, for example by bolus injection or continuous intravenous infusion. Formulations for injection may be presented in unit dosage form, e.g. in ampoules or multi-dose containers, including an added preservative. They may take such forms as suspensions, solutions or emulsions in oily or aqueous vehicles, and may contain formulating agents such as isotonizing, suspending, stabilizing and/or dispersing agents. Alternatively, the active ingredient may be present in powder form for mixing with a suitable vehicle, e.g. sterile pyrogen-free water, before use.

The compounds of formula (I) may also be formulated in rectal compositions such as suppositories or retention enemas, e.g. containing conventional suppository bases such as cocoa butter and/or other glycerides.

Those of skill in the treatment of diseases linked to the mediation of the ligand-gated ion channels will easily determine the therapeutically effective amount of a compound of formula (I) from the test results presented hereinafter. In general it is contemplated that a therapeutically effective dose will be from about 0.001 mg/kg to about 50 mg/kg of body weight, more preferably from about 0.01 mg/kg to about 10 mg/kg of body weight of the patient to be treated. It may be appropriate to administer the therapeutically effective dose in the form of two or more sub-doses at appropriate intervals throughout the day. Said sub-doses may be formulated as unit dosage forms, for example each containing from about 0.1 mg to about 1000 mg, more particularly from about 1 to about 500 mg, of the active ingredient per unit dosage form.

As used herein, a "therapeutically effective amount" of a compound, is the quantity of a compound which, when administered to an individual or animal, results in a sufficiently high level of that compound in the individual or animal to cause a discernible GPR120 receptor modulating response.

The exact dosage and frequency of administration depends on the particular compound of formula (I) used, the particular condition being treated, the severity of the condition being treated, the age, weight and general physical condition of the particular patient as well as the other medication, the patient may be taking, as is well known to those skilled in the art. Furthermore, said "therapeutically effective amount" may be lowered or increased depending on the response of the treated patient and/or depending on the evaluation of the physician prescribing the compounds of the instant invention. The effective daily amount ranges mentioned hereinabove are therefore only guidelines.

Nomenclature and Structures

In general, the nomenclature used in this Application is based on ChemSketch™ (ACDLabs) and generated according to the IUPAC systematic nomenclature. Chemical structures shown herein were prepared using ISIS© version 2.2. Any open valency appearing on a carbon, oxygen, sulfur, or nitrogen atom in the structures herein indicates the presence of a hydrogen atom unless indicated otherwise. Where a nitrogen-containing heteroaryl ring is shown with an open valency on a nitrogen atom and variables such as $R^1$, $R^2$, $R^3$ etc. are shown on the heteroaryl ring, such variables may be bound or joined to the open valency nitrogen. Where a chiral center exists in a structure but no specific stereochemistry is shown for the chiral center, both enantiomers associated with the chiral center are encompassed by the structure. Where a structure shown herein may exist in multiple tautomeric forms, all such tautomers are encompassed by the structure. The atoms represented in the structure herein are intended to encompass all naturally occurring isotopes of such atoms. Thus, for example, the hydrogen atoms represented herein are meant to include deuterium and tritium, and the carbon atoms are meant to include $^{13}C$ and $^{14}C$ isotopes.

Abbreviations

Abbreviations which are used in the description of the Schemes and the Examples that follows are:

AcOH: Acetic acid; Anh: Anhydrous; AcONa: Sodium acetate; Boc: Tert-butyl-carbonate; Boc$_2$O: Di-tert-butyl dicarbonate; CC: Column Chromatography; DAST: Diethylaminosulfur trifluoride; DCM: Dichloromethane; DEA: Diethylamine; DIAD: Diisopropylazodicarboxylate; DIBAL: Diisobutylaluminium hydride; DIPEA: Diisopropylethylenamine; DMAP: Dimethylaminopyridine; DMF: Dimethylformamide; DMSO: Dimethylsulfoxide; Et$_2$O: Diethyl ether; EtOAc: Ethyl acetate; EtOH: Ethanol; ESI: Electrospray ionization; HBTU: N,N,N',N'-Tetramethyl-O-(1H-benzotriazol-1-yl)uronium hexafluorophosphate; h: hour; Hrs hours; M: Molar; MeCN: Acetonitrile; MeOH: Methanol; Min: Minute(s); Ni-Raney: Nickel-Raney; NMR: Nuclear Magnetic Resonance; rt: Room Temperature; TFA Trifluoroacetic acid; THF: Tetrahydrofuran; TLC: Thin Layer Chromatography; TMSCN Trimethylsilylcyanide; UPLC-MS: UltraPerformance LiquidChromatography-Mass Spectrometry; XPhos: 4,5-bis(diphenylphosphino)-9,9-dimethylxantene.

Experimental Part

Compounds of formula (I) can be prepared according to different procedures described in the following general methods.

General Synthetic Schemes

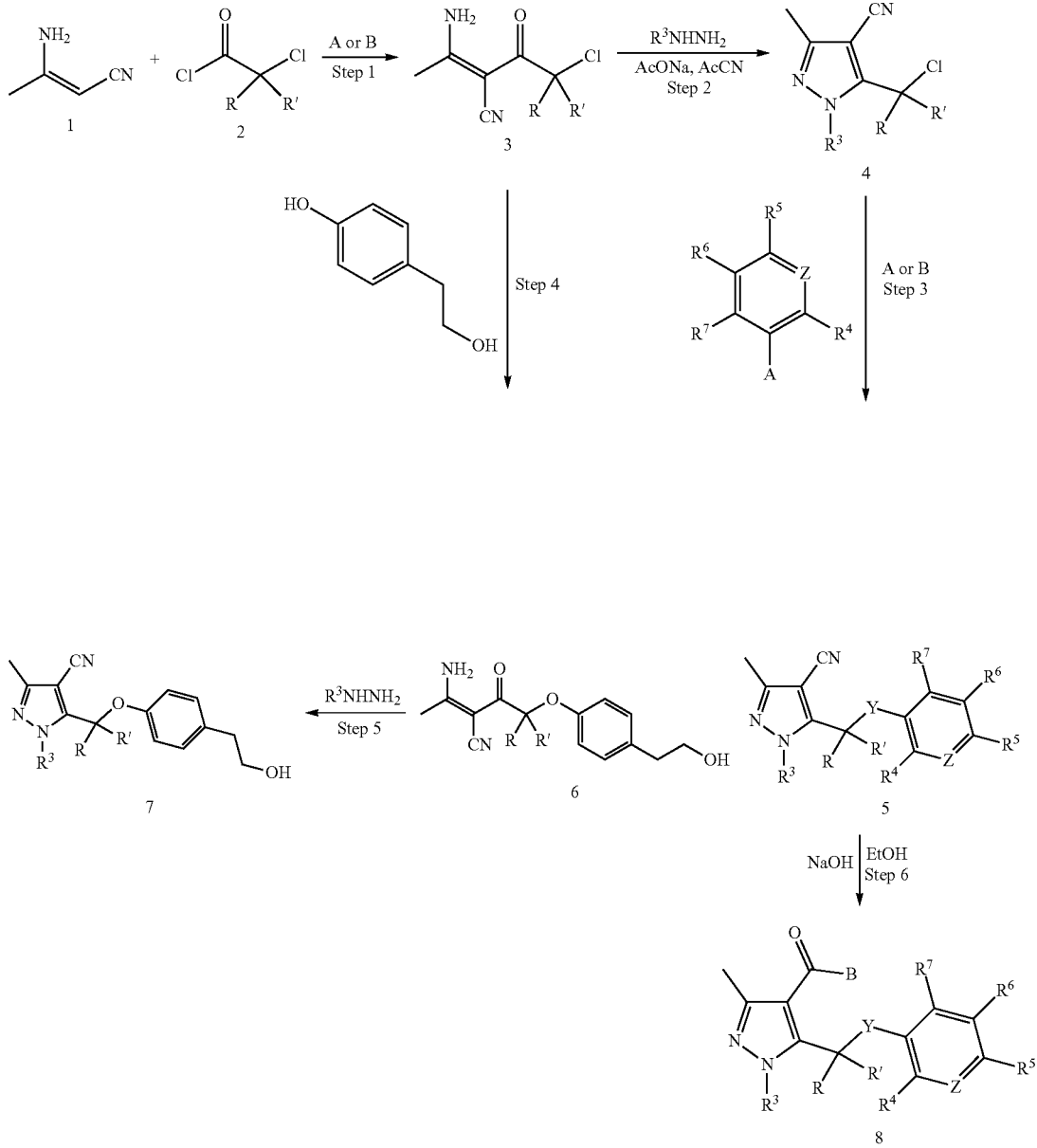

Scheme 1

Step 1.

Method A. A mixture of 3-aminocrotononitrile 1 (1.0 eq) and pyridine (1.2 eq) in anhydrous toluene was cooled to −5° C. in ice-water salt bath. The appropriate acyl chloride 2 (1.0 eq) in anhydrous toluene was added dropwise, and the reaction mixture was stirred at the same temperature for 2 h. Water was added, and the layers were separated. The aqueous phase was extracted with ethyl acetate (×3). The combined organic layers were washed with 1 N HCl (×2), brine (×3), dried over $Na_2SO_4$, filtered and concentrated to small volume. The precipitate was collected to provide the desired product.

Method B. To a solution of 3-aminocrotononitrile 1 (1.0 eq) in benzene was added pyridine (2.5 eq), followed by dropwise addition of appropriate acyl chloride 2 (1.2 eq) in benzene at 0° C. The reaction mixture was stirred at 0° C. to room temperature for 3 h. After completion of reaction, the reaction mixture was poured into ice water and extracted with ethyl acetate (×3). The combined organic layer was washed with saturated $NaHCO_3$ solution (×2) and 10% citric acid solution (×2). The organic layer was dried over $Na_2SO_4$, filtered and evaporated under reduced pressure. The crude product was suspended in DCM to give a precipitate that was collected to provide the desired product.

Step 2. The appropriate substituted hydrazine (1.0 eq) was added to a mixture of the compound 3 (1.0 eq), and sodium acetate in acetonitrile. The reaction mixture was stirred at room temperature overnight. 1 N HCl was added, and the resulted mixture was extracted with ethyl acetate (×3). The combined organic layers were washed with brine (×3), dried over $Na_2SO_4$, filtered and evaporated. The desired product was obtained after purification of the crude material as reported in the specific examples.

Step 3.

Method A. A mixture of the chloride 4 (1.0 eq), the appropriate alcohol (1.0 eq), and $K_2CO_3$ or $Cs_2CO_3$ (2.0 eq) in acetonitrile or N,N-dimethylformamide was stirred for a time period between 2 h and overnight at a temperature ranging between room temperature and the reflux temperature. After cooling to rt, $H_2O$ was added and the reaction mixture was extracted with EtOAc (×3). The combined organic layers were washed with brine, dried over $Na_2SO_4$, filtered and evaporated under vacuum. The desired product was obtained after purification of the crude material as reported in the specific examples.

Method B. The appropriate alcohol was added to a cooled suspension of NaH (2.0 eq) in dry DMF. After 5 min the reaction mixture was warmed to rt and stirred for additional 30 min. The alkyl chloride 4 (1.2 eq) was added and the resulting mixture was stirred at rt for a time period between 1 h and overnight. The reaction mixture was quenched with water and extracted with EtOAc (×3). The combined organic layers were washed with brine (×3), dried over $Na_2SO_4$, filtered and evaporated under reduced pressure. The crude product was purified by flash silica gel column chromatography as reported in the specific examples.

Step 4. To a solution of 3 (1.0 eq) and 4-(2-hydroxyethyl)phenol (1.2 eq) in acetonitrile was added potassium carbonate (3.0 eq) and heated at 80° C. for 16 h. After 16 h, the reaction mixture was filtered under vacuum and washed with EtOAc. The filtrate was evaporated under vacuum to give crude, which was purified by flash silica gel column chromatography as reported in the specific examples.

Step 5.

Method A. To a suspension of 6 (1.0 eq) and the appropriate substituted hydrazine (ranging between 1.1 and 1.5 eq) in acetonitrile was added sodium acetate (ranging between 2.0 and 3.0 eq) and the reaction mixture was heated to temperature ranging from 700 to 110° C. for 1 h or 2 h under microwave irradiation. After completion of reaction, the reaction mixture was acidified with diluted HCl and extracted with ethyl acetate (×3). The organic layer was washed with brine, dried over anhydrous $Na_2SO_4$ and evaporated under reduced pressure to afford the crude product that was purified as reported in the specific examples.

Method B. To a suspension of 6 (1.0 eq) and the appropriate substituted hydrazine (ranging between 1.2 and 1.5 eq) in acetonitrile, was added sodium acetate (3.0 eq) and the reaction mixture was heated to 110° C. for 2 h under microwave irradiation. After completion of reaction, the reaction mixture was quenched with water and extracted with EtOAc (×3). The organic layer was washed with brine (×2), dried over anhydrous $Na_2SO_4$, filtered and evaporated under reduced pressure to afford impure product that was purified as reported in the specific examples.

Method C. A suspension of 6 (1.0 eq), appropriate hydrazine (ranging between 1.0 and 1.5 eq) and sodium acetate (3.0 eq) in acetonitrile was heated in microwave at 110° C. for 2 h. After 2 h, the reaction mixture was poured in 10% citric acid solution and extracted with ethyl acetate (×3). The combined organic layer was dried over anhydrous $Na_2SO_4$ and evaporated under reduced pressure to afford the crude product that was purified as reported in the specific examples.

Method D. To a suspension of 6 (1.0 eq) and the appropriate substituted hydrazine (ranging between 1.0 and 1.5 eq) in acetonitrile was added sodium acetate (ranging between 1.4 and 3.0 eq) and the reaction mixture was heated to 110° C. for 1 h under microwave irradiation. After completion of reaction, the reaction mixture was filtered under vacuum and filtrate was evaporated under reduced pressure to afford the crude product that was purified as reported in the specific examples.

Method E. A suspension of 6 (1.0 eq), appropriate substituted hydrazine (ranging between 1.8 and 2.4 eq) and potassium acetate (ranging between 3.0 and 5.3 eq) in acetic acid: water (1:1) was heated at 90° C. for a time period between 3 h and 16 h. The solvents were evaporated under vacuum. The residue was neutralized with saturated $NaHCO_3$ solution and extracted with ethyl acetate (×3). The combined organic layer was dried over anhydrous $Na_2SO_4$ and evaporated under reduced pressure to afford the crude product that was purified as reported in the specific examples.

Method F. To a suspension of 6 (1.0 eq) and the appropriate substituted hydrazine (ranging between 1.0 and 1.2 eq) in acetonitrile was added sodium acetate (3.0 eq) and the reaction mixture was heated to 110° C. for 6 h. After completion of reaction, the reaction mixture was filtered and filtrate was evaporated under reduced pressure to afford the crude product that was purified as reported in the specific examples.

Step 6. A mixture of 5 (1.0 eq) and 3N sodium hydroxide (1.0 eq) in ethanol was heated to reflux temperature for 12 h. After cooling, the reaction mixture was acidified with 2N hydrochloric acid and extracted with dichloromethane. The combined organic layers were washed with brine, dried over $Na_2SO_4$, filtered and evaporated under reduced pressure to afford the crude product that was purified as reported in the specific examples.

Scheme 2

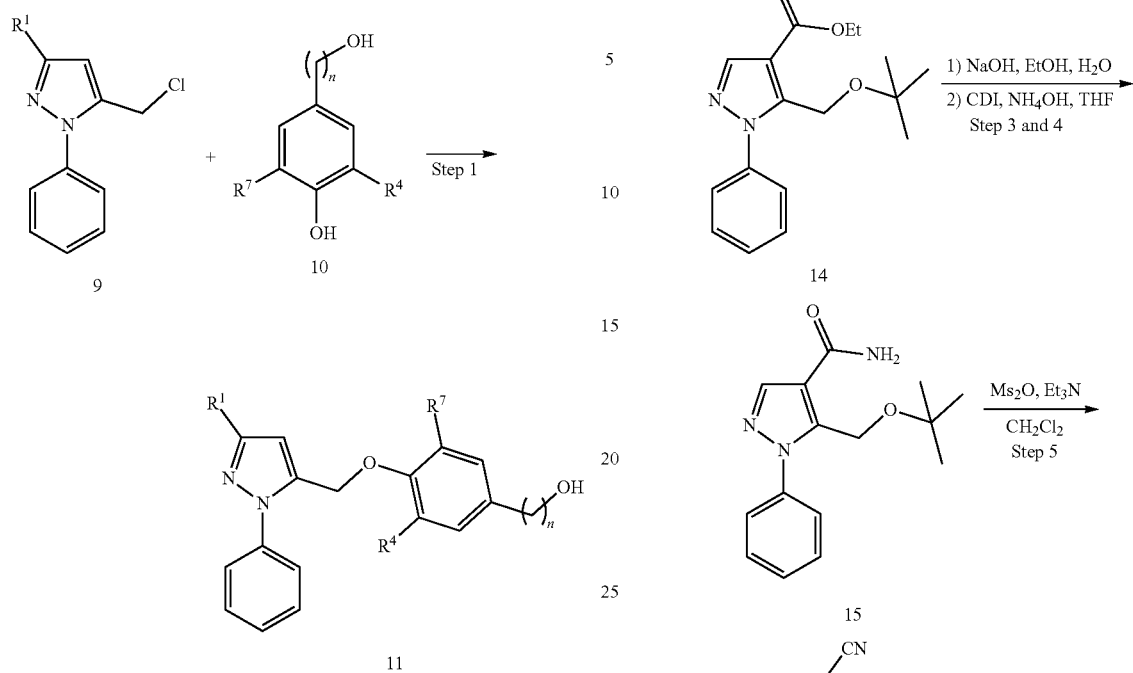

Step 1. A mixture of the chloride 1 (1.0 eq), the appropriate alcohol 2 (1.0 eq), and K₂CO₃ or Cs₂CO₃ (2.0 eq) in acetonitrile or N,N-dimethylformamide was stirred for a time period between 2 h and overnight at a temperature ranging between room temperature and the reflux temperature. After cooling to rt, H₂O was added and the reaction mixture was extracted with EtOAc (×3). The combined organic layers were washed with brine, dried over Na₂SO₄, filtered and evaporated under vacuum. The desired product was obtained after purification of the crude material as reported in the specific examples.

Scheme 3

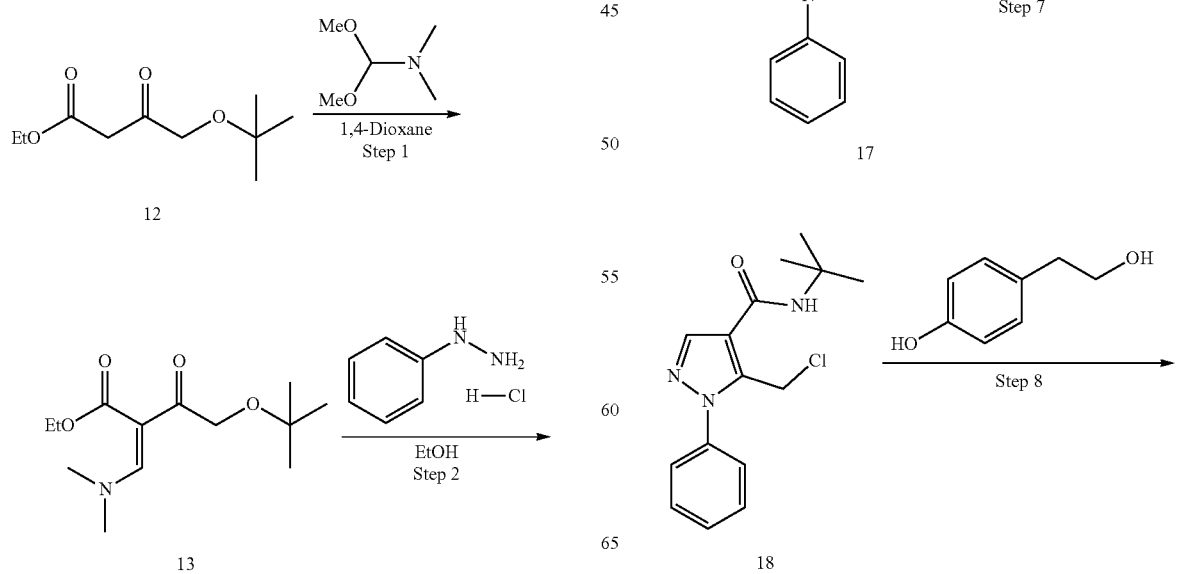

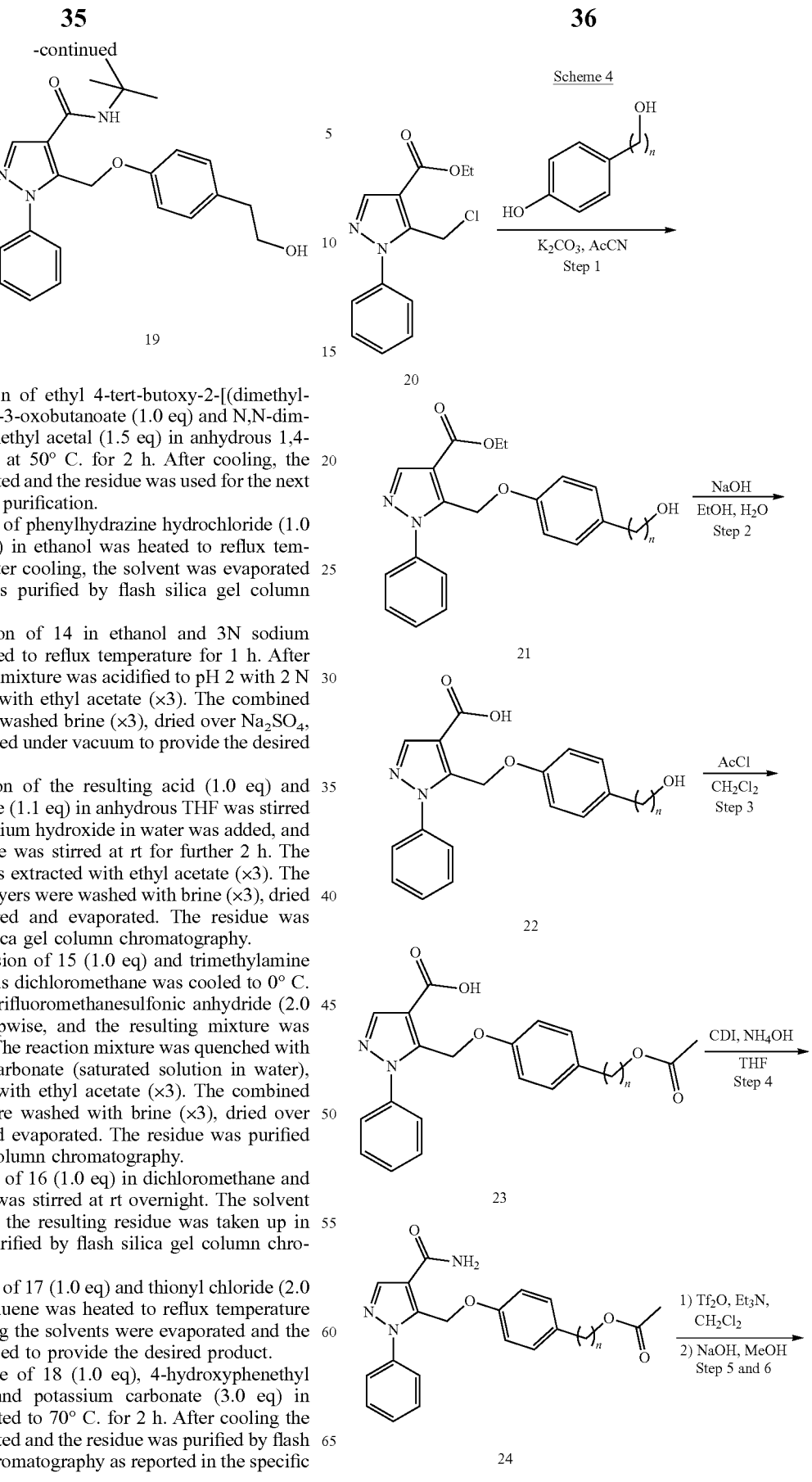

Scheme 4

Step 1. A solution of ethyl 4-tert-butoxy-2-[(dimethyl-amino)methylidene]-3-oxobutanoate (1.0 eq) and N,N-dimethylformamide dimethyl acetal (1.5 eq) in anhydrous 1,4-dioxane was stirred at 50° C. for 2 h. After cooling, the solvent was evaporated and the residue was used for the next step without further purification.

Step 2. A mixture of phenylhydrazine hydrochloride (1.0 eq), and 13 (1.0 eq) in ethanol was heated to reflux temperature for 1 h. After cooling, the solvent was evaporated and the residue was purified by flash silica gel column chromatography.

Step 3. A solution of 14 in ethanol and 3N sodium hydroxide was heated to reflux temperature for 1 h. After cooling the reaction mixture was acidified to pH 2 with 2 N HCl, and extracted with ethyl acetate (×3). The combined organic layers were washed brine (×3), dried over Na$_2$SO$_4$, filtered and evaporated under vacuum to provide the desired product.

Step 4. A solution of the resulting acid (1.0 eq) and carbonyl diimidazole (1.1 eq) in anhydrous THF was stirred at rt for 1 h. Ammonium hydroxide in water was added, and the resulting mixture was stirred at rt for further 2 h. The reaction mixture was extracted with ethyl acetate (×3). The combined organic layers were washed with brine (×3), dried over Na$_2$SO$_4$, filtered and evaporated. The residue was purified by flash silica gel column chromatography.

Step 5. A suspension of 15 (1.0 eq) and trimethylamine (2.0 eq) in anhydrous dichloromethane was cooled to 0° C. in ice-water bath. Trifluoromethanesulfonic anhydride (2.0 eq) was added dropwise, and the resulting mixture was stirred at rt for 3 h. The reaction mixture was quenched with sodium hydrogen carbonate (saturated solution in water), and then extracted with ethyl acetate (×3). The combined organic extracts were washed with brine (×3), dried over Na$_2$SO$_4$, filtered and evaporated. The residue was purified by flash silica gel column chromatography.

Step 6. A mixture of 16 (1.0 eq) in dichloromethane and trifluoroacetic acid was stirred at rt overnight. The solvent was evaporated and the resulting residue was taken up in CH$_2$C2 and then purified by flash silica gel column chromatography.

Step 7. A solution of 17 (1.0 eq) and thionyl chloride (2.0 eq) in anhydrous toluene was heated to reflux temperature for 1 h. After cooling the solvents were evaporated and the residue was well dried to provide the desired product.

Step 8. A mixture of 18 (1.0 eq), 4-hydroxyphenethyl alcohol (1.0 eq), and potassium carbonate (3.0 eq) in acetonitrile was heated to 70° C. for 2 h. After cooling the solvent was evaporated and the residue was purified by flash silica gel column chromatography as reported in the specific examples.

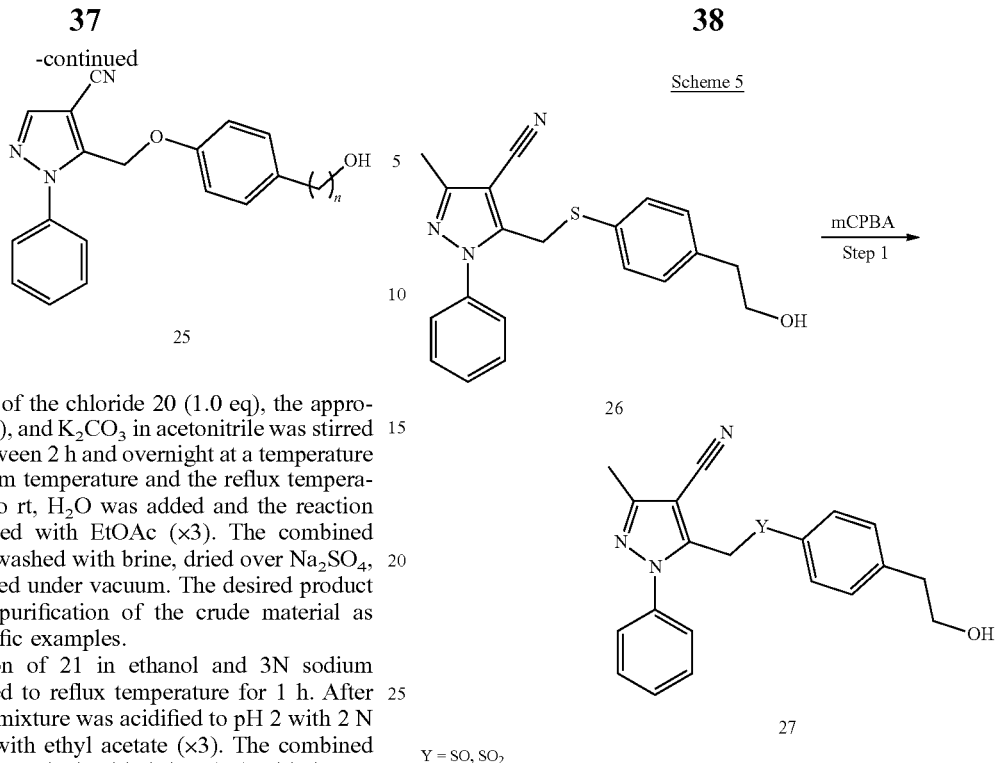

Step 1. A mixture of the chloride 20 (1.0 eq), the appropriate alcohol (1.0 eq), and K$_2$CO$_3$ in acetonitrile was stirred for a time period between 2 h and overnight at a temperature ranging between room temperature and the reflux temperature. After cooling to rt, H$_2$O was added and the reaction mixture was extracted with EtOAc (×3). The combined organic layers were washed with brine, dried over Na$_2$SO$_4$, filtered and evaporated under vacuum. The desired product was obtained after purification of the crude material as reported in the specific examples.

Step 2. A solution of 21 in ethanol and 3N sodium hydroxide was heated to reflux temperature for 1 h. After cooling the reaction mixture was acidified to pH 2 with 2 N HCl, and extracted with ethyl acetate (×3). The combined organic layers were washed with brine (×3), dried over Na$_2$SO$_4$, filtered and evaporated to provide the desired product.

Step 3. Pyridine (3.0 eq) was added dropwise to an ice-water bath cooled mixture of 22 (1.0 eq) and acetyl chloride (2.0 eq) in anhydrous dichloromethane. The resulting mixture was stirred at rt for 1 h. Water was added and the resulting mixture was stirred at rt for 1 h. The reaction mixture was transferred in a separatory funnel and the layers were separated. The aqueous phase was extracted 2 times with dichloromethane. The combined organic layers were washed with brine (×3), dried over Na$_2$SO$_4$, filtered and evaporated. The residue was used for the next step without further purification.

Step 4. Carbonyl diimidazole (1.1 eq) was added to a mixture of 23 (1.0 eq) in anhydrous THF. The reaction mixture was stirred at rt for 1 h. Ammonium hydroxide was added and the resulting mixture was stirred at rt for 1 h. The reaction mixture was diluted with water and extracted with ethyl acetate (×3). The combined organic layers were washed with brine (×3), dried over Na$_2$SO$_4$, filtered and evaporated. The residue was purified by flash silica gel column chromatography as reported in the specific examples.

Step 5 and 6. A suspension of 24 (1.0 eq) and trimethylamine (2.0 eq) in anhydrous dichloromethane was cooled to 0° C. in ice-water bath. Trifluoromethanesulfonic anhydride (1.08 eq) was added dropwise, and the resulting mixture was stirred at rt for 3 h. The reaction mixture was quenched with sodium hydrogen carbonate (saturated solution in water), and then extracted with ethyl acetate (×3). The combined organic extracts were washed with brine (×3), dried over Na$_2$SO$_4$, filtered and evaporated. The residue was dissolved in methanol and 3N NaOH and stirred at rt overnight. The reaction mixture was acidified to pH 2 by addition of 2N HCl and extracted with ethyl acetate (×3). The combined organic extracts were washed with brine (×3), dried over Na$_2$SO$_4$, filtered and evaporated. The residue was purified by flash silica gel column chromatography as reported in the specific examples.

Step 1. A solution of 26 (1.0 eq.) in dichloromethane was cooled to 0° C. in ice-water bath. 3-chloroperbenzoic acid (1.2 or 2.5 eq) was added portionwise, and the reaction mixture was allowed to warm up to rt and stirred for 1 h. The reaction mixture was diluted with dichloromethane, and washed with a saturated solution of sodium bicarbonate (×3) and brine (×3). The organic layer was dried over Na$_2$SO$_4$, filtered and evaporated under reduced pressure. The residue was purified by flash silica gel column chromatography as reported in the specific examples.

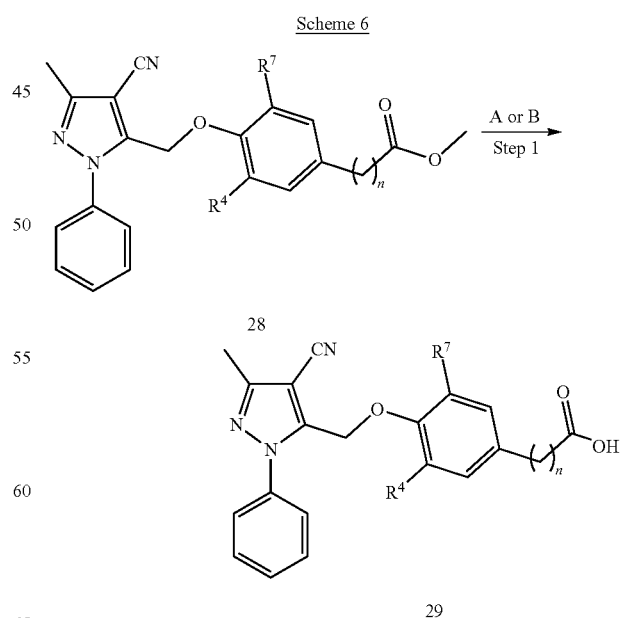

Step 1.

Method A. To a cooled solution of 28 (1.0 eq) in MeOH, 3N NaOH (3.0 eq) was added dropwise. The reaction mixture was allowed to warm to rt and stirred overnight. The most of MeOH was evaporated and the residue was diluted with EtOAc and H₂O. The aqueous phase was acidified with 2N HCl and extracted with EtOAc (×3). The combined organic layers were washed with brine, dried (Na₂SO₄), filtered and evaporated under reduced pressure. The crude product was purified as reported in the specific examples.

Method B. To a stirred solution of 28 (1.0 eq) in THF:water (1:1) followed by addition of LiOH H₂O (10 eq) at room temperature and stirred for 14 h. After completion of reaction, the reaction mixtures were then quenched by the addition of 20 mL of water and acidify using dil. HCl. The resulting solution was extracted with ethyl acetate (×3). The combined organic layer was washed with brine (×2), dried over anhydrous Na₂SO₄ and evaporated to afford the desired product.

Scheme 7

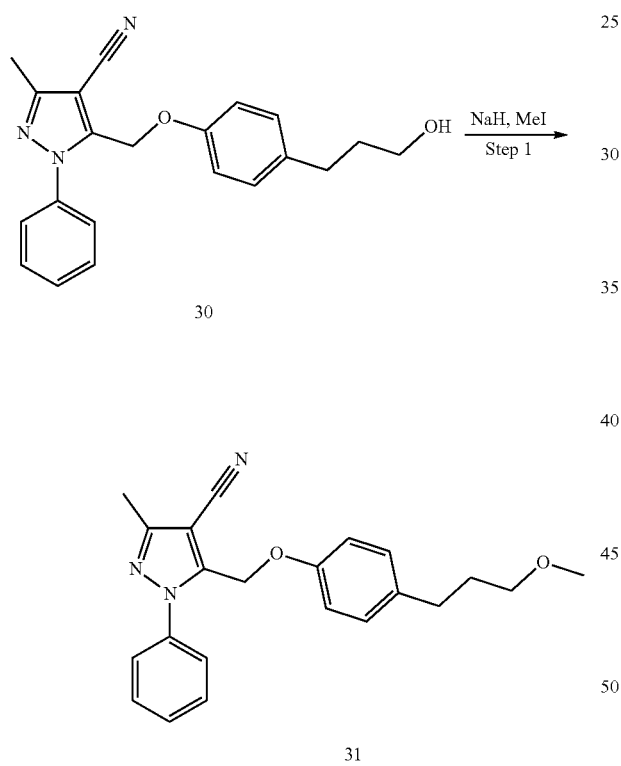

Scheme 8

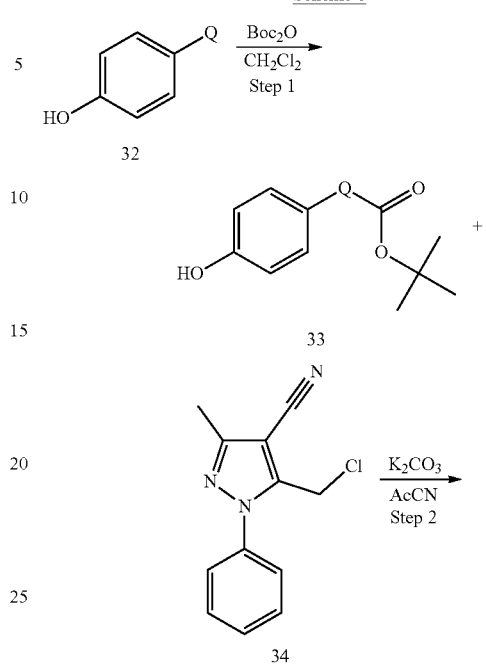

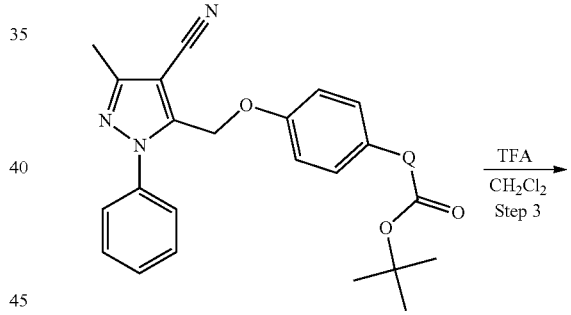

Step 1. To a stirred solution of 30 (0.12 g, 0.35 mmol) in DMF, NaH (60% in mineral oil) (0.02 g, 0.41 mmol) was added at 0° C. and stirred for 30 min followed by dropwise addition of MeI (0.033 mL, 0.53 mmol) at 0° C. The resulting solution was stirred at 50° C. for 12 h. After completion of reaction, the reaction mixture was then quenched by the addition of water and extracted with ethyl acetate (×3). The combined organic layer was washed with brine solution (×2), dried over anhydrous sodium sulphate and evaporated to afford impure product. The impure product was purified by flash chromatography as reported in the specific example.

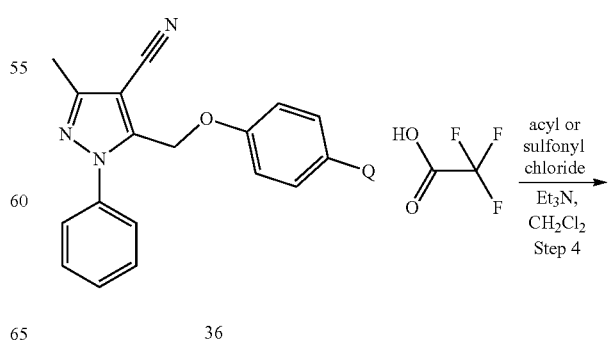

-continued

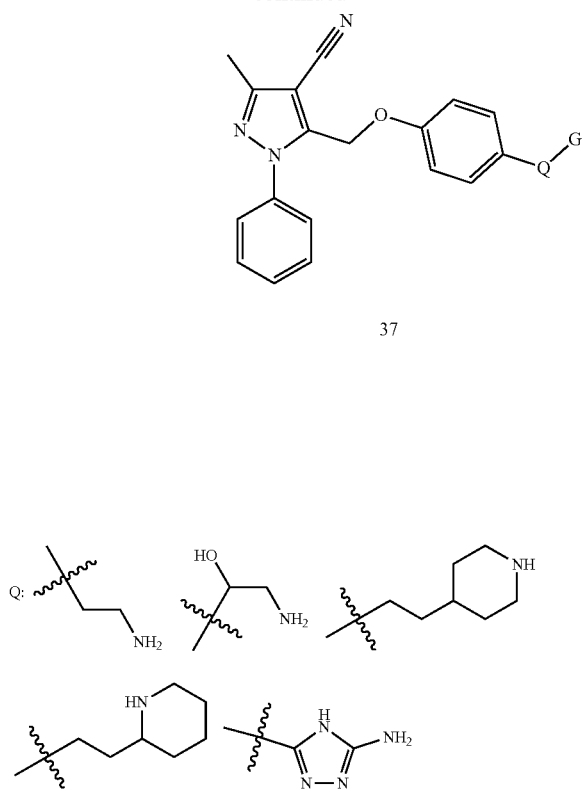

37

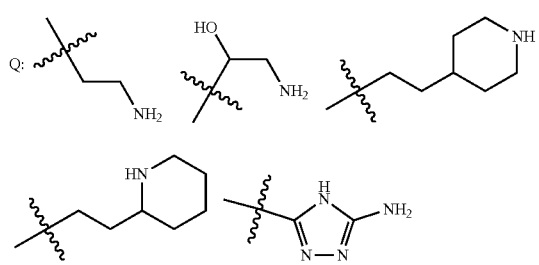

Scheme 9

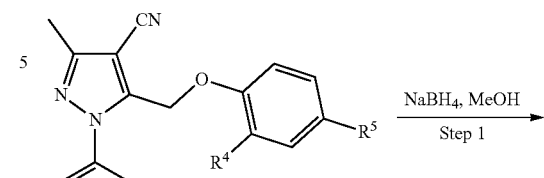

38

$R^4 = CF_3, R^5 = CHO$ $R^4 = H, R^5 =$ 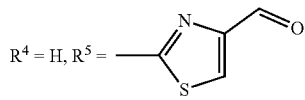

$R^4 = H, R^5 =$ 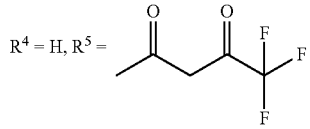

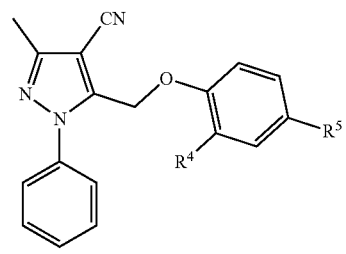

39

$R^4 = CF_3, R^5 = CH_2OH$ $R^4 = H, R^5 =$ 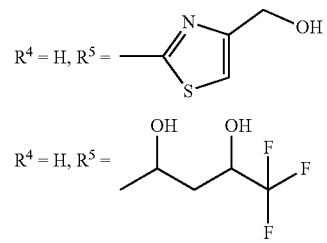

$R^4 = H, R^5 =$ 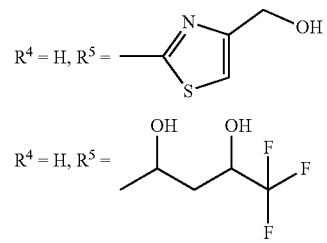

Step 1. A solution of the appropriate amine (1.0 eq) and di-tert-butyl dicarbonate (1.2 eq) in methanol was stirred at rt overnight. The reaction mixture was diluted with water and extracted with ethyl acetate (×3). The combined organic layers were washed with brine (×3), dried over $Na_2SO_4$, filtered and evaporated under reduced pressure. The residue was used for the next step without further purification.

Step 2. A mixture of the chloride 34 (1.0 eq), the appropriate protected amine 33 (1.0 eq), and $K_2CO_3$ in acetonitrile was stirred for a time period between 2 h and overnight at a temperature ranging between room temperature and the reflux temperature. After cooling to rt, $H_2O$ was added and the reaction mixture was extracted with EtOAc (×3). The combined organic layers were washed with brine, dried over $Na_2SO_4$, filtered and evaporated under vacuum. The desired product was obtained after purification of the crude material as reported in the specific examples.

Step 3. A solution of the appropriate intermediate 35 in dichloromethane and trifluoroacetic acid (1:1) was stirred at rt for 1 h. The solvent was evaporated under reduced pressure and the residue was taken up in $CH_2Cl_2$ to provide the desired product.

Step 4. The appropriate acyl or sulfonyl chloride (1.2 eq) was added dropwise to a mixture of 37 and triethylamine in anhydrous dichloromethane. The reaction mixture was stirred at rt for 2 h, and diluted with dichloromethane. 2N HCl was added and the layers were separated. The aqueous phase was extracted with dichloromethane (×2), and the combined organic layers were washed with brine (×3), dried over $Na_2SO_4$, filtered and evaporated under vacuum. The residue was purified by flash silica gel column chromatography as reported in the specific example.

Step 1. A solution of 38 (1.0 eq) in methanol was cooled in ice-water bath. Sodium borohydride (1.5 eq) was added and the resulting mixture was stirred at rt for 2 h. The reaction mixture was diluted with water and then extracted with ethyl acetate (×3). The combined organic layers were washed with brine (×3), dried over $Na_2SO_4$, filtered and evaporated under vacuum. The residue was purified by flash silica gel column chromatography as reported in the specific example.

SPECIFIC EXAMPLES

Example 1

5-[(4-cyanophenoxy)methyl]-3-methyl-1-phenyl-pyrazole-4-carbonitrile

The compound of example 1 is commercially available.

Example 2

5-[[2-chloro-4-(hydroxymethyl)phenoxy]methyl]-3-methyl-1-phenyl-pyrazole-4-carbonitrile The compound of example 2 is commercially available.

Example 3

5-[(4-Methoxyphenoxy)methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-methoxyphenol (CAS: 150-76-5), and $Cs_2CO_3$ at 60° C. for 3 h and purified by flash silica gel chromatography using a linear gradient of ethyl acetate in hexane from 0% to 40% (y=94%). Colorless oil.

Example 4

3-Methyl-5-[(4-methylphenoxy)methyl]-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-methylphenol (CAS: 106-44-5), and $Cs_2CO_3$ at 60° C. for 3 h and purified by flash silica gel chromatography using a linear gradient of ethyl acetate in hexane from 0% to 40% (y=71%). Colorless oil.

Example 5

5-[[4-(Hydroxymethyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-hydroxybenzyl alcohol (CAS: 623-05-2), and $Cs_2CO_3$ at 60° C. for 3 h and purified by flash silica gel chromatography using a linear gradient of ethyl acetate in hexane from 0% to 50% (y=89%).

Example 6

5-[[4-(2-Hydroxyethyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-hydroxyphenethyl alcohol (CAS: 501-94-0), and $Cs_2CO_3$ at 60° C. for 3 h and purified by flash silica gel chromatography using a linear gradient of ethyl acetate in hexane from 0% to 50% (y=91%). White solid.

Example 7

5-[(2-chloro-4-cyano-phenoxy)methyl]-3-methyl-1-phenyl-pyrazole-4-carbonitrile

The compound of example 7 is commercially available.

Example 8

3-methyl-5-(phenoxymethyl)-1-phenyl-pyrazole-4-carbonitrile

The compound of example 8 is commercially available.

Example 9

5-[(4-Cyano-2,6-difluorophenoxy)methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 3,5-difluoro-4-hydroxybenzonitrile (CAS: 2967-54-6), and $Cs_2CO_3$ at 60° C. for 2 h and purified by flash silica gel chromatography using a linear gradient of ethyl acetate in hexane from 0% to 50% (y=78%). White solid.

Example 10

5-[(4-Cyano-2-fluorophenoxy)methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 3-fluoro-4-hydroxybenzonitrile (CAS: 405-04-9), and $Cs_2CO_3$ at 60° C. for 2 h. The product precipitated after adding $H_2O$ to the reaction mixture. It was obtained pure after filtration (y=94%). White solid.

Example 11

5-[(4-Cyano-2-methylphenoxy)methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-hydroxy-3-methyl benzonitrile (CAS: 15777-70-5), and $Cs_2CO_3$ at 60° C. for 2 h. The product precipitated after adding $H_2O$ to the reaction mixture. It was obtained pure after filtration (y=87%). White solid.

Example 12

5-[(4-Cyano-2,6-dimethylphenoxy)methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-hydroxy-3,5-dimethylbenzonitrile (CAS: 4198-90-7), and $Cs_2CO_3$ at 60° C. for 2 h. The product precipitated after adding $H_2O$ to the reaction mixture. It was obtained pure after filtration (y=63%). White solid.

Example 13

5-[(4-Cyano-2,3-difluorophenoxy)methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 2,3-difluoro-4-hydroxybenzonitrile (CAS: 126162-38-7), and $Cs_2CO_3$ at 60° C. for 2 h. The product precipitated after adding $H_2O$ to the reaction mixture. It was obtained pure after filtration (y=88%). White solid.

Example 14

5-[[2,3-Difluoro-4-(hydroxymethyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-H-pyrazole-4-carbonitrile (CAS: 698367-00-9), 2,3-difluoro-4-(hydroxymethyl)phenol (CAS: 1472068-00-0), and $Cs_2CO_3$ at 60° C. for 2 h. The product precipitated after adding $H_2O$ to the reaction mixture. It was obtained pure after filtration (y=80%). White solid.

Example 15

5-[(4-Cyano-2,3-dimethylphenoxy)methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-hydroxy-2,3-dimethylbenzonitrile (CAS: 448961-58-8), and $Cs_2CO_3$ at 60° C. for 2 h. The product precipitated after adding $H_2O$ to the reaction mixture. It was obtained pure after filtration (y=78%). White solid.

Example 16

5-[[4-(Hydroxymethyl)-2-methylphenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-H-pyrazole-4-carbonitrile (CAS: 698367-00-9), 4-(hydroxymethyl)-2-methylphenol (CAS: 18299-15-5), and $Cs_2CO_3$ at 80° C. for 4 h and purified by flash silica gel chromatography using a linear gradient of ethyl acetate in hexane from 0% to 60% (y=61%). Colorless oil.

Example 17

5-[[4-(Hydroxymethyl)-2,6-dimethylphenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-H-pyrazole-4-carbonitrile (CAS: 698367-00-9), 4-(hydroxymethyl)-2,6-dimethylphenol (CAS: 4397-14-2), and $Cs_2CO_3$ at 60° C. for 2 h. The product precipitated after adding $H_2O$ to the reaction mixture. It was obtained pure after filtration (y=59%). White solid.

Example 18

5-[(4-Fluorophenoxy)methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-fluorophenol (CAS: 371-41-5), and $Cs_2CO_3$ at 60° C. for 2 h. The product precipitated after adding $H_2O$ to the reaction mixture. It was obtained pure after filtration (y=70%). White solid.

Example 19

5-[(4-Ethylphenoxy)methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-ethylphenol (CAS: 123-07-9), and $Cs_2CO_3$ at 80° C. for 4 h and purified by flash silica gel chromatography using a linear gradient of ethyl acetate in hexane from 0% to 20% (y=70%). Colorless oil.

Example 20

5-[[2-Fluoro-4-(hydroxymethyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-H-pyrazole-4-carbonitrile (CAS: 698367-00-9), 2-fluoro-4-(hydroxymethyl)phenol (CAS: 96740-93-1), and $K_2CO_3$ at 60° C. for 3 h and purified by flash silica gel chromatography using a linear gradient of ethyl acetate in hexane from 0% to 40% (y=94%). White solid.

Example 21

5-[[2,6-Difluoro-4-(hydroxymethyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-H-pyrazole-4-carbonitrile (CAS: 698367-00-9), 2,6-difluoro-4-(hydroxymethyl)phenol (CAS: 206198-07-4), and $Cs_2CO_3$ at 60° C. for 3 h and purified by flash silica gel chromatography using a linear gradient of ethyl acetate in hexane from 0% to 100% (y=64%). White solid.

Example 22

5-[(3,5-Dimethylphenoxy)methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 3,5-dimethylphenol (CAS: 108-68-9), and $Cs_2CO_3$ at 85° C. for 4 h and purified by flash silica gel chromatography using a linear gradient of ethyl acetate in hexane from 0% to 40% (y=67%). Colorless oil.

Example 23

5-[[2-(Hydroxymethyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 2-hydroxybenzyl alcohol (CAS: 90-01-7), and $Cs_2CO_3$ at 85° C. for 4 h and purified by flash silica gel chromatography using a linear gradient of ethyl acetate in hexane from 0% to 40% (y=82%). Colorless oil.

Example 24

5-[[3-(Hydroxymethyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 3-hydroxybenzyl alcohol (CAS: 620-24-6), and $Cs_2CO_3$ at 85° C. for 4 h and purified by flash silica gel chromatography using a linear gradient of ethyl acetate in hexane from 0% to 40% (y=58%). Colorless oil.

Example 25

5-[(2,6-Dimethylphenoxy)methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 2,6-dimethylphenol (CAS: 576-26-1), and $Cs_2CO_3$ at 50° C. for 12 h and purified by flash silica gel chromatography using a linear gradient of ethyl acetate in hexane from 0% to 40% (y=57%). White solid.

Example 26

3-Methyl-5-[(2-methylphenoxy)methyl]-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 2-methylphenol (CAS: 95-48-7), and $Cs_2CO_3$ at 50° C. for 12 h and purified by flash silica gel chromatography using a linear gradient of ethyl acetate in hexane from 0% to 40% (y=50%). White solid.

Example 27

5-[(2,5-Dimethylphenoxy)methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 2,5-dimethylphenol (CAS: 95-87-4), and $Cs_2CO_3$ at 50° C. for 12 h and purified by flash silica gel chromatography using a linear gradient of ethyl acetate in hexane from 0% to 40% (y=72%). Colorless oil.

Example 28

3-Methyl-5-[(3-methylphenoxy)methyl]-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 3-methylphenol (CAS: 108-39-4) and $Cs_2CO_3$ at 50° C. for 12 h and purified by flash silica gel chromatography using a linear gradient of ethyl acetate in hexane from 0% to 40% (y=81%). Colorless oil.

Example 29

5-[[4-(Cyanomethyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-hydroxyphenylacetonitrile (CAS: 14191-95-8), and $Cs_2CO_3$ at 50° C. for 12 h and purified by flash silica gel chromatography using a linear gradient of ethyl acetate in hexane from 0% to 60% (y=67%). Colorless oil.

Example 30

5-[(2,3-Dimethylphenoxy)methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 2,3-dimethylphenol (CAS: 526-75-0), and $Cs_2CO_3$ at 50° C. for 12 h and purified by flash silica gel chromatography using a linear gradient of ethyl acetate in hexane from 0% to 20% (y=79%). Colorless oil.

Example 31

5-[[4-(2-Cyanoethyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 3-(4-hydroxyphenyl)propionitrile (CAS: 17362-17-3), and $Cs_2CO_3$ at 50° C. for 12 h and purified by flash silica gel chromatography using a linear gradient of ethyl acetate in hexane from 0% to 40% (y=79%). Colorless oil.

Example 32

5-[[2,6-Difluoro-4-(3-hydroxypropyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-H-pyrazole-4-carbonitrile (CAS: 698367-00-9), 2,6-difluoro-4-(3-hydroxypropyl)phenol (CAS: 1895507-21-7), and $K_2CO_3$ at 50° C. for 12 h and purified by flash silica gel chromatography using a linear gradient of ethyl acetate in hexane from 10% to 80% (y=89%). White solid.

Example 33

5-[[2-Fluoro-4-(2-hydroxyethyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-H-pyrazole-4-carbonitrile (CAS: 698367-00-9), 2-fluoro-4-(2-hydroxyethyl)phenol (CAS: 5497-21-2), and $K_2CO_3$ at 60° C. for 12 h and purified by flash silica gel chromatography using a linear gradient of ethyl acetate in hexane from 10% to 60% (y=95%). White solid.

Example 34

3-Methyl-1-phenyl-5-[(2,3,4-trimethylphenoxy)methyl]-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 2,3,4-trimethylphenol (CAS: 526-85-2), and $K_2CO_3$ at 60° C. for 2 h and purified by flash silica gel chromatography using a linear gradient of ethyl acetate in hexane from 0% to 40% (y=79%). White solid.

Example 35

5-[[4-(3-Hydroxypropyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-(3-hydroxypropyl)phenol (CAS: 10210-17-0), and $K_2CO_3$ at 60° C. for 2 h and purified by flash silica gel chromatography using a linear gradient of ethyl acetate in hexane from 10% to 65% (y=81%). White solid.

Example 36

5-[[2-(2-Hydroxyethoxy)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 2-(2-hydroxyethoxy)phenol (CAS: 4792-78-3), and $K_2CO_3$ at 60° C. for 2 h and purified by flash silica gel chromatography using a linear gradient of ethyl acetate in hexane from 15% to 70% (y=71%). Colorless oil.

Example 37

N-[2-[(4-Cyano-3-methyl-1-phenyl-1H-pyrazol-5-yl)methoxy]phenyl]acetamide. The title compound was prepared by the general procedure (scheme 1, step 3, method A) from 5-(chloromethyl)-3-methyl-1-phenyl-1H-pyrazole-4-carbonitrile (CAS: 698367-00-9), 2-acetamidophenol (CAS: 614-80-2), and $K_2CO_3$ at 60° C. for 2 h and purified by flash silica gel chromatography using a linear gradient of ethyl acetate in hexane from 15% to 70% (y=73%). Colorless oil.

Example 38

5-[[3-(2-Hydroxyethyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 3-hydroxyphenethyl alcohol (CAS: 13398-94-2), and $K_2CO_3$ at 60° C. for 2 h and purified by flash silica gel chromatography using a linear gradient of ethyl acetate in hexane from 15% to 70% (y=77%). Colorless oil.

Example 39

5-[(2-Ethylphenoxy)methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 2-ethylphenol (CAS: 90-00-6), and $K_2CO_3$ at 60° C. for 2 h and purified by flash silica gel chromatography using a linear gradient of ethyl acetate in hexane from 15% to 70% (y=72%). Colorless oil.

Example 40

5-[(3-Fluorophenoxy)methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 3-fluorophenol (CAS: 372-20-3), and $K_2CO_3$ at 60° C. for 2 h and purified by flash silica gel chromatography using a linear gradient of ethyl acetate in hexane from 15% to 70% (y=75%). Colorless oil.

Example 41

5-[(3-Chlorophenoxy)methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 3-chlorophenol (CAS: 108-43-0), and $K_2CO_3$ at 60° C. for 2 h and purified by flash silica gel chromatography using a linear gradient of ethyl acetate in hexane from 15% to 70% (y=71%). Colorless oil.

Example 42

5-[[2-Fluoro-4-(3-hydroxypropyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-H-pyrazole-4-carbonitrile (CAS: 698367-00-9), 2-fluoro-4-(3-hydroxypropyl)phenol (CAS: 839694-33-6), and $K_2CO_3$ at 70° C. overnight and purified by flash silica gel chromatography using a linear gradient of ethyl acetate in hexane from 15% to 70% (y=52%). Yellowish oil.

Example 43

5-[[2,6-Difluoro-4-(3-hydroxy-2-methylpropyl)phenoxy]methyl]-3-methyl-1-phenyl-1H-pyrazole-4-carbonitrile. 4-(3-Hydroxy-2-methylpropyl)phenol (Intermediate 1). A solution of lithium aluminum hydride (2.0M in anhydrous tetrahydrofuran, 1.64 mL, 1.64 mmol) was added dropwise to a 0° C. cooled solution of ethyl 3-(3,5-difluoro-4-hydroxyphenyl)-2-methylpropanoate (CAS: 1224103-93-8) in anhydrous tetrahydrofuran (1.64 mL). The reaction mixture was stirred at 60° C. overnight. Water was added (caution: hydrogen evolution and exothermic reaction), and the reaction mixture was acidified with 2N hydrochloric acid. The resulting mixture was extracted with ethyl acetate (3 times). The combined organic layers were washed with brine (3 times), dried over $Na_2SO_4$, filtered and evaporated to provide Intermediate 1 as yellow solid (y=99%). 5-[[2,6-Difluoro-4-(3-hydroxy-2-methylpropyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), intermediate 1, and $K_2CO_3$ at 70° C. overnight and purified by flash silica gel chromatography using a linear gradient of ethyl acetate in hexane from 0% to 50% (y=60%). Yellowish oil.

Example 44

3-Methyl-1-phenyl-5-[[4-(trifluoromethyl)phenoxy]methyl]-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-(trifluoromethyl)phenol (CAS: 402-45-9), and $K_2CO_3$ at 70° C. overnight and purified by flash silica gel chromatography using a linear gradient of ethyl acetate in hexane from 0% to 50% (y=39%). White solid.

Example 45

5-[[4-(1-Hydroxypropyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-hydroxy-N-(2-hydroxyethyl)-N-methylbenzamide (CAS: 1183771-00-7), and $K_2CO_3$ at 60° C. for 3 h and purified by flash silica gel chromatography using a linear gradient of ethyl acetate in hexane from 50% to 100% and then methanol in ethyl acetate from 0% to 15% (y=37%). Yellow solid.

Example 46

5-[[4-(2-Hydroxypropan-2-yl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-H-pyrazole-4-carbonitrile (CAS: 698367-00-9), 4-hydroxy-N-(2,2,2-trifluoroethyl)benzamide (CAS: 1019343-45-3), and $K_2CO_3$ at 60° C. for 3 h and purified by flash silica gel chromatography using a linear gradient of ethyl acetate in hexane from 50% to 100% and then methanol in ethyl acetate from 0% to 15% (y=85%). White solid.

Example 47

5-[[4-(3-Hydroxybutyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-(3-hydroxybutyl)phenol (CAS: 69617-84-1), and $K_2CO_3$ at 60° C. for 3 h and purified by flash silica gel chromatography using a linear gradient of ethyl acetate in hexane from 0% to 65% (y=61%). Yellow oil.

Example 48

5-[[4-(2-Isopropyloxyethoxymethyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-H-pyrazole-4-carbonitrile (CAS: 698367-00-9), 4-(1,3-thiazol-4-yl)phenol (CAS: 68535-57-9), and $K_2CO_3$ at 60° C. for 3 h and purified by flash silica gel chromatography using a linear gradient of ethyl acetate in hexane from 0% to 65% (y=97%). Yellowish oil.

Example 49

2-[4-[(4-Cyano-3-methyl-1-phenyl-1H-pyrazol-5-yl)methoxy]phenyl]-N-(2-hydroxyethyl)acetamide. The title compound was prepared by the general procedure (scheme 1, step 3, method A) from 5-(chloromethyl)-3-methyl-1-phenyl-H-pyrazole-4-carbonitrile (CAS: 698367-00-9), N-(2-hydroxyethyl)-2-(4-hydroxyphenyl)acetamide (CAS: 855928-60-8), and $K_2CO_3$ at 60° C. for 3 h and purified by flash silica gel chromatography using a linear gradient of ethyl acetate in hexane from 50% to 100% and then methanol in ethyl acetate from 0% to 15% (y=63%). White solid.

Example 50

5-[[4-(1-Hydroxypropyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-(1-hydroxypropyl)phenol (CAS: 22805-42-1), and $K_2CO_3$ at 60° C. for 3 h and purified by flash silica gel chromatography using a linear gradient of ethyl acetate in hexane from 0% to 65% (y=23%). Colorless oil.

Example 51

5-[[4-(2-Hydroxypropan-2-yl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-H-pyrazole-4-carbonitrile (CAS: 698367-00-9), 4-(2-hydroxypropan-2-yl)phenol (CAS: 2948-47-2), and $K_2CO_3$ at 60° C. for 3 h and purified by flash silica gel chromatography using a linear gradient of ethyl acetate in hexane from 0% to 65% (y=71%). Yellow oil.

Example 52

5-[[4-(2-Isopropyloxyethoxymethyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-H-pyrazole-4-carbonitrile (CAS: 698367-00-9), 4-{[2-(propan-2-yloxy)ethoxy]methyl}phenol (CAS: 177034-57-0), and $K_2CO_3$ at 60° C. for 3 h and purified by flash silica gel chromatography using a linear gradient of ethyl acetate in hexane from 0% to 65% (y=64%). Colorless oil.

Example 53

5-[[4-(3-Hydroxypropyl)-2-methoxyphenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-H-pyrazole-4-carbonitrile (CAS: 698367-00-9), 4-(3-hydroxypropyl)-2-methoxyphenol (CAS: 2305-13-7), and $K_2CO_3$ at 70° C. for 2 h and purified by flash silica gel chromatography using a linear gradient of ethyl acetate in hexane from 15% to 70% (y=84%). White solid.

Example 54

5-[[4-(1-Hydroxyethyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-(1-hydroxyethyl)phenol (CAS: 2380-91-8), and $K_2CO_3$ at 70° C. for 2 h and purified by flash silica gel chromatography using a linear gradient of ethyl acetate in hexane from 15% to 70% (y=90%). White solid.

Example 55

5-[[4-(Methoxymethyl)phenoxy]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-(methoxymethyl)phenol (CAS: 5355-17-9), and $K_2CO_3$ at 70° C. for 2 h and purified by flash silica gel chromatography using a linear gradient of ethyl acetate in hexane from 15% to 70% (y=88%). Colorless oil.

Example 56

5-{[4-(2-Methoxyethyl)phenoxy]methyl}-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-(2-methoxyethyl)phenol (CAS: 5355-17-9), and $K_2CO_3$ at 60° C. for 6 h and purified by flash silica gel chromatography using a linear gradient of ethyl acetate in hexane from 30% to 35% (y=28%). Colorless oil.

Example 57

5-[[4-(2-Hydroxyethyl)anilino]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 2-(4-aminophenyl)ethanol (CAS: 104-10-9), and $K_2CO_3$ at 60° C. overnight and purified by flash silica gel chromatography using a linear gradient of ethyl acetate in hexane from 20% to 80% (y=32%). Colorless oil.

Example 58

5-[[4-(2-Hydroxyethyl)-N-methylanilino]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-H-pyrazole-4-carbonitrile (CAS: 698367-00-9), 2-[4-(methylamino)phenyl]ethanol (CAS: 812640-16-7), and $K_2CO_3$ at 70° C. overnight and purified by flash silica gel chromatography using a linear gradient of ethyl acetate in hexane from 20% to 80% (y=41%). Colorless oil.

Example 59

5-[[[4-(2-Hydroxyethyl)phenyl]thio]methyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 2-(4-sulfanylphenyl)ethanol (CAS: 242791-24-8), and $K_2CO_3$ at 60° C. for 2 h and purified by flash silica gel chromatography using a linear gradient of ethyl acetate in hexane from 15% to 70% (y=98%). Colorless oil.

Example 60

5-[(4-Cyano-3-methyl-1-phenyl-1H-pyrazol-5-yl)methoxy]pyridine-2-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 5-hydroxypyridine-2-carbonitrile (CAS: 86869-14-9), and $Cs_2CO_3$ at 50° C. for 12 h and purified by flash silica gel chromatography using a linear gradient of ethyl acetate in hexane from 10% to 60% (y=79%). White solid.

Example 61

5-(2H-Indazol-5-yloxymethyl)-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 5-hydroxy-1H-indazole (CAS: 15579-15-4), and $K_2CO_3$ at 60° C. for 3 h and purified by flash silica gel chromatography using a linear gradient of ethyl acetate in hexane from 10% to 65% (y=81%). White solid.

Example 62

5-(Isoquinolin-7-yloxymethyl)-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 7-hydroxyisoquinoline (CAS: 7651-83-4), and $K_2CO_3$ at 60° C. for 2 h and purified by flash silica gel chromatography using a linear gradient of ethyl acetate in hexane from 15% to 70% (y=80%). Colorless oil.

Example 63

3-Methyl-1-phenyl-5-(quinolin-8-yloxymethyl)-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 8-hydroxyisoquinoline (CAS: 148-24-3), and $K_2CO_3$ at 60° C. for 2 h and purified by flash silica gel chromatography using a linear gradient of ethyl acetate in hexane from 15% to 70% (y=81%). Colorless oil.

Example 64

3-[(4-Cyano-3-methyl-1-phenyl-1H-pyrazol-5-yl)methoxy]pyridine-2-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 2-cyano-3-hydroxy pyridine (CAS: 932-35-4), and $K_2CO_3$ at 60° C. for 2 h and purified by flash silica gel chromatography using a linear gradient of ethyl acetate in hexane from 15% to 70% (y=83%). Colorless oil.

Example 65

5-[(2-Fluoropyridin-3-yl)oxymethyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 2-fluoro-3-hydroxypyridine (CAS: 174669-74-0), and $K_2CO_3$ at 70° C. overnight and purified by flash silica gel chromatography using a linear gradient of ethyl acetate in hexane from 0% to 100% (y=38%). White solid.

Example 66

5-[(5-Fluoropyridin-3-yl)oxymethyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 3-fluoro-5-hydroxypyridine (CAS: 209328-55-2), and $K_2CO_3$ at 70° C. overnight and purified by flash silica gel chromatography using a linear gradient of ethyl acetate in hexane from 0% to 100% (y=63%). White solid.

Example 67

5-[[6-(Hydroxymethyl)pyridin-3-yl]oxymethyl]-3-methyl-1-phenyl-1H-pyrazole-4-carbonitrile. The title compound was prepared by the general procedure (scheme 1, step 3, method A) from 5-(chloromethyl)-3-methyl-1-phenyl-H-pyrazole-4-carbonitrile (CAS: 698367-00-9), 6-(hydroxymethyl)pyridin-3-ol (CAS: 40222-77-3), and $K_2CO_3$ at 70° C. overnight and purified by flash silica gel chromatography using a linear gradient of ethyl acetate in hexane from 0% to 100% and then methanol in ethyl acetate from 0% to 15% (y=35%). White solid.

Example 68

3-Methyl-5-[(4-methylpyridin-3-yl)oxymethyl]-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 4-methylpyridin-3-ol (CAS: 1121-19-3), and $K_2CO_3$ at 70° C. overnight and purified by flash silica gel chromatography using a linear gradient of ethyl acetate in hexane from 0% to 100% (y=31%). Brown solid.

Example 69

3-Methyl-5-[(6-methylpyridin-3-yl)oxymethyl]-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 5-hydroxy-2-methylpyridine (CAS: 1121-78-4), and $K_2CO_3$ at 70° C. overnight and purified by flash silica gel chromatography using a linear gradient of ethyl acetate in hexane from 0% to 100% (y=76%). Yellow solid.

Example 70

5-[(2,4-Dimethylpyridin-3-yl)oxymethyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 2,4-dimethyl-3-hydroxypyridine (CAS: 27296-76-0), and $K_2CO_3$ at 70° C. overnight and purified by flash silica gel chromatography using a linear gradient of ethyl acetate in hexane from 0% to 100% (y=76%). White solid.

Example 71

5-[(2,6-Difluoropyridin-3-yl)oxymethyl]-3-methyl-1-phenyl-1H-pyrazole-4-carbonitrile. The title compound was prepared by the general procedure (scheme 1, step 3, method A) from 5-(chloromethyl)-3-methyl-1-phenyl-1H-pyrazole-4-carbonitrile (CAS: 698367-00-9), 2,6-difluoropyridin-3-ol (CAS: 6602-33-1), and $K_2CO_3$ at 70° C. overnight and purified by flash silica gel chromatography using a linear gradient of ethyl acetate in hexane from 0% to 100% (y=36%). Yellow solid.

Example 72

5-[[4-(2-Hydroxyethyl)phenoxy]methyl]-3-methyl-1-(2-methylphenyl)-1H-pyrazole-4-carbonitrile. 5-(Chloromethyl)-3-methyl-1-(2-methylphenyl)-1H-pyrazole-4-carbonitrile (Intermediate 2). The title compound was prepared by the general procedure (scheme 1, step 2) from 3-amino-2-(chloroacetyl)but-2-enenitrile (CAS: 170652-68-3) and o-tolylhydrazine hydrochloride (CAS: 635-26-7) (y=29%).

5-[[4-(2-Hydroxyethyl)phenoxy]methyl]-3-methyl-1-(2-methylphenyl)-1H-pyrazole-4-carbonitrile. The title compound was prepared by the general procedure (scheme 1, step 3, method A) from intermediate 2, 4-(2-hydroxyethyl)phenol (CAS: 501-94-0), and $K_2CO_3$ at 70° C. overnight and purified by flash silica gel chromatography using a linear gradient of ethyl acetate in hexane from 10% to 60% (y=45%).

Example 73

5-[[4-(2-Hydroxyethyl)phenoxy]methyl]-3-methyl-1-(3-methylphenyl)-1H-pyrazole-4-carbonitrile 5-(Chloromethyl)-3-methyl-1-(3-methylphenyl)-1H-pyrazole-4-carbonitrile (Intermediate 3). The title compound was prepared by the general procedure (scheme 1, step 2) from 3-amino-2-(chloroacetyl)but-2-enenitrile (CAS: 170652-68-3) and m-tolylhydrazine hydrochloride (CAS: 637-04-7) (y=32%).

5-[[4-(2-Hydroxyethyl)phenoxy]methyl]-3-methyl-1-(3-methylphenyl)-1H-pyrazole-4-carbonitrile. The title compound was prepared by the general procedure (scheme 1, step 3, method A) from intermediate 3, 4-(2-hydroxyethyl)phenol (CAS: 501-94-0), and $K_2CO_3$ at 70° C. overnight and purified by flash silica gel chromatography using a linear gradient of ethyl acetate in hexane from 10% to 60% (y=51%). White solid.

Example 74

5-[[4-(2-Hydroxyethyl)phenoxy]methyl]-3-methyl-1-(4-methylphenyl)-1H-pyrazole-4-carbonitrile 5-(Chloromethyl)-3-methyl-1-(4-methylphenyl)-1H-pyrazole-4-carbonitrile (Intermediate 4). The title compound was prepared by the general procedure (scheme 1, step 2) from 3-amino-2-(chloroacetyl)but-2-enenitrile (CAS: 170652-68-3) and p-tolylhydrazine hydrochloride (CAS: 637-60-5) (y=30%).

5-[[4-(2-Hydroxyethyl)phenoxy]methyl]-3-methyl-1-(4-methylphenyl)-1H-pyrazole-4-carbonitrile. The title compound was prepared by the general procedure (scheme 1, step 3, method A) from intermediate 4, 4-(2-hydroxyethyl)phenol (CAS: 501-94-0), and $K_2CO_3$ at 70° C. overnight and purified by flash silica gel chromatography using a linear gradient of ethyl acetate in hexane from 10% to 60% (y=80%). Brown solid.

Example 75

1-(3-Chlorophenyl)-5-[[4-(2-hydroxyethyl)phenoxy]methyl]-3-methyl-1H-pyrazole-4-carbonitrile 5-(Chloromethyl)-1-(3-chlorophenyl)-3-methyl-1H-pyrazole-4-carbonitrile (Intermediate 5). The title compound was prepared by the general procedure (scheme 1, step 2) from 3-amino-2-(chloroacetyl)but-2-enenitrile (CAS: 170652-68-3) and 3-chlorophenylhydrazine hydrochloride (CAS: 2312-23-4) (y=30%).

1-(3-Chlorophenyl)-5-[[4-(2-hydroxyethyl)phenoxy]methyl]-3-methyl-1H-pyrazole-4-carbonitrile. The title compound was prepared by the general procedure (scheme 1, step 3, method A) from intermediate 5, 4-(2-hydroxyethyl)phenol (CAS: 501-94-0), and $K_2CO_3$ at 70° C. overnight and purified by flash silica gel chromatography using a linear gradient of ethyl acetate in hexane from 10% to 60% (y=46%). Yellow oil.

Example 76

1-(4-Chlorophenyl)-5-[[4-(2-hydroxyethyl)phenoxy]methyl]-3-methyl-1H-pyrazole-4-carbonitrile 5-(Chloromethyl)-1-(4-chlorophenyl)-3-methyl-1H-pyrazole-4-carbonitrile (Intermediate 6). The title compound was prepared by the general procedure (scheme 1, step 2) from 3-amino-2-(chloroacetyl)but-2-enenitrile (CAS: 170652-68-3) and 4-chlorophenylhydrazine hydrochloride (CAS: 1073-70-7) (y=31%).

1-(4-Chlorophenyl)-5-[[4-(2-hydroxyethyl)phenoxy]methyl]-3-methyl-1H-pyrazole-4-carbonitrile. The title compound was prepared by the general procedure (scheme 1, step 3, method A) from intermediate 6, 4-(2-hydroxyethyl)phenol (CAS: 501-94-0), and $K_2CO_3$ at 70° C. overnight and purified by flash silica gel chromatography using a linear gradient of ethyl acetate in hexane from 10% to 60% (y=46%). White solid.

Example 77

5-[[4-(2-Hydroxyethyl)phenoxy]methyl]-3-methyl-1-[3-(trifluoromethyl)phenyl]-1H-pyrazole-4-carbonitrile 5-(Chloromethyl)-1-(4-chlorophenyl)-3-methyl-1H-pyrazole-4-carbonitrile (Intermediate 7). The title compound was prepared by the general procedure (scheme 1, step 2) from 3-amino-2-(chloroacetyl)but-2-enenitrile (CAS: 170652-68-3) and 3-(trifluoromethyl)phenyl]hydrazine (CAS: 368-78-5) (y=36%).
5-[[4-(2-Hydroxyethyl)phenoxy]methyl]-3-methyl-1-[3-(trifluoromethyl)phenyl]-1H-pyrazole-4-carbonitrile. The title compound was prepared by the general procedure (scheme 1, step 3, method A) from intermediate 7, 4-(2-hydroxyethyl)phenol (CAS: 501-94-0), and $K_2CO_3$ at 70° C. overnight and purified by flash silica gel chromatography using a linear gradient of ethyl acetate in hexane from 10% to 60% (y=40%). Yellow oil.

Example 78

1-(4-Ethylphenyl)-5-[[4-(2-hydroxyethyl)phenoxy]methyl]-3-methyl-1H-pyrazole-4-carbonitrile 5-(Chloromethyl)-1-(4-ethylphenyl)-3-methyl-1H-pyrazole-4-carbonitrile (Intermediate 8). The title compound was prepared by the general procedure (scheme 1, step 2) from 3-amino-2-(chloroacetyl)but-2-enenitrile (CAS: 170652-68-3) and 4-ethylphenylhydrazine hydrochloride (CAS: 53661-18-0) (y=32%). 1-(4-Ethylphenyl)-5-[[4-(2-hydroxyethyl)phenoxy]methyl]-3-methyl-1H-pyrazole-4-carbonitrile. The title compound was prepared by the general procedure (scheme 1, step 3, method A) from intermediate 8, 4-(2-hydroxyethyl)phenol (CAS: 501-94-0), and $K_2CO_3$ at 70° C. overnight and purified by flash silica gel chromatography using a linear gradient of ethyl acetate in hexane from 10% to 60% (y=43%). Colorless oil.

Example 79

5-[[4-(2-Hydroxyethyl)phenoxy]methyl]-1-(3-methoxyphenyl)-3-methyl-1H-pyrazole-4-carbonitrile 5-(chloromethyl)-1-(3-methoxyphenyl)-3-methyl-1H-pyrazole-4-carbonitrile (Intermediate 9). The title compound was prepared by the general procedure (scheme 1, step 2) from 3-amino-2-(chloroacetyl)but-2-enenitrile (CAS: 170652-68-3) and 3-methoxyphenylhydrazine hydrochloride (CAS: 39232-91-2) (y=29%).
5-[[4-(2-Hydroxyethyl)phenoxy]methyl]-1-(3-methoxyphenyl)-3-methyl-1H-pyrazole-4-carbonitrile. The title compound was prepared by the general procedure (scheme 1, step 3, method A) from intermediate 9, 4-(2-hydroxyethyl)phenol (CAS: 501-94-0), and $K_2CO_3$ at 70° C. overnight and purified by flash silica gel chromatography using a linear gradient of ethyl acetate in hexane from 10% to 60% (y=13%). Colorless oil.

Example 80

5-[[4-(2-Hydroxyethyl)phenoxy]methyl]-1-(4-methoxyphenyl)-3-methyl-1H-pyrazole-4-carbonitrile 5-(Chloromethyl)-1-(4-methoxyphenyl)-3-methyl-1H-pyrazole-4-carbonitrile (Intermediate 10). The title compound was prepared by the general procedure (scheme 1, step 2) from 3-amino-2-(chloroacetyl)but-2-enenitrile (CAS: 170652-68-3) and 4-methoxyphenylhydrazine hydrochloride (CAS: 19501-58-7) (y=26%).
5-[[4-(2-Hydroxyethyl)phenoxy]methyl]-1-(4-methoxyphenyl)-3-methyl-1H-pyrazole-4-carbonitrile. The title compound was prepared by the general procedure (scheme 1, step 3, method A) from intermediate 10, 4-(2-hydroxyethyl)phenol (CAS: 501-94-0), and $K_2CO_3$ at 70° C. overnight and purified by flash silica gel chromatography using a linear gradient of ethyl acetate in hexane from 10% to 60% (y=73%). Yellow solid.

Example 81

5-[[4-(2-Hydroxyethyl)phenoxy]methyl]-3-methyl-1-[3-(trifluoromethoxy)phenyl]-1H-pyrazole-4-carbonitrile 5-(Chloromethyl)-3-methyl-1-[3-(trifluoromethoxy)phenyl]-1H-pyrazole-4-carbonitrile (Intermediate 11). The title compound was prepared by the general procedure (scheme 1, step 2) from 3-amino-2-(chloroacetyl)but-2-enenitrile (CAS: 170652-68-3) and (3-(trifluoromethoxy)phenyl)hydrazine hydrochloride (CAS: 133115-55-6) (y=31%).
5-[[4-(2-Hydroxyethyl)phenoxy]methyl]-3-methyl-1-[3-(trifluoromethoxy)phenyl]-1H-pyrazole-4-carbonitrile. The title compound was prepared by the general procedure (scheme 1, step 3, method A) from intermediate 11, 4-(2-hydroxyethyl)phenol (CAS: 501-94-0), and $K_2CO_3$ at 70° C. overnight and purified by flash silica gel chromatography using a linear gradient of ethyl acetate in hexane from 10% to 60% (y=7%). Yellowish solid.

Example 82

1-(2-Fluorophenyl)-5-[[4-(2-hydroxyethyl)phenoxy]methyl]-3-methyl-1H-pyrazole-4-carbonitrile 5-(Chloromethyl)-1-(2-fluorophenyl)-3-methyl-1H-pyrazole-4-carbonitrile (Intermediate 12). The title compound was prepared by the general procedure (scheme 1, step 2) from 3-amino-2-(chloroacetyl)but-2-enenitrile (CAS: 170652-68-3) and 2-fluorophenylhydrazine hydrochloride (CAS: 2368-80-1) (y=35%).
1-(2-Fluorophenyl)-5-[[4-(2-hydroxyethyl)phenoxy]methyl]-3-methyl-1H-pyrazole-4-carbonitrile. The title compound was prepared by the general procedure (scheme 1, step 3, method A) from intermediate 12, 4-(2-hydroxyethyl)phenol (CAS: 501-94-0), and $K_2CO_3$ at 70° C. overnight and purified by flash silica gel chromatography using a linear gradient of ethyl acetate in hexane from 10% to 60% (y=67%). Yellow oil.

Example 83

1-(4-Fluorophenyl)-3-methyl-5-(phenoxymethyl)-1H-pyrazole-4-carbonitrile 5-(Chloromethyl)-1-(4-fluorophenyl)-3-methyl-1H-pyrazole-4-carbonitrile (Intermediate 13). The title compound was prepared by the general procedure (scheme 1, step 2) from 3-amino-2-(chloroacetyl)but-2-enenitrile (CAS: 170652-68-3) and 4-fluorophenylhydrazine (CAS: 371-14-2) (y=37%).
1-(4-Fluorophenyl)-3-methyl-5-(phenoxymethyl)-1H-pyrazole-4-carbonitrile. The title compound was prepared by the general procedure (scheme 1, step 3, method A) from intermediate 13, phenol (CAS: 108-95-2), and K$_2$CO$_3$ at room temperature for 2 h and purified by flash silica gel chromatography using ethyl acetate in hexane (10%) as eluant (y=35%). Light yellow oil.

Example 84

1-(4-Fluorophenyl)-5-[[4-(2-hydroxyethyl)phenoxy]methyl]-3-methyl-1H-pyrazole-4-carbonitrile. The title compound was prepared by the general procedure (scheme 1, step 3, method A) from intermediate 13, 4-(2-hydroxyethyl)phenol (CAS: 501-94-0), and K$_2$CO$_3$ at 80° C. for 16 h and purified by flash silica gel chromatography using ethyl acetate in hexane (27%) as eluant (y=43%). White solid.

Example 85

5-[(3-Fluorophenoxy)methyl]-1-(4-fluorophenyl)-3-methyl-1H-pyrazole-4-carbonitrile. The title compound was prepared by the general procedure (scheme 1, step 3, method A) from intermediate 13, 3-fluorophenol (CAS: 372-20-3), and K$_2$CO$_3$ at 50° C. for 2 h and purified by flash silica gel chromatography using ethyl acetate in hexane (7%) as eluant (y=61%). Light yellow solid.

Example 86

1-(4-Fluorophenyl)-3-methyl-5-[(2-methylphenoxy)methyl]-1H-pyrazole-4-carbonitrile. The title compound was prepared by the general procedure (scheme 1, step 3, method A) from intermediate 13, o-cresol (CAS: 95-48-7), and K$_2$CO$_3$ at 50° C. for 2 h and purified by flash silica gel chromatography using ethyl acetate in hexane (6% as eluant (y=26%). White solid.

Example 87

1-(4-Fluorophenyl)-5-[[4-(3-hydroxypropyl)phenoxy]methyl]-3-methyl-1H-pyrazole-4-carbonitrile. The title compound was prepared by the general procedure (scheme 1, step 3, method A) from intermediate 13, 4-(3-hydroxypropyl)phenol (CAS: 10210-17-0), and K$_2$CO$_3$ at 80° C. for 4 h and purified by flash silica gel chromatography using ethyl acetate in hexane (30%) as eluant (y=55%). White solid.

Example 88

1-Benzyl-5-[[4-(2-hydroxyethyl)phenoxy]methyl]-3-methyl-1H-pyrazole-4-carbonitrile 1-Benzyl-5-(chloromethyl)-3-methyl-1H-pyrazole-4-carbonitrile (Intermediate 14). The title compound was prepared by the general procedure (scheme 1, step 2) from 3-amino-2-(chloroacetyl)but-2-enenitrile (CAS: 170652-68-3) and benzylhydrazine dihydrochloride (CAS: 20570-96-1) (y=32%).

1-Benzyl-5-[[4-(2-hydroxyethyl)phenoxy]methyl]-3-methyl-1H-pyrazole-4-carbonitrile. The title compound was prepared by the general procedure (scheme 1, step 3, method A) from intermediate 14, 4-(2-hydroxyethyl)phenol (CAS: 501-94-0), and K$_2$CO$_3$ at 60° C. for 3 h and purified by flash silica gel chromatography using a linear gradient of ethyl acetate in hexane from 15% to 65% as eluant (y=88%). Colorless oil.

Example 89

1-Benzyl-5-[[4-(3-hydroxypropyl)phenoxy]methyl]-3-methyl-1H-pyrazole-4-carbonitrile. The title compound was prepared by the general procedure (scheme 1, step 3, method A) from intermediate 14, 4-(3-hydroxypropyl)phenol (CAS: 10210-17-0), and K$_2$CO$_3$ at 60° C. for 3 h and purified by flash silica gel chromatography using a linear gradient of ethyl acetate in hexane from 15% to 65% as eluant (y=92%). Colorless oil.

Example 90

1-Benzyl-5-[[2,6-difluoro-4-(3-hydroxypropyl)phenoxy]methyl]-3-methyl-1H-pyrazole-4-carbonitrile. The title compound was prepared by the general procedure (scheme 1, step 3, method A) from intermediate 14, 2,6-difluoro-4-(3-hydroxypropyl)phenol (CAS: 1895507-21-7), and K$_2$CO$_3$ at 60° C. for 3 h and purified by flash silica gel chromatography using a linear gradient of ethyl acetate in hexane from 15% to 65% as eluant (y=60%). Colorless oil.

Example 91

5-[4-(2-Hydroxyethyl)phenoxymethyl]-1-[(4-methoxyphenyl)methyl]-3-methyl-1H-pyrazole-4-carbonitrile 5-(Chloromethyl)-1-(4-methoxybenzyl)-3-methyl-1H-pyrazole-4-carbonitrile (Intermediate 15). The title compound was prepared by the general procedure (scheme 1, step 2) from 3-amino-2-(chloroacetyl)but-2-enenitrile (CAS: 170652-68-3) and (4-methoxybenzyl)hydrazine (CAS: 140-69-2) (y=13%).

5-[4-(2-Hydroxyethyl)phenoxymethyl]-1-[(4-methoxyphenyl)methyl]-3-methyl-1H-pyrazole-4-carbonitrile. The title compound was prepared by the general procedure (scheme 1, step 3, method A) from intermediate 15, 4-(2-hydroxyethyl)phenol (CAS: 501-94-0), and K$_2$CO$_3$ at 60° C. for 2 h and purified by flash silica gel chromatography using a linear gradient of ethyl acetate in hexane from 15% to 70% as eluant (y=88%). Yellowish oil.

Example 92

5-[1-[4-(2-Hydroxyethyl)phenoxy]ethyl]-3-methyl-1-phenyl-1H-pyrazole-4-carbonitrile 2-(1-Aminoethylidene)-4-chloro-3-oxopentanenitrile (Intermediate 16). The title compound was prepared by the general procedure (scheme 1, step 1) from 2-chloropropionyl chloride (CAS: 7623-09-8) (y=31%).

5-(1-Chloroethyl)-3-methyl-1-phenyl-1H-pyrazole-4-carbonitrile (Intermediate 17). The title compound was prepared by the general procedure (scheme 1, step 2) from intermediate 16 and phenylhydrazine hydrochloride (CAS: 59-88-1) (y=20%).

5-[1-[4-(2-Hydroxyethyl)phenoxy]ethyl]-3-methyl-1-phenyl-1H-pyrazole-4-carbonitrile. The title compound was prepared by the general procedure (scheme 1, step 3, method A) from intermediate 17, 4-(2-hydroxyethyl)phenol (CAS: 501-94-0), and K$_2$CO$_3$ at reflux temperature for 4 h and purified by flash silica gel chromatography using a linear gradient of ethyl acetate in hexane from 15% to 70% (y=78%). Colorless oil.

Example 93

5-[1-[2,6-Difluoro-4-(3-hydroxypropyl)phenoxy]ethyl]-3-methyl-1-phenyl-1H-pyrazole-4-carbonitrile. The title compound was prepared by the general procedure (scheme 1, step 3, method A) from intermediate 17, 2,6-difluoro-4-(3-hydroxypropyl)phenol (CAS: 1895507-21-7), and K₂CO₃ at reflux temperature for 4 h and purified by flash silica gel chromatography using a linear gradient of ethyl acetate in hexane from 15% to 70% (y=81%). Colorless oil.

Example 94

5-[difluoro-[4-(2-hydroxyethyl)phenoxy]methyl]-3-methyl-1-phenyl-1H-pyrazole-4-carbonitrile 2-(1-Aminoethylidene)-4-chloro-3-oxopentanenitrile (Intermediate 18). The title compound was prepared by the general procedure (scheme 1, step 1) from chloro(difluoro)acetyl chloride (CAS: 354-24-5) (y=31%).
5-(1-Chloroethyl)-3-methyl-1-phenyl-1H-pyrazole-4-carbonitrile (Intermediate 19). The title compound was prepared by the general procedure (scheme 1, step 2) from intermediate 18 and phenylhydrazine hydrochloride (CAS: 59-88-1) (y=20%).
5-[difluoro-[4-(2-hydroxyethyl)phenoxy]methyl]-3-methyl-1-phenyl-1H-pyrazole-4-carbonitrile. The title compound was prepared by the general procedure (scheme 1, step 3, method A) from intermediate 19, 4-(2-hydroxyethyl)phenol (CAS: 501-94-0), and K₂CO₃ at 140° C. for 4 h and purified by flash silica gel chromatography using a linear gradient of ethyl acetate in hexane from 10% to 60% (y=78%). Colorless oil.

Example 95

5-{Difluoro[4-(3-hydroxypropyl)phenoxy]methyl}-3-methyl-1-phenyl-1H-pyrazole-4-carbonitrile. The title compound was prepared by the general procedure (scheme 1, step 3, method A) from intermediate 19, 4-(3-hydroxypropyl)phenol (CAS: 10210-17-0), and K₂CO₃ at 140° C. for 4 h and purified by flash silica gel chromatography using a linear gradient of ethyl acetate in hexane from 10% to 60% (y=71%). Yellow solid.

Example 96

5-{[2,6-Difluoro-4-(3-hydroxypropyl)phenoxy](difluoro)methyl}-3-methyl-1-phenyl-1H-pyrazole-4-carbonitrile.
The title compound was prepared by the general procedure (scheme 1, step 3, method A) from intermediate 19, 2,6-difluoro-4-(3-hydroxypropyl)phenol (CAS: 1895507-21-7), and K₂CO₃ at 140° C. for 4 h and purified by flash silica gel chromatography using a linear gradient of ethyl acetate in hexane from 10% to 60% (y=78%). Yellow oil.

Example 97

5-[(4-Cyanophenyl)methoxymethyl]-3-methyl-1-phenyl-1H-pyrazole-4-carbonitrile. The title compound was prepared by the general procedure (scheme 1, step 3, method B) from 5-(chloromethyl)-3-methyl-1-phenyl-1H-pyrazole-4-carbonitrile (CAS: 698367-00-9) and 4-(hydroxymethyl)benzonitrile (CAS: 874-89-5) overnight and purified by flash silica gel chromatography using a linear gradient of ethyl acetate in hexane from 0% to 40% (y=25%). Colorless oil.

Example 98

5-(Benzyloxymethyl)-1-(4-fluorophenyl)-3-methyl-1H-pyrazole-4-carbonitrile. The title compound was prepared by the general procedure (scheme 1, step 3, method B) from 5-(chloromethyl)-3-methyl-1-phenyl-1H-pyrazole-4-carbonitrile (CAS: 698367-00-9) and phenylmethanol (CAS: 100-51-6) for 1 h and purified by flash silica gel chromatography using a linear gradient of ethyl acetate in hexane from 7% to 10% (y=31%). White solid.

Example 99

1-(2-Ethylphenyl)-5-[[4-(2-hydroxyethyl)phenoxy]methyl]-3-methyl-1H-pyrazole-4-carbonitrile 3-Amino-2-{[4-(2-hydroxyethyl)phenoxy]acetyl}but-2-enenitrile (Intermediate 20). The title compound was prepared by the general procedure (scheme 1, step 4) from 3-amino-2-(chloroacetyl)but-2-enenitrile (CAS: 170652-68-3) and 4-(2-hydroxyethyl)phenol (CAS: 501-94-0). The crude product was purified by flash chromatography using 70% of ethyl acetate in hexane (y=40%).
1-(2-Ethylphenyl)-5-[[4-(2-hydroxyethyl)phenoxy]methyl]-3-methyl-1H-pyrazole-4-carbonitrile. The title compound was prepared by the general procedure (scheme 1, step 5, Method A) using Intermediate 20 and (2-ethylphenyl)hydrazine hydrochloride (CAS: 19398-06-2), at 110° C. for 1 h and purified by flash silica gel chromatography using 30%-40% of ethyl acetate in hexane (y=72%). Light yellow solid.

Example 100

5-[[4-(2-Hydroxyethyl)phenoxy]methyl]-3-methyl-1-(4-methylsulfonylphenyl)-1H-pyrazole-4-carbonitrile. The title compound was prepared by the general procedure (scheme 1, step 5, Method A) using Intermediate 20 and (4-(methylsulfonyl)phenyl)hydrazine hydrochloride (CAS: 17852-67-4) at 70° C. for 2 h and purified by flash silica gel chromatography using 50%-60% of ethyl acetate in hexane and then by preparative HPLC using 20%-55% of acetonitrile in water (y=17%). White solid.

Example 101

1-(3-Fluorophenyl)-5-[[4-(2-hydroxyethyl)phenoxy]methyl]-3-methyl-1H-pyrazole-4-carbonitrile. The title compound was prepared by the general procedure (scheme 1, step 5, Method A) using Intermediate 20 and (3-fluorophenyl)hydrazine hydrochloride (CAS: 2924-16-5) at 100° C. for 1 h and purified by flash silica gel chromatography using 30%-35% of ethyl acetate in hexane and then by preparative HPLC using 25%-70% of acetonitrile in water (y=15%). White solid.

Example 102

5-[[4-(2-Hydroxyethyl)phenoxy]methyl]-3-methyl-1-pyridin-2-yl-1H-pyrazole-4-carbonitrile. The title compound was prepared by the general procedure (scheme 1, step 5, Method E) using Intermediate 20 and 2-hydrazinylpyridine (CAS: 4930-98-7) at 90° C. for 16 h and purified by flash silica gel chromatography using 40% of ethyl acetate in hexane (y=10%). White solid.

Example 103

5-[[4-(2-Hydroxyethyl)phenoxy]methyl]-3-methyl-1-pyridin-3-yl-1H-pyrazole-4-carbonitrile. The title compound was prepared by the general procedure (scheme 1, step 5, Method C) using Intermediate 20 and 3-hydrazinylpyridine dihydrochloride (CAS: 364727-74-2) at 100° C. for 2 h and purified by flash silica gel chromatography using 2% of methanol in dichloromethane (y=8%). White solid.

Example 104

5-[[4-(2-Hydroxyethyl)phenoxy]methyl]-3-methyl-1-pyridin-4-yl-1H-pyrazole-4-carbonitrile. The title compound was prepared by the general procedure (scheme 1, step 5, Method C) using Intermediate 20 and 4-hydrazinylpyridine (CAS: 27256-91-3) at 100° C. for 2 h and purified by flash silica gel chromatography using 2% of methanol in dichloromethane and then by preparative HPLC using 35-100% water containing 0.1% ammonia in acetonitrile (y=21%). White solid.

Example 105

5-[[4-(2-Hydroxyethyl)phenoxy]methyl]-3-methyl-1-pyrimidin-2-yl-1H-pyrazole-4-carbonitrile. The title compound was prepared by the general procedure (scheme 1, step 5, Method E) using Intermediate 20 and 4-hydrazinylpyridine (CAS: 7504-94-1) at 90° C. for 3 h and purified by trituration in ethyl acetate (y=41%). White solid.

Example 106

5-[[4-(2-Hydroxyethyl)phenoxy]methyl]-3-methyl-1-pyridazin-3-yl-1H-pyrazole-4-carbonitrile. The title compound was prepared by the general procedure (scheme 1, step 5, Method E) using Intermediate 20 and 4-hydrazinylpyridine (CAS: 7504-94-1) at 90° C. for 4 h and purified by flash silica gel chromatography using 40% of ethyl acetate in hexane (y=16%). White solid.

Example 107

1-(4-Cyanophenyl)-5-[[4-(2-hydroxyethyl)phenoxy]methyl]-3-methyl-1H-pyrazole-4-carbonitrile. The title compound was prepared by the general procedure (scheme 1, step 5, Method C) using Intermediate 20 and 4-hydrazinylbenzonitrile hydrochloride (CAS: 2863-98-1) at 110° C. for 2 h and purified by flash silica gel chromatography using 30%-40% of ethyl acetate in hexane (y=39%). White solid.

Example 108

1-(3-Cyanophenyl)-5-[[4-(2-hydroxyethyl)phenoxy]methyl]-3-methyl-1H-pyrazole-4-carbonitrile. The title compound was prepared by the general procedure (scheme 1, step 5, Method C) using Intermediate 20 and 3-hydrazinylbenzonitrile hydrochloride (CAS: 2881-99-4) at 110° C. for 2 h and purified by flash silica gel chromatography using 30%-35% of ethyl acetate in hexane (y=39%). White solid.

Example 109

5-[[4-(2-Hydroxyethyl)phenoxy]methyl]-3-methyl-1-[4-(trifluoromethyl)phenyl]-1H-pyrazole-4-carbonitrile. The title compound was prepared by the general procedure (scheme 1, step 5, Method D) using Intermediate 20 and (4-(trifluoromethyl)phenyl)hydrazine (CAS: 368-90-1) at 110° C. for 1 h and purified by flash silica gel chromatography using 30%-35% of ethyl acetate in hexane (y=16%).

Example 110

1-(3-Bromopyridin-2-yl)-5-{[4-(2-hydroxyethyl)phenoxy]methyl}-3-methyl-1H-pyrazole-4-carbonitrile. The title compound was prepared by the general procedure (scheme 1, step 5, Method B) using Intermediate 20 and 3-bromo-2-hydrazinylpyridine (CAS: 54231-41-3) at 110° C. for 2 h and purified by flash silica gel chromatography using 35%-40% of ethyl acetate in hexane (y=40%). Yellow oil.

Example 111

1-(2,6-Dichlorophenyl)-5-{[4-(2-hydroxyethyl)phenoxy]methyl}-3-methyl-1H-pyrazole-4-carbonitrile. The title compound was prepared by the general procedure (scheme 1, step 5, Method B) using Intermediate 20 and (2,6-dichlorophenyl)hydrazine hydrochloride (CAS: 50709-36-9) at 110° C. for 2 h and purified by flash silica gel chromatography using 35%-75% of ethyl acetate in hexane (y=28%). White solid.

Example 112

1-(2,6-Difluorophenyl)-5-{[4-(2-hydroxyethyl)phenoxy]methyl}-3-methyl-1H-pyrazole-4-carbonitrile. The title compound was prepared by the general procedure (scheme 1, step 5, Method B) using Intermediate 20 and (2,6-difluorophenyl)hydrazine hydrochloride (CAS: 502496-26-6) at 110° C. for 2 h and purified by flash silica gel chromatography using 35%-75% of ethyl acetate in hexane (y=28%). White solid.

Example 113

1-(2-Chlorophenyl)-5-{[4-(2-hydroxyethyl)phenoxy]methyl}-3-methyl-1H-pyrazole-4-carbonitrile. The title compound was prepared by the general procedure (scheme 1, step 5, Method A) using Intermediate 20 and (2-chlorophenyl)hydrazine hydrochloride (CAS: 41052-75-9) at 110° C. for 1 h and purified by flash silica gel chromatography using 30%-40% of ethyl acetate in hexane (y=35%). Yellow solid.

Example 114

1-(2,4-Difluorophenyl)-5-{[4-(2-hydroxyethyl)phenoxy]methyl}-3-methyl-1H-pyrazole-4-carbonitrile. The title compound was prepared by the general procedure (scheme 1, step 5, Method A) using Intermediate 20 and (2,4-difluorophenyl)hydrazine hydrochloride (CAS: 51523-79-6) at 110° C. for 1 h and purified by flash silica gel chromatography using 30%-40% of ethyl acetate in hexane (y=49%). Yellow solid.

Example 115

5-{[4-(2-Hydroxyethyl)phenoxy]methyl}-3-methyl-1-[4-(trifluoromethoxy)phenyl]-1H-pyrazole-4-carbonitrile. The title compound was prepared by the general procedure (scheme 1, step 5, Method D) using Intermediate 20 and (4-(trifluoromethyl)phenyl)hydrazine (CAS: 13957-54-5) at 110° C. for 1 h and purified by flash silica gel chromatography using 30%-35% of ethyl acetate in hexane (y=17%). Yellow oil.

Example 116

1-(6-Chloropyridazin-3-yl)-5-{[4-(2-hydroxyethyl)phenoxy]methyl}-3-methyl-1H-pyrazole-4-carbonitrile. The title compound was prepared by the general procedure (scheme 1, step 5, Method F) using Intermediate 20 and 3-chloro-6-hydrazinylpyridazine (CAS: 17284-97-8) at 110° C. for 1 h and purified by flash silica gel chromatography using 30%-35% of ethyl acetate in hexane (y=7%). White solid.

Example 117

1-Cyclopentyl-5-{[4-(2-hydroxyethyl)phenoxy]methyl}-3-methyl-1H-pyrazole-4-carbonitrile. The title compound was prepared by the general procedure (scheme 1, step 5, Method A) using Intermediate 20 and cyclopentylhydrazine hydrochloride (CAS: 24214-72-0) at 110° C. for 2 h and purified by flash silica gel chromatography using 30%-35% of ethyl acetate in hexane (y=13%). White semisolid.

Example 118

1-Cyclohexyl-5-{[4-(2-hydroxyethyl)phenoxy]methyl}-3-methyl-1H-pyrazole-4-carbonitrile. The title compound was prepared by the general procedure (scheme 1, step 5, Method A) using Intermediate 20 and cyclohexylhydrazine hydrochloride (CAS: 24214-73-1) at 110° C. for 2 h and purified by flash silica gel chromatography using 40%-50% of ethyl acetate in hexane (y=20%). White semisolid.

Example 119

1-(4,4-Difluorocyclohexyl)-5-{[4-(2-hydroxyethyl)phenoxy]methyl}-3-methyl-1H-pyrazole-4-carbonitrile. The title compound was prepared by the general procedure (scheme 1, step 5, Method C) using Intermediate 20 and (4,4-difluorocyclohexyl)hydrazine hydrochloride (CAS: 1548590-10-8) at 110° C. for 2 h and purified by flash silica gel chromatography using 50% of ethyl acetate in hexane (y=46%). White solid.

Example 120

5-{[2,6-Difluoro-4-(3-hydroxypropyl)phenoxy]methyl}-3-methyl-1-phenyl-1H-pyrazole-4-carboxamide. The title compound was prepared by the described general procedure (scheme 1, step 6) from Example 32. The crude product was purified by flash silica gel column chromatography using a linear gradient of ethyl acetate in hexane from 20% to 80% as eluant to provide the desired product (y=60%). White solid.

Example 121A and Example 121B

5-{[2-Fluoro-4-(2-hydroxyethyl)phenoxy]methyl}-3-methyl-1-phenyl-1H-pyrazole-4-carboxamide and 5-{[2-fluoro-4-(2-hydroxyethyl)phenoxy]methyl}-3-methyl-1-phenyl-1H-pyrazole-4-carboxylic acid. The title compounds were prepared by the described general procedure (scheme 1, step 6) from Example 33. The crude product was purified by prep HPLC on RP-C18 column (35% to 70% CH$_3$CN/H$_2$O) gave two products Example 121A and Example 121B in a ratio of 40% to 60%. White solids.

Example 122

2-{4-[(1-Phenyl-1H-pyrazol-5-yl)methoxy]phenyl}ethanol. The title compound was prepared by the general procedure (scheme 2, step 1) from 5-(chloromethyl)-1-phenyl-1H-pyrazole (CAS: 1138009-85-4), 2-(4-hydroxyphenyl)ethanol (CAS: 501-94-0), and K$_2$CO$_3$ at 60° C. overnight and purified by flash silica gel chromatography using 50% of ethyl acetate in hexane (y=95%). Colorless oil.

Example 123

{3-Fluoro-4-[(1-phenyl-1H-pyrazol-5-yl)methoxy]phenyl}methanol. The title compound was prepared by the general procedure (scheme 2, step 1) from 5-(chloromethyl)-1-phenyl-1H-pyrazole (CAS: 1138009-85-4), 2-fluoro-4-(hydroxymethyl)phenol (CAS: 96740-93-1), and K$_2$CO$_3$ at 60° C. overnight and purified by flash silica gel chromatography using a linear gradient of ethyl acetate in hexane from 10% to 80% (y=96%). Colorless oil.

Example 124

{3,5-Difluoro-4-[(1-phenyl-1H-pyrazol-5-yl)methoxy]phenyl}methanol. The title compound was prepared by the general procedure (scheme 2, step 1) from 5-(chloromethyl)-1-phenyl-1H-pyrazole (CAS: 1138009-85-4), 2,6-difluoro-4-(hydroxymethyl)phenol (CAS: 206198-07-4), and K$_2$CO$_3$ at 60° C. overnight and purified by flash silica gel chromatography using a linear gradient of ethyl acetate in hexane from 20% to 80% (y=88%). Colorless oil.

Example 125

{3-Fluoro-4-[(3-methyl-1-phenyl-1H-pyrazol-5-yl)methoxy]phenyl}methanol. The title compound was prepared by the general procedure (scheme 2, step 1) from 5-(chloromethyl)-3-methyl-1-phenyl-1H-pyrazole (CAS: 1824317-98-7), 2-fluoro-4-(hydroxymethyl)phenol (CAS: 96740-93-1), and K$_2$CO$_3$ at 60° C. 12 h. The crude product was purified by flash silica gel chromatography using a linear gradient of ethyl acetate in hexane from 20% to 80% (y=88%). White solid.

Example 126

2-{4-[(3-Methyl-1-phenyl-1H-pyrazol-5-yl)methoxy]phenyl}ethanol. The title compound was prepared by the general procedure (scheme 2, step 1) from 5-(chloromethyl)-3-methyl-1-phenyl-1H-pyrazole (CAS: 1824317-98-7), 2-(4-hydroxyphenyl)ethanol (CAS: 501-94-0), and K$_2$CO$_3$ at 60° C. 12 h. The crude product was purified by flash silica gel chromatography using a linear gradient of ethyl acetate in hexane from 0% to 50% (y=74%). White solid.

Example 127

{3,5-Difluoro-4-[(3-methyl-1-phenyl-1H-pyrazol-5-yl)methoxy]phenyl}methanol. The title compound was prepared by the general procedure (scheme 2, step 1) from 5-(chloromethyl)-3-methyl-1-phenyl-1H-pyrazole (CAS: 1824317-98-7), 2,6-difluoro-4-(hydroxymethyl)phenol (CAS: 206198-07-4), and K$_2$CO$_3$ at 60° C. 12 h. The crude product was purified by flash silica gel chromatography using a linear gradient of ethyl acetate in hexane from 0% to 50% (y=79%). White solid.

Example 128

N-tert-Butyl-5-[4-(2-hydroxyethyl)phenoxymethyl]-1-phenyl-1H-pyrazole-4-carboxamide Ethyl 4-tert-Butoxy-2-[(dimethylamino)methylidene]-3-oxobutanoate (Intermediate 21). It was synthesized as reported in the scheme 3, step 1 (y=99%). Brown oil.

Ethyl 5-(tert-Butoxymethyl)-1-phenyl-1H-pyrazole-4-carboxylate (Intermediate 22). It was synthesized as described in the scheme 3, step 2 from Intermediate 21. The crude product was purified by silica gel column chromatography using a linear gradient of ethyl acetate in hexane from 0% to 35% as eluant to provide the desired product (y=67%). Colorless oil.

5-(tert-Butoxymethyl)-1-phenyl-1H-pyrazole-4-carboxylic acid (Intermediate 23). It was synthesized as reported in the scheme 3, step 3 from Intermediate 22 (y=96%). White solid.

5-(tert-Butoxymethyl)-1-phenyl-1H-pyrazole-4-carboxamide (Intermediate 24). It was synthesized as reported in the scheme 3, step 4 from Intermediate 23. The crude product was purified by silica gel column chromatography using a linear gradient of ethyl acetate in hexane from 40% to 95% as eluant to provide the desired product (y=79%). White solid.

5-(tert-Butoxymethyl)-1-phenyl-1H-pyrazole-4-carbonitrile (Intermediate 25). It was synthesized as described in the scheme 3, step 5 from Intermediate 24. The crude product was purified by silica gel column chromatography using a linear gradient of ethyl acetate in hexane from 0 to 50% as eluant to provide the desired product (y=33%). Yellowish oil.

N-tert-Butyl-5-(hydroxymethyl)-1-phenyl-1H-pyrazole-4-carboxamide (Intermediate 26). It was synthesized as reported in the scheme 3, step 6 from Intermediate 25. The crude product was purified by silica gel column chromatography using a linear gradient of ethyl acetate in hexane from 10 to 60% as eluant to provide the desired product (y=42%). White solid.

5-(Chloromethyl)-1-phenyl-1H-pyrazole-4-carbonitrile (Intermediate 27). It was synthesized as reported in the scheme 3, step 7 from Intermediate 26 (y=100%). White solid.

N-tert-Butyl-5-[4-(2-hydroxyethyl)phenoxymethyl]-1-phenyl-1H-pyrazole-4-carboxamide. The compound was synthesized as reported in the scheme 3, step 8 from Intermediate 27. The crude product was purified by silica gel column chromatography using a linear gradient of ethyl acetate in hexane from 15 to 70% as eluant, to provide the desired product (y=97%). White solid.

Example 129

5-{[4-(2-Hydroxyethyl)phenoxy]methyl}-1-phenyl-1H-pyrazole-4-carbonitrile

Ethyl 5-{[4-(2-hydroxyethyl)phenoxy]methyl}-1-phenyl-1H-pyrazole-4-carboxylate (Intermediate 28). It was prepared by the general procedure (scheme 4, step 1) from ethyl 5-(chloromethyl)-1-phenyl-1H-pyrazole-4-carboxylate (CAS Number: 137487-61-7), 4-hydroxyphenethyl alcohol (CAS: 501-94-0), and $K_2CO_3$ at 70° C. for 2 h and purified by flash silica gel chromatography using a linear gradient of ethyl acetate in hexane from 15% to 70% (y=91%).

5-{[4-(2-Hydroxyethyl)phenoxy]methyl}-1-phenyl-1H-pyrazole-4-carboxylic acid (Intermediate 29). It was prepared by the general procedure (scheme 4, step 2) from Intermediate 28 (y=94%).

5-({4-[2-(Acetyloxy)ethyl]phenoxy}methyl)-1-phenyl-1H-pyrazole-4-carboxylic acid (Intermediate 30). It was prepared by the general procedure (scheme 4, step 3) from Intermediate 29 (y=94%).

2-{4-[(4-Carbamoyl-1-phenyl-1H-pyrazol-5-yl)methoxy]phenyl}ethyl acetate (Intermediate 31). It was prepared by the general procedure (scheme 4, step 4) from Intermediate 30. The crude product was purified by silica gel column chromatography using a linear gradient of ethyl acetate in hexane from 50 to 95% as eluant to provide the desired product as white solid (y=55%).

5-{[4-(2-Hydroxyethyl)phenoxy]methyl}-1-phenyl-1H-pyrazole-4-carbonitrile. It was prepared by the general procedure (scheme 4, step 5 and 6) from Intermediate 31. The crude product was purified by silica gel column chromatography using a linear gradient of ethyl acetate in hexane from 15% to 70% as eluant to provide the desired product (y=78%). Yellowish oil.

Example 130

5-{[4-(3-Hydroxypropyl)phenoxy]methyl}-1-phenyl-1H-pyrazole-4-carbonitrile

Ethyl 5-{[4-(2-Hydroxyethyl)phenoxy]methyl}-1-phenyl-1H-pyrazole-4-carboxylate (Intermediate 32). It was prepared by the general procedure (scheme 4, step 1) from ethyl 5-(chloromethyl)-1-phenyl-1H-pyrazole-4-carboxylate (CAS: 137487-61-7), 4-(3-hydroxypropyl)phenol (CAS: 10210-17-0), and $K_2CO_3$ at 70° C. for 2 h and purified by flash silica gel chromatography using a linear gradient of ethyl acetate in hexane from 15% to 70% (y=84%).

5-{[4-(3-Hydroxypropyl)phenoxy]methyl}-1-phenyl-1H-pyrazole-4-carboxylic acid (Intermediate 33). It was prepared by the general procedure (scheme 4, step 2) from Intermediate 32 (y=99%).

5-{4-[3-(Acetyloxy)propyl]phenoxymethyl}-1-phenyl-1H-pyrazole-4-carboxylic acid (Intermediate 34). It was prepared by the general procedure (scheme 4, step 3) from Intermediate 33 (y=93%).

2-{4-[(4-Carbamoyl-1-phenyl-1H-pyrazol-5-yl)methoxy]phenyl}ethyl acetate (Intermediate 35). It was prepared by the general procedure (scheme 4, step 4) from Intermediate 34. The crude product was purified by silica gel column chromatography using a linear gradient of ethyl acetate in hexane from 50 to 95% as eluant to provide the desired product as white solid (y=45%).

5-{[4-(3-Hydroxypropyl)phenoxy]methyl}-1-phenyl-1H-pyrazole-4-carbonitrile. It was prepared by the general procedure (scheme 4, step 5 and 6) from Intermediate 35. The crude product was purified by silica gel column chromatography using a linear gradient of ethyl acetate in hexane from 15 to 70% as eluant to provide the desired product (y=75%). Yellowish oil.

Example 131

5-({[4-(2-Hydroxyethyl)phenyl]sulfinyl}methyl)-3-methyl-1-phenyl-1H-pyrazole-4-carbonitrile. The title compound was prepared by the general procedure (scheme 5, step 1) using 1.2 eq of 3-chloroperbenzoic acid. The crude product was purified by silica gel column chromatography using a linear gradient of ethyl acetate in hexane from 10% to 65% (y=76%). White solid.

Example 132

5-({[4-(2-Hydroxyethyl)phenyl]sulfonyl}methyl)-3-methyl-1-phenyl-1H-pyrazole-4-carbonitrile. The title compound was prepared by the general procedure (scheme 5, step 1) using 2.5 eq of 3-chloroperbenzoic acid. The crude product was purified by silica gel column chromatography using a linear gradient of ethyl acetate in hexane from 10% to 65% (y=64%). White solid.

Example 133

3-{4-[(4-Cyano-3-methyl-1-phenyl-1H-pyrazol-5-yl)methoxy]phenyl}propanoic acid

Methyl 3-{4-[(4-cyano-3-methyl-1-phenyl-1H-pyrazol-5-yl)methoxy]-3,5-difluorophenyl}propanoate (intermediate 35). It was prepared by the general procedure (scheme 1, step 3, method A) from 5-(chloromethyl)-3-methyl-1-phenyl-H-pyrazole-4-carbonitrile (CAS: 698367-00-9) methyl 3-(3,5-difluoro-4-hydroxyphenyl)propanoate (CAS: 1782078-07-2), and $K_2CO_3$ at 60° C. for 3 h and purified by flash silica gel chromatography using a linear gradient of ethyl acetate in hexane from 0% to 40% (y=81%).
3-{4-[(4-Cyano-3-methyl-1-phenyl-1H-pyrazol-5-yl)methoxy]phenyl}propanoic acid. The title compound was prepared by hydrolysis of the product intermediate 35, according to the procedure described in general synthetic Scheme 6, Method A. HPLC on RP-C18 column (10% to 95% $CH_3CN/H_2O$) gave the pure product (y=91%). White solid.

Example 134

2-(4-((4-Cyano-3-methyl-1-phenyl-1H-pyrazol-5-yl)methoxy)phenyl)acetic acid

Ethyl {4-[(4-cyano-3-methyl-1-phenyl-1H-pyrazol-5-yl)methoxy]phenyl}acetate (intermediate 36). It was prepared by the general procedure (scheme 1, step 3, method A) from 5-(chloromethyl)-3-methyl-1-phenyl-H-pyrazole-4-carbonitrile (CAS: 698367-00-9 methyl 3-(3,5-difluoro-4-hydroxyphenyl)propanoate (17138-28-2), and $K_2CO_3$ at 60° C. for 8 h and purified by flash silica gel chromatography using 20-25% ethyl acetate in hexane (y 48%). 2-(4-((4-Cyano-3-methyl-1-phenyl-1H-pyrazol-5-yl)methoxy)phenyl)acetic acid. The title compound was prepared by hydrolysis of the product intermediate 36, according to the procedure described in general synthetic Scheme 6, Method B (y=35%). White solid.

Example 135

5-{[4-(3-Methoxypropyl)phenoxy]methyl}-3-methyl-1-phenyl-1H-pyrazole-4-carbonitrile. The title compound was prepared by the general procedure (Scheme 7, step 1). The crude product was purified by silica gel column chromatography using 15-20% ethyl acetate in hexanes as gradient (y=18%). Yellow oil.

Example 136

3-Methyl-1-phenyl-5-[[4-(2-piperidin-4-ylethyl)phenoxy]methyl]-1H-pyrazole-4-carbonitrile tert-butyl 4-(2-{4-[(4-cyano-3-methyl-1-phenyl-1H-pyrazol-5-yl)methoxy]phenyl}ethyl)piperidine-1-carboxylate (intermediate 37). It was prepared by the general procedure (scheme 8, step 2) from 5-(chloromethyl)-3-methyl-1-phenyl-1H-pyrazole-4-carbonitrile (CAS: 698367-00-9), tert-butyl 4-[2-(4-hydroxyphenyl)ethyl]-piperidine-1-carboxylate (CAS: 1403315-71-8), and $K_2CO_3$ at 60° C. for 2 h and purified by flash silica gel chromatography using a linear gradient of ethyl acetate in hexane from 15% to 70% (y=66%).
3-Methyl-1-phenyl-5-[[4-(2-piperidin-4-ylethyl)phenoxy]methyl]-1H-pyrazole-4-carbonitrile. The title compound was prepared by the general procedure (scheme 8, step 3) from intermediate 37 (y=99%). White solid.

Example 137

5-[[4-(2-Amino-1-hydroxyethyl)phenoxy]methyl]-3-methyl-1-phenyl-1H-pyrazole-4-carbonitrile tert-butyl [2-hydroxy-2-(4-hydroxyphenyl)ethyl]carbamate (Intermediate 38). The intermediate 38 was synthesized by general procedure (scheme 8, step 1) from 4-(2-amino-1-hydroxyethyl)phenol (CAS: 104-14-3) (y=84%).
tert-butyl N-(2-{4-[(4-cyano-3-methyl-1-phenyl-1H-pyrazol-5-yl)methoxy]phenyl}-2-hydroxyethyl)carbamate (intermediate 39). It was prepared by the general procedure (scheme 8, step 2) from 5-(chloromethyl)-3-methyl-1-phenyl-1H-pyrazole-4-carbonitrile (CAS: 698367-00-9), intermediate 38, and $K_2CO_3$ at 60° C. for 2 h and purified by flash silica gel chromatography using a linear gradient of ethyl acetate in hexane from 15% to 70% (y=59%).
5-[[4-(2-Amino-1-hydroxyethyl)phenoxy]methyl]-3-methyl-1-phenyl-1H-pyrazole-4-carbonitrile. The title compound was prepared by the general procedure (scheme 8, step 3) from intermediate 38 (y=99%). Colorless oil.

Example 138

3-Methyl-1-phenyl-5-[[4-(2-piperidin-2-ylethyl)phenoxy]methyl]-1H-pyrazole-4-carbonitrile tert-butyl 2-[2-(4-hydroxyphenyl)ethyl]piperidine-1-carboxylate (Intermediate 39). The intermediate 39 was synthesized by general procedure (scheme 8, step 1) from 4-[2-(2-piperidinyl)ethyl]phenol (CAS: 408312-63-0) (y=89%).
tert-butyl 2-(2-{4-[(3,4-dimethyl-1-phenyl-1H-pyrazol-5-yl)methoxy]phenyl}-ethyl)piperidine-1-carboxylate (intermediate 40). It was prepared by the general procedure (scheme 8, step 2) from 5-(chloromethyl)-3-methyl-1-phenyl-H-pyrazole-4-carbonitrile (CAS: 698367-00-9), intermediate 39, and $K_2CO_3$ at 60° C. for 2 h and purified by flash silica gel chromatography using a linear gradient of ethyl acetate in hexane from 15% to 70% (y=79%).
3-Methyl-1-phenyl-5-[[4-(2-piperidin-2-ylethyl)phenoxy]methyl]-1H-pyrazole-4-carbonitrile. The title compound was prepared by the general procedure (scheme 8, step 3) from intermediate 40 (y=99%). White solid.

Example 139

5-[[4-(5-Amino-4H-1,2,4-triazol-3-yl)phenoxy]methyl]-3-methyl-1-phenyl-1H-pyrazole-4-carbonitrile tert-butyl [5-(4-hydroxyphenyl)-4H-1,2,4-triazol-3-yl]carbamate (Intermediate 41). The intermediate 41 was synthesized by general procedure (scheme 8, step 1) from 4-(3-amino-1H-1,2,4-triazol-5-yl)phenol (CAS: 92352-27-7) (y=81%).
tert-butyl N-(5-{4-[(4-cyano-3-methyl-1-phenyl-1H-pyrazol-5-yl)methoxy]-phenyl}-4H-1,2,4-triazol-3-yl)carbamate (intermediate 42). It was prepared by the general procedure (scheme 8, step 2) from 5-(chloromethyl)-3-methyl-1-phenyl-1H-pyrazole-4-carbonitrile (CAS: 698367-00-9), intermediate 41, and $K_2CO_3$ at 60° C. for 2 h and purified by flash silica gel chromatography using a linear gradient of ethyl acetate in hexane from 15% to 70% (y=71%).

5-[[4-(5-Amino-4H-1,2,4-triazol-3-yl)phenoxy]methyl]-3-methyl-1-phenyl-1H-pyrazole-4-carbonitrile. The title compound was prepared by the general procedure (scheme 8, step 3) from intermediate 41 (y=99%). White solid.

Example 140

5-[[4-(2-Aminoethyl)phenoxy]methyl]-3-methyl-1-phenyl-1H-pyrazole-4-carbonitrile tert-Butyl N-(2-{4-[(4-cyano-3-methyl-1-phenyl-1H-pyrazol-5-yl)methoxy]-phenyl}ethyl)carbamate (Intermediate 42). The intermediate 42 was synthesized by general procedure (scheme 8, step 2) from 5-(chloromethyl)-3-methyl-1-phenyl-1H-pyrazole-4-carbonitrile (CAS: 698367-00-9), tert-butyl [2-(4-hydroxyphenyl)ethyl]carbamate (CAS: 64318-28-1), and $K_2CO_3$ at 60° C. for 3 h and purified by flash silica gel chromatography using a linear gradient of ethyl acetate in hexane from 0% to 40% (y=81%).

5-[[4-(2-Aminoethyl)phenoxy]methyl]-3-methyl-1-phenyl-1H-pyrazole-4-carbonitrile. The title compound was prepared by the general procedure (scheme 8, step 3) from Intermediate 42 (y=99%). White solid.

Example 141

N-(2-{4-[(4-Cyano-3-methyl-1-phenyl-1H-pyrazol-5-yl)methoxy]phenyl}ethyl)acetamide. The title compound was prepared by the general procedure (scheme 8, step 4) from Example 140 and acetyl chloride (CAS: 75-36-5). The crude product was purified by silica gel column chromatography using a linear gradient of ethyl acetate in hexane from 50% to 100% and the 100% of ethyl acetate (y=72%). White solid.

Example 142

N-(2-{4-[(4-Cyano-3-methyl-1-phenyl-1H-pyrazol-5-yl)methoxy]phenyl}ethyl)benzamide. The title compound was prepared by the general procedure (scheme 8, step 4) from Example 140 and benzoyl chloride (CAS: 98-88-4). The crude product was purified by silica gel column chromatography using a linear gradient of ethyl acetate in hexane from 20% to 60% (y=62%). White solid.

Example 143

N-(2-{4-[(4-Cyano-3-methyl-1-phenyl-1H-pyrazol-5-yl)methoxy]phenyl}ethyl)methanesulfonamide. The title compound was prepared by the general procedure (scheme 8, step 4) from Example 140 and methanesulfonyl chloride (CAS: 124-63-0). The crude product was purified by silica gel column chromatography using a linear gradient of ethyl acetate in hexane from 20% to 60% (y=44%). White solid.

Example 144

N-(2-{4-[(4-Cyano-3-methyl-1-phenyl-1H-pyrazol-5-yl)methoxy]phenyl}ethyl)benzenesulfonamide. The title compound was prepared by the general procedure (scheme 8, step 4) from Example 140 and benzenesulfonyl chloride (CAS: 98-09-9). The crude product was purified by silica gel column chromatography using a linear gradient of ethyl acetate in hexane from 10% to 50% (y=58%). White solid.

Example 145

N-(2-{4-[(4-Cyano-3-methyl-1-phenyl-1H-pyrazol-5-yl)methoxy]phenyl}ethyl)-2-phenylacetamide. The title compound was prepared by the general procedure (scheme 8, step 4) from Example 140 and phenylacetyl chloride (CAS: 103-8-0). The crude product was purified by silica gel column chromatography using a linear gradient of ethyl acetate in hexane from 15% to 60% (y=71%). White solid.

Example 146

5-[[4-[4-(Hydroxymethyl)-1,3-thiazol-2-yl]phenoxy]methyl]-3-methyl-1-phenyl-1H-pyrazole-4-carbonitrile 5-{[4-(4-Formyl-1,3-thiazol-2-yl)phenoxy]methyl}-3-methyl-1-phenyl-1H-pyrazole-4-carbonitrile (intermediate 43). It was prepared by the general procedure (scheme 1, step 3, method A) from 5-(chloromethyl)-3-methyl-1-phenyl-H-pyrazole-4-carbonitrile (CAS: 698367-00-9), 2-(4-hydroxyphenyl)-1,3-thiazole-4-carbaldehyde (CAS: 885278-87-5), and $K_2CO_3$ at 60° C. for 2 h and purified by flash silica gel chromatography using a linear gradient of ethyl acetate in hexane from 0% to 30% (y=89%).

5-[[4-[4-(Hydroxymethyl)-1,3-thiazol-2-yl]phenoxy]methyl]-3-methyl-1-phenyl-1H-pyrazole-4-carbonitrile. The title compound was prepared by the general procedure (scheme 9, step 1) from intermediate 43 and purified by flash silica gel chromatography using a linear gradient of ethyl acetate in hexane from 15% to 70% (y=69%). Colorless oil.

Example 147

5-[[4-(Hydroxymethyl)-2-(trifluoromethyl)phenoxy]methyl]-3-methyl-1-phenyl-1H-pyrazole-4-carbonitrile 5-{[4-Formyl-2-(trifluoromethyl)phenoxy]methyl}-3-methyl-1-phenyl-1H-pyrazole-4-carbonitrile (intermediate 44). It was prepared by the general procedure (scheme 1, step 3, method A) from 5-(chloromethyl)-3-methyl-1-phenyl-H-pyrazole-4-carbonitrile (CAS: 698367-00-9), 4-hydroxy-3-(trifluoromethyl)benzaldehyde (CAS: 220227-98-5), and $K_2CO_3$ at 60° C. for 2 h and purified by flash silica gel chromatography using a linear gradient of ethyl acetate in hexane from 0% to 30% (y=93%).

5-[[4-(Hydroxymethyl)-2-(trifluoromethyl)phenoxy]methyl]-3-methyl-1-phenyl-1H-pyrazole-4-carbonitrile. The title compound was prepared by the general procedure (scheme 9, step 1) from intermediate 44 and purified by flash silica gel chromatography using a linear gradient of ethyl acetate in hexane from 15% to 70% (y=82%). Colorless oil.

Example 148

3-Methyl-1-phenyl-5-[[4-(4,4,4-trifluoro-1,3-dihydroxybutyl)phenoxy]methyl]-1H-pyrazole-4-carbonitrile 5-{[4-Formyl-2-(trifluoromethyl)phenoxy]methyl}-3-methyl-1-phenyl-1H-pyrazole-4-carbonitrile (intermediate 45). It was prepared by the general procedure (scheme 1, step 3, method A) from 5-(chloromethyl)-3-methyl-1-phenyl-H-pyrazole-4-carbonitrile (CAS: 698367-00-9), 4,4,4-trifluoro-1-(4-hydroxyphenyl)butane-1,3-dione (CAS: 57965-22-7), and K$_2$CO$_3$ at 70° C. for 2 h and purified by flash silica gel chromatography using a linear gradient of ethyl acetate in hexane from 15% to 70% (y=71%).

3-Methyl-1-phenyl-5-[[4-(4,4,4-trifluoro-1,3-dihydroxybutyl)phenoxy]methyl]-1H-pyrazole-4-carbonitrile. The title compound was prepared by the general procedure (scheme 9, step 1) from intermediate 45 and purified by flash silica gel chromatography using a linear gradient of ethyl acetate in hexane from 20% to 80% (y=79%). White solid.

Example 149

5-[[4-(3-hydroxypropyl)phenoxy]methyl]-3-methyl-1-(2-pyridyl)pyrazole-4-carbonitrile 5-(Chloromethyl)-3-methyl-1-(pyridin-2-yl)-1H-pyrazole-4-carbonitrile (Intermediate 46). The title compound was prepared by the general procedure (scheme 1, step 2) from 3-amino-2-(chloroacetyl)but-2-enenitrile (CAS: 170652-68-3) and 2-Hydrazinopyridine (CAS: 4930-98-7) (y=22%).

5-[[4-(3-Hydroxypropyl)phenoxy]methyl]-3-methyl-1-(2-pyridyl)pyrazole-4-carbonitrile. The title compound was prepared by the general procedure (scheme 1, step 3, method A) from intermediate 46, 3-(4-hydroxyphenyl)-1-propanol (CAS: 10210-17-0), and K$_2$CO$_3$ at 60° C. for 3 h. After cooling, the solvent was evaporated and the residue was purified by flash silica gel chromatography a linear gradient of ethyl acetate in hexane from 10 to 60% as eluent to provide the desired product (y=61%). White solid.

Example 150

5-[[4-(3-Hydroxypropyl)phenoxy]methyl]-3-methyl-1-(p-tolyl)pyrazole-4-carbonitrile. The title compound was prepared by the general procedure (scheme 1, step 3, method A) from intermediate 4, 3-(4-hydroxyphenyl)-1-propanol (CAS: 10210-17-0), and K$_2$CO$_3$ at 60° C. for 3 h. After cooling, the solvent was evaporated and the residue was purified by flash silica gel chromatography a linear gradient of ethyl acetate in hexane from 10 to 40% as eluent to provide the desired product (y=55%). White solid.

Example 151

1-(4-Ethylphenyl)-5-[[4-(3-hydroxypropyl)phenoxy]methyl]-3-methyl-pyrazole-4-carbonitrile. The title compound was prepared by the general procedure (scheme 1, step 3, method A) from intermediate 8, 3-(4-hydroxyphenyl)-1-propanol (CAS: 10210-17-0), and K$_2$CO$_3$ at 60° C. for 3 h. After cooling, the solvent was evaporated and the residue was purified by flash silica gel chromatography a linear gradient of ethyl acetate in hexane from 10 to 30% as eluent to provide the desired product (y=65%). White solid.

Example 152

1-(4-Chlorophenyl)-5-[[4-(3-hydroxypropyl)phenoxy]methyl]-3-methyl-pyrazole-4-carbonitrile. The title compound was prepared by the general procedure (scheme 1, step 3, method A) from intermediate 6, 3-(4-hydroxyphenyl)-1-propanol (CAS: 10210-17-0), and K$_2$CO$_3$ at 60° C. for 3 h. After cooling, the solvent was evaporated and the residue was purified by flash silica gel chromatography a linear gradient of ethyl acetate in hexane from 10 to 30% as eluent to provide the desired product (y=63%). White solid.

Example 153

1-Cyclopentyl-5-[[4-(3-hydroxypropyl)phenoxy]methyl]-3-methyl-pyrazole-4-carbonitrile 5-(Chloromethyl)-1-cyclopentyl-3-methyl-1H-pyrazole-4-carbonitrile (Intermediate 47). The title compound was prepared by the general procedure (scheme 1, step 2) from 3-amino-2-(chloroacetyl)but-2-enenitrile (CAS: 170652-68-3) and cyclopentylhydrazine hydrochloride (CAS: 24214-72-0) (y=18%).

1-Cyclopentyl-5-[[4-(3-hydroxypropyl)phenoxy]methyl]-3-methyl-pyrazole-4-carbonitrile. The title compound was prepared by the general procedure (scheme 1, step 3, method A) from intermediate 47, 3-(4-hydroxyphenyl)-1-propanol (CAS: 10210-17-0), and K$_2$CO$_3$ at 60° C. for 3 h. After cooling, the solvent was evaporated and the residue was purified by flash silica gel chromatography a linear gradient of ethyl acetate in hexane from 10 to 30% as eluent to provide the desired product (y=65%). White solid.

Example 154

1-(5-Fluoro-2-pyridyl)-5-[[4-(3-hydroxypropyl)phenoxy]methyl]-3-methyl-pyrazole-4-carbonitrile 5-(Chloromethyl)-1-(5-fluoropyridin-2-yl)-3-methyl-1H-pyrazole-4-carbonitrile (Intermediate 48). The title compound was prepared by the general procedure (scheme 1, step 2) from 3-amino-2-(chloroacetyl)but-2-enenitrile (CAS: 170652-68-3) and (5-fluoro-pyridin-2-yl)-hydrazine (CAS: 145934-90-3) (y=31%).

1-(5-Fluoro-2-pyridyl)-5-[[4-(3-hydroxypropyl)phenoxy]methyl]-3-methyl-pyrazole-4-carbonitrile. The title compound was prepared by the general procedure (scheme 1, step 3, method A) from intermediate 48, 3-(4-hydroxyphenyl)-1-propanol (CAS: 10210-17-0), and K$_2$CO$_3$ at 60° C. for 3 h. After cooling, the solvent was evaporated and the residue was purified by flash silica gel chromatography a linear gradient of ethyl acetate in hexane from 10 to 30% as eluent to provide the desired product (y=71%). White solid.

Example 155

1-(5-Chloro-2-pyridyl)-5-[[4-(3-hydroxypropyl)phenoxy]methyl]-3-methyl-pyrazole-4-carbonitrile 5-(Chloromethyl)-1-(5-chloropyridin-2-yl)-3-methyl-1H-pyrazole-4-carbonitrile (Intermediate 49). The title compound was prepared by the general procedure (scheme 1, step 2) from 3-amino-2-(chloroacetyl)but-2-enenitrile (CAS: 170652-68-3) and 5-Chloro-2-hydrazinopyridine (CAS: 27032-63-9) (y=32%).

1-(5-Chloro-2-pyridyl)-5-[[4-(3-hydroxypropyl)phenoxy]methyl]-3-methyl-pyrazole-4-carbonitrile. The title compound was prepared by the general procedure (scheme 1, step 3, method A) from intermediate 49, 3-(4-hydroxyphenyl)-1-propanol (CAS: 10210-17-0), and K$_2$CO$_3$ at 60° C. for 3 h. After cooling, the solvent was evaporated and the residue was purified by flash silica gel chromatography a linear gradient of ethyl acetate in hexane from 10 to 60% as eluent to provide the desired product (y=81%). White solid.

Example 156

5-[[4-(3-Hydroxypropyl)phenoxy]methyl]-3-methyl-1-(5-methyl-2-pyridyl)pyrazole-4-carbonitrile 5-(Chloromethyl)-3-methyl-1-(5-methylpyridin-2-yl)-1H-pyrazole-4-carbonitrile (Intermediate 50). The title compound was prepared by the general procedure (scheme 1, step 2) from 3-amino-2-(chloroacetyl)but-2-enenitrile (CAS: 170652-68-3) and 2-hydrazinyl-5-methylpyridine (CAS: 4931-01-5) (y=29%).

5-[[4-(3-Hydroxypropyl)phenoxy]methyl]-3-methyl-1-(5-methyl-2-pyridyl)pyrazole-4-carbonitrile. The title compound was prepared by the general procedure (scheme 1, step 3, method A) from intermediate 50, 3-(4-hydroxyphenyl)-1-propanol (CAS: 10210-17-0), and $K_2CO_3$ at 60° C. for 3 h. After cooling, the solvent was evaporated and the residue was purified by flash silica gel chromatography a linear gradient of ethyl acetate in hexane from 10 to 60% as eluent to provide the desired product (y=75%). White solid.

Example 157

5-[[4-(3-Hydroxypropyl)phenoxy]methyl]-1-(5-methoxy-2-pyridyl)-3-methyl-pyrazole-4-carbonitrile 5-(Chloromethyl)-1-(5-methoxypyridin-2-yl)-3-methyl-1H-pyrazole-4-carbonitrile (Intermediate 51). The title compound was prepared by the general procedure (scheme 1, step 2) from 3-amino-2-(chloroacetyl)but-2-enenitrile (CAS: 170652-68-3) and 2-hydrazinyl-5-methoxypyridine (CAS: 741287-82-1) (y=32%).

5-[[4-(3-Hydroxypropyl)phenoxy]methyl]-1-(5-methoxy-2-pyridyl)-3-methyl-pyrazole-4-carbonitrile. The title compound was prepared by the general procedure (scheme 1, step 3, method A) from intermediate 51, 3-(4-hydroxyphenyl)-1-propanol (CAS: 10210-17-0), and $K_2CO_3$ at 60° C. for 3 h. After cooling, the solvent was evaporated and the residue was purified by flash silica gel chromatography a linear gradient of ethyl acetate in hexane from 10 to 60% as eluent to provide the desired product (y=65%). White solid.

Example 158

5-[[2,6-Difluoro-4-(3-hydroxypropyl)phenoxy]methyl]-3-methyl-1-(2-pyridyl)pyrazole-4-carbonitrile. The title compound was prepared by the general procedure (scheme 1, step 3, method A) from intermediate 46, 4-(hydroxymethyl)-2,6-dimethylphenol (CAS: 4397-14-2), and $K_2CO_3$ at reflux temperature for 4 h. After cooling, the solvent was evaporated and the residue was purified by flash silica gel chromatography a linear gradient of ethyl acetate in hexane from 15 to 70% as eluent to provide the desired product (y=90%). Colorless oil.

Example 159

5-[[2,6-Difluoro-4-(3-hydroxypropyl)phenoxy]methyl]-3-methyl-1-(p-tolyl)pyrazole-4-carbonitrile. The title compound was prepared by the general procedure (scheme 1, step 3, method A) from intermediate 4,4-(hydroxymethyl)-2,6-dimethylphenol (CAS: 4397-14-2), and $K_2CO_3$ at reflux temperature for 4 h. After cooling, the solvent was evaporated and the residue was purified by flash silica gel chromatography a linear gradient of ethyl acetate in hexane from 15 to 70% as eluent to provide the desired product (y=96%). Colorless oil.

Example 160

5-[[2,6-Difluoro-4-(3-hydroxypropyl)phenoxy]methyl]-1-(4-ethylphenyl)-3-methyl-pyrazole-4-carbonitrile. The title compound was prepared by the general procedure (scheme 1, step 3, method A) from intermediate 8, 4-(hydroxymethyl)-2,6-dimethylphenol (CAS: 4397-14-2), and $K_2CO_3$ at reflux temperature for 4 h. After cooling, the solvent was evaporated and the residue was purified by flash silica gel chromatography a linear gradient of ethyl acetate in hexane from 15 to 70% as eluent to provide the desired product (y=94%). Colorless oil.

Example 161

5-[[2,6-Difluoro-4-(3-hydroxypropyl)phenoxy]methyl]-1-(4-methoxyphenyl)-3-methyl-pyrazole-4-carbonitrile. The title compound was prepared by the general procedure (scheme 1, step 3, method A) from intermediate 10, 4-(hydroxymethyl)-2,6-dimethylphenol (CAS: 4397-14-2), and $K_2CO_3$ at reflux temperature for 4 h. After cooling, the solvent was evaporated and the residue was purified by flash silica gel chromatography a linear gradient of ethyl acetate in hexane from 15 to 70% as eluent to provide the desired product (y=66%). Colorless oil.

Example 162

1-(4-Chlorophenyl)-5-[[2,6-difluoro-4-(3-hydroxypropyl)phenoxy]methyl]-3-methyl-pyrazole-4-carbonitrile. The title compound was prepared by the general procedure (scheme 1, step 3, method A) from intermediate 6, 4-(hydroxymethyl)-2,6-dimethylphenol (CAS: 4397-14-2), and $K_2CO_3$ at reflux temperature for 4 h. After cooling, the solvent was evaporated and the residue was purified by flash silica gel chromatography a linear gradient of ethyl acetate in hexane from 15 to 70% as eluent to provide the desired product (y=89%). Colorless oil.

Example 163

1-Cyclopentyl-5-[[2,6-difluoro-4-(3-hydroxypropyl)phenoxy]methyl]-3-methyl-pyrazole-4-carbonitrile. The title compound was prepared by the general procedure (scheme 1, step 3, method A) from intermediate 47, 4-(hydroxymethyl)-2,6-dimethylphenol (CAS: 4397-14-2), and $K_2CO_3$ at reflux temperature for 4 h. After cooling, the solvent was evaporated and the residue was purified by flash silica gel chromatography a linear gradient of ethyl acetate in hexane from 15 to 70% as eluent to provide the desired product (y=86%). Colorless oil.

Example 164

5-[[2,6-Difluoro-4-(3-hydroxypropyl)phenoxy]methyl]-1-(5-fluoro-2-pyridyl)-3-methyl-pyrazole-4-carbonitrile.
The title compound was prepared by the general procedure (scheme 1, step 3, method A) from intermediate 48, 4-(hydroxymethyl)-2,6-dimethylphenol (CAS: 4397-14-2), and $K_2CO_3$ at reflux temperature for 4 h. After cooling, the solvent was evaporated and the residue was purified by flash silica gel chromatography a linear gradient of ethyl acetate

Example 165

5-[[2,6-Difluoro-4-(3-hydroxypropyl)phenoxy]methyl]-3-methyl-1-(5-methyl-2-pyridyl)pyrazole-4-carbonitrile. The title compound was prepared by the general procedure (scheme 1, step 3, method A) from intermediate 49, 4-(hydroxymethyl)-2,6-dimethylphenol (CAS: 4397-14-2), and $K_2CO_3$ at reflux temperature for 4 h. After cooling, the solvent was evaporated and the residue was purified by flash silica gel chromatography a linear gradient of ethyl acetate in hexane from 15 to 70% as eluent to provide the desired product (y=82%). Colorless oil.

Example 166

1-(5-Chloro-2-pyridyl)-5-[[2,6-difluoro-4-(3-hydroxypropyl)phenoxy]methyl]-3-methyl-pyrazole-4-carbonitrile. The title compound was prepared by the general procedure (scheme 1, step 3, method A) from intermediate 50, 4-(hydroxymethyl)-2,6-dimethylphenol (CAS: 4397-14-2), and $K_2CO_3$ at reflux temperature for 4 h. After cooling, the solvent was evaporated and the residue was purified by flash silica gel chromatography a linear gradient of ethyl acetate in hexane from 15 to 70% as eluent to provide the desired product (y=89%). Colorless oil.

Example 167

5-[[2,6-Difluoro-4-(3-hydroxypropyl)phenoxy]methyl]-1-(5-methoxy-2-pyridyl)-3-methyl-pyrazole-4-carbonitrile. The title compound was prepared by the general procedure (scheme 1, step 3, method A) from intermediate 51, 4-(hydroxymethyl)-2,6-dimethylphenol (CAS: 4397-14-2), and $K_2CO_3$ at reflux temperature for 4 h. After cooling, the solvent was evaporated and the residue was purified by flash silica gel chromatography a linear gradient of ethyl acetate in hexane from 15 to 70% as eluent to provide the desired product (y=89%). Colorless oil.

| Example | Structure |
| --- | --- |
| 1 | *(structure image)* |
| 2 | *(structure image)* |
| 3 | *(structure image)* |

-continued
| Example | Structure |
|---|---|
| 4 | 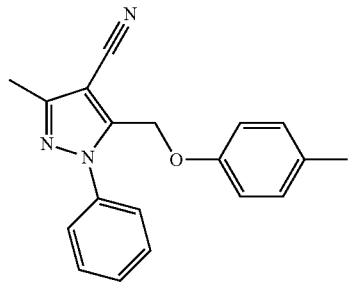 |
| 5 | 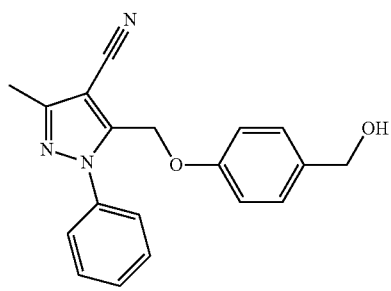 [SMILES: Cc1nn(-c2ccccc2)c(COc2ccc(CO)cc2)c1C#N] |
| 6 | 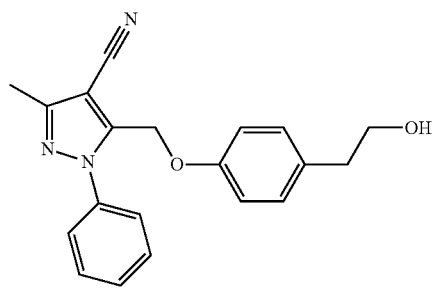 [SMILES: Cc1nn(-c2ccccc2)c(COc2ccc(CCO)cc2)c1C#N] |
| 7 | 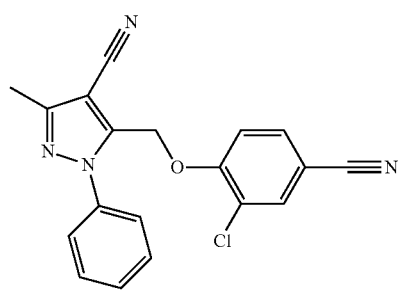 [SMILES: Cc1nn(-c2ccccc2)c(COc2ccc(C#N)cc2Cl)c1C#N] |
| 8 | 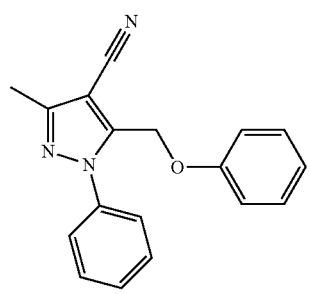 [SMILES: Cc1nn(-c2ccccc2)c(COc2ccccc2)c1C#N] |

-continued
| Example | Structure |
|---|---|
| 9 | 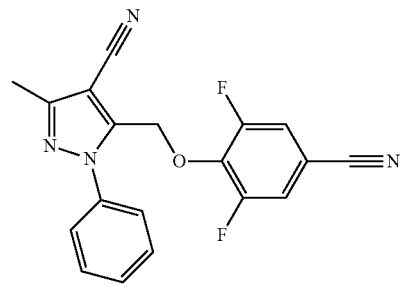 [SMILES: Cc1nn(-c2ccccc2)c(COc2c(F)cc(C#N)cc2F)c1C#N] |
| 10 | 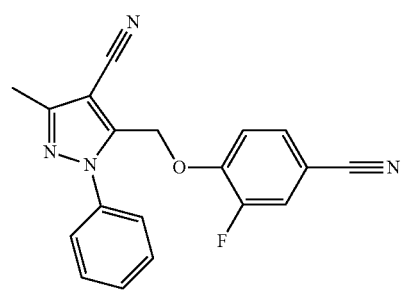 [SMILES: Cc1nn(-c2ccccc2)c(COc2ccc(C#N)cc2F)c1C#N] |
| 11 | 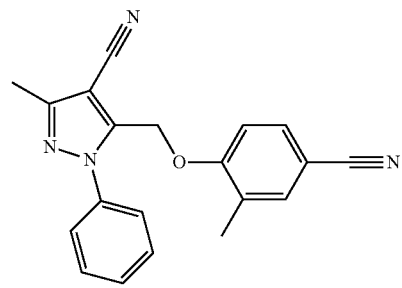 [SMILES: Cc1cc(C#N)ccc1OCc1c(C#N)c(C)nn1-c1ccccc1] |
| 12 | 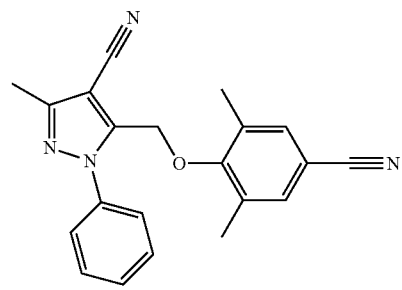 [SMILES: Cc1cc(C#N)cc(C)c1OCc1c(C#N)c(C)nn1-c1ccccc1] |
| 13 | 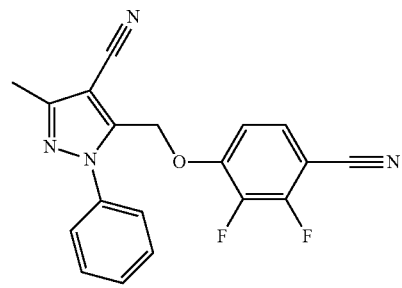 [SMILES: Cc1nn(-c2ccccc2)c(COc2ccc(C#N)c(F)c2F)c1C#N] |

| Example | Structure |
|---------|-----------|
| 14 | 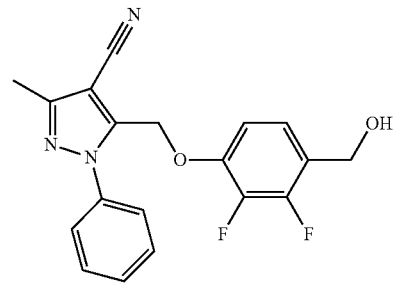 [SMILES: Cc1nn(-c2ccccc2)c(COc2ccc(CO)c(F)c2F)c1C#N] |
| 15 | 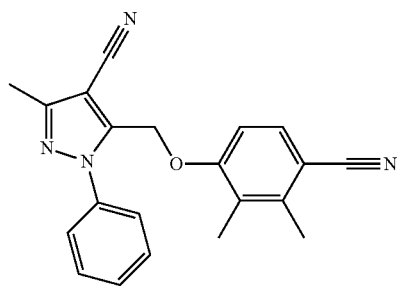 [SMILES: Cc1nn(-c2ccccc2)c(COc2ccc(C#N)c(C)c2C)c1C#N] |
| 16 | 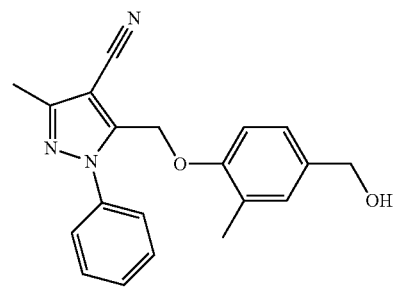 [SMILES: Cc1cc(CO)ccc1OCc1c(C#N)c(C)nn1-c1ccccc1] |
| 17 | 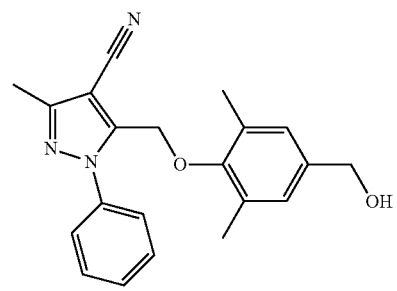 [SMILES: Cc1cc(CO)cc(C)c1OCc1c(C#N)c(C)nn1-c1ccccc1] |
| 18 | 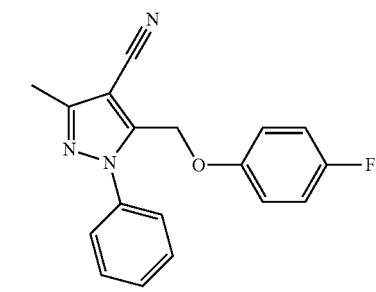 [SMILES: Cc1nn(-c2ccccc2)c(COc2ccc(F)cc2)c1C#N] |

-continued

| Example | Structure |
|---|---|
| 19 | 3-methyl-5-((4-ethylphenoxy)methyl)-1-phenyl-1H-pyrazole-4-carbonitrile |
| 20 | 5-((2-fluoro-4-(hydroxymethyl)phenoxy)methyl)-3-methyl-1-phenyl-1H-pyrazole-4-carbonitrile |
| 21 | 5-((2,6-difluoro-4-(hydroxymethyl)phenoxy)methyl)-3-methyl-1-phenyl-1H-pyrazole-4-carbonitrile |
| 22 | 5-((3,5-dimethylphenoxy)methyl)-3-methyl-1-phenyl-1H-pyrazole-4-carbonitrile |
| 23 | 5-((2-(hydroxymethyl)phenoxy)methyl)-3-methyl-1-phenyl-1H-pyrazole-4-carbonitrile |

-continued
| Example | Structure |
|---|---|
| 24 | 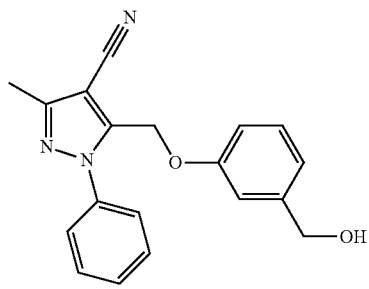 [SMILES: Cc1nn(-c2ccccc2)c(COc2cccc(CO)c2)c1C#N] |
| 25 | 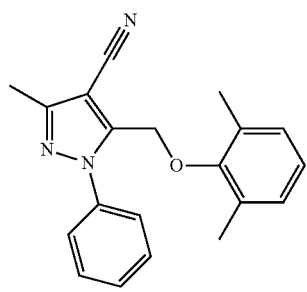 [SMILES: Cc1cccc(C)c1OCc1c(C#N)c(C)nn1-c1ccccc1] |
| 26 | 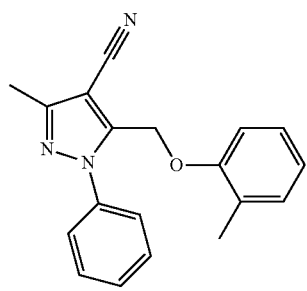 [SMILES: Cc1ccccc1OCc1c(C#N)c(C)nn1-c1ccccc1] |
| 27 | 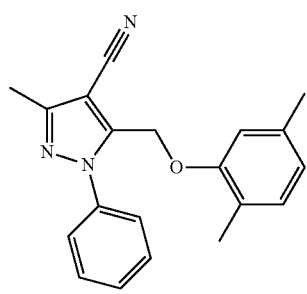 |
| 28 | 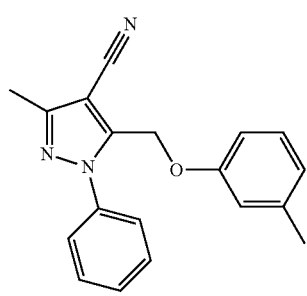 |

-continued

| Example | Structure |
|---------|-----------|
| 29 | 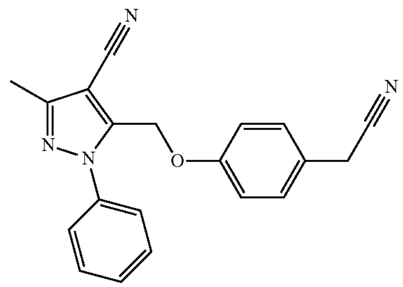 [SMILES: Cc1nn(-c2ccccc2)c(COc2ccc(CC#N)cc2)c1C#N] |
| 30 | 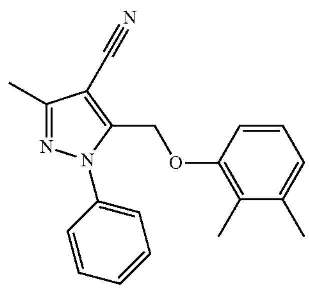 |
| 31 | 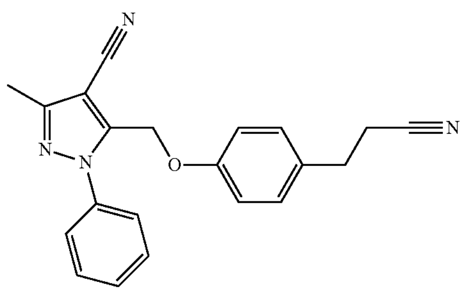 [SMILES: Cc1nn(-c2ccccc2)c(COc2ccc(CCC#N)cc2)c1C#N] |
| 32 | 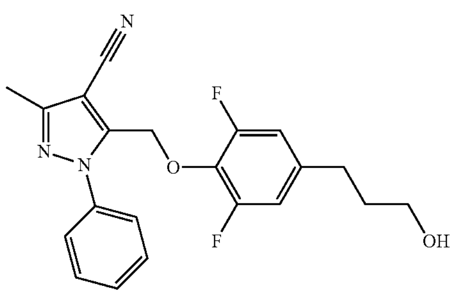 [SMILES: Cc1nn(-c2ccccc2)c(COc2c(F)cc(CCCO)cc2F)c1C#N] |
| 33 | 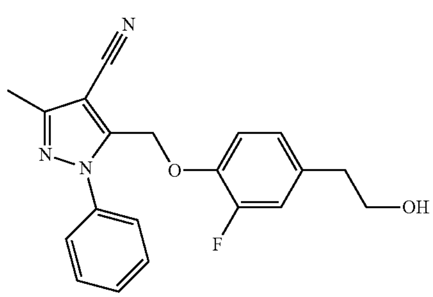 [SMILES: Cc1nn(-c2ccccc2)c(COc2ccc(CCO)cc2F)c1C#N] |

-continued
| Example | Structure |
|---|---|
| 34 | 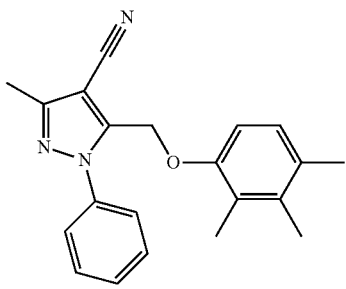 |
| 35 | 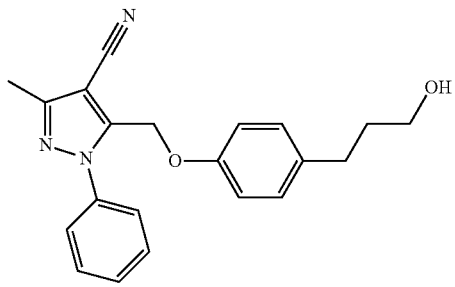 [SMILES: Cc1nn(-c2ccccc2)c(COc2ccc(CCCO)cc2)c1C#N] |
| 36 | 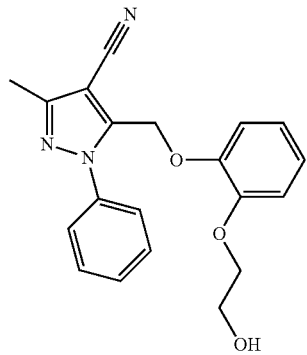 [SMILES: Cc1nn(-c2ccccc2)c(COc2ccccc2OCCO)c1C#N] |
| 37 | 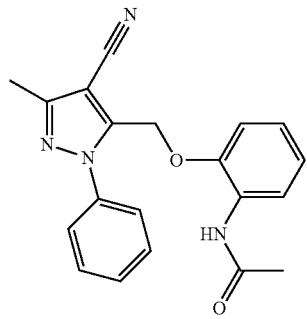 [SMILES: CC(=O)Nc1ccccc1OCc1c(C#N)c(C)nn1-c1ccccc1] |
| 38 | 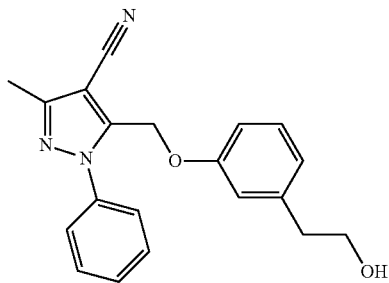 [SMILES: Cc1nn(-c2ccccc2)c(COc2cccc(CCO)c2)c1C#N] |

-continued
| Example | Structure |
|---|---|
| 39 | 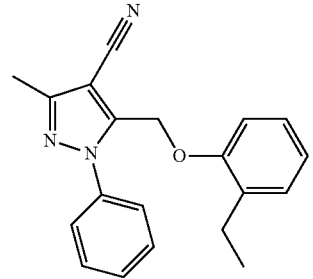 [SMILES: CCc1ccccc1OCc1c(C#N)c(C)nn1-c1ccccc1] |
| 40 | 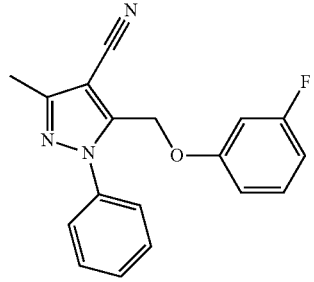 [SMILES: Cc1nn(-c2ccccc2)c(COc2cccc(F)c2)c1C#N] |
| 41 | 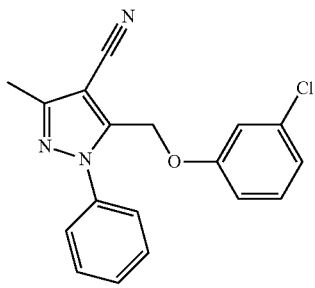 [SMILES: Cc1nn(-c2ccccc2)c(COc2cccc(Cl)c2)c1C#N] |
| 42 | 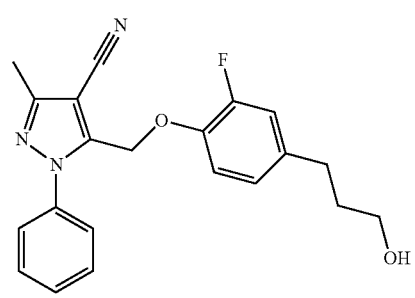 [SMILES: Cc1nn(-c2ccccc2)c(COc2ccc(CCCO)cc2F)c1C#N] |
| 43 | 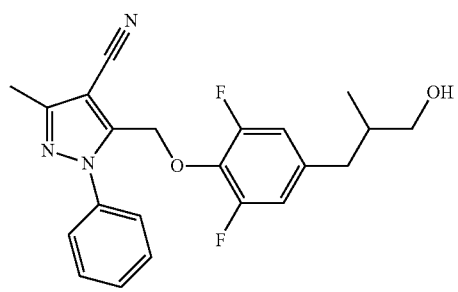 [SMILES: Cc1nn(-c2ccccc2)c(COc2c(F)cc(CC(C)CO)cc2F)c1C#N] |

-continued
| Example | Structure |
|---|---|
| 43A | 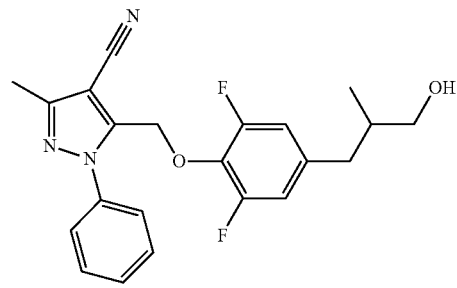 [SMILES: Cc1nn(-c2ccccc2)c(COc2c(F)cc(CC(C)CO)cc2F)c1C#N] |
| 43B | 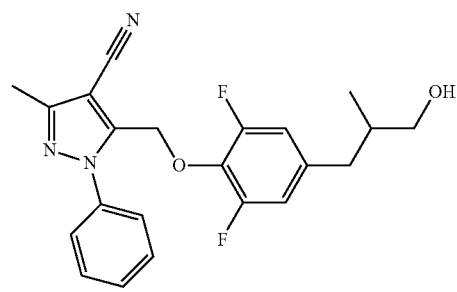 [SMILES: Cc1nn(-c2ccccc2)c(COc2c(F)cc(CC(C)CO)cc2F)c1C#N] |
| 44 | 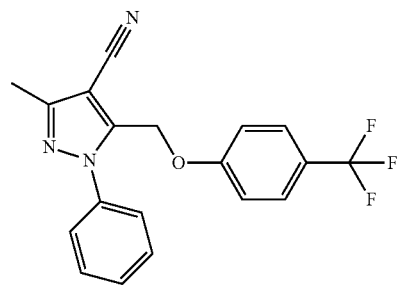 [SMILES: Cc1nn(-c2ccccc2)c(COc2ccc(C(F)(F)F)cc2)c1C#N] |
| 45 | 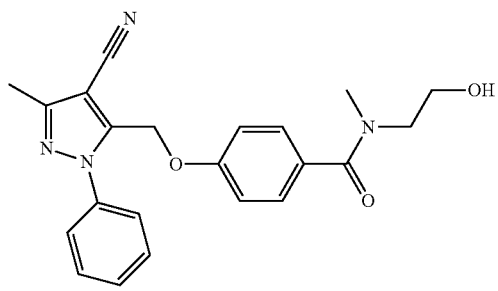 [SMILES: Cc1nn(-c2ccccc2)c(COc2ccc(C(=O)N(C)CCO)cc2)c1C#N] |
| 46 | 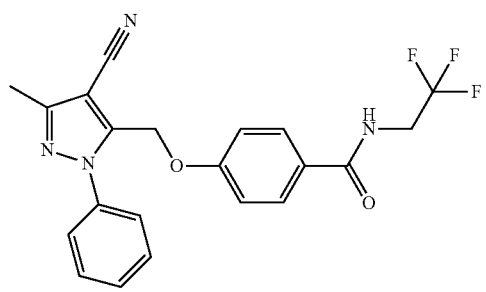 [SMILES: Cc1nn(-c2ccccc2)c(COc2ccc(C(=O)NCC(F)(F)F)cc2)c1C#N] |

-continued
| Example | Structure |
|---------|-----------|
| 47 | 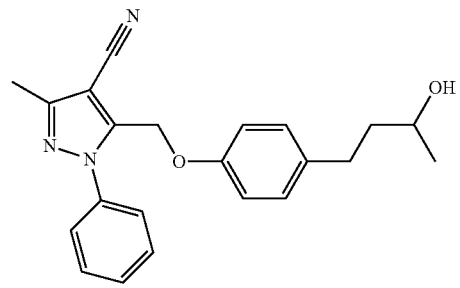 [SMILES: Cc1nn(-c2ccccc2)c(COc2ccc(CCC(C)O)cc2)c1C#N] |
| 47A | 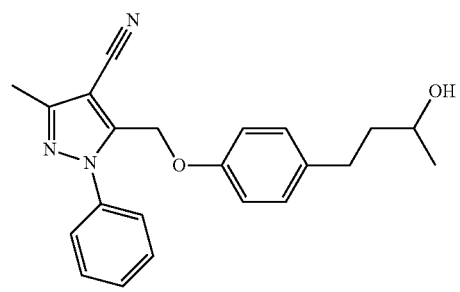 [SMILES: Cc1nn(-c2ccccc2)c(COc2ccc(CCC(C)O)cc2)c1C#N] |
| 47B | 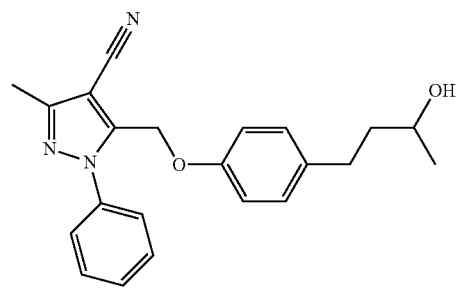 [SMILES: Cc1nn(-c2ccccc2)c(COc2ccc(CCC(C)O)cc2)c1C#N] |
| 48 | 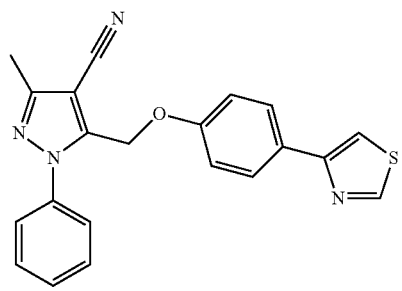 [SMILES: Cc1nn(-c2ccccc2)c(COc2ccc(-c3cscn3)cc2)c1C#N] |
| 49 | 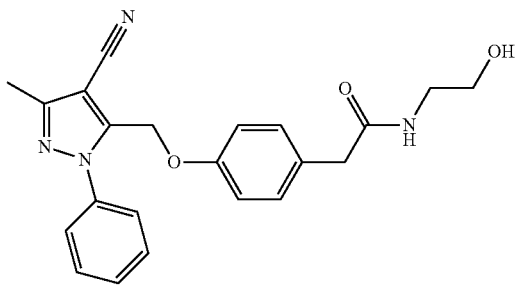 [SMILES: Cc1nn(-c2ccccc2)c(COc2ccc(CC(=O)NCCO)cc2)c1C#N] |

-continued
| Example | Structure |
|---|---|
| 50 | 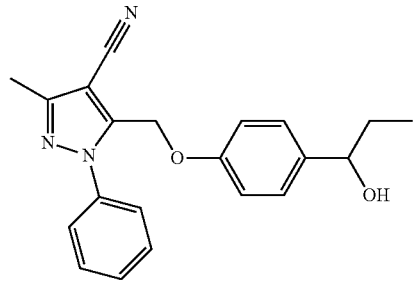 [SMILES: CCC(O)c1ccc(OCc2c(C#N)c(C)nn2-c2ccccc2)cc1] |
| 51 | 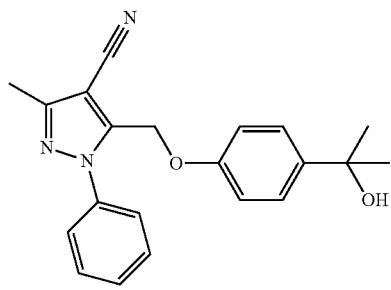 [SMILES: Cc1nn(-c2ccccc2)c(COc2ccc(C(C)(C)O)cc2)c1C#N] |
| 52 | 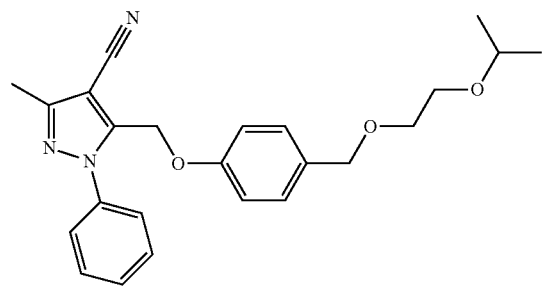 [SMILES: Cc1nn(-c2ccccc2)c(COc2ccc(COCCOC(C)C)cc2)c1C#N] |
| 53 | 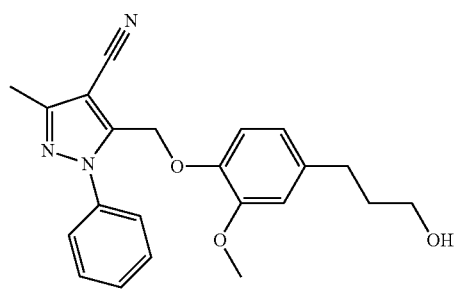 [SMILES: COc1cc(CCCO)ccc1OCc1c(C#N)c(C)nn1-c1ccccc1] |
| 54 | 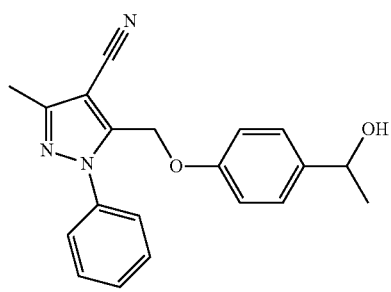 [SMILES: Cc1nn(-c2ccccc2)c(COc2ccc(C(C)O)cc2)c1C#N] |

-continued
| Example | Structure |
|---------|-----------|
| 55 | 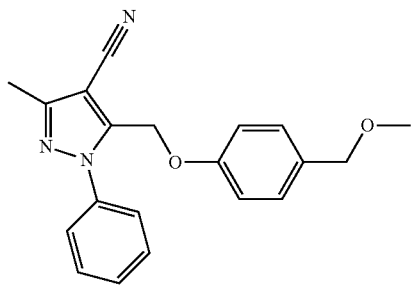 |
| 56 | 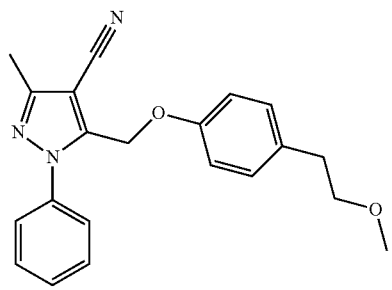 |
| 57 | 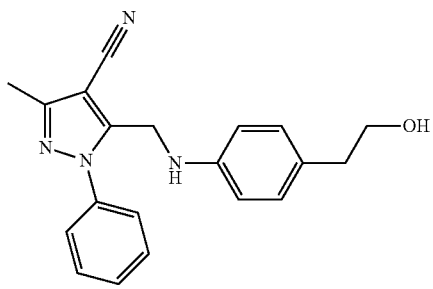 [SMILES: Cc1nn(-c2ccccc2)c(CNc2ccc(CCO)cc2)c1C#N] |
| 58 | 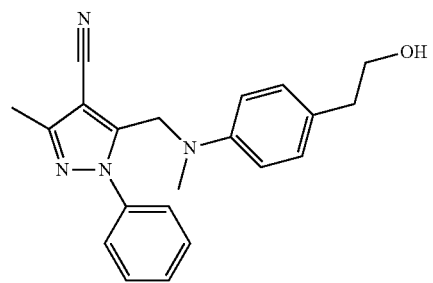 [SMILES: Cc1nn(-c2ccccc2)c(CN(C)c2ccc(CCO)cc2)c1C#N] |
| 59 | 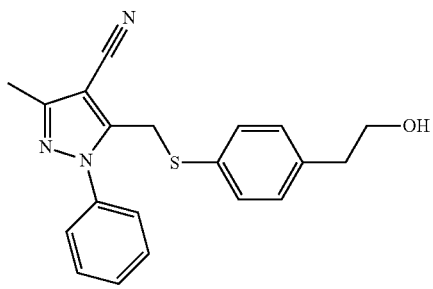 [SMILES: Cc1nn(-c2ccccc2)c(CSc2ccc(CCO)cc2)c1C#N] |

-continued
| Example | Structure |
|---|---|
| 60 | 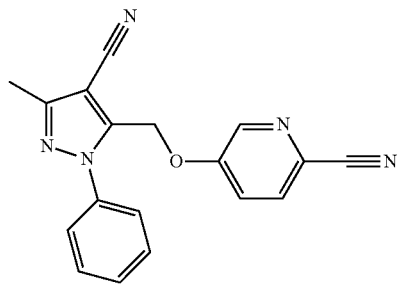 [SMILES: Cc1nn(-c2ccccc2)c(COc2ccc(C#N)nc2)c1C#N] |
| 61 | 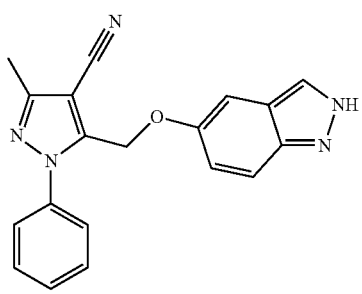 [SMILES: Cc1nn(-c2ccccc2)c(COc2ccc3n[nH]cc3c2)c1C#N] |
| 62 | 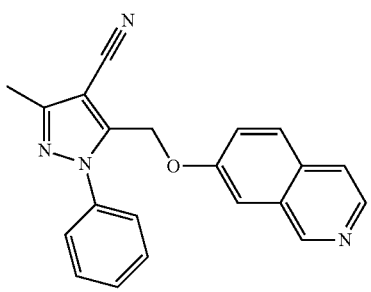 [SMILES: Cc1nn(-c2ccccc2)c(COc2ccc3ccncc3c2)c1C#N] |
| 63 | 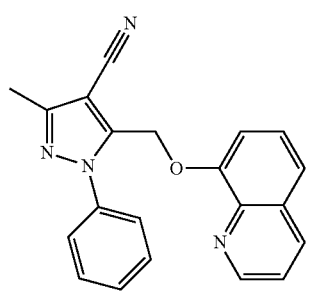 [SMILES: Cc1nn(-c2ccccc2)c(COc2cccc3cccnc23)c1C#N] |
| 64 | 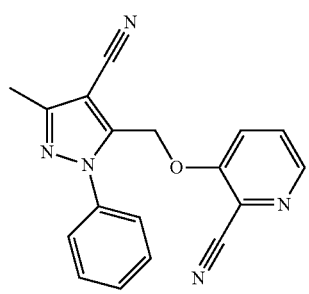 [SMILES: Cc1nn(-c2ccccc2)c(COc2cccnc2C#N)c1C#N] |

-continued
| Example | Structure |
|---|---|
| 65 | 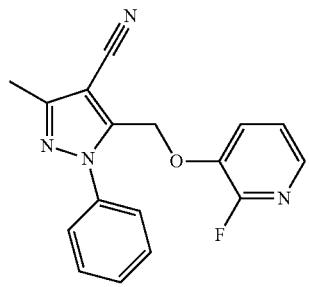 |
| 66 | 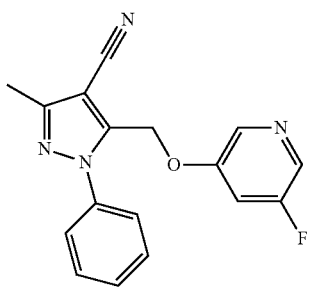 [SMILES: Cc1nn(-c2ccccc2)c(COc2cncc(F)c2)c1C#N] |
| 67 | 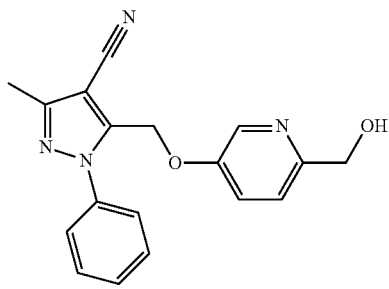 [SMILES: Cc1nn(-c2ccccc2)c(COc2ccc(CO)nc2)c1C#N] |
| 68 | 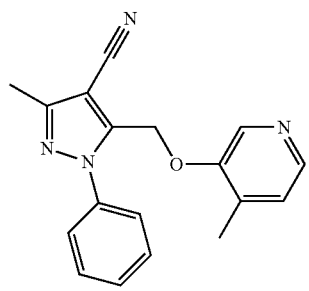 |
| 69 | 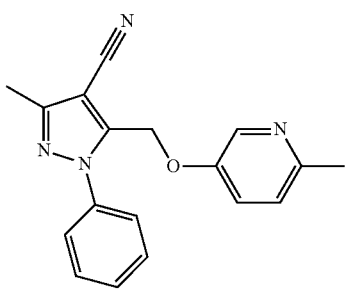 |

-continued
| Example | Structure |
|---|---|
| 70 | 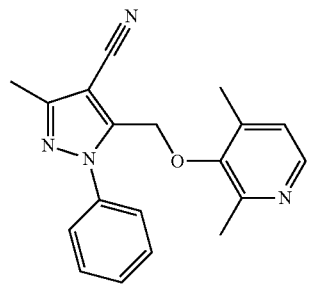 [SMILES: Cc1ccnc(C)c1OCc1c(C#N)c(C)nn1-c1ccccc1] |
| 71 | 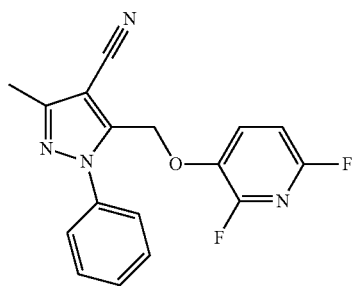 [SMILES: Cc1nn(-c2ccccc2)c(COc2ccc(F)nc2F)c1C#N] |
| 72 | 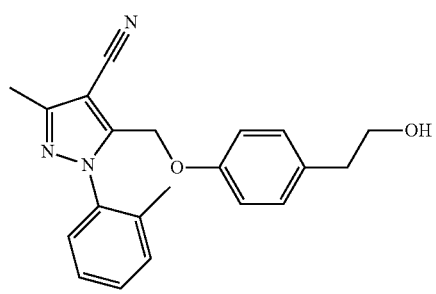 [SMILES: Cc1ccccc1-n1nc(C)c(C#N)c1COc1ccc(CCO)cc1] |
| 73 | 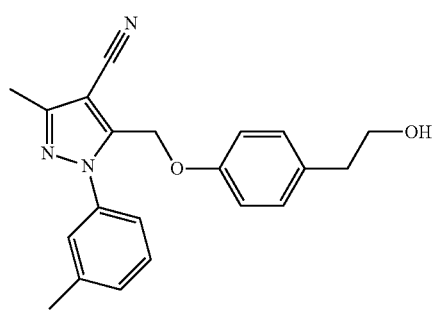 [SMILES: Cc1cccc(-n2nc(C)c(C#N)c2COc2ccc(CCO)cc2)c1] |
| 74 | 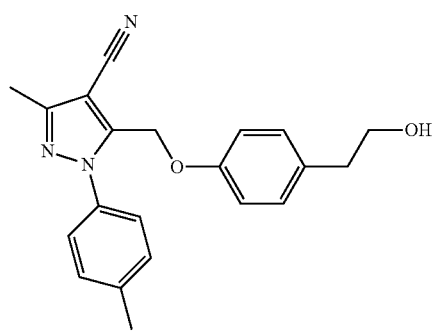 [SMILES: Cc1ccc(-n2nc(C)c(C#N)c2COc2ccc(CCO)cc2)cc1] |

-continued
| Example | Structure |
|---|---|
| 75 | 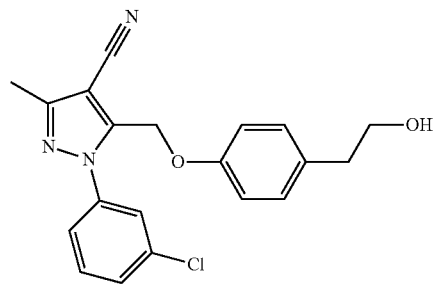 [SMILES: Cc1nn(-c2cccc(Cl)c2)c(COc2ccc(CCO)cc2)c1C#N] |
| 76 | 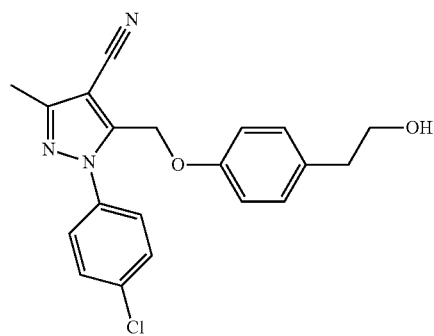 [SMILES: Cc1nn(-c2ccc(Cl)cc2)c(COc2ccc(CCO)cc2)c1C#N] |
| 77 | 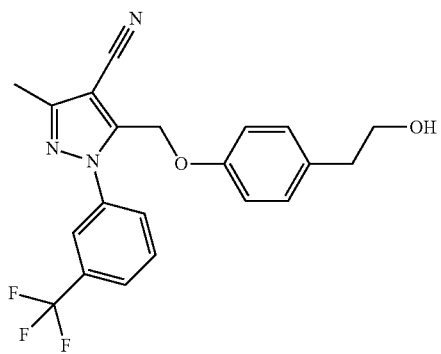 [SMILES: Cc1nn(-c2cccc(C(F)(F)F)c2)c(COc2ccc(CCO)cc2)c1C#N] |
| 78 | 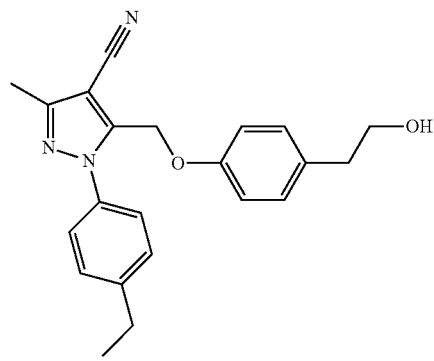 [SMILES: CCc1ccc(-n2nc(C)c(C#N)c2COc2ccc(CCO)cc2)cc1] |

-continued
| Example | Structure |
|---|---|
| 79 | 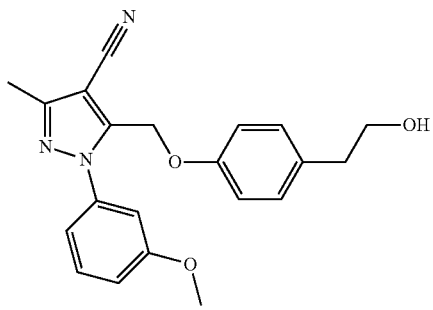 [SMILES: COc1cccc(-n2nc(C)c(C#N)c2COc2ccc(CCO)cc2)c1] |
| 80 | 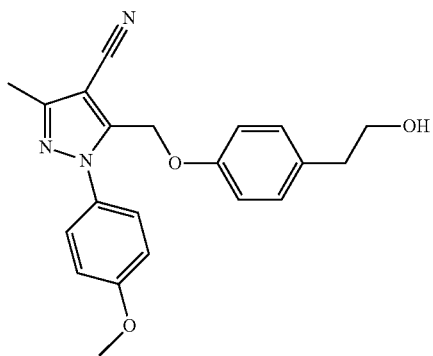 [SMILES: COc1ccc(-n2nc(C)c(C#N)c2COc2ccc(CCO)cc2)cc1] |
| 81 | 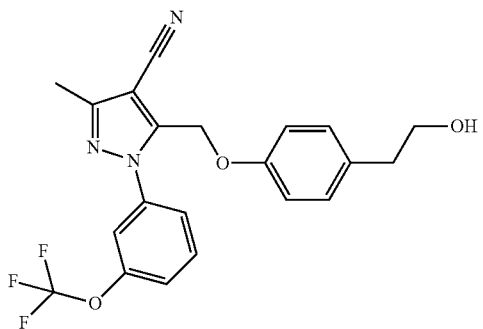 [SMILES: Cc1nn(-c2cccc(OC(F)(F)F)c2)c(COc2ccc(CCO)cc2)c1C#N] |
| 82 | 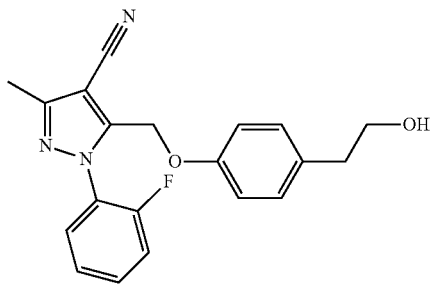 |

-continued
| Example | Structure |
|---|---|
| 83 | 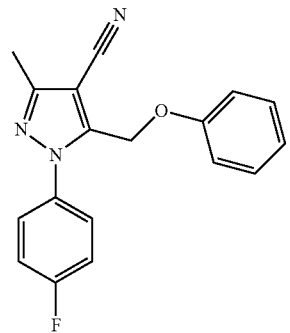 [SMILES: Cc1nn(-c2ccc(F)cc2)c(COc2ccccc2)c1C#N] |
| 84 | 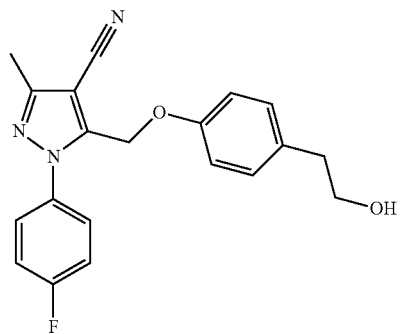 [SMILES: Cc1nn(-c2ccc(F)cc2)c(COc2ccc(CCO)cc2)c1C#N] |
| 85 | 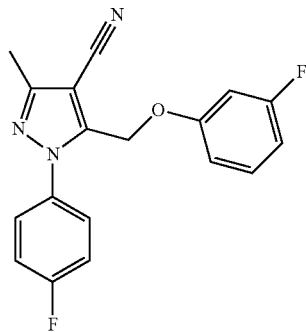 [SMILES: Cc1nn(-c2ccc(F)cc2)c(COc2cccc(F)c2)c1C#N] |
| 86 | 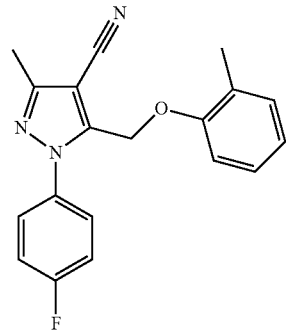 [SMILES: Cc1ccccc1OCc1c(C#N)c(C)nn1-c1ccc(F)cc1] |

| Example | Structure |
|---|---|
| 87 | 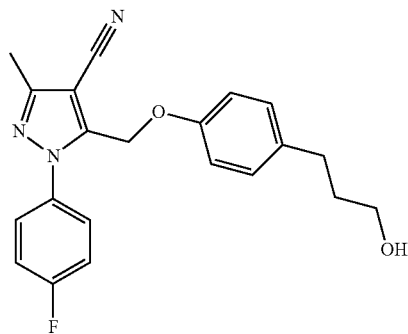 [SMILES: Cc1nn(-c2ccc(F)cc2)c(COc2ccc(CCCO)cc2)c1C#N] |
| 88 | 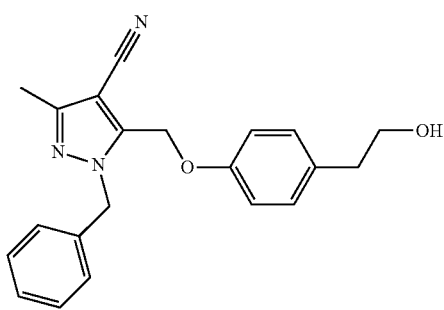 [SMILES: Cc1nn(Cc2ccccc2)c(COc2ccc(CCO)cc2)c1C#N] |
| 89 | 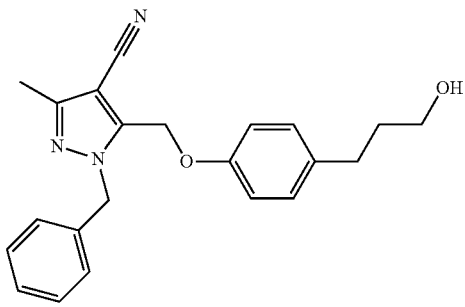 [SMILES: Cc1nn(Cc2ccccc2)c(COc2ccc(CCCO)cc2)c1C#N] |
| 90 | 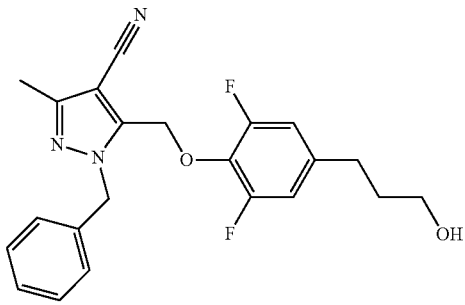 [SMILES: Cc1nn(Cc2ccccc2)c(COc2c(F)cc(CCCO)cc2F)c1C#N] |
| 91 | 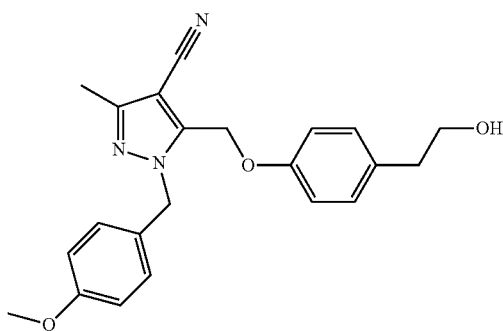 [SMILES: COc1ccc(Cn2nc(C)c(C#N)c2COc2ccc(CCO)cc2)cc1] |

-continued
| Example | Structure |
|---|---|
| 92 | 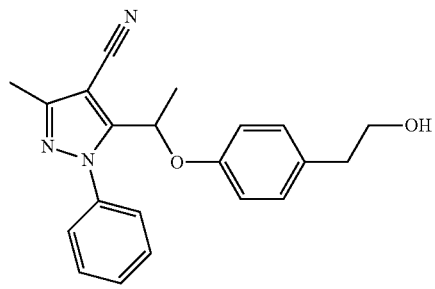 [SMILES: Cc1nn(-c2ccccc2)c(C(C)Oc2ccc(CCO)cc2)c1C#N] |
| 93 | 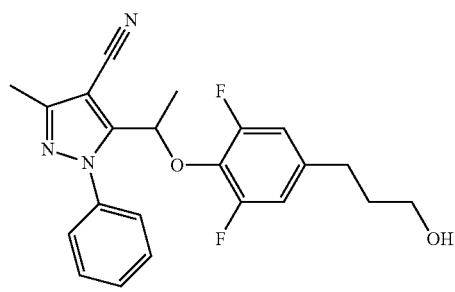 [SMILES: Cc1nn(-c2ccccc2)c(C(C)Oc2c(F)cc(CCCO)cc2F)c1C#N] |
| 94 | 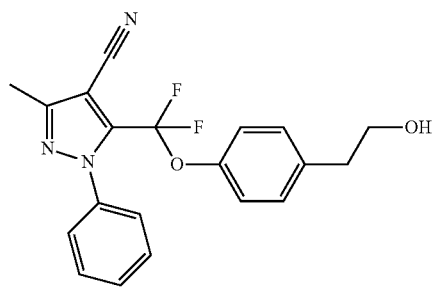 [SMILES: Cc1nn(-c2ccccc2)c(C(F)(F)Oc2ccc(CCO)cc2)c1C#N] |
| 95 | 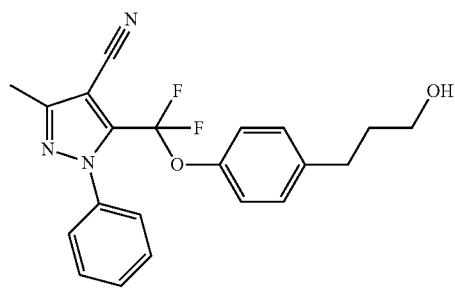 [SMILES: Cc1nn(-c2ccccc2)c(C(F)(F)Oc2ccc(CCCO)cc2)c1C#N] |
| 96 | 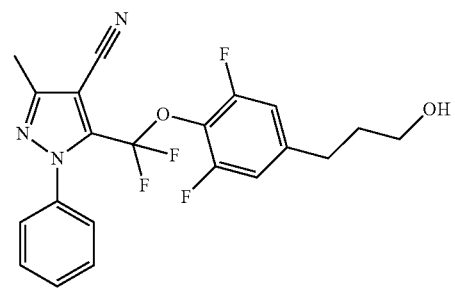 [SMILES: Cc1nn(-c2ccccc2)c(C(F)(F)Oc2c(F)cc(CCCO)cc2F)c1C#N] |

-continued

| Example | Structure |
|---|---|
| 97 | (structure) |
| 98 | (structure) |
| 99 | (structure) |
| 100 | (structure) |

-continued
| Example | Structure |
|---------|-----------|
| 101 | 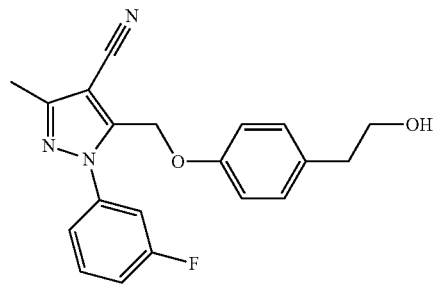 |
| 102 | 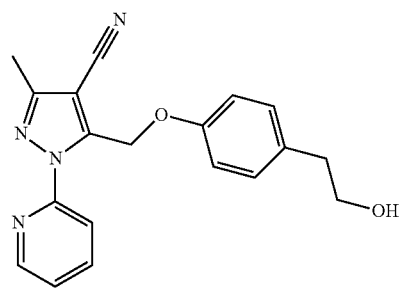 |
| 103 | 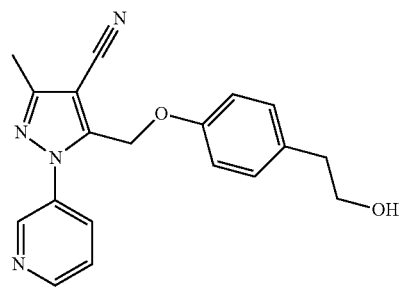 |
| 104 | 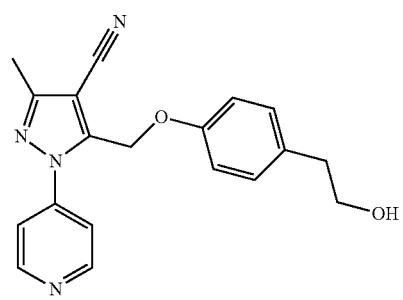 [SMILES: Cc1nn(-c2ccncc2)c(COc2ccc(CCO)cc2)c1C#N] |
| 105 | 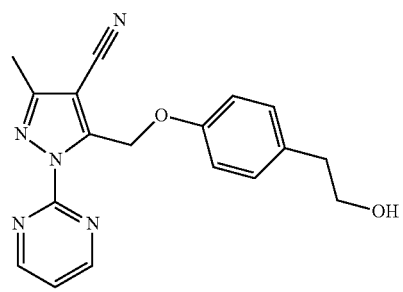 [SMILES: Cc1nn(-c2ncccn2)c(COc2ccc(CCO)cc2)c1C#N] |

-continued
| Example | Structure |
|---|---|
| 106 | 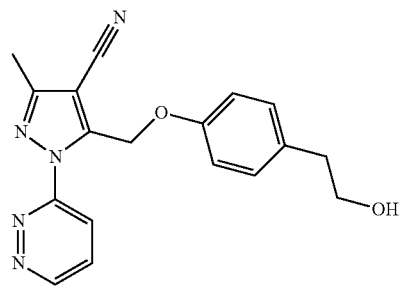 [SMILES: Cc1nn(-c2cccnn2)c(COc2ccc(CCO)cc2)c1C#N] |
| 107 | 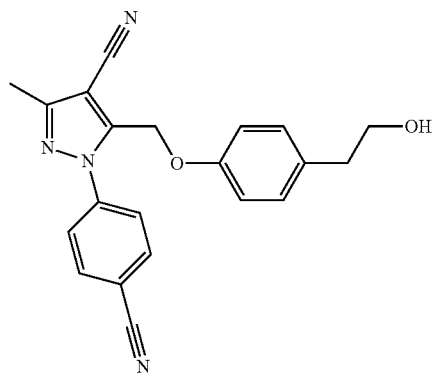 [SMILES: Cc1nn(-c2ccc(C#N)cc2)c(COc2ccc(CCO)cc2)c1C#N] |
| 108 | 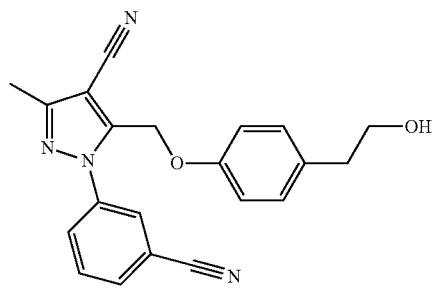 [SMILES: Cc1nn(-c2cccc(C#N)c2)c(COc2ccc(CCO)cc2)c1C#N] |
| 109 | 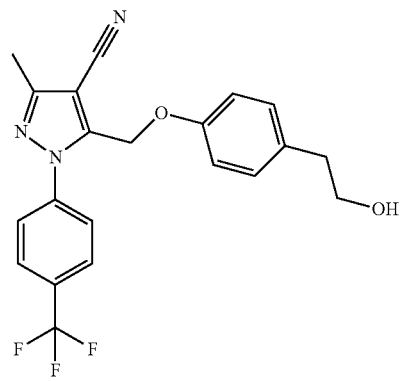 [SMILES: Cc1nn(-c2ccc(C(F)(F)F)cc2)c(COc2ccc(CCO)cc2)c1C#N] |

-continued
| Example | Structure |
|---|---|
| 110 | 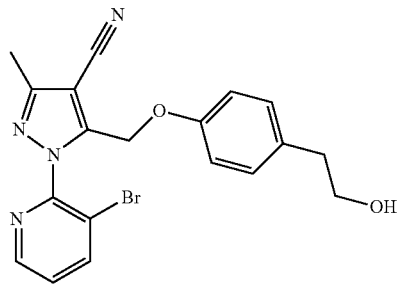 [SMILES: Cc1nn(-c2ncccc2Br)c(COc2ccc(CCO)cc2)c1C#N] |
| 111 | 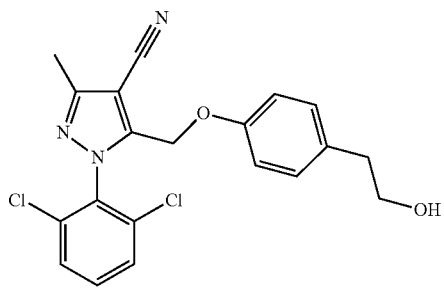 [SMILES: Cc1nn(-c2c(Cl)cccc2Cl)c(COc2ccc(CCO)cc2)c1C#N] |
| 112 | 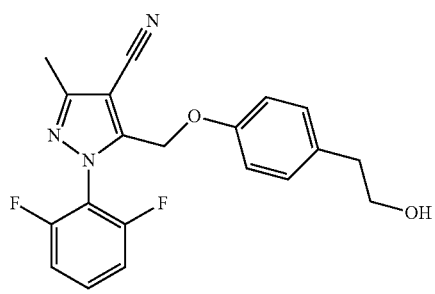 [SMILES: Cc1nn(-c2c(F)cccc2F)c(COc2ccc(CCO)cc2)c1C#N] |
| 113 | 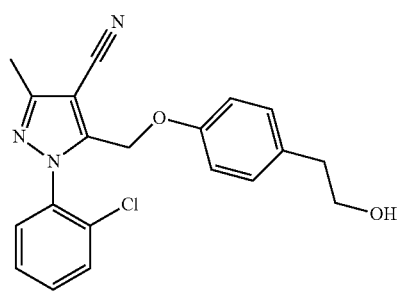 [SMILES: Cc1nn(-c2ccccc2Cl)c(COc2ccc(CCO)cc2)c1C#N] |
| 114 | 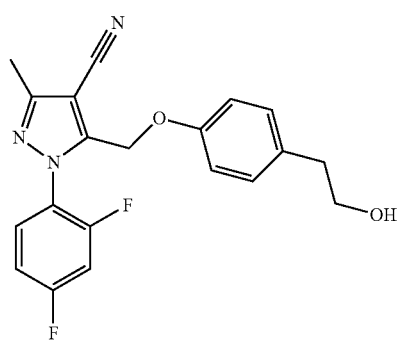 [SMILES: Cc1nn(-c2ccc(F)cc2F)c(COc2ccc(CCO)cc2)c1C#N] |

| Example | Structure |
|---|---|
| 115 | 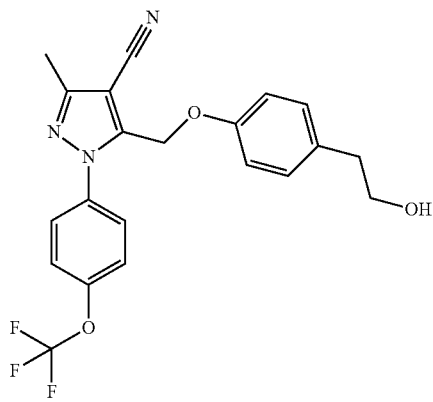 [SMILES: Cc1nn(-c2ccc(OC(F)(F)F)cc2)c(COc2ccc(CCO)cc2)c1C#N] |
| 116 | 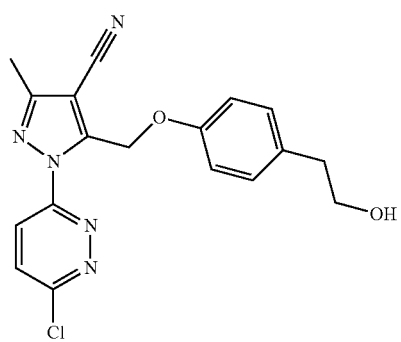 [SMILES: Cc1nn(-c2ccc(Cl)nn2)c(COc2ccc(CCO)cc2)c1C#N] |
| 117 | 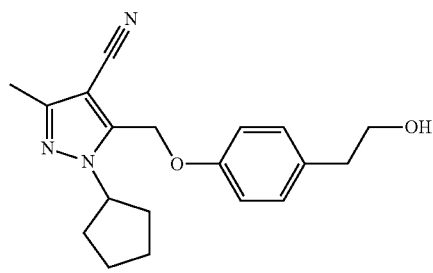 [SMILES: Cc1nn(C2CCCC2)c(COc2ccc(CCO)cc2)c1C#N] |
| 118 | 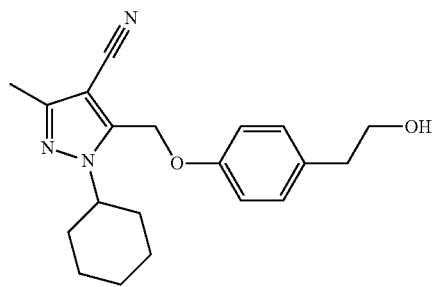 [SMILES: Cc1nn(C2CCCCC2)c(COc2ccc(CCO)cc2)c1C#N] |

| Example | Structure |
|---|---|
| 119 | 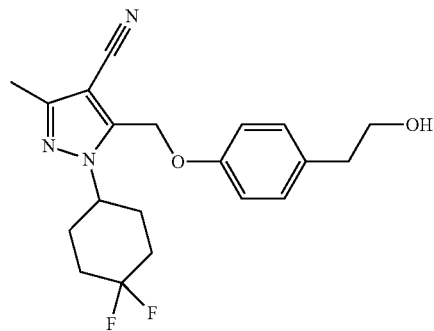 [SMILES: Cc1nn(C2CCC(F)(F)CC2)c(COc2ccc(CCO)cc2)c1C#N] |
| 120 | 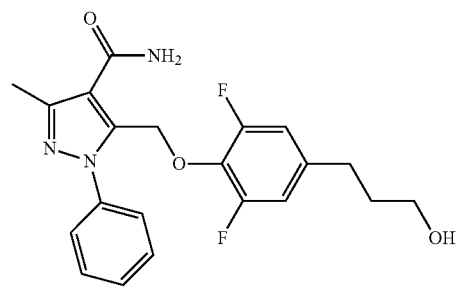 [SMILES: Cc1nn(-c2ccccc2)c(COc2c(F)cc(CCCO)cc2F)c1C(N)=O] |
| 121A | 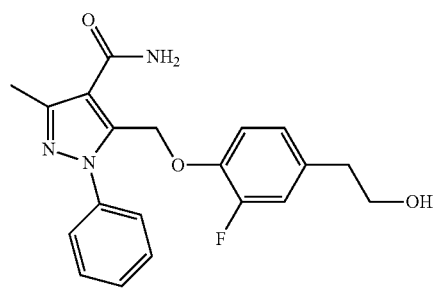 |
| 121B | 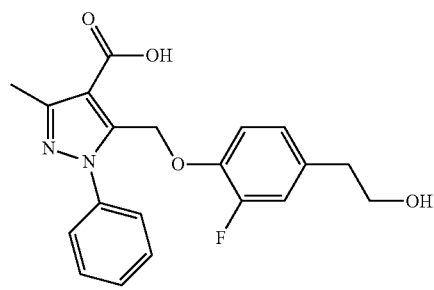 [SMILES: Cc1nn(-c2ccccc2)c(COc2ccc(CCO)cc2F)c1C(=O)O] |
| 122 | 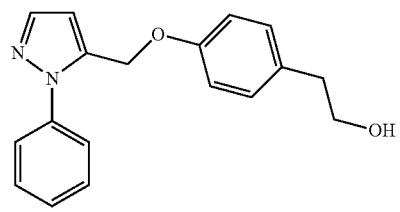 [SMILES: OCCc1ccc(OCc2ccnn2-c2ccccc2)cc1] |

-continued
| Example | Structure |
|---|---|
| 123 | 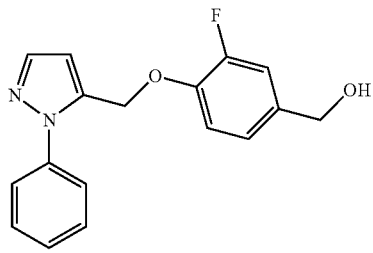 [SMILES: OCc1ccc(OCc2ccnn2-c2ccccc2)c(F)c1] |
| 124 | 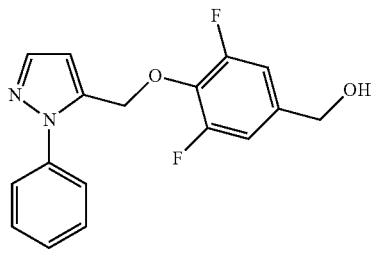 [SMILES: OCc1cc(F)c(OCc2ccnn2-c2ccccc2)c(F)c1] |
| 125 | 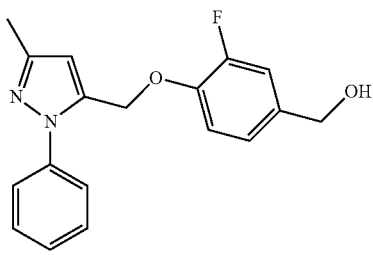 [SMILES: Cc1cc(COc2ccc(CO)cc2F)n(-c2ccccc2)n1] |
| 126 | 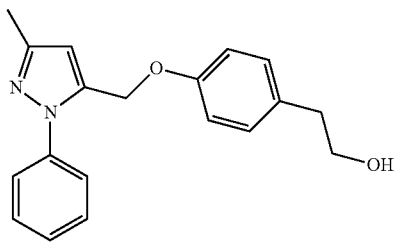 [SMILES: Cc1cc(COc2ccc(CCO)cc2)n(-c2ccccc2)n1] |
| 127 | 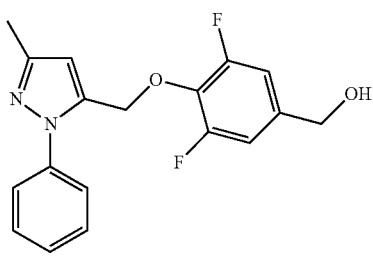 [SMILES: Cc1cc(COc2c(F)cc(CO)cc2F)n(-c2ccccc2)n1] |

-continued
| Example | Structure |
|---|---|
| 128 | 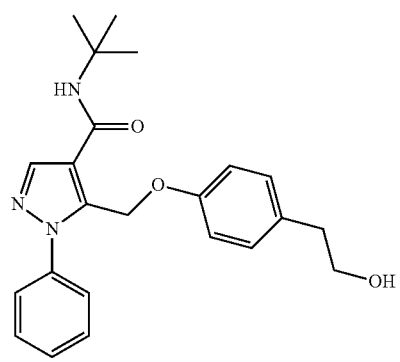 [SMILES: CC(C)(C)NC(=O)c1cnn(-c2ccccc2)c1COc1ccc(CCO)cc1] |
| 129 | 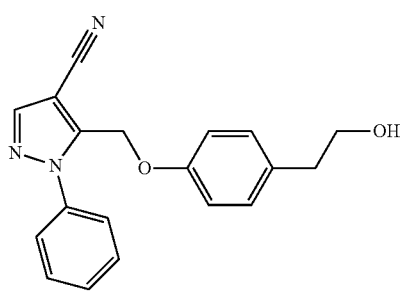 [SMILES: N#Cc1cnn(-c2ccccc2)c1COc1ccc(CCO)cc1] |
| 130 | 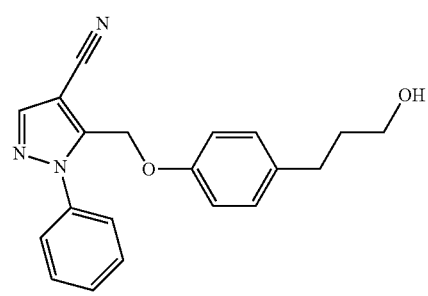 [SMILES: N#Cc1cnn(-c2ccccc2)c1COc1ccc(CCCO)cc1] |
| 131 | 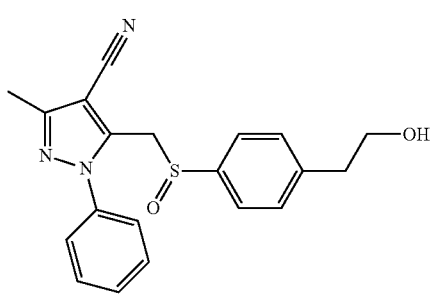 [SMILES: Cc1nn(-c2ccccc2)c(CS(=O)c2ccc(CCO)cc2)c1C#N] |
| 132 | 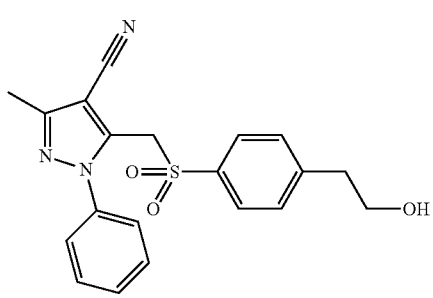 [SMILES: Cc1nn(-c2ccccc2)c(CS(=O)(=O)c2ccc(CCO)cc2)c1C#N] |

| Example | Structure |
|---|---|
| 133 | 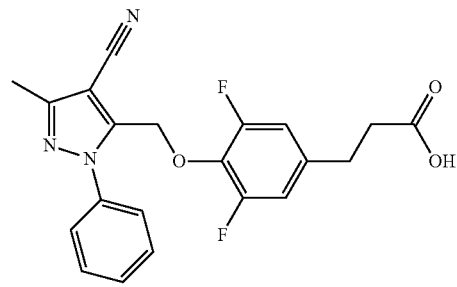 [SMILES: Cc1nn(-c2ccccc2)c(COc2c(F)cc(CCC(=O)O)cc2F)c1C#N] |
| 134 | 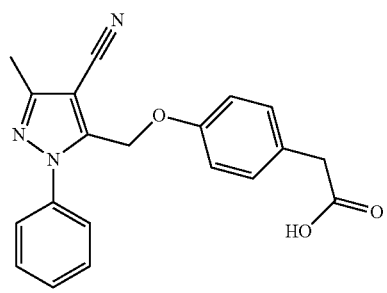 [SMILES: Cc1nn(-c2ccccc2)c(COc2ccc(CC(=O)O)cc2)c1C#N] |
| 135 | 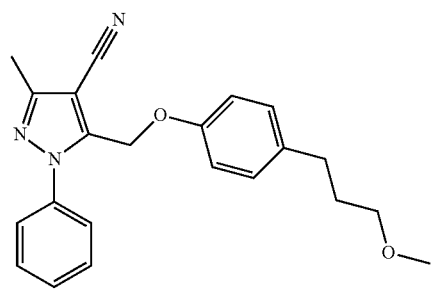 |
| 136 | 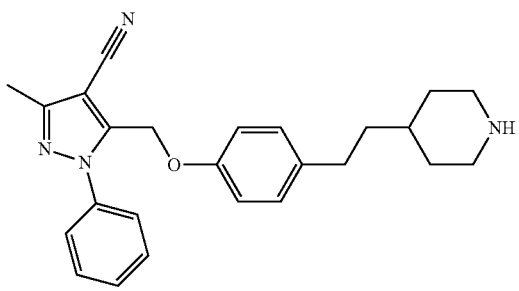 [SMILES: Cc1nn(-c2ccccc2)c(COc2ccc(CCC3CCNCC3)cc2)c1C#N] |
| 137 | 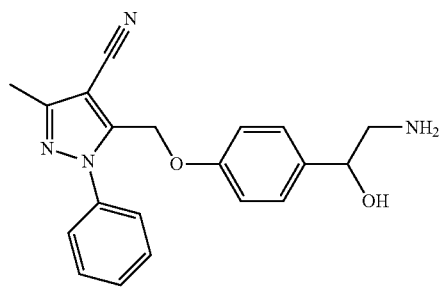 [SMILES: Cc1nn(-c2ccccc2)c(COc2ccc(C(O)CN)cc2)c1C#N] |

-continued

| Example | Structure |
|---|---|
| 138 | 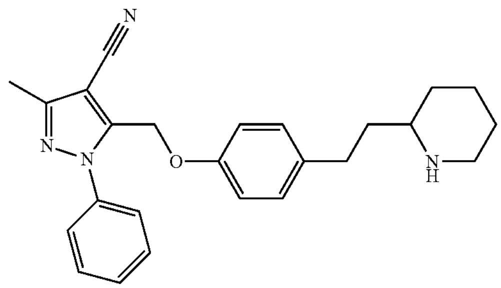 [SMILES: Cc1nn(-c2ccccc2)c(COc2ccc(CCC3CCCCN3)cc2)c1C#N] |
| 139 | 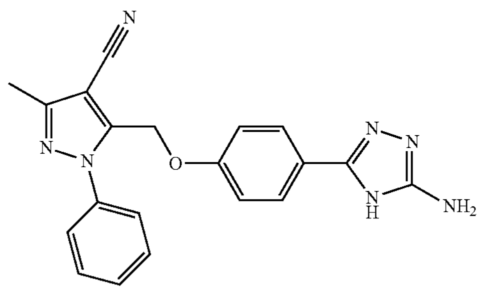 [SMILES: Cc1nn(-c2ccccc2)c(COc2ccc(-c3nnc(N)[nH]3)cc2)c1C#N] |
| 140 | 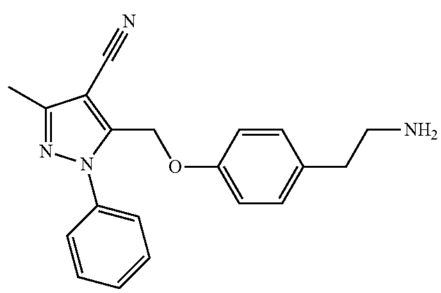 [SMILES: Cc1nn(-c2ccccc2)c(COc2ccc(CCN)cc2)c1C#N] |
| 141 | 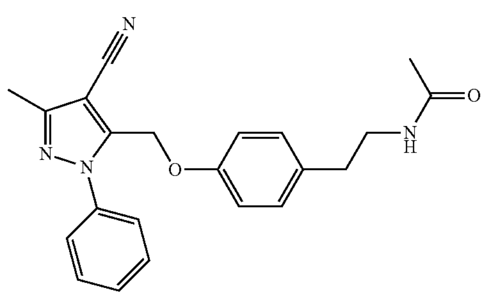 [SMILES: CC(=O)NCCc1ccc(OCc2c(C#N)c(C)nn2-c2ccccc2)cc1] |
| 142 | 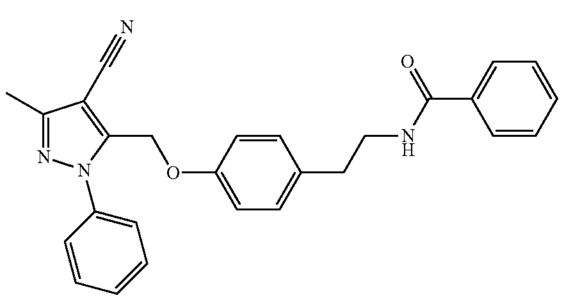 [SMILES: Cc1nn(-c2ccccc2)c(COc2ccc(CCNC(=O)c3ccccc3)cc2)c1C#N] |

-continued
| Example | Structure |
|---|---|
| 143 | 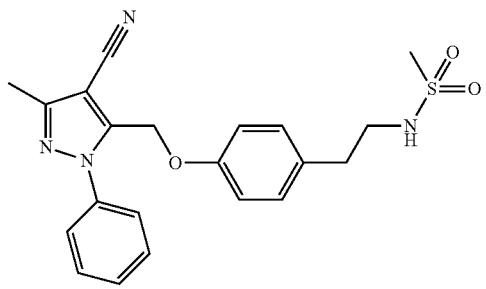 [SMILES: Cc1nn(-c2ccccc2)c(COc2ccc(CCNS(C)(=O)=O)cc2)c1C#N] |
| 144 | 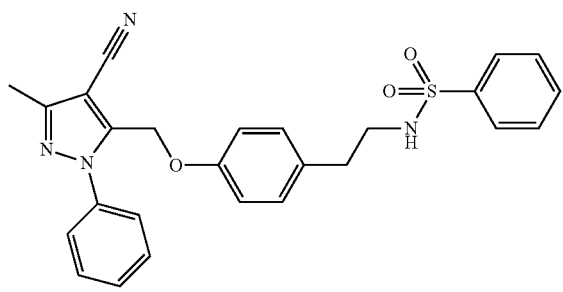 [SMILES: Cc1nn(-c2ccccc2)c(COc2ccc(CCNS(=O)(=O)c3ccccc3)cc2)c1C#N] |
| 145 | 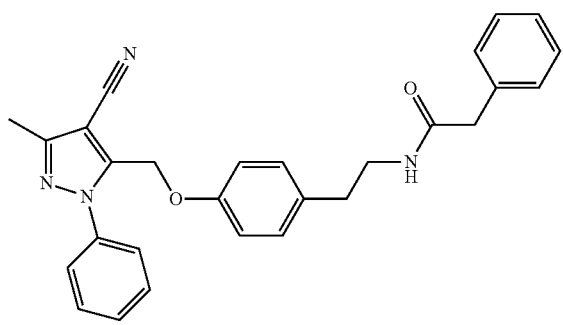 [SMILES: Cc1nn(-c2ccccc2)c(COc2ccc(CCNC(=O)Cc3ccccc3)cc2)c1C#N] |
| 146 | 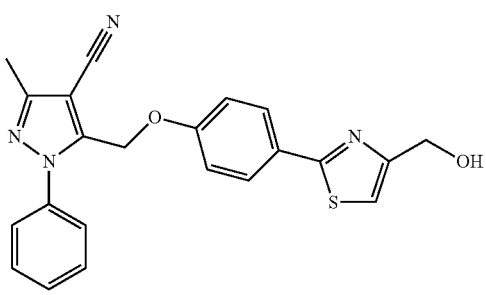 [SMILES: Cc1nn(-c2ccccc2)c(COc2ccc(-c3nc(CO)cs3)cc2)c1C#N] |
| 147 | 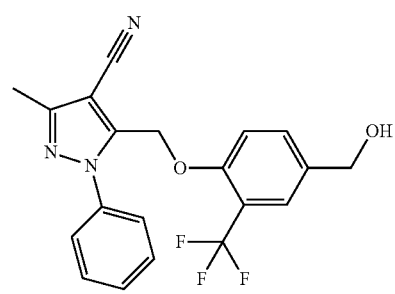 [SMILES: Cc1nn(-c2ccccc2)c(COc2ccc(CO)cc2C(F)(F)F)c1C#N] |

| Example | Structure |
|---|---|
| 148 | 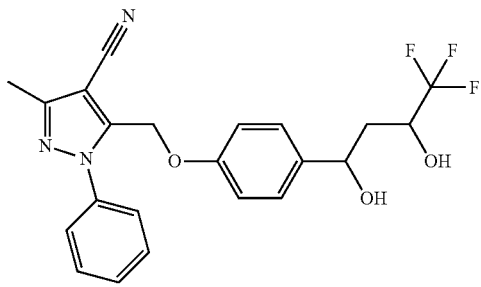 [SMILES: Cc1nn(-c2ccccc2)c(COc2ccc(C(O)CC(O)C(F)(F)F)cc2)c1C#N] |
| 149 | 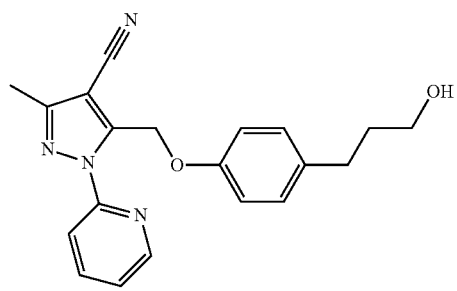 [SMILES: Cc1nn(-c2ccccn2)c(COc2ccc(CCCO)cc2)c1C#N] |
| 150 | 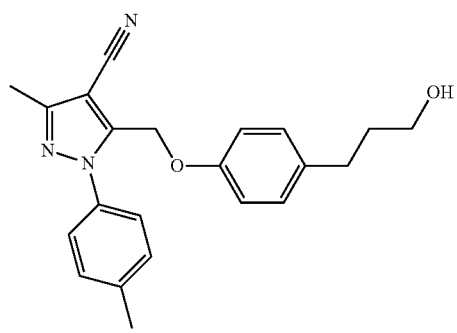 [SMILES: Cc1ccc(-n2nc(C)c(C#N)c2COc2ccc(CCCO)cc2)cc1] |
| 151 | 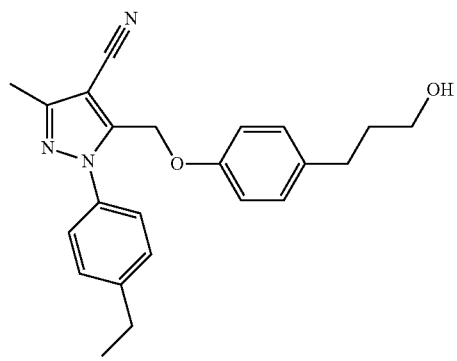 [SMILES: CCc1ccc(-n2nc(C)c(C#N)c2COc2ccc(CCCO)cc2)cc1] |
| 152 | 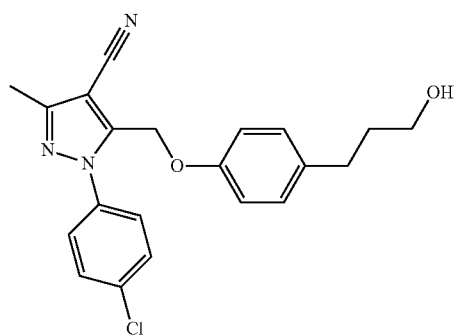 [SMILES: Cc1nn(-c2ccc(Cl)cc2)c(COc2ccc(CCCO)cc2)c1C#N] |

-continued
| Example | Structure |
|---|---|
| 153 | 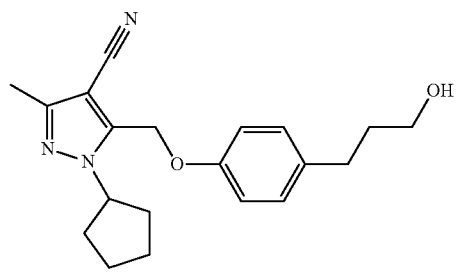 [SMILES: Cc1nn(C2CCCC2)c(COc2ccc(CCCO)cc2)c1C#N] |
| 154 | 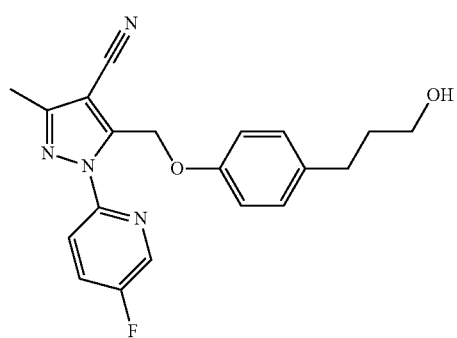 [SMILES: Cc1nn(-c2ccc(F)cn2)c(COc2ccc(CCCO)cc2)c1C#N] |
| 155 | 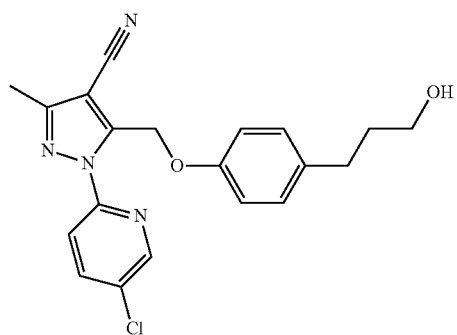 |
| 156 | 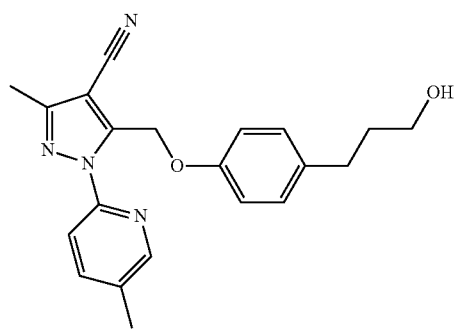 [SMILES: Cc1ccc(-n2nc(C)c(C#N)c2COc2ccc(CCCO)cc2)nc1] |

| Example | Structure |
|---------|-----------|
| 157 | 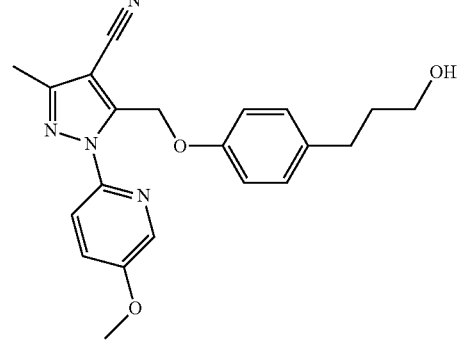 |
| 158 | 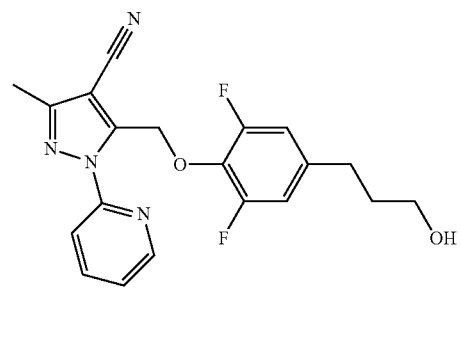 |
| 159 | 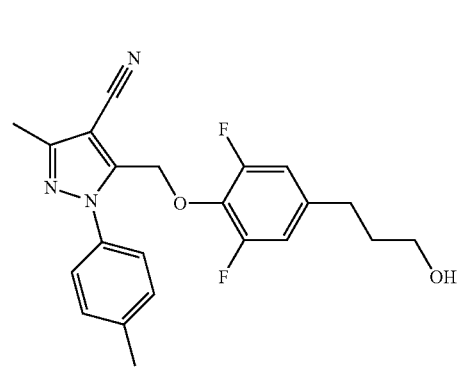 [SMILES: Cc1ccc(-n2nc(C)c(C#N)c2COc2c(F)cc(CCCO)cc2F)cc1] |
| 160 | 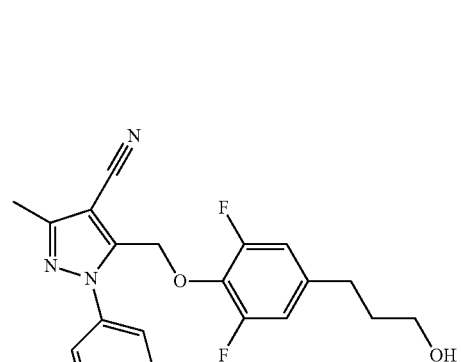 |

-continued
| Example | Structure |
|---|---|
| 161 | 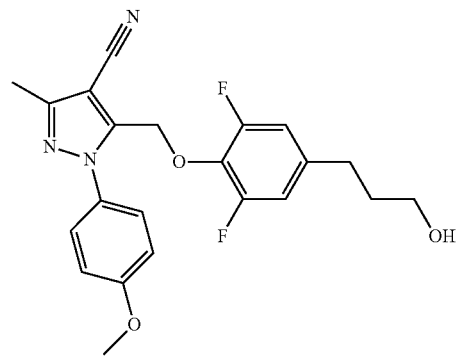 [SMILES: COc1ccc(-n2nc(C)c(C#N)c2COc2c(F)cc(CCCO)cc2F)cc1] |
| 162 | 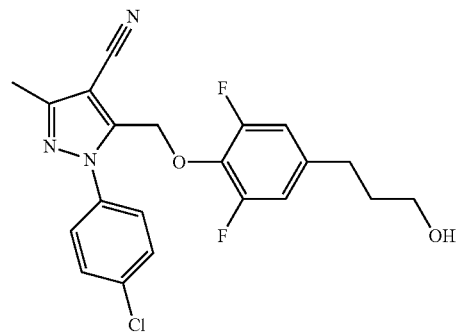 [SMILES: Cc1nn(-c2ccc(Cl)cc2)c(COc2c(F)cc(CCCO)cc2F)c1C#N] |
| 163 | 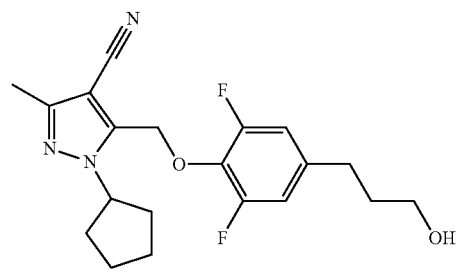 [SMILES: Cc1nn(C2CCCC2)c(COc2c(F)cc(CCCO)cc2F)c1C#N] |
| 164 | 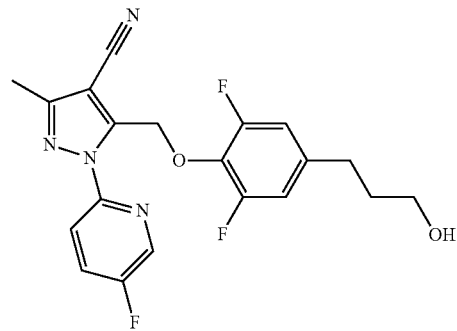 [SMILES: Cc1nn(-c2ccc(F)cn2)c(COc2c(F)cc(CCCO)cc2F)c1C#N] |

-continued

| Example | Structure |
|---------|-----------|
| 165 | 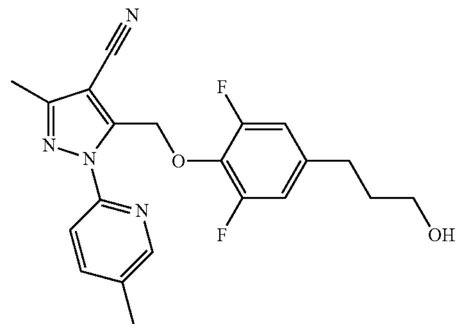 [SMILES: Cc1ccc(-n2nc(C)c(C#N)c2COc2c(F)cc(CCCO)cc2F)nc1] |
| 166 | 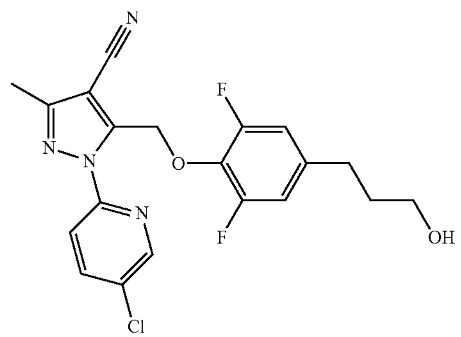 [SMILES: Cc1nn(-c2ccc(Cl)cn2)c(COc2c(F)cc(CCCO)cc2F)c1C#N] |
| 167 | 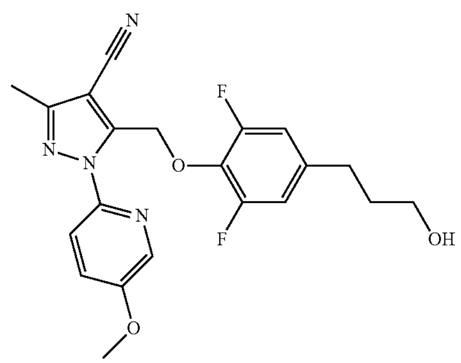 [SMILES: COc1ccc(-n2nc(C)c(C#N)c2COc2c(F)cc(CCCO)cc2F)nc1] |

Analytical Part
System Purification
HPLC Preparative

HPLC system WATERS Quaternary Gradient Mobile 535 equipped with WATERS UV/Visible Detector 2489 set to a dual-wavelength UV detection. Two mobile phases were used, mobile phase A: water (MilliQ) 0.05% TFA; mobile phase B: acetonitrile (Chromasolv Sigma-Aldrich) 0.05% TFA, and the run gradient conditions were set specifically for each compound. The purifications were achieved on a XBRIDGE Waters Column C18 5 μm 19×150. An injection volume between 100 and 500 μl was used and the flow was 15 ml/min.

Racemate Separations

The two enantiomers examples 43A and 43B were obtained by resolution of the racemic mixture example 43 using a WATERS Quaternary Gradient Mobile 2535 equipped with WATERS UV/Visible Detector 2489 set to a dual-wavelength UV detection at 250 and 265 nm. The chiral resolution was achieved on the Kromasil 5-Amycoat column (250 mm×4.6 mm, particle size 5 m) using Hexane (Chromasolv Sigma-Aldrich)-Ethanol (Chromasolv Sigma-Aldrich) 95-5 (v/v) as isocratic mobile phase; The sample was eluted from the column at a flow rate of 1.0 ml/min at room temperature (Pressure: ≈500 psi). The mixture was dissolved in Ethanol at concentration of 1% (w/v) and the injection volume was 100 μL.

The two enantiomers examples 47A and 47B were obtained by resolution of the racemic mixture example 47 using a WATERS Quaternary Gradient Mobile 2535 equipped with WATERS UV/Visible Detector 2489 set to a dual-wavelength UV detection at 250 and 265 nm. The chiral resolution was achieved on the Kromasil 5-Amycoat column (250 mm×4.6 mm, particle size 5 m) using Hexane (Chromasolv Sigma-Aldrich)-Isopropanol (Chromasolv Sigma-Aldrich) 80-20 (v/v) as isocratic mobile phase; The sample was eluted from the column at a flow rate of 1.0 ml/min at room temperature (Pressure: z 600 psi). The mixture was dissolved in Ethanol at concentration of 1% (w/v) and the injection volume was 100 μL.

LCMS

LCMS General Procedure

The HPLC measurement was performed using a Dionex 3000 module comprising a quaternary pump with degasser, an autosampler, a column oven (set at 29° C.), a diode-array detector DAD and a column as specified in the respective methods below. Flow from the column was split to a MS spectrometer. The MS detector (LCQ Fleet Thermo Scientific) was configured with an electrospray ionization source. Mass spectra were acquired by scanning from 50 to 800 in 0.48 second. The capillary needle voltage was 5 kV in positive and negative ionization mode and the source temperature was maintained at 275° C. Nitrogen was used as the nebulizer gas, the flow was 8 l/min. Data acquisition was performed with Thermo Xcalibur Qual Browser.

LCMS-Procedure 1

In addition to general procedure: Reversed phase HPLC was carried out on a Kinetex XB-C18 column Phenomenex (1.7 µm, 50×2.1 mm) with a flow rate of 0.300 ml/min. Two mobile phases were used, mobile phase A: ammonium formate buffer solution at pH 3.5; mobile phase B: acetonitrile (Chromasolv Sigma-Aldrich), and they were employed to run a gradient conditions from 15% B for 0.5 minutes, from 1% to 98% in 4.0 minutes, 98% B for 1.35 minutes and 15% B in 0.10 minutes and hold these conditions for 2.75 minutes in order to reequilibrate the column (Total Run Time 8.7 minutes). An injection volume of 1 µl was used.

LCMS-Procedure 2

LC-MS was carried out on Waters BEH C18 (1.7 µm, 50×2.1 mm). Column flow was 0.55 ml/min and mobile phase were used (A) 5 mm Ammonium Acetate in water followed by 0.1% Formic acid and (B) 0.1% Formic Acid in Acetonitrile. They were employed to run a gradient conditions from 5% B for 0.4 minutes, from 5% to 95% in 2.1 minutes, 95% B for 0.8 minutes and 5% B in 0.01 minutes and hold these conditions for 0.69 minutes in order to reequilibrate the column (Total Run Time 4.0 minutes). The mass spectra were recorded with a Waters SQ detector at 125° C. The mass spectrometer was equipped with an electrospray ion source (ESI) operated in a positive and negative ion mode and was set to scan between m/z 80-800.

TABLE 1

Retention time ($R_t$) in minutes, $[M + H]^+$ and/or $[M - H]^-$ peak, LCMS procedure

| Example | RT (min) | $[M + H]^+$ | $[M - H]^-$ | LC-MS | Example | RT (min) | $[M + H]^+$ | $[M - H]^-$ | LC-MS |
|---|---|---|---|---|---|---|---|---|---|
| 1 | 5.3 | 315.1 | 313.6 | 1 | 2 | 5.0 | 354.4 | 352.6 | 1 |
| 3 | 5.5 | 320.3 | 318.9 | 1 | 4 | 5.8 | 304.3 | 302.9 | 1 |
| 5 | 4.8 | 320.6 | 318.9 | 1 | 6 | 4.9 | 334.5 | 332.8 | 1 |
| 7 | 5.6 | 349.2 | 347.7 | 1 | 8 | 5.6 | 290.2 | 288.7 | 1 |
| 9 | 5.5 | 351.0 | — | 1 | 10 | 5.3 | 333.0 | 331.6 | 1 |
| 11 | 5.5 | 328.2 | 327.7 | 1 | 12 | 5.7 | 343.1 | — | 1 |
| 13 | 5.5 | 351.0 | — | 1 | 14 | 5.0 | 356.6 | 354.6 | 1 |
| 15 | 5.7 | 343.2 | 341.6 | 1 | 16 | 5.0 | 334.2 | 332.5 | 1 |
| 17 | 5.1 | 348.4 | — | 1 | 18 | 5.6 | 308.2 | 306.7 | 1 |
| 19 | 6.1 | 318.4 | 316.7 | 1 | 20 | 4.9 | 338.2 | — | 1 |
| 21 | 5.0 | 356.3 | — | 1 | 22 | 6.0 | 318.3 | 316.9 | 1 |
| 23 | 4.9 | 320.1 | 318.5 | 1 | 24 | 4.8 | 320.7 | 318.6 | 1 |
| 25 | 6.0 | 318.4 | 316.3 | 1 | 26 | 5.8 | 304.3 | 302.5 | 1 |
| 27 | 6.0 | 318.4 | 316.5 | 1 | 28 | 5.8 | 304.3 | 302.6 | 1 |
| 29 | 5.2 | 330.4 | — | 1 | 30 | 6.0 | 318.3 | 316.4 | 1 |
| 31 | 5.3 | 343.9 | 341.6 | 1 | 32 | 5.1 | 384.6 | — | 1 |
| 33 | 4.9 | 352.1 | 350.2 | 1 | 34 | 6.2 | 332.5 | 330.9 | 1 |
| 35 | 5.0 | 348.3 | — | 1 | 36 | 4.9 | 350.4 | 348.4 | 1 |
| 37 | 4.9 | 347.3 | 345.3 | 1 | 38 | 4.9 | 334.6 | 332.4 | 1 |
| 39 | 6.0 | 318.0 | 316.2 | 1 | 40 | 5.6 | 308.0 | 306.3 | 1 |
| 41 | 5.8 | 324.1 | 322.3 | 1 | 42 | 5.0 | 366.6 | 364.5 | 1 |
| 43 | 5.3 | 398.3 | — | 1 | 43A | 5.3 | 398.3 | — | 1 |
| 43B | 5.3 | 398.3 | — | 1 | 44 | 5.9 | — | 356.2 | 1 |
| 45 | 4.4 | 391.3 | 389.3 | 1 | 46 | 5.1 | 415.3 | — | 1 |
| 47 | 5.2 | 362.5 | 360.6 | 1 | 47A | 5.2 | 362.5 | 360.6 | 1 |
| 47B | 5.2 | 362.5 | 360.6 | 1 | 48 | 5.4 | — | 371.3 | 1 |
| 49 | 4.3 | 391.4 | — | 1 | 50 | 5.1 | 348.0 | 346.2 | 1 |
| 51 | 5.0 | 348.4 | — | 1 | 52 | 5.8 | — | 404.2 | 1 |
| 53 | 4.9 | 378.4 | — | 1 | 54 | 4.9 | 334.5 | 332.5 | 1 |
| 55 | 5.4 | 362.5 | 360.6 | 1 | 56 | 2.6 | 348.2 | — | 2 |
| 57 | 4.5 | 333.9 | — | 1 | 58 | 4.8 | 347.3 | — | 1 |
| 59 | 4.9 | 350.4 | 348.2 | 1 | 60 | 5.0 | 316.1 | 314.5 | 1 |
| 61 | 4.8 | 330.2 | — | 1 | 62 | 4.8 | 341.2 | 339.2 | 1 |
| 63 | 4.7 | 341.3 | 339.2 | 1 | 64 | 4.7 | 316.3 | 314.3 | 1 |
| 65 | 4.9 | 307.1 | — | 1 | 66 | 4.9 | 309.2 | — | 1 |
| 67 | 4.2 | 321.4 | — | 1 | 68 | 4.6 | 305.2 | — | 1 |
| 69 | 4.6 | 305.2 | — | 1 | 70 | 4.5 | 319.2 | — | 1 |
| 71 | 5.3 | — | 325.5 | 1 | 72 | 4.9 | 348.3 | — | 1 |
| 73 | 5.0 | 348.5 | 346.4 | 1 | 74 | 5.1 | 348.9 | — | 1 |
| 75 | 5.2 | — | 366.3 | 1 | 76 | 5.2 | — | 366.3 | 1 |
| 77 | 5.2 | 402.0 | 400.3 | 1 | 78 | 5.3 | 363.2 | — | 1 |
| 79 | 4.9 | 364.5 | — | 1 | 80 | 4.9 | 364.3 | — | 1 |
| 81 | 5.3 | 418.1 | 416.3 | 1 | 82 | 4.7 | 352.3 | 350.2 | 1 |
| 83 | 2.8 | 308.2 | — | 2 | 84 | 2.3 | 352.2 | — | 2 |
| 85 | 2.7 | 326.2 | — | 2 | 86 | 2.8 | 322.2 | — | 2 |
| 87 | 2.4 | 366.2 | — | 2 | 88 | 4.9 | 348.1 | 346.2 | 1 |
| 89 | 5.0 | 362.2 | 360.3 | 1 | 90 | 5.1 | 398.2 | — | 1 |
| 91 | 4.8 | 378.5 | — | 1 | 92 | 4.8 | 348.2 | — | 1 |
| 93 | 5.1 | 398.1 | — | 1 | 94 | 5.2 | 370.0 | 368.2 | 1 |

TABLE 1-continued

Retention time (R$_t$) in minutes, [M + H]$^+$ and/or [M − H]$^-$ peak, LCMS procedure

| Example | RT (min) | [M + H]$^+$ | [M − H]$^-$ | LC-MS | Example | RT (min) | [M + H]$^+$ | [M − H]$^-$ | LC-MS |
|---|---|---|---|---|---|---|---|---|---|
| 95 | 5.3 | 384.1 | 382.0 | 1 | 96 | 5.4 | 450.2 | — | 1 |
| 97 | 5.4 | 329.2 | — | 1 | 98 | 2.7 | 322.2 | — | 2 |
| 99 | 2.4 | 362.2 | — | 2 | 100 | 2.1 | 412.2 | — | 2 |
| 101 | 2.5 | 352.2 | — | 2 | 102 | 1.9 | 335.5 | — | 2 |
| 103 | 1.6 | 335.6 | — | 2 | 104 | 1.6 | 335.5 | — | 2 |
| 105 | 1.9 | 336.2 | — | 2 | 106 | 2.0 | 336.2 | — | 2 |
| 107 | 1.8 | 359.6 | — | 2 | 108 | 2.4 | 359.2 | — | 2 |
| 109 | 2.5 | 402.2 | — | 2 | 110 | 2.7 | 413.2 | — | 2 |
| 111 | 2.4 | 404.2 | — | 2 | 112 | 2.8 | 370.6 | — | 2 |
| 113 | 4.4 | 368.0 | — | 2 | 114 | 2.3 | 370.2 | — | 2 |
| 115 | 2.5 | 418.2 | — | 2 | 116 | 2.2 | 370.2 | — | 2 |
| 117 | 2.6 | 326.2 | — | 2 | 118 | 2.6 | 340.2 | — | 2 |
| 119 | 2.0 | 375.7 | — | 2 | 120 | 4.3 | 401.9 | — | 1 |
| 121A | 4.2 | 370.1 | 368.6 | 1 | 121B | 4.5 | 371.2 | 369.3 | 1 |
| 123 | 4.5 | 299.2 | — | 1 | 122 | 4.5 | 295.2 | — | 1 |
| 125 | 4.7 | 313.2 | — | 1 | 124 | 4.8 | 317.1 | — | 1 |
| 127 | 4.8 | 331.1 | — | 1 | 126 | 4.7 | 309.2 | — | 1 |
| 129 | 4.7 | 320.1 | 318.2 | 1 | 128 | 4.8 | 394.0 | 392.5 | 1 |
| 131 | 4.0 | 366.0 | — | 1 | 130 | 4.8 | 334.6 | 332.3 | 1 |
| 133 | 5.1 | 398.6 | 396.5 | 1 | 132 | 4.3 | 382.2 | — | 1 |
| 135 | 2.8 | 362.2 | — | 2 | 134 | 2.3 | 348.2 | — | 1 |
| 137 | 3.8 | 349.0 | — | 1 | 136 | 4.5 | 401.3 | — | 1 |
| 139 | 4.3 | 372.1 | 370.0 | 1 | 138 | 4.5 | 401.3 | — | 1 |
| 141 | 4.7 | 375.3 | — | 1 | 140 | 4.0 | 333.3 | — | 1 |
| 143 | 5.0 | 411.3 | — | 1 | 142 | 5.3 | 437.1 | — | 1 |
| 145 | 5.3 | 451.1 | — | 1 | 144 | 5.5 | 473.0 | 471.2 | 1 |
| 147 | 5.1 | 388.0 | 386.2 | 1 | 146 | 4.9 | 403.1 | 401.2 | 1 |
| 148 | 5.0 | 432.5 | — | 1 | 149 | 5.0 | 349.3 | — | 1 |
| 150 | 5.3 | 362.4 | — | 1 | 151 | 5.5 | 376.4 | 374.2 | 1 |
| 152 | 5.3 | 382.2 | 380.3 | 1 | 153 | 5.3 | 340.8 | 338.6 | 1 |
| 154 | 5.2 | 367.4 | 365.3 | 1 | 155 | 5.3 | 382.3 | 380.3 | 1 |
| 156 | 5.2 | 362.4 | 360.3 | 1 | 157 | 5.1 | 379.2 | 377.4 | 1 |
| 158 | 5.1 | 385.2 | — | 1 | 159 | 5.4 | 398.1 | — | 1 |
| 160 | 5.6 | 412.3 | — | 1 | 161 | 5.2 | 414.2 | — | 1 |
| 162 | 5.5 | — | 461.7* | 1 | 163 | 5.4 | 376.0 | — | 1 |
| 164 | 5.2 | 403.0 | — | 1 | 165 | 5.3 | 399.2 | — | 1 |
| 166 | 5.4 | — | 466.5* | 1 | 167 | 5.1 | 415.2 | — | 1 |

NMR Characterization $^1$H NMR spectra were recorded on a Varian Mercury NMR 400 MHz spectrometer using CDCl$_3$, DMSO-d or CD$_3$OD as solvents. Chemical shifts (δ) are reported in parts per million (ppm) relative to tetramethylsilane (TMS), which was used as internal standard.

TABLE 2

NMR data of compounds

| Ex. | $^1$H-NMR 400 |
|---|---|
| 1 | $^1$H NMR (CHLOROFORM-d) δ ppm 2.46 (s, 3 H) 5.11 (s, 2 H) 6.97 (d, J = 8.80 Hz, 2 H) 7.48 (s, 5 H) 7.60 (d, J = 8.80 Hz, 2 H) |
| 2 | $^1$H NMR (CHLOROFORM-d) δ ppm 2.45 (s, 3 H) 4.56 (s, 2 H) 5.05 (s, 2 H) 6.96 (d, J = 8.34 Hz, 1 H) 7.18 (dd, J = 8.34, 1.65 Hz, 1 H) 7.37 (d, J = 1.65 Hz, 1 H) 7.40-7.52 (m, 3 H) 7.59-7.66 (m, 2 H) |
| 3 | $^1$H NMR (CHLOROFORM-d) δ ppm 2.46 (s, 3 H) 3.76 (s, 3 H) 4.99 (s, 2 H) 6.79-6.89 (m, 4 H) 7.42-7.52 (m, 3 H) 7.53-7.59 (m, 2 H) |
| 4 | $^1$H NMR (CHLOROFORM-d) δ ppm 2.31 (s, 3 H) 2.48 (s, 3 H) 5.02 (s, 2 H) 6.82 (br d, J = 8.43 Hz, 2 H) 7.10 (br d, J = 8.25 Hz, 2 H) 7.43-7.53 (m, 3 H) 7.53-7.59 (m, 2 H) |
| 5 | $^1$H NMR (METHANOL-d4) δ ppm 2.39 (s, 3 H) 4.52 (s, 2 H) 5.10 (s, 2 H) 6.87 (d, J = 8.61 Hz, 2 H) 7.26 (d, J = 8.41 Hz, 2 H) 7.45-7.57 (m, 5 H) |
| 6 | $^1$H NMR (CHLOROFORM-d) δ ppm 2.44 (s, 3 H) 2.79 (t, J = 6.55 Hz, 2 H) 3.79 (t, J = 6.55 Hz, 2 H) 5.01 (s, 2 H) 6.86 (d, J = 8.34 Hz, 2 H) 7.14 (d, J = 8.34 Hz, 2 H) 7.40-7.56 (m, 5 H) |
| 7 | $^1$H NMR (CHLOROFORM-d) δ ppm 2.48 (s, 3 H) 5.15 (s, 2 H) 7.05 (d, J = 8.52 Hz, 1 H) 7.44-7.52 (m, 3 H) 7.53-7.60 (m, 3 H) 7.69 (d, J = 1.83 Hz, 1H) |
| 8 | $^1$H NMR (CHLOROFORM-d) δ ppm 2.48 (s, 3 H) 5.05 (s, 2 H) 6.93 (d, J = 8.06 Hz, 2 H) 7.00-7.07 (m, 1 H) 7.31 (t, J = 7.93 Hz, 3 H) 7.43-7.52 (m, 3 H) 7.52-7.60 (m, 2 H) |
| 9 | $^1$H NMR (CHLOROFORM-d) δ ppm 2.43 (s, 3 H) 5.21 (s, 2 H) 7.21-7.29 (m, 2 H) 7.44-7.55 (m, 3 H) 7.59 (br d, J = 7.24 Hz, 2 H) |
| 10 | $^1$H NMR (CHLOROFORM-d) δ ppm 2.45 (s, 3 H) 5.15 (s, 2 H) 7.07 (t, J = 8.16 Hz, 1 H) 7.34-7.45 (m, 2 H) 7.45-7.56 (m, 5 H) |

TABLE 2-continued

NMR data of compounds

| Ex. | $^1$H-NMR 400 |
|---|---|
| 11 | $^1$H NMR (CHLOROFORM-d) δ ppm 2.14 (s, 3 H) 2.45 (s, 3 H) 5.14 (s, 2 H) 6.81 (d, J = 8.52 Hz, 1 H) 7.37-7.54 (m, 7 H) |
| 12 | $^1$H NMR (CHLOROFORM-d) δ ppm 2.13 (s, 6 H) 2.46 (s, 3 H) 4.87 (s, 2 H) 7.29 (s, 2 H) 7.48-7.61 (m, 5 H) |
| 13 | $^1$H NMR (CHLOROFORM-d) δ ppm 2.48 (s, 3 H) 5.19 (s, 2 H) 6.90 (br, 1 H) 7.37 (br, 1 H) 7.51 (br, 5 H) |
| 14 | $^1$H NMR (DMSO-d) δ ppm 2.32 (s, 3 H) 4.44 (br d, J = 2.20 Hz, 2 H) 5.26 (s, 2 H) 6.92 (br t, J = 7.70 Hz, 1 H) 7.05-7.17 (m, 1 H) 7.40-7.57 (m, 5 H) |
| 15 | $^1$H NMR (CHLOROFORM-d) δ ppm 2.09 (s, 3 H) 2.45 (s, 3 H) 2.47 (s, 3 H) 5.12 (s, 2 H) 6.70 (d, J = 8.61 Hz, 1 H) 7.41 (br d, J = 8.61 Hz, 1 H) 7.51-7.44 (m, 5 H) |
| 16 | $^1$H NMR (CHLOROFORM-d) δ ppm 2.15 (s, 3 H) 2.47 (s, 3 H) 4.55 (s, 2 H) 5.06 (s, 2 H) 6.75 (d, J = 8.25 Hz, 1 H) 7.11 (br d, J = 8.25 Hz, 1 H) 7.14 (s, 1 H) 7.41-7.57 (m, 5 H) |
| 17 | $^1$H NMR (CHLOROFORM-d) δ ppm 2.12 (s, 6 H) 2.46 (s, 3 H) 4.53 (s, 2 H) 4.82 (s, 2 H) 6.98 (s, 2 H) 7.52 (br d, J = 6.78 Hz, 3 H) 7.62 (br d, J = 6.78 Hz, 2 H) |
| 18 | $^1$H NMR (CHLOROFORM-d) δ ppm 2.46 (s, 3 H) 5.01 (s, 2 H) 6.81-6.90 (m, 2 H) 6.94-7.03 (m, 2 H) 7.42-7.57 (m, 5 H) |
| 19 | $^1$H NMR (CHLOROFORM-d) δ ppm 1.23 (t, J = 7.61 Hz, 3 H) 2.48 (s, 3 H) 2.62 (q, J = 7.61 Hz, 2 H) 5.03 (s, 2 H) 6.87 (d, J = 8.52 Hz, 2 H) 7.14 (d, J = 8.43 Hz, 2 H) 7.42-7.52 (m, 3 H) 7.53-7.60 (m, 2 H) |
| 20 | $^1$H NMR (CHLOROFORM-d) δ ppm 2.44 (s, 3 H) 4.57 (s, 2 H) 5.06 (s, 2 H) 6.93-7.04 (m, 2 H) 7.10 (m, 1 H) 7.44-7.53 (m, 3 H) 7.58 (m, 2 H) |
| 21 | $^1$H NMR (DMSO-d) δ ppm 2.36 (s, 3 H) 4.46 (d, J = 5.50 Hz, 2 H) 5.15 (s, 2 H) 5.43 (t, J = 5.50 Hz, OH) 7.03 (br d, J = 8.98 Hz, 2 H) 7.49-7.67 (m, 5 H) |
| 22 | $^1$H NMR (CHLOROFORM-d) δ ppm 2.30 (s, 6 H) 2.49 (s, 3 H) 5.03 (s, 2 H) 6.57 (s, 2 H) 6.69 (s, 1 H) 7.43-7.53 (m, 3 H) 7.55-7.59 (m, 2 H) |
| 23 | $^1$H NMR (CHLOROFORM-d) δ ppm 2.46 (s, 3 H) 4.59 (s, 2 H) 5.12 (s, 2 H) 6.79 (d, J = 8.25 Hz, 1 H) 7.00 (t, J = 7.74 Hz, 1 H) 7.22 (br t, J = 7.74 Hz, 1 H) 7.35 (d, J = 7.15 Hz, 1 H) 7.44-7.53 (m, 5 H) |
| 24 | $^1$H NMR (CHLOROFORM-d) δ ppm 2.39-2.48 (m, 3 H) 4.61 (s, 2 H) 5.02 (s, 2 H) 6.78-6.84 (m, 1 H) 6.92-7.00 (m, 2 H) 7.24 (t, J = 7.79 Hz, 1 H) 7.41-7.49 (m, 3 H) 7.49-7.55 (m, 2 H) |
| 25 | $^1$H NMR (CHLOROFORM-d) δ ppm 2.16 (s, 6 H) 2.49 (s, 3 H) 4.86 (s, 2 H) 6.94-7.04 (m, 3 H) 7.49-7.58 (m, 3 H) 7.64 (dd, J = 7.84, 1.51 Hz, 2 H) |
| 26 | $^1$H NMR (CHLOROFORM-d) δ ppm 2.18 (s, 3 H) 2.47-2.53 (m, 3 H) 5.07 (s, 2 H) 6.81 (d, J = 7.97 Hz, 1 H) 6.91-6.99 (m, 1 H) 7.12-7.20 (m, 2 H) 7.44-7.53 (m, 3 H) 7.53-7.59 (m, 2 H) |
| 27 | $^1$H NMR (CHLOROFORM-d) δ ppm 2.14 (s, 3 H) 2.32 (s, 3 H) 2.50 (s, 3 H) 5.07 (s, 2 H) 6.65 (s, 1 H) 6.76 (br d, J = 7.51 Hz, 1 H) 7.05 (d, J = 7.51 Hz, 1 H) 7.46-7.54 (m, 3 H) 7.55-7.60 (m, 2 H) |
| 28 | $^1$H NMR (CHLOROFORM-d) δ ppm 2.34 (s, 3 H) 2.48 (s, 3 H) 5.04 (s, 2 H) 6.69-6.79 (m, 2 H) 6.86 (s, 1 H) 7.19 (t, J = 7.79 Hz, 1 H) 7.44-7.53 (m, 3 H) 7.53-7.59 (m, 2 H) |
| 29 | $^1$H NMR (CHLOROFORM-d) δ ppm 2.45 (s, 3 H) 3.68 (s, 2 H) 5.04 (s, 2 H) 6.90 (d, J = 8.61 Hz, 2 H) 7.24 (br d, J = 8.61 Hz, 2 H) 7.42-7.55 (m, 5 H) |
| 30 | $^1$H NMR (CHLOROFORM-d) δ ppm 2.11 (s, 3 H) 2.29 (s, 3 H) 2.50 (s, 3 H) 5.05 (s, 2 H) 6.69 (d, J = 8.16 Hz, 1 H) 6.87 (d, J = 7.51 Hz, 1 H) 7.01-7.08 (m, 1 H) 7.42-7.53 (m, 3 H) 7.54-7.60 (m, 2 H) |
| 31 | $^1$H NMR (CHLOROFORM-d) δ ppm 2.46 (s, 3 H) 2.58 (t, J = 7.24 Hz, 2 H) 2.90 (t, J = 7.24 Hz, 2 H) 5.03 (s, 2 H) 6.88 (d, J = 8.52 Hz, 2 H) 7.17 (d, J = 8.52 Hz, 2 H) 7.42-7.57 (m, 5 H) |
| 32 | $^1$H NMR (CHLOROFORM-d) δ ppm 1.82-1.89 (m, 2 H) 2.44 (s, 3 H) 2.66 (t, J = 7.61 Hz, 2 H) 3.64 (t, J = 6.28 Hz, 2 H) 5.05 (s, 2 H) 6.77 (d, J = 8.98 Hz, 2H) 7.46-7.57 (m, 3 H) 7.70 (br d, J = 7.24 Hz, 2 H) |
| 33 | $^1$H NMR (CHLOROFORM-d) δ ppm 2.45 (s, 3 H) 2.80 (t, J = 6.28 Hz, 2 H) 3.78-3.88 (m, 2 H) 5.04 (s, 2 H) 6.90-7.05 (m, 3 H) 7.43-7.57 (m, 3 H) 7.61 (br d, J = 7.24 Hz, 2 H) |
| 34 | $^1$H NMR (CHLOROFORM-d) δ ppm 2.14 (s, 3 H) 2.20 (s, 3 H) 2.26 (s, 3 H) 2.50 (s, 3 H) 5.03 (s, 2 H) 6.61 (d, J = 8.25 Hz, 1 H) 6.95 (d, J = 8.25 Hz, 1 H) 7.43-7.62 (m, 5 H) |
| 35 | $^1$H NMR (CHLOROFORM-d) δ ppm 1.80-1.94 (m, 2 H) 2.47 (s, 3 H) 2.67 (t, J = 7.65 Hz, 2 H) 3.66 (t, J = 6.42 Hz, 2 H) 5.02 (s, 2 H) 6.85 (d, J = 8.52 Hz, 2 H) 7.13 (d, J = 8.52 Hz, 2 H) 7.41-7.59 (m, 5 H) |
| 36 | $^1$H NMR (CHLOROFORM-d) δ ppm 2.43 (s, 3 H) 3.84-4.00 (m, 2 H) 4.00-4.14 (m, 2 H) 5.09 (s, 2 H) 6.81-6.95 (m, 3 H) 6.95-7.10 (m, 1 H) 7.44-7.64 (m, 5 H) |
| 37 | $^1$H NMR (CHLOROFORM-d) δ ppm 2.18 (s, 3 H) 2.47 (s, 3 H) 5.16 (s, 2 H) 6.73 (br d, J = 7.24 Hz, 1 H) 6.90-7.04 (m, 2 H) 7.27-7.47 (m, 2 H) 7.47-7.58 (m, 3 H) 7.89 (br s, NH) 8.34 (br d, J = 7.51 Hz, 1 H) |
| 38 | $^1$H NMR (CHLOROFORM-d) δ ppm 2.46 (s, 3 H) 2.83 (t, J = 6.51 Hz, 2 H) 3.84 (t, J = 6.51 Hz, 2 H) 5.05 (s, 2 H) 6.78 (dd, J = 8.16, 2.02 Hz, 1 H) 6.82 (s, 1 H) 6.91 (d, J = 7.51 Hz, 1 H) 7.24 (t, J = 7.84 Hz, 1 H) 7.44-7.52 (m, 3 H) 7.53-7.58 (m, 2 H) |

TABLE 2-continued

NMR data of compounds

| Ex. | $^1$H-NMR 400 |
|---|---|
| 39 | $^1$H NMR (CHLOROFORM-d) δ ppm 1.18 (t, J = 7.51 Hz, 3 H) 2.51 (s, 3 H) 2.61 (q, J = 7.51 Hz, 2 H) 5.08 (s, 2 H) 6.84 (d, J = 8.06 Hz, 1 H) 6.96-7.03 (m, 1H) 7.14-7.18 (m, 1 H) 7.19-7.24 (m, 1 H) 7.45-7.53 (m, 3 H) 7.55-7.61 (m, 2 H) |
| 40 | $^1$H NMR (CHLOROFORM-d) δ ppm 2.46 (s, 3 H) 5.02 (s, 2 H) 6.61 (dd, J = 10.40, 1.97 Hz, 1 H) 6.68-6.76 (m, 2 H) 7.20-7.28 (m, 1 H) 7.44-7.53 (m, 5 H) |
| 41 | $^1$H NMR (CHLOROFORM-d) δ ppm 2.48 (s, 3 H) 5.03 (s, 2 H) 6.83 (dd, J = 8.34, 2.20 Hz, 1 H) 6.90 (t, J = 1.88 Hz, 1 H) 7.01 (d, J = 8.06 Hz, 1 H) 7.13-7.33 (m, 1 H) 7.45-7.54 (m, 5 H) |
| 42 | $^1$H NMR (CHLOROFORM-d) δ ppm 1.79-1.90 (q, 2 H) 2.46 (s, 3 H) 2.65 (t, J = 7.65 Hz, 2 H) 3.64 (t, J = 6.32 Hz, 2 H) 5.05 (s, 2 H) 6.86-6.97 (m, 3 H) 7.44-7.54 (m, 3 H) 7.60 (br d, J = 6.78 Hz, 2 H) |
| 43 | $^1$H NMR (CHLOROFORM-d) δ ppm 0.93 (d, J = 6.84 Hz, 3 H) 1.87-1.97 (m, 1 H) 2.40 (br dd, J = 13.46, 8.12 Hz, 1 H) 2.45 (s, 3 H) 2.74 (br dd, J = 13.46, 6.19 Hz, 1 H) 3.51 (br d, J = 5.77 Hz, 2 H) 5.07 (s, 2 H) 6.77 (br d, J = 8.76 Hz, 2 H) 7.45-7.58 (m, 3 H) 7.72 (br d, J = 7.26 Hz, 2 H) |
| 43A | $^1$H NMR (CHLOROFORM-d) δ ppm 0.93 (d, J = 6.84 Hz, 3 H) 1.87-1.97 (m, 1 H) 2.40 (br dd, J = 13.46, 8.12 Hz, 1 H) 2.45 (s, 3 H) 2.74 (br dd, J = 13.46, 6.19 Hz, 1 H) 3.51 (br d, J = 5.77 Hz, 2 H) 5.07 (s, 2 H) 6.77 (br d, J = 8.76 Hz, 2 H) 7.45-7.58 (m, 3 H) 7.72 (br d, J = 7.26 Hz, 2 H) |
| 43B | $^1$H NMR (CHLOROFORM-d) δ ppm 0.93 (d, J = 6.84 Hz, 3 H) 1.87-1.97 (m, 1 H) 2.40 (br dd, J = 13.46, 8.12 Hz, 1 H) 2.45 (s, 3 H) 2.74 (br dd, J = 13.46, 6.19 Hz, 1 H) 3.51 (br d, J = 5.77 Hz, 2 H) 5.07 (s, 2 H) 6.77 (br d, J = 8.76 Hz, 2 H) 7.45-7.58 (m, 3 H) 7.72 (br d, J = 7.26 Hz, 2 H) |
| 44 | $^1$H NMR (CHLOROFORM-d) δ ppm 2.49 (s, 3 H) 5.10 (s, 2 H) 6.99 (d, J = 8.61 Hz, 2 H) 7.46-7.53 (m, 5 H) 7.58 (d, J = 8.71 Hz, 2 H) |
| 45 | 1H NMR (DMSO-d) δ ppm 2.39 (s, 3 H) 2.95 (s, 3 H) 3.49 (br s, 4 H) 4.78 (br t, J = 5.13 Hz, OH) 5.26 (s, 2 H) 6.98 (d, J = 8.61 Hz, 2 H) 7.38 (d, J = 8.61 Hz, 2 H) 7.49-7.61 (m, 5 H) |
| 46 | $^1$H NMR (CHLOROFORM-d) δ ppm 2.46 (s, 3 H) 3.98-4.15 (m, 2 H) 5.09 (s, 2 H) 6.92 (br d, J = 8.43 Hz, 2 H) 7.43-7.52 (m, 5 H) 7.78 (d, J = 8.43 Hz, 2 H) |
| 47 | $^1$H NMR (CHLOROFORM-d) δ ppm 1.24 (d, J = 6.19 Hz, 3 H) 1.69-1.80 (m, 2 H) 2.48 (s, 3 H) 2.59-2.67 (m, 1 H) 2.69-2.76 (m, 1 H) 3.82 (sxt, J = 6.19 Hz, 1 H) 5.02 (s, 2 H) 6.85 (d, J = 8.54 Hz, 2 H) 7.14 (d, J = 8.54 Hz, 2 H) 7.45-7.51 (m, 3 H) 7.53-7.57 (m, 2 H) |
| 47A | $^1$H NMR (CHLOROFORM-d) δ ppm 1.24 (d, J = 6.19 Hz, 3 H) 1.69-1.80 (m, 2 H) 2.48 (s, 3 H) 2.59-2.67 (m, 1 H) 2.69-2.76 (m, 1 H) 3.82 (sxt, J = 6.19 Hz, 1 H) 5.02 (s, 2 H) 6.85 (d, J = 8.54 Hz, 2 H) 7.14 (d, J = 8.54 Hz, 2 H) 7.45-7.51 (m, 3 H) 7.53-7.57 (m, 2 H) |
| 47B | $^1$H NMR (CHLOROFORM-d) δ ppm 1.24 (d, J = 6.19 Hz, 3 H) 1.69-1.80 (m, 2 H) 2.48 (s, 3 H) 2.59-2.67 (m, 1 H) 2.69-2.76 (m, 1 H) 3.82 (sxt, J = 6.19 Hz, 1 H) 5.02 (s, 2 H) 6.85 (d, J = 8.54 Hz, 2 H) 7.14 (d, J = 8.54 Hz, 2 H) 7.45-7.51 (m, 3 H) 7.53 -7.57 (m, 2 H) |
| 48 | $^1$H NMR (CHLOROFORM-d) δ ppm 2.47 (s, 3 H) 5.08 (s, 2 H) 6.96 (m, J = 8.80 Hz, 2 H) 7.40-7.56 (m, 6 H) 7.87 (m, J = 8.80 Hz, 2 H) 8.84 (d, J = 1.74 Hz, 1 H) |
| 49 | $^1$H NMR (CHLOROFORM-d) δ ppm 2.43 (s, 3 H) 3.33 (q, J = 5.25, J = 10.31 Hz, 2 H) 3.50 (s, 2 H) 3.61 (t, J = 5.25 Hz, 2 H) 5.01 (s, 2 H) 6.88 (d, J = 8.43 Hz, 2 H) 7.18 (d, J = 8.43 Hz, 2 H) 7.37-7.60 (m, 5 H) |
| 50 | $^1$H NMR (CHLOROFORM-d) δ ppm 0.83 (t, J = 7.34 Hz, 3 H) 1.64-1.75 (m, 1 H) 1.75-1.86 (m, 1 H) 2.45 (s, 3 H) 4.53 (t, J = 6.60 Hz, 1 H) 5.02 (s, 2 H) 6.88 (d, J = 8.52 Hz, 2 H) 7.26 (d, J = 8.52 Hz, 2 H) 7.41-7.55 (m, 5 H) |
| 51 | $^1$H NMR (CHLOROFORM-d) ä ppm 1.55 (s, 6 H) 2.45 (s, 3 H) 5.02 (s, 2 H) 6.87 (d, J = 8.61 Hz, 2 H) 7.41 (d, J = 8.61 Hz, 2 H) 7.43-7.56 (m, 5 H) |
| 52 | $^1$H NMR (CHLOROFORM-d) δ ppm 1.16 (d, J = 6.26 Hz, 6 H) 2.46 (s, 3 H) 3.58-3.65 (m, 5 H) 4.50 (s, 2 H) 5.02 (s, 2 H) 6.87 (m, J = 8.61 Hz, 2 H) 7.28 (m, J = 8.61 Hz, 2 H) 7.40-7.56 (m, 5 H) |
| 53 | $^1$H NMR (CHLOROFORM-d) δ ppm 1.82-1.91 (m, 2 H) 2.44 (s, 3 H) 2.66 (t, J = 7.69 Hz, 2 H) 3.65 (t, J = 6.41 Hz, 2 H) 3.80 (s, 3 H) 5.02 (s, 2 H) 6.67-6.71 (m, 1 H) 6.75 (d, J = 1.28 Hz, 1 H) 6.83 (d, J = 8.12 Hz, 1 H) 7.42-7.51 (m, 3 H) 7.67 (d, J = 7.48 Hz, 2 H) |
| 54 | $^1$H NMR (CHLOROFORM-d) δ ppm 1.43 (d, J = 6.41 Hz, 3 H) 2.44 (s, 3 H) 4.81 (q, J = 6.41 Hz, 1 H) 5.02 (s, 2 H) 6.87 (d, J = 8.54 Hz, 2 H) 7.28 (d, J = 8.54 Hz, 2 H) 7.40-7.55 (m, 5 H) |
| 55 | $^1$H NMR ( CHLOROFORM-d) δ ppm 2.42-2.51 (m, 3 H) 3.30-3.43 (m, 3 H) 4.38 (s, 2 H) 5.03 (s, 2 H) 6.89 (d, J = 8.54 Hz, 2 H) 7.27 (d, J = 8.33 Hz, 2 H) 7.41-7.49 (m, 3 H) 7.50-7.55 (m, 2 H) |
| 56 | $^1$H NMR (DMSO-d) δ 2.38 (s, 3H) 2.73 (t, J = 6.6 Hz, 2H), 3.22 (s, 3H), 3.48 (t, J = 6.8 Hz, 2H), 6.85 (d, J = 8.8 Hz, 2H), 5.17 (s, 2H), 7.14 (d, J = 8.4 Hz, 2H), 7.58-7.52 (m, 5H), |
| 57 | $^1$H NMR (CHLOROFORM-d) δ ppm 2.41 (s, 3 H) 2.67-2.82 (t, J = 6.55 2 H) 3.78 (t, J = 6.55 Hz, 2 H) 4.44 (s, 2 H) 6.46 (d, J = 8.34 Hz, 2 H) 7.01 (d, J = 8.34 Hz, 2 H) 7.43-7.58 (m, 5 H) |

TABLE 2-continued

NMR data of compounds

| Ex. | ¹H-NMR 400 |
|---|---|
| 58 | ¹H NMR (CHLOROFORM-d) δ ppm 2.41 (s, 3 H) 2.74 (t, J = 6.46 Hz, 2 H) 2.91 (s, 3 H) 3.77 (t, J = 6.37 Hz, 2 H) 4.48 (s, 2 H) 6.55 (d, J = 8.43 Hz, 2 H) 7.04 (br d, J = 8.43 Hz, 2 H) 7.39-7.53 (m, 5 H) |
| 59 | ¹H NMR (CHLOROFORM-d) δ ppm 2.31 (s, 3 H) 2.80 (t, J = 6.05 Hz, 2 H) 3.78 (t, J = 6.05 Hz, 2 H) 3.91 (s, 2 H) 7.15 (d, J = 7.97 Hz, 2 H) 7.27 (d, J = 7.97 Hz, 2 H) 7.38-7.50 (m, 5 H) |
| 60 | ¹H NMR (CHLOROFORM-d) δ ppm 2.46 (s, 3 H) 5.18 (s, 2 H) 7.30 (dd, J = 8.61, 2.75 Hz, 1 H) 7.43-7.54 (m, 5 H) 7.66 (d, J = 8.61 Hz, 1 H) 8.34 (d, J = 2.75 Hz, 1 H) |
| 61 | ¹H NMR (CHLOROFORM-d) δ ppm 2.48 (s, 3 H) 5.09 (s, 2 H) 7.08 (br d, J = 8.98 Hz, 1 H) 7.12 (s, 1 H) 7.41 (br d, J = 8.89 Hz, 1 H) 7.44-7.52 (m, 3 H) 7.53-7.59 (m, 2 H) 7.99 (s, 1 H) |
| 62 | ¹H NMR (CHLOROFORM-d) δ ppm 2.48 (s, 3 H) 5.21 (s, 2 H) 7.21 (d, J = 1.92 Hz, 1 H) 7.38 (dd, J = 8.94, 2.43 Hz, 1 H) 7.44-7.57 (m, 5 H) 7.60 (d, J = 5.59 Hz, 1 H) 7.77 (d, J = 8.98 Hz, 1 H) 8.44 (d, J = 5.68 Hz, 1 H) 9.11 (s, 1 H) |
| 63 | ¹H NMR (CHLOROFORM-d) δ ppm 2.45 (s, 3 H) 5.31 (s, 2 H) 7.13 (d, J = 7.51 Hz, 1 H) 7.36 (dd, J = 5.13, 1.56 Hz, 3 H) 7.40-7.45 (m, 2 H) 7.47-7.52 (m, 1 H) 7.68-7.74 (m, 2 H) 8.14 (dd, J = 8.34, 1.28 Hz, 1 H) 8.93 (dd, J = 4.03, 1.47 Hz, 1 H) |
| 64 | ¹H NMR (CHLOROFORM-d) δ ppm 2.48 (s, 3 H) 5.19 (s, 2 H) 7.48-7.56 (m, 5 H) 7.57-7.62 (m, 2 H) 8.37 (dd, J = 3.57, 2.02 Hz, 1 H) |
| 65 | ¹H NMR (CHLOROFORM-d) δ ppm 2.46 (s, 3 H) 5.11 (s, 2 H) 7.11-7.17 (m, 1 H) 7.40 (br t, J = 8.86 Hz, 1 H) 7.45-7.60 (m, 5 H) 7.86 (br d, J = 3.52 Hz, 1 H) |
| 66 | ¹H NMR (CHLOROFORM-d) δ ppm 2.47 (s, 3 H) 5.10 (s, 2 H) 6.99 (dt, J = 9.72, 2.24 Hz, 1 H) 7.42-7.55 (m, 5 H) 8.09-8.24 (m, 2 H) |
| 67 | ¹H NMR (CHLOROFORM-d) δ ppm 2.46 (s, 3 H) 4.69 (s, 2 H) 5.09 (s, 2 H) 7.20-7.29 (m, 2 H) 7.43-7.52 (m, 5 H) 8.20 (s, 1 H) |
| 68 | ¹H NMR (CHLOROFORM-d) δ ppm 2.26 (s, 3 H) 2.48 (s, 3 H) 5.16 (s, 2 H) 7.10 (br d, J = 4.49 Hz, 1 H) 7.50 (br s, 5 H) 8.05-8.28 (m, 2 H) |
| 69 | ¹H NMR (CHLOROFORM-d) δ ppm 2.45 (s, 3 H) 2.49 (s, 3 H) 5.06 (s, 2 H) 7.08 (br d, J = 8.12 Hz, 1 H) 7.12-7.18 (m, 1 H) 7.42-7.52 (m, 5 H) 8.12 (br s, 1 H) |
| 70 | ¹H NMR (CHLOROFORM-d) δ ppm 2.15 (s, 3 H) 2.29 (s, 3 H) 2.45 (s, 3 H) 4.84 (s, 2 H) 6.92 (br d, J = 4.49 Hz, 1 H) 7.51 (m, 3 H) 7.57 (m, 2 H) 8.13 (br d, J = 4.49 Hz, 1 H) |
| 71 | ¹H NMR (CHLOROFORM-d) δ ppm 2.47 (s, 3 H) 5.10 (s, 2 H) 6.79 (dd, J = 8.33, 3.20 Hz, 1 H) 7.47-7.61 (m, 6 H) |
| 72 | ¹H NMR (CHLOROFORM-d) δ ppm 2.08 (s, 3 H) 2.46 (s, 3 H) 2.77 (t, J = 6.51 Hz, 2 H) 3.78 (t, J = 6.51 Hz, 2 H) 4.87 (s, 2 H) 6.74 (d, J = 8.61 Hz, 2 H) 7.09 (d, J = 8.43 Hz, 2 H) 7.20-7.43 (m, 4 H) |
| 73 | ¹H NMR (CHLOROFORM-d) δ ppm 2.36 (s, 3 H) 2.45 (s, 3 H) 2.81 (t, J = 6.55 Hz, 2 H) 3.81 (t, J = 6.55 Hz, 2 H) 5.00 (s, 2 H) 6.87 (d, J = 8.61 Hz, 2 H) 7.16 (d, J = 8.61 Hz, 2 H) 7.17-7.36 (m, 4 H) |
| 74 | ¹H NMR (CHLOROFORM-d) δ ppm 2.40 (s, 3 H) 2.44 (s, 3 H) 2.80 (t, J = 6.51 Hz, 2 H) 3.81 (t, J = 6.51 Hz, 2 H) 4.99 (s, 2 H) 6.86 (d, J = 8.52 Hz, 2 H) 7.15 (d, J = 8.52 Hz, 2 H) 7.26 (d, J = 8.16 Hz, 2 H) 7.40 (d, J = 8.16 Hz, 2 H) |
| 75 | ¹H NMR (CHLOROFORM-d) δ ppm 2.48 (s, 3 H) 2.85 (t, J = 6.46 Hz, 2 H) 3.85 (t, J = 6.46 Hz, 2 H) 5.05 (s, 2 H) 6.92 (d, J = 8.52 Hz, 2 H) 7.20 (d, J = 8.52 Hz, 2 H) 7.39-7.52 (m, 3 H) 7.65 (m, 1 H) |
| 76 | ¹H NMR (CHLOROFORM-d) δ ppm 2.46 (s, 3 H) 2.83 (t, J = 6.51 Hz, 2 H) 3.84 (t, J = 6.51 Hz, 2 H) 5.01 (s, 2 H) 6.88 (d, J = 8.61 Hz, 2 H) 7.19 (d, J = 8.61 Hz, 2 H) 7.43-7.48 (m, 2 H) 7.50-7.55 (m, 2 H) |
| 77 | ¹H NMR (CHLOROFORM-d) δ ppm 2.48 (s, 3 H) 2.83 (t, J = 6.51 Hz, 2 H) 3.84 (t, J = 6.51 Hz, 2 H) 5.04 (s, 2 H) 6.89 (d, J = 8.52 Hz, 2 H) 7.19 (d, J = 8.52 Hz, 2 H) 7.60-7.66 (m, 1 H) 7.69 (br d, J = 7.97 Hz, 1 H) 7.80 (br d, J = 7.97 Hz, 1 H) 7.92 (s, 1 H) |
| 78 | ¹H NMR (CHLOROFORM-d) δ ppm 1.26 (t, J = 7.61 Hz, 3 H) 2.46 (s, 3 H) 2.71 (q, J = 7.61 Hz, 2 H) 2.82 (t, J = 6.51 Hz, 2 H) 3.83 (t, J = 6.51 Hz, 2 H) 5.01 (s, 2 H) 6.88 (d, J = 8.52 Hz, 2 H) 7.17 (d, J = 8.52 Hz, 2 H) 7.30 (d, J = 8.34 Hz, 2 H) 7.44 (d, J = 8.34 Hz, 2 H) |
| 79 | ¹H NMR (METHANOL-d4) δ ppm 2.42 (s, 3 H) 2.76 (t, J = 7.04 Hz, 2 H) 3.71 (t, J = 7.04 Hz, 2 H) 3.75 (s, 3 H) 5.10 (s, 2 H) 6.86 (d, J = 8.61 Hz, 2 H) 7.04-7.08 (m, 1 H) 7.10-7.18 (m, 4 H) 7.42 (t, J = 8.41 Hz, 1 H) |
| 80 | ¹H NMR (METHANOL-d4) δ ppm 2.38 (s, 3 H) 2.74 (t, J = 7.04 Hz, 2 H) 3.69 (t, J = 7.04 Hz, 2 H) 3.82 (s, 3 H) 5.02 (s, 2 H) 6.82 (d, J = 8.61 Hz, 2 H) 6.98-7.04 (m, 2 H) 7.12 (d, J = 8.61 Hz, 2 H) 7.38-7.44 (m, 2 H) |
| 81 | ¹H NMR (CHLOROFORM-d) δ ppm 2.47 (s, 3 H) 2.83 (t, J = 6.51 Hz, 2 H) 3.84 (t, J = 6.51 Hz, 2 H) 5.05 (s, 2 H) 6.89 (d, J = 8.61 Hz, 2 H) 7.19 (d, J = 8.61 Hz, 2 H) 7.32 (br d, J = 7.42 Hz, 1 H) 7.49-7.58 (m, 1 H) 7.51-7.56 (m, 3 H) |
| 82 | ¹H NMR (CHLOROFORM-d) δ ppm 2.45 (s, 3 H) 2.77 (t, J = 6.55 Hz, 2 H) 3.78 (t, J = 6.55 Hz, 2 H) 5.04 (s, 2 H) 6.72 (d, J = 8.52 Hz, 2 H) 7.09 (d, J = 8.52 Hz, 2 H) 7.20-7.32 (m, 2 H) 7.43-7.52 (m, 2 H) |

TABLE 2-continued

NMR data of compounds

| Ex. | ¹H-NMR 400 |
|---|---|
| 83 | ¹H NMR (DMSO) + 2.38 (s, 3H) 5.21 (s, 2H), 6.94 (d, J = 8.0 Hz, 2H), 7.00 (t, J = 7.4 Hz, 1H), 7.33-7.27 (m, 2H), 7.43-7.39 (m, 2H), 7.66-7.62 (m, 2H) |
| 84 | ¹NMR (DMSO) δ 2.20 (s, 3H), 4.42 (s, 2H), 9.43 (bs, 1H), 10.25 (bs, 1H) |
| 85 | ¹H NMR (METHANOL-d4) δ 2.46 (s, 3H), 5.16 (s, 2H), 6.78-6.71 (m, 3H) 7.33-7.27 (m, 3H), 7.62-7.57 (m, 2H) |
| 86 | ¹H NMR (METHANOL-d4) δ 2.11 (s, 3H), 2.45 (s, 3H), 5.17 (s, 2H), 6.84 (d, J = 7.6 Hz, 1H), 6.90 (t, J = 7 Hz, 1H), 7.28-7.11 (m, 2H), 7.33-7.28 (m, 2H), 7.62-7.59 (m, 2H) |
| 87 | ¹H NMR (METHANOL-d4) δ 1.85-1.79 (m, 2H) 2.44 (s, 3H), 2.64 (t, J = 7.6 Hz, 2H), 3.56 (t, J = 6.4 Hz, 2H), 5.11 (s, 2H), 6.85 (d, J = 8.8 Hz, 2H), 7.14 (d, J = 8.4 Hz, 2H), 7.62-7.58 (m, 2H), 7.75 (t, J = 8.6 Hz, 2H) |
| 88 | ¹H NMR (CHLOROFORM-d) δ ppm 2.38 (s, 3 H) 2.80 (t, J = 6.60 Hz, 2 H) 3.80 (t, J = 6.60 Hz, 2 H) 4.99 (s, 2 H) 5.36 (s, 2 H) 6.82 (d, J = 8.25 Hz, 2 H) 7.15 (br d, J = 8.43 Hz, 4 H) 7.28-7.35 (m, 3 H) |
| 89 | ¹H NMR (CHLOROFORM-d) δ ppm 1.81-1.90 (m, 2 H) 2.38 (s, 3 H) 2.65 (t, J = 7.70 Hz, 2 H) 3.64 (t, J = 6.42 Hz, 2 H) 4.98 (s, 2 H) 5.36 (s, 2 H) 6.80 (d, J = 8.61 Hz, 2 H) 7.12 (d, J = 8.61 Hz, 2 H) 7.16 (dd, J = 6.92, 2.25 Hz, 2 H) 7.28-7.34 (m, 3 H) |
| 90 | ¹H NMR (CHLOROFORM-d) δ ppm 1.79-1.88 (m, 2 H) 2.36 (s, 3 H) 2.65 (t, J = 7.70 Hz, 2 H) 3.64 (t, J = 6.28 Hz, 2 H) 5.05 (s, 2 H) 5.49 (s, 2 H) 6.73-6.80 (m, 2 H) 7.19-7.26 (m, 2 H) 7.29-7.38 (m, 3 H) |
| 91 | ¹H NMR (CHLOROFORM-d) δ ppm 2.36 (s, 3 H) 2.80 (t, J = 6.55 Hz, 2 H) 3.77 (s, 2 H) 3.80 (t, J = 6.55 Hz 2H) 4.98 (s, 2 H) 5.28 (s, 2 H) 6.84 (m, 4 H) 7.14 (m, 4 H) |
| 92 | ¹H NMR (CHLOROFORM-d) δ ppm 1.76 (d, J = 6.51 Hz, 3 H) 2.40 (s, 3 H) 2.77 (t, J = 6.55 Hz, 2 H) 3.79 (t, J = 6.55 Hz, 2 H) 5.35 (q, J = 6.51 Hz, 1 H) 6.67 (d, J = 8.52 Hz, 2 H) 7.06 (d, J = 8.52 Hz, 2 H) 7.31-7.39 (m, 2 H) 7.49-7.57 (m, 3 H) |
| 93 | ¹H NMR (CHLOROFORM-d) δ ppm 1.72 (d, J = 6.69 Hz, 3 H) 1.78-1.89 (m, 2 H) 2.44 (s, 3 H) 2.64 (t, J = 7.70 Hz, 2 H) 3.65 (t, J = 6.28 Hz, 2 H) 5.31 (q, J = 6.69 Hz, 1 H) 6.69 (d, J = 8.80 Hz, 2 H) 7.32 (dd, J = 7.42, 1.74 Hz, 2 H) 7.43-7.49 (m, 3 H) |
| 94 | ¹H NMR (CHLOROFORM-d) δ ppm 2.50 (s, 3 H) 2.82 (t, J = 6.51 Hz, 2 H) 3.81 (t, J = 6.51 Hz, 2 H) 6.91 (d, J = 8.25 Hz, 2 H) 7.16 (d, J = 8.25 Hz, 2 H) 7.48-7.57 (m, 5 H) |
| 95 | ¹H NMR (CHLOROFORM-d) δ ppm 1.78-1.90 (m, 2 H) 2.50 (s, 3 H) 2.58-2.70 (m, 2 H) 3.65 (q, J = 6.23 Hz, 2 H) 6.87 (d, J = 8.52 Hz, 2 H) 7.11 (d, J = 8.52 Hz, 2 H) 7.47-7.58 (m, 5 H) |
| 96 | ¹H NMR (CHLOROFORM-d) δ ppm 1.79-1.88 (m, 2 H) 2.50 (s, 3 H) 2.64-2.72 (m, 2 H) 3.64 (t, J = 6.23 Hz, 2 H) 6.79 (d, J = 8.43 Hz, 2 H) 7.46-7.55 (m, 5H) |
| 97 | ¹H NMR (CHLOROFORM-d) δ ppm 2.47 (s, 3 H) 4.61 (s, 2 H) 4.67 (s, 2 H) 7.42 (d, J = 8.16 Hz, 2 H) 7.47-7.57 (m, 5 H) 7.64 (d, J = 8.16 Hz, 2 H) |
| 98 | ¹H NMR (DMSO-d) δ 2.36 (s, 3H), 4.53 (s, 2H), 4.59 (s, 2H), 7.45-7.21 (m, 7H), 7.63-7.59 (m, 2H) |
| 99 | ¹H NMR (DMSO-d) δ 1.04 (t, J = 7.6 Hz, 3H), 2.35-2.29 (m, 2H), 2.38 (s, 3H), 2.62 (t, J = 7 Hz, 2H), 3.54-3.50 (m, 2H), 4.58 (t, J = 5.2 Hz, 1H), 4.94 (s, 2H), 6.97 (d, J = 8.8 Hz, 2H), 7.09 (d, J = 8.4 Hz, 2H), 7.37-7.35 (m, 2H), 7.51-7.47 (m, 2H), |
| 100 | ¹H NMR (DMSO d) δ 2.40 (s, 3H), 2.65 (t, J = 7.0 Hz, 2H), 3.30 (s, 3H), 3.55 (dd, J = 6.8 and 12.4 Hz, 2H), 4.61 (t, J = 5.2 Hz, 1H), 5.29 (s, 2H), 6.87 (d, J = 8.4 Hz, 2H), 7.14 (d, J = 8.4 Hz, 2H), 7.88 (d, J = 8.4 Hz, 2H), 8.11 (d, J = 8.8 Hz, 2H) |
| 101 | ¹H NMR (DMSO-d) δ 2.38 (s, 3H), 2.65 (t, J = 7.0 Hz, 2H), 3.54 (dd, J = 7.2 and 12.4 Hz, 2H), 4.61 (t, J = 5.2 Hz, 1H), 5.23 (s, 2H), 6.85 (d, J = 8.8 Hz, 2H), 7.13 (d, J = 8.4 Hz, 2H), 7.43-7.35 (m, 1H), 7.45 (d, J = 8.0 Hz, 1H), 7.51 (d, J = 9.6 Hz, 1H), 7.61 (dd, J = 8.0 and 14.8 Hz, 1H) |
| 102 | ¹H NMR (METHANOL-d₄) δ 2.20 (s, 3H); 2.64 (t, J = 7 Hz, 2H), 3.54 (q, J = 7 Hz, 2H), 4.61 (t, J = 5.2 Hz, 1H), 4.85 (s, 2H), 6.77 (d, J = 8.8 Hz, 2H), 7.10 (d, J = 8.4 Hz, 2H), 9.30 (bs, 1H), 10.26 (bs, 1H) |
| 103 | ¹H NMR (DMSO-d) δ 2.46 (s, 3H), 2.77 (t, J = 7 Hz, 2H), 3.72 (t, J = 7 Hz, 2H), 5.19 (s, 2H), 6.86 (d, J = 8.8 Hz, 2H), 7.17 (d, J = 8.4 Hz, 2H), 7.64-7.60 (m, 1H), 8.10-8.07 (m, 1H), 8.67 (d, J = 4.8 Hz, 1H), 8.81 (d, J = 2.4 Hz, 1H) |
| 104 | ¹H NMR (METHANOL-d₄) δ 2.46 (s, 3H), 2.79 (t, J = 7 Hz, 2H), 3.73 (t, J = 7 Hz, 2H), 5.29 (s, 2H), 6.92 (d, J = 8.8 Hz, 2H), 7.20 (d, J = 8.4 Hz, 2H), 8.71 (dd, J = 1.2 and 4.4 Hz, 2H), 7.75 (dd, J = 1.6 and 4.8 Hz, 2H), |
| 105 | ¹H NMR (METHANOL-d₄) δ 2.48 (s, 3H), 2.79 (t, J = 7Hz, 2H), 3.73 (t, J = 7 Hz, 2H), 5.74 (s, 2H), 6.95 (d, J = 8.8 Hz, 2H), 7.19 (d, J = 8.4 Hz, 2H), 7.52 (t, J = 5 Hz, 1 H), 8.89 (d, J = 5.2 Hz, 2H), |
| 106 | ¹H NMR (METHANOL-d₄) δ 2.48 (s, 3H), 2.78 (t, J = 7 Hz, 2H), 3.73 (t, J = 7 Hz, 2H), 5.78 (s, 2H), 6.97 (d, J = 8.4 Hz, 2H), 7.18 (d, J = 8.8 Hz, 2H), 7.96 (dd, J = ~.4 and 8.8 Hz, 1 H), 8.32 (dd, J = 1.6 and 9.2 Hz, 1 H), 9.21 (dd, J = 1.2 and 4.8 Hz, 1 H), |
| 107 | ¹H NMR (METHANOL-d₄) δ 2.46 (s, 3H), 2.78 (t, J = 7 Hz, 2H), 3.73 (t, J = 7 Hz, 2H), 5.21 (s, 2H), 6.88 (d, J = 8.8 Hz, 2H), 7. 18 (d, J = 8 Hz, 2H), 7.81 (d, J = 8.4 Hz, 2H), 7.92 (d, J = 8.8 Hz, 2H), |

TABLE 2-continued

NMR data of compounds

| Ex. | ¹H-NMR 400 |
|---|---|
| 108 | ¹H NMR (METHANOL-d₄) δ 2.46 (s, 3H), 2.78 (t, J = 7 Hz, 2H), 3.73 (t, J = 7 Hz, 2H), 5.20 (s, 2H) , 6.87 (d, J = 8.8 Hz, 2H), 7.18 (d, J = 8.8 Hz, 2H), 7.73 (t, J = 7.8 Hz, 1 H), 7.93-7.87 (m, 2H) 8. 01 (s, 1 H), |
| 109 | ¹H NMR (DMSO) δ 2.40 (s, 3H), 2.66 (t, J = 6 Hz, 2H), 3.54 (d, J = 5.2 Hz, 2H), 4.60 (bs, 1 H), 5.27 (s, 2H), 6.86 (d, J = 8.0 Hz, 2H), 7.95 (d, J = 8Hz, 2H), 7.13 (d, J = 7.6 Hz, 2H), 7.83 (d, J = 8Hz, 2H), Hz, 2H), |
| 110 | ¹H NMR (CDCl₃) δ 1.42-1.49 (m, 1H), 2.49 (s, 3H), 2.79 (t, J = 6.4 Hz, 2H), 3.84-3.79 (m, 2H), 5.21 (s, 2H), 6.70 (d, J = 8.4 Hz, 2H), 7.10 (d, J = 8.8 Hz, 2H), 7.36 (dd, 4.8 and 8 Hz, 1H), 8.14 (dd, J = 1.6 and 8.4 Hz, 1H), 8.51 (dd, J = 1.6 and 4.8 Hz, 1H), |
| 111 | ¹H NMR (CDCl₃) δ 1.40 (t, J = 5.8 Hz, 1 H). 2.51 (s, 3H), 2.80 (t, J = 6.6 Hz, 2H), 3.82 (q, J = 6.4; 2H), 4.99 (s, 2H),), 6.75 (d, J = 2 Hz, 2H), 7.12 (d; J = 8.0 Hz, 2H) 7.44-7.40 (m, 1H) 7.50-7.48 · (m, 2H),), |
| 112 | ¹H NMR (DMSO) δ 2.38 (s, 3H), 2.62 (t, J = 7 Hz, 2H), 3.52 (dd, J = 6.8 and 12 Hz, 2H), 4.58 (t, J = 5 Hz, 1H), 5.11 (s, 2H), 6.73 (d, J = 8.8 Hz, 2H), 7.08 (d, J = 8.4 Hz, 2H), 7.42 (t, J = 8.4 Hz, 2H), 7.74-7.69 (m, 1H), |
| 113 | ¹H NMR (DMSO-d) δ 2.38 (s, 3H) 2.62 (t, J = 7 Hz, 2H), 3.52 (t, J = 7 Hz, 2H), 4.61 (bs, 1H), 5.02 (s, 2H), 6.09 (d, J = 8.4 Hz, 2H), 6.74 (d, J = 8.4 Hz, 2H), 7.40 (d , J = 8 Hz, 1H), 7.55-7.51 (m, 1 H),7.64-7.59 (m, 2H), |
| 114 | ¹H NMR (DMSO-d) δ 2.37 (s, 3H), 2.63 (t, J = 7 Hz, 2H), 3.52-3.51 (m, 2H), 4.61-4.59 (t, J = 5.2 Hz, 1H), 5.10 (s, 2H), 6.76 (d, J = 8.8 Hz, 2H), 7.11 (d, J = 8.4 Hz, 2H), 7.29 (t, J = 8 Hz 1 8), 7.66-7.60 (m, 1H), 7.75-7.69 (m, 1H), |
| 115 | ¹H NMR (CHLOROFORM-d) δ 1.46 (t, J = 6 Hz, 1H), 2.48 (s, 3H), 2.85 (t, J = 6.4 Hz, 2H), 3.88-3.84 (m, 2H), 5.04 (s, 2H), 6.89 (d, J = 8.4 Hz, 2H), 7.20 (d, J = 8.4 Hz, 2H), 7.35 (d, J = 8.4 Hz, 2H), 7.64 (d, J = 8.8 Hz, 2H), |
| 116 | ¹H NMR (DMSO) δ 2.41 (s, 3H); 2.66 (t, J = 7 Hz, 2H), 3.58-3.55 (m, 2H), 4.61 (t, J = 5.2 Hz, 1H), 5.69 (s, 2H), 6.91 (d, J = 8.4 Hz, 2H), 7.15 (d, J = 8.4 Hz, 2H), 8.18 (d, J = 9.2 Hz, 1H), 8.28 (d, J = 9.2 Hz, 1H), |
| 117 | ¹H NMR (DMSO) δ 1.65-1.55 (m, 2H), 1.94-1.75 (m, 4H), 2.13-1.95 (m, 2H), 2.27 (s, 3H), 2.66 (t, J = 7.0 Hz, 2H), 3.55 (dd, J = 6.8 and 12 Hz, 2H), 4.62 (t, J = 5.0 Hz, 1H), 4.83-4.78 (m, 1H), 5.24 (s, 2H), 6.96 (d, J = 8.4 Hz, 2H), 7.17 (d, J = 8.4 Hz, 2H) |
| 118 | ¹H NMR (DMSO) δ 1.24-1.10 (m, 1H), 1.41-1.25 (m, 2H), 1.69-1.40 (m, 1H), 1.90-1.70 (m, 6H), 2.27 (s, 3H), 2.66 (t, J = 7.2 Hz, 2H), 3.55 (dd, J = 7.2 and 12.4 Hz, 2H), 4.30-4.15 (m, 1H), 4.62 (t, J = 5.2 Hz, 1H), 5.25 (s, 2H), 6.95 (d, J = 8.8 Hz, 2H), 7.17 (d, J = 8.4 Hz, 2H) |
| 119 | ¹H NMR (DMSO) δ 2.16-1.95 (m, J = 8.8 Hz, 2H) 2.67 (t, J = 7.2 Hz, 2H), 2.82 (s,3H) 3.56 (q, J = 7 Hz, 2H), 4.55 (bs, 1 H), 4.61 (t, J = 5.2 Hz, 1 H), 5.28 (s, 2H), 6.97 (d, J = 8.8 Hz, 2H), 7.18 (d, J = 8.8 Hz, 2H), |
| 120 | ¹H NMR (METHANOL-d₄) δ ppm 1.72-1.88 (m, 2 H) 2.45 (s, 3 H) 2.58-2.67 (m, 2 H) 3.55 (t, J = 6.26 Hz, 2 H) 5.22 (s, 2 H) 6.74-6.84 (m, 2 H) 7.43-7.59 (m, 5 H) |
| 121A | ¹H NMR (METHANOL-d₄) δ ppm 2.47 (s, 3 H) 2.74 (t, J = 6.85 Hz, 2 H) 3.72 (t, J = 6.85 Hz, 2 H) 5.19 (s, 2 H) 6.86-7.03 (m, 3 H) 7.50 (s, 5 H) |
| 121B | ¹H NMR (METHANOL-d₄) δ ppm 2.51 (s, 3 H) 2.74 (t, J = 6.85 Hz, 2 H) 3.71 (t, J = 6.85 Hz, 2 H) 5.27 (s, 2 H) 6.87-7.02 (m, 3 H) 7.43-7.52 (m, 3 H) 7.52-7.61 (m, 2 H) |
| 122 | ¹H NMR (CHLOROFORM-d) δ ppm 2.80 (t, J = 6.60 Hz, 2 H) 3.80 (t, J = 6.60 Hz, 2 H) 4.98 (s, 2 H) 6.56 (s, 1 H) 6.87 (d, J = 8.43 Hz, 2 H) 7.14 (d, J = 8.34 Hz, 2 H) 7.34-7.41 (m, 1 H) 7.42-7.49 (m, 2 H) 7.59 (br d, J = 7.79 Hz, 2 H) 7.69 (s, 1 H) |
| 123 | ¹H NMR (CHLOROFORM-d) δ ppm 4.56 (s, 2 H) 5.05 (s, 2 H) 6.53 (d, J = 1.37 Hz, 1 H) 6.85-6.92 (m, 1 H) 6.96-7.01 (m, 1 H) 7.09 (br d, J = 11.82 Hz, 1 H) 7.36-7.43 (m, 1 H) 7.43-7.50 (m, 2 H) 7.60 (d, J = 7.97 Hz, 2 H) 7.65 (d, J = 1.37 Hz, 1 H) |
| 124 | ¹H NMR (CHLOROFORM-d) δ ppm 2.90 (t, J = 4.67, OH) 4.55 (d, J = 4.67 Hz, 2 H) 5.09 (s, 2 H) 6.43 (d, J = 1.56 Hz, 1 H) 6.81-6.89 (m, 2 H) 7.38-7.45 (m, 1 H) 7.47-7.54 (m, 2 H) 7.58-7.62 (m, 1 H) 7.60 (d, J = 1.37 Hz, 1 H) 7.69 (d, J = 7.70 Hz, 2 H) |
| 125 | ¹H NMR (CHLOROFORM-d) δ ppm 2.34 (s, 3 H) 4.57 (s, 2 H) 5.00 (s, 2 H) 6.33 (s, 1 H) 6.84-6.92 (m, 1 H) 6.98 (d, J = 8.16 Hz, 1 H) 7.09 (d, J = 11.82 Hz, 1 H) 7.32-7.40 (m, 1 H) 7.44 (t, J = 7.61 Hz, 2 H) 7.57 (br d, J = 8.16 Hz, 2 H) |
| 126 | ¹H NMR (CHLOROFORM-d) δ ppm 2.36 (s, 3 H) 2.79 (t, J = 6.64 Hz, 2 H) 3.78 (t, J = 6.64 Hz, 2 H) 4.93 (s, 2 H) 6.36 (s, 1 H) 6.87 (d, J = 8.43 Hz, 2 H) 7.13 (br d, J = 8.43 Hz, 2 H) 7.31-7.38 (m, 1 H) 7.43 (t, J = 7.65 Hz, 2 H) 7.56 (br d, J = 7.70 Hz, 2 H) |
| 127 | ¹H NMR (CHLOROFORM-d) δ ppm 2.29 (s, 3 H) 3.81 (t, J = 3.67 Hz, OH) 4.47 (d, J = 3.67 Hz, 2 H) 5.01 (s, 2 H) 6.24 (s, 1 H) 6.79 (d, J = 8.61 Hz, 2 H) 7.34-7.41 (m, 2 H) 7.42-7.50 (m, 2 H) 7.63 (br d, J = 7.79 Hz, 2 H) |
| 128 | ¹H NMR (CHLOROFORM-d) δ ppm 1.35 (s, 9 H) 2.79 (t, J = 6.68 Hz, 2 H) 3.79 (t, J = 6.68 Hz, 2 H) 5.12 (s, 2 H) 6.31 (s, 1 H) 6.87 (d, J = 8.44 Hz, 2 H) 7.14 (d, J = 8.44 Hz, 2 H) 7.38-7.46 (m, 3 H) 7.46-7.50 (m, 2 H) 7.98 (s, 1 H) |
| 129 | ¹H NMR (CHLOROFORM-d) δ ppm 2.82 (t, J = 6.51 Hz, 2 H) 3.83 (t, J = 6.51 Hz, 2 H) 5.06 (s, 2 H) 6.87 (d, J = 8.52 Hz, 2 H) 7.17 (d, J = 8.52 Hz, 2 H) 7.44-7.61 (m, 5 H) 7.97 (s, 1 H) |

TABLE 2-continued

NMR data of compounds

| Ex. | ¹H-NMR 400 |
|---|---|
| 130 | ¹H NMR (CHLOROFORM-d) δ ppm 1.82-1.91 (m, 2 H) 2.67 (t, J = 7.70 Hz, 2 H) 3.66 (t, J = 6.42 Hz, 2 H) 5.06 (s, 2 H) 6.85 (d, J = 8.52 Hz, 2 H) 7.14 (d, J = 8.52 Hz, 2 H) 7.47-7.54 (m, 3 H) 7.54-7.60 (m, 2 H) 7.98 (s, 1 H) |
| 131 | ¹H NMR (CHLOROFORM-d) δ ppm 2.37 (s, 3 H) 2.93 (t, J = 5.77 Hz, 2 H) 3.90 (t, J = 5.77 Hz, 2 H) 4.08 (d, J = 13.56 Hz, 1 H) 4.27 (d, J = 13.56 Hz, 1 H) 7.38-7.57 (m, 9 H) |
| 132 | ¹H NMR (CHLOROFORM-d) δ ppm 2.36 (s, 3 H) 2.96 (t, J = 5.64 Hz, 2 H) 3.90 (t, J = 5.64 Hz, 2 H) 4.46 (s, 2 H) 7.48 (d, J = 8.16 Hz, 2 H) 7.51-7.57 (m, 5 H) 7.72 (d, J = 8.16 Hz, 2 H) |
| 133 | ¹H NMR (CHLOROFORM-d) δ ppm 2.44 (s, 3 H) 2.66 (t, J = 7.76 Hz, 2 H) 2.90 (t, J = 7.76 Hz, 2 H) 5.07 (s, 2 H) 6.80 (br d, J = 8.61 Hz, 2 H) 7.46-7.57 (m, 3 H) 7.69 (br d, J = 7.51 Hz, 2 H) |
| 134 | ¹H NMR (DMSO-d) δ 2.08 (s, 3H). 3.49 (s, 2H), 5.19 (s, 2H); 6.87 (d, J = 8.4 Hz, 2H), 7.18 (d, J = 8.4 Hz, 2H), 7.57-7.50 (m, 5H), 12.28 (bs, 1H), |
| 135 | ¹H NMR (CHLOROFORM-d) δ 1.91-1.84 (m, 2H). 2.49 (s, 3H), 2.66 (t, J = 7.6 Hz, 2H), 3.41-3.36 (m, 5H), 5.03 (s, 2H), 6.86 (d, J = 8 Hz, 2H), 7.14 (d, J = 8.4 Hz, 2H), 7.57-7.47 (m, 5H), |
| 136 | ¹H NMR (CHLOROFORM-d) δ ppm 1.40-1.57 (m, 3 H) 1.57-1.68 (m, 2 H) 1.94 (br d, J = 11.82 Hz, 2 H) 2.48 (s, 3 H) 2.60 (br t, J = 7.42 Hz, 2 H) 2.76-3.01 (m, 2 H) 3.46 (br d, J = 11.00 Hz, 2 H) 5.02 (s, 2 H) 6.85 (br d, J = 8.43 Hz, 2 H) 7.09 (br d, J = 8.43 Hz, 2 H) 7.44-7.57 (m, 5 H) |
| 137 | ¹H NMR (CHLOROFORM-d) δ ppm 2.40 (s, 3 H) 3.12-3.28 (m, 2 H) 4.94 (br s, 1 H) 4.99 (s, 2 H) 6.85 (br d, J = 8.06 Hz, 2 H) 7.15-7.26 (m, 2 H) 7.40-7.59 (m, 5 H) 9.50 (br s, NH2) |
| 138 | ¹H NMR (CHLOROFORM-d) δ ppm 1.36-1.50 (m, 1 H) 1.56 (q, J = 11.64 Hz, 1 H) 1.65-2.07 (m, 5 H) 2.45 (s, 3 H) 2.53-2.69 (m, 2 H) 2.82 (br d, J = 10.91 Hz, 1 H) 2.94 (br s, 1 H) 3.30 (br d, J = 12.01 Hz, 1 H) 3.77 (br t, J = 6.42 Hz, 1 H) 4.98 (s, 2 H) 6.81 (d, J = 8.52 Hz, 2 H) 7.06 (d, J = 8.52 Hz, 2 H) 7.40-7.56 (m, 5 H) |
| 139 | ¹H NMR (METHANOL-d₄) δ ppm 2.43 (s, 3 H) 5.24 (s, 2 H) 7.08 (d, J = 8.61 Hz, 2 H) 7.47-7.62 (m, 5 H) 7.71-7.94 (d, J = 8.61 Hz, 2 H) |
| 140 | ¹H NMR (METHANOL-d4) δ ppm 2.41 (s, 3 H) 2.90 (t, J = 7.63 Hz, 2 H) 3.14 (t, J = 7.63 Hz, 2 H) 5.12 (s, 2 H) 6.91 (d, J = 8.61 Hz, 2 H) 7.20 (d, J = 8.61 Hz, 2 H) 7.47-7.59 (m, 5 H) |
| 141 | ¹H NMR (CHLOROFORM-d) δ ppm 1.94 (s, 3 H) 2.46 (s, 3 H) 2.77 (t, J = 6.83 Hz, 2 H) 3.48 (q, J = 6.63 Hz, 2 H) 5.02 (s, 2 H) 6.88 (d, J = 8.52 Hz, 2 H) 7.13 (d, J = 8.43 Hz, 2 H) 7.43-7.60 (m, 5 H) |
| 142 | ¹H NMR (CHLOROFORM-d) δ ppm 2.46 (s, 3 H) 2.90 (t, J = 6.69 Hz, 2 H) 3.69 (q, J = 6.69 Hz, 2 H) 5.03 (s, 2 H) 6.30 (br s, NH) 6.88 (br d, J = 8.43 Hz, 2 H) 7.17 (br d, J = 8.34 Hz, 2 H) 7.38-7.60 (m, 8 H) 7.72 (br d, J = 7.42 Hz, 2 H) |
| 143 | ¹H NMR (CHLOROFORM-d) δ ppm 2.47 (s, 3 H) 2.81-2.88 (br s, 5 H) 3.37 (q, J = 6.63 Hz, 2 H) 4.41 (br s, NH) 5.03 (s, 2 H) 6.88 (m, J = 8.52 Hz, 2 H) 7.15 (m, J = 8.43 Hz, 2 H) 7.44-7.59 (m, 5 H) |
| 144 | ¹H NMR (CHLOROFORM-d) δ ppm 2.47 (s, 3 H) 2.72 (t, J = 6.69 Hz, 2 H) 3.20 (q, J = 6.69 Hz, 2 H) 4.62 (br t, NH) 5.01 (s, 2 H) 6.82 (d, J = 8.43 Hz, 2 H) 7.01 (d, J = 8.43 Hz, 2 H) 7.43-7.60 (m, 8 H) 7.82 (d, J = 7.51 Hz, 2 H) |
| 145 | ¹H NMR (CHLOROFORM-d) δ ppm 2.47 (s, 3 H) 2.67 (t, J = 6.74 Hz, 2 H) 3.42 (q, J = 6.74 Hz, 2 H) 3.52 (s, 2 H) 5.00 (s, 2 H) 5.41 (br s, NH) 6.78 (d, J = 8.34 Hz, 2 H) 6.95 (d, J = 8.43 Hz, 2 H) 7.18 (br d, J = 6.97 Hz, 2 H) 7.23-7.35 (m, 3 H) 7.42-7.59 (m, 5 H) |
| 146 | ¹H NMR (CHLOROFORM-d) δ ppm 2.47 (s, 3 H) 4.78 (s, 2 H) 5.08 (s, 2 H) 6.93 (m, J = 8.71 Hz, 2 H) 7.11 (s, 1 H) 7.42-7.54 (m, 5 H) 7.85 (m, J = 8.71 Hz, 2 H) |
| 147 | ¹H NMR (CHLOROFORM-d) δ ppm 2.47 (s, 3 H) 4.64 (s, 2 H) 5.08 (s, 2 H) 7.06 (d, J = 8.52 Hz, 1 H) 7.27-7.51 (m, 4 H) 7.53-7.63 (m, 3 H) |
| 148 | ¹H NMR (CHLOROFORM-d) δ ppm 1.91-2.11 (m, 2 H) 2.45 (s, 3 H) 3.72 (br t, J = 6.37 Hz, 1 H) 4.90 (br dd, J = 9.49, 3.62 Hz, 1 H) 5.03 (s, 2 H) 6.90 (d, J = 8.43 Hz, 2 H) 7.26-7.34 (m, 2 H) 7.42-7.60 (m, 5 H) |
| 149 | ¹H NMR (CDCl₃) δ ppm 1.79-1.90 (m, 2 H) 2.41-2.48 (m, 3 H) 2.64 (t, J = 7.65 Hz, 2 H) 3.65 (t, J = 6.42 Hz, 2 H) 5.62-5.70 (m, 2 H) 6.91 (d, J = 8.52 Hz, 2 H) 7.11 (d, J = 8.52 Hz, 2 H) 7.20-7.30 (m, 1 H) 7.83-7.89 (m, 1 H) 7.90-7.95 (m, 1 H) 8.38-8.43 (m, 1 H) |
| 150 | ¹H NMR (CDCl₃) δ ppm 1.79-1.88 (m, 2 H) 2.38 (s, 3 H) 2.44 (s, 3 H) 2.64 (t, J = 7.70 Hz, 2 H) 3.60-3.67 (m, 2 H) 4.97 (s, 2 H) 6.83 (d, J = 8.52 Hz, 2 H) 7.11 (d, J = 8.52 Hz, 2 H) 7.24 (d, J = 8.34 Hz, 2 H) 7.39 (d, J = 8.34 Hz, 2 H) |
| 151 | ¹H NMR (CDCl₃) δ ppm 1.24 (t, J = 7.56 Hz, 3 H) 1.74-1.89 (m, 2 H) 2.44 (s, 3 H) 2.54-2.75 (m, 4 H) 3.55-3.69 (m, 2 H) 4.99 (s, 2 H) 6.83 (d, J = 8.34 Hz, 2 H) 7.10 (m, J = 8.34 Hz, 2 H) 7.27 (m, J = 8.25 Hz, 2 H) 7.41 (m, J = 8.25 Hz, 2 H) |
| 152 | ¹H NMR (CDCl₃) δ ppm 1.78-1.91 (m, 2 H) 2.44 (s, 3 H) 2.62 (t, 7.62 Hz, 2 H) 3.65 (t, J = 6.26 Hz, 2 H) 4.98 (s, 2 H) 6.83 (d, J = 8.34 Hz, 2 H) 7.12 (d, J = 8.34 Hz, 2 H) 7.42 (d, J = 8.74 Hz, 2 H) 7.49 (d, J = 8.74 Hz, 2 H) |
| 153 | ¹H NMR (CDCl₃) δ ppm 1.56-1.70 (m, 2H) 1.82-1.97 (br.s, 4H) 2.02-2.11 (m, 4 H) 2.35 (s, 3 H) 2.66 (t, J = 6.42 Hz, 2 H) 3.65 (t, J = 7.42 Hz, 2 H) 4.68 (quin, J = 7.56 Hz, 1 H) 5.07 (s, 2 H) 6.89 (d, J = 8.61 Hz, 2 H) 7.15 (d, J = 8.52 Hz, 2 H) |

TABLE 2-continued

NMR data of compounds

| Ex. | $^1$H-NMR 400 |
|---|---|
| 154 | $^1$H NMR (CDCl$_3$) δ ppm 1.80-1.89 (m, 2 H) 2.43 (s, 3 H) 2.64 (t, J = 7.74 Hz, 2 H) 3.65 (t, J = 6.42 Hz, 2 H) 5.60 (s, 2 H) 6.89 (d, J = 8.61 Hz, 2 H) 7.11 (d, J = 8.52 Hz, 2 H) 7.59 (ddd, J = 9.00, 7.49, 2.93 Hz, 1 H) 7.95 (dd, J = 9.07, 3.85 Hz, 1 H) 8.24 (d, J = 2.84 Hz, 1 H) |
| 155 | $^1$H NMR (CDCl$_3$) δ ppm 1.86 (q, J = 8.20, 6.92 Hz, 2 H) 2.44 (s, 3 H) 2.65 (t, J = 7.65 Hz, 2 H) 3.66 (t, J = 6.42 Hz, 2 H) 5.61 (s, 2 H) 6.90 (d, J = 8.52 Hz, 2 H) 7.12 (d, J = 8.52 Hz, 2 H) 7.82 (dd, J = 8.80, 2.47 Hz, 1 H) 7.92 (d, J = 8.80 Hz, 1 H) 8.34 (d, J = 2.29 Hz, 1 H) |
| 156 | $^1$H NMR (CDCl$_3$) δ ppm 1.84 (q, J = 8.29, 6.92 Hz, 2 H) 2.36 (s, 3 H) 2.43 (s, 3 H) 2.64 (t, J = 7.65 Hz, 2 H) 3.64 (t, J = 6.42 Hz, 2 H) 5.62 (s, 2 H) 6.90 (m, J = 8.52 Hz, 2 H) 7.10 (m, J = 8.52 Hz, 2 H) 7.65 (dd, J = 8.39, 1.88 Hz, 1 H) 7.79 (d, J = 8.34 Hz, 1 H) 8.21 (s, 1 H) |
| 157 | $^1$H NMR (CDCl$_3$) δ ppm 1.84 (q, J = 8.29, 6.92 Hz, 2 H) 2.43 (s, 3 H) 2.64 (t, J = 7.65 Hz, 2 H) 3.65 (t, J = 6.42 Hz, 2 H) 3.89 (s, 3 H) 5.58 (s, 2 H) 6.89 (m, J = 8.61 Hz, 2 H) 7.10 (m, J = 8.52 Hz, 2 H) 7.25-7.42 (m, 1 H) 7.80 (d, J = 8.98 Hz, 1 H) 8.06 (d, J = 2.93 Hz, 1 H) |
| 158 | $^1$H NMR (CDCl$_3$) δ ppm 1.73-1.84 (m, 2 H) 2.42 (s, 3 H) 2.59 (t, J = 7.65 Hz, 2 H) 3.59 (t, J = 6.28 Hz, 2 H) 5.70 (s, 2 H) 6.68 (d, J = 8.80 Hz, 2 H) 7.23 (s, 1 H) 7.76-7.91 (m, 2 H) 8.31 (br d, J = 4.49 Hz, 1 H) |
| 159 | $^1$H NMR (CDCl$_3$) δ ppm 1.82 (m, 2 H) 2.40 (br s, 6 H) 2.64 (t, J = 7.61 Hz, 2 H) 3.61 (t, J = 6.32 Hz, 2 H) 5.02 (s, 2 H) 6.75 (d, J = 8.89 Hz, 2 H) 7.29 (d, J = 8.16 Hz, 2 H) 7.54 (d, J = 8.25 Hz, 2 H) |
| 160 | $^1$H NMR (CDCl$_3$) δ ppm 1.26 (t, J = 7.51 Hz, 3 H) 1.77-2.03 (m, 2 H) 2.40 (s, 3 H) 2.64 (m, 2 H) 2.71 (m, 2 H) 3.62 (t, J = 6.28 Hz, 2 H) 5.03 (s, 2 H) 6.75 (br d, J = 8.89 Hz, 2 H) 7.32 (m, J = 8.16 Hz, 2 H) 7.56 (m, J = 8.25 Hz, 2 H) |
| 161 | $^1$H NMR (CDCl$_3$) δ ppm 1.77-1.87 (m, 2 H) 2.40 (s, 3 H) 2.64 (t, J = 7.65 Hz, 2 H) 3.61 (t, J = 6.28 Hz, 2 H) 3.84 (s, 3 H) 5.00 (s, 2 H) 6.74 (d, J = 8.89 Hz, 2 H) 6.98 (d, J = 8.80 Hz, 2 H) 7.56 (d, J = 8.80 Hz, 2 H) |
| 162 | $^1$H NMR (CDCl$_3$) δ ppm 1.76-2.03 (m, 3 H) 2.41 (s, 3 H) 2.66 (t, J = 7.65 Hz, 2 H) 3.63 (t, J = 6.28 Hz, 2 H) 5.02 (s, 2 H) 6.76 (d, J = 8.98 Hz, 2 H) 7.48 (d, J = 8.80 Hz, 2 H) 7.67 (d, J = 8.80 Hz, 2 H) |
| 163 | $^1$H NMR (CDCl$_3$) δ ppm 1.61-1.72 (m, 2 H) 1.77-1.85 (m, 2 H) 1.87-2.16 (m, 6 H) 2.30 (s, 3 H) 2.63 (t, J = 7.70 Hz, 2 H) 3.57-3.65 (m, 2 H) 4.83 (quin, J = 7.56 Hz, 1 H) 5.10 (s, 2 H) 6.74 (d, J = 9.07 Hz, 2H) |
| 164 | $^1$H NMR (CDCl$_3$) δ ppm 1.74-1.85 (m, 2 H) 2.41 (s, 3 H) 2.60 (t, J = 7.70 Hz, 2H) 3.60 (t, J = 6.28 Hz, 2 H) 5.64 (s, 2 H) 6.64-6.72 (m, 2 H) 7.56 (ddd, J = 8.98, 7.51, 2.93 Hz, 1 H) 7.84-7.93 (m, 1 H) 8.17 (d, J = 2.84 Hz, 1 H) |
| 165 | $^1$H NMR (CDCl$_3$) δ ppm 1.75-1.84 (m, 2 H) 2.34 (s, 3 H) 2.42 (s, 3 H) 2.60 (t, J = 7.65 Hz, 2 H) 3.61 (t, J = 6.28 Hz, 2 H) 5.67 (s, 2 H) 6.64-6.72 (m, 2 H) 7.63 (dd, J = 8.29, 1.79 Hz, 1 H) 7.74 (d, J = 8.25 Hz, 1 H) 8.15 (s, 1 H) |
| 166 | $^1$H NMR (CDCl$_3$) δ ppm 1.76-1.84 (m, 2 H) 2.42 (s, 3 H) 2.61 (t, J = 7.70 Hz, 2 H) 3.61 (t, J = 6.32 Hz, 2 H) 5.67 (s, 2 H) 6.64-6.72 (m, 2 H) 7.76-7.82 (m, 1 H) 7.83-7.88 (m, 1 H) 8.26 (d, J = 2.20 Hz, 1 H) |
| 167 | $^1$H NMR (CDCl$_3$) δ ppm 1.75-1.84 (m, 2 H) 2.41 (s, 3 H) 2.60 (t, J = 7.65 Hz, 2 H) 3.60 (t, J = 6.32 Hz, 2 H) 3.87 (s, 3 H) 5.61 (s, 2 H) 6.64-6.71 (m, 2 H) 7.34 (dd, J = 8.94, 2.98 Hz, 1 H) 7.73-7.78 (m, 1 H) 8.00 (d, J = 2.84 Hz, 1 H) |

Pharmacology

Compounds of the invention were tested for GPR120 agonism in a CHO mitoPhotinaGPR120 cell based assay with fluorescent readout in Agonist Mode in dose response in quadruplicate with intra-plate modality.

CHO mitoPhotinaGPR120 cells were seeded at 7.500 c/w in 384 MTP (black walled, clear bottom). Twenty (20) h after seeding, growth medium was manually removed and cells were starved in the presence of 25 µL/w of Standard Tyrode's Buffer. After 3 h, cells were loaded with 20 µL/w of 0.5× Fluo-8 No Wash (AAT Bioquest, Inc.) Ca2+ sensitive dye prepared in Standard Tyrode's Buffer. Cells were incubated for 1 h at room temperature in the dark. Ten (10) µL/w 3× of controls and compounds were diluted in Standard Tyrode's Buffer+0.01% fatty acid free BSA (final concentration=0.0033%) and injected at the FLIPRTetra®, recording the kinetic calcium traces for 3 minutes. Standard Tyrode's buffer composition: 5 mM KCl, 130 mM NaCl, 2 mM CaCl2, 5 mM NaHCO3, 1 mM MgCl2, 20 mM HEPES, pH7.4. GPR120 small molecule agonists GSK137647A and TUG-891 were used as active GPR120 agonist reference compounds.

The following examples are meant to illustrate, but in no way to limit, the claimed invention.

TABLE 3

Biological activity

| Example | GPR120 agonism EC$_{50}$ µM) |
|---|---|
| 1 | 1.29 |
| 2 | 1.24 |
| 3 | 1.31 |
| 4 | 1.67 |
| 5 | 2.31 |
| 6 | 1.10 |
| 8 | 1.52 |
| 10 | 3.39 |
| 14 | 3.09 |
| 16 | 0.86 |
| 17 | 1.01 |
| 18 | 1.41 |
| 20 | 1.77 |
| 21 | 1.33 |
| 23 | 8.13 |
| 24 | 7.31 |

TABLE 3-continued

Biological activity

| Example | GPR120 agonism EC$_{50}$ μM) |
|---|---|
| 25 | 0.94 |
| 26 | 0.58 |
| 29 | 4.22 |
| 30 | 0.71 |
| 32 | 0.09 |
| 33 | 1.27 |
| 35 | 0.15 |
| 39 | 7.24 |
| 40 | 0.79 |
| 42 | 0.49 |
| 43 | 0.45 |
| 43A | 0.34 |
| 43B | 1.69 |
| 47 | 1.65 |
| 47A | 0.50 |
| 47B | 2.36 |
| 49 | 18.42 |
| 53 | 0.52 |
| 54 | 18.35 |
| 55 | 2.03 |
| 56 | 5.00 |
| 59 | 2.63 |
| 61 | 1.02 |
| 62 | 2.60 |
| 63 | 16.38 |
| 64 | 19.06 |
| 65 | 3.56 |
| 68 | 8.32 |
| 69 | 9.82 |
| 70 | 2.30 |
| 71 | 5.69 |
| 73 | 1.98 |
| 74 | 0.49 |
| 75 | 4.61 |
| 76 | 0.76 |
| 77 | 9.03 |
| 78 | 0.38 |
| 79 | 1.64 |
| 80 | 0.64 |
| 82 | 3.41 |
| 83 | 2.22 |
| 84 | 1.54 |
| 85 | 4.55 |
| 86 | 1.58 |
| 87 | 0.18 |
| 88 | 11.16 |
| 89 | 0.99 |
| 90 | 0.31 |
| 91 | 16.51 |
| 92 | 3.66 |
| 93 | 0.33 |
| 94 | 1.35 |
| 95 | 0.83 |
| 96 | 0.52 |
| 97 | 2.80 |
| 98 | 9.90 |
| 101 | 1.48 |
| 102 | 0.53 |
| 103 | 9.22 |
| 104 | 10.44 |
| 105 | 12.55 |
| 106 | 2.49 |
| 107 | 8.15 |
| 109 | 3.22 |
| 112 | 10.18 |
| 114 | 5.55 |
| 115 | 4.62 |
| 116 | 1.63 |
| 117 | 1.20 |
| 118 | 2.24 |
| 126 | 5.92 |
| 129 | 3.33 |
| 130 | 0.19 |
| 133 | 9.73 |
| 136 | 17.68 |
| 146 | 3.36 |
| 147 | 1.49 |
| 149 | 0.15 |
| 150 | 0.15 |
| 151 | 0.24 |
| 152 | 0.51 |
| 153 | 0.18 |
| 154 | 0.21 |
| 155 | 0.81 |
| 156 | 0.19 |
| 157 | 0.28 |
| 158 | 0.13 |
| 159 | 0.19 |
| 160 | 0.3 |
| 161 | 0.23 |
| 162 | 0.43 |
| 163 | 0.099 |
| 164 | 0.19 |
| 165 | 0.17 |
| 166 | 0.22 |
| 167 | 0.21 |
| GSK137639A | 4.48 |
| TUG-891 | 0.94 |

The invention claimed is:
1. A compound of formula (I) or a pharmaceutically acceptable salt thereof:

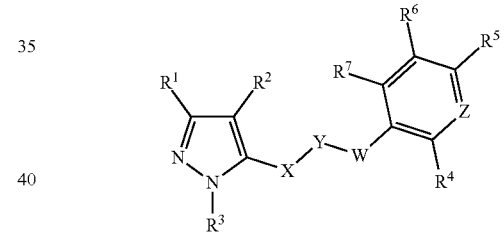

(I)

including any stereochemically isomeric form thereof, wherein:

X is a methylene group, unsubstituted or substituted by a methyl group or one or more halogen atoms;

Y is selected from: —O—; —NR$^8$—, wherein R$^8$ is hydrogen or C$_1$-C$_6$ alkyl; —S—; —SO— and —SO$_2$—;

W is a single bond;

Z is —CR$^9$—, wherein R$^9$ is hydrogen, halogen, C$_1$-C$_6$ alkyl, C$_1$-C$_4$ hydroxyalkyl;

R$^1$ is selected from hydrogen; C$_1$-C$_6$ alkyl and C$_3$-C$_{10}$ cycloalkyl;

R$^2$ is CN or trifluoromethyl;

R$^3$ is aryl; hetaryl; benzyl; C$_1$-C$_4$ alkyl or C$_3$-C$_{10}$ cycloalkyl;

which can be unsubstituted or substituted by one or more substituents selected from halogen, C$_1$-C$_4$ alkyl (unsubstituted or substituted by halogen), C$_1$-C$_4$ alkyloxy (unsubstituted or substituted by halogens), CN and R$^{12}$SO$_2$—, wherein R$^{12}$ is a C$_1$-C$_6$ alkyl or cycloalkyl;

each of R$^4$, R$^6$ and R$^7$ is independently selected from the group consisting of hydrogen; halogen; CN; C$_1$-C$_6$ alkyl (unsubstituted or substituted by halogen or hydroxyl); C$_1$-C$_4$ alkyloxy (unsubstituted or substituted by halogen or hydroxyl); —CONH$_2$; —NHCOCH$_3$ and —NO$_2$;

R$^5$ is —(CH$_2$)$_n$—OH, wherein n is 1-3;

or

R$^6$ and R$^7$, taken together with the aromatic ring to which they are bound, form a group:

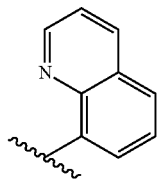 [SMILES: *c1cccc2cccnc12]

with the proviso that the compound of formula (I) is not:

5-[(4-cyanophenoxy)methyl]-3-methyl-1-phenyl-pyrazole-4-carbonitrile,

5-[[2-chloro-4-(hydroxymethyl)phenoxy]methyl]3-methyl-1-phenyl-pyrazole-4-carbonitrile;

5-[(2-chloro-4-cyano-phenoxy)methyl]-3-methyl-1-phenyl-pyrazole-4-carbonitrile; and 3-methyl-5-(phenoxymethyl)-1-phenyl-pyrazole-4-carbonitrile.

2. The compound of Formula (I) according to claim 1 or a pharmaceutically acceptable salt thereof wherein:

X is a methylene group, unsubstituted or substituted by a methyl group or one or more halogen atoms selected from F and Cl;

Y is selected from: —O—; —NR$^8$—, wherein R$^8$ is hydrogen or C$_1$-C$_4$ alkyl; —S—; —SO— and —SO$_2$—;

W is a single bond;

Z is selected from —CR$^9$—, wherein R$^9$ is hydrogen, halogen selected from Cl or F, C$_1$-C$_4$ alkyl, C$_1$-C$_4$ hydroxyalkyl;

R$^1$ is selected from hydrogen; C$_1$-C$_4$ alkyl and C$_3$-C$_6$ cycloalkyl;

R$^2$ is CN or trifluoromethyl;

R$^3$ is phenyl unsubstituted or substituted by one or more substituents selected from Br, Cl, F or C$_1$-C$_4$ alkyl (unsubstituted or substituted by F, Cl or Br), C$_1$-C$_4$ alkyloxy (unsubstituted or substituted by F, Cl or Br), CN, and R$^{12}$SO$_2$—, wherein R$^{12}$ is a C$_1$-C$_4$ alkyl; hetaryl unsubstituted or substituted by one or more substituents selected from Br, Cl, F, C$_1$-C$_4$ alkyl or C$_1$-C$_4$ alkyloxy; benzyl unsubstituted or substituted by C$_1$-C$_4$ alkyl, C$_1$-C$_4$ alkyloxy, C$_3$-C$_6$ cycloalkyl; each of R$^4$, R$^6$ and R$^7$ is independently selected from the group consisting of hydrogen; halogen selected from F, Cl or Br; CN; C$_1$-C$_4$ alkyl (unsubstituted or substituted by F, Cl, Br or hydroxyl); C$_1$-C$_4$ alkyloxy (unsubstituted or substituted by hydroxyl); —CONH$_2$; and —NHCOCH$_3$;

R$^5$ is —(CH$_2$)$_n$—OH, wherein n is 1-3;

or R$^5$ and R$^6$, taken together with the aromatic ring to which they are bound, form a group:

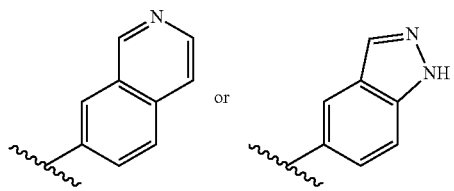 [SMILES: *c1ccc2ccncc2c1 ; *c1ccc2[nH]ncc2c1]

or

R$^6$ and R$^7$, taken together with the aromatic ring to which they are bound, form a group:

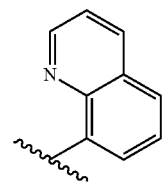

with the proviso that the compound of formula (I) is not:

5-[(4-cyanophenoxy)methyl]-3-methyl-1-phenyl-pyrazole-4-carbonitrile,

5-[[2-chloro-4-(hydroxymethyl)phenoxy]methyl]-3-methyl-1-phenyl-pyrazole-4-carbonitrile;

5-[(2-chloro-4-cyano-phenoxy)methyl]-3-methyl-1-phenyl-pyrazole-4-carbonitrile; and 3-methyl-5-(phenoxymethyl)-1-phenyl-pyrazole-4-carbonitrile.

3. The compound of Formula (I) according to claim 2 or a salt thereof wherein:

X is —CH$_2$—, unsubstituted or substituted by a methyl group or F;

Y is selected from: —O—; —NR$^8$—, wherein R$^8$ is H or methyl or ethyl; —S—; —SO— or —SO$_2$—;

W is a single bond;

Z is selected from: CR$^9$, wherein R$^9$ is an H, Cl or F; methyl, ethyl; hydroxymethyl, hydroxyethyl;

R$^1$ is selected from: hydrogen, methyl, ethyl, cyclopropyl;

R$^2$ is CN or trifluoromethyl;

R$^3$ is selected from the group consisting of phenyl unsubstituted or substituted by Cl, F, methyl (unsubstituted or substituted by F), ethyl (unsubstituted or substituted by F), methoxy (unsubstituted or substituted by F), cyano, R$^{12}$SO$_2$—, wherein R$^{12}$ is methyl); pyridine (unsubstituted or substituted by Br, Cl, F, methyl or methoxy); pyrimidine; pyrazine (unsubstituted or substituted by Cl); benzyl (unsubstituted or substituted by methoxy); isopropyl; t-butyl; cyclopentyl (unsubstituted or substituted by F); cyclohexyl (unsubstituted or substituted by F);

each of R$^4$, R$^6$ and R$^7$ is independently selected from the group consisting of hydrogen; Cl; F; CN; methyl (unsubstituted or substituted by hydroxyl or F); ethyl (unsubstituted or substituted by hydroxyl); C$_1$-C$_4$ alkyloxy, selected from methoxy and ethoxy unsubstituted or substituted by hydroxyl; —CONH$_2$; —NHCOCH$_3$ or NO$_2$;

R$^5$ is —(CH$_2$)$_n$—OH, wherein n is 1-3;

or

R$^6$ and R$^7$ taken together with the aromatic ring to which they are bound form a group:

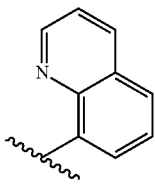

with the proviso that the compound of formula (I) is not:
5-[(4-cyanophenoxy)methyl]-3-methyl-1-phenyl-pyrazole-4-carbonitrile,
5-[[2-chloro-4-(hydroxymethyl)phenoxy]methyl]-3-methyl-1-phenyl-pyrazole-4-carbonitrile;
5-[(2-chloro-4-cyano-phenoxy)methyl]-3-methyl-1-phenyl-pyrazole-4-carbonitrile; and
3-methyl-5-(phenoxymethyl)-1-phenyl-pyrazole-4-carbonitrile.

4. The compound of Formula (I) according to claim 3 wherein
X is —CH$_2$—;
Y is selected from: —O—, —NH—, —NCH$_3$—, —S—, —SO—, or —SO$_2$—;
W is a single bond;
Z is selected from CR$^9$, wherein R$^9$ is H, Cl or F, methyl, hydroxymethyl or hydroxyethyl;
R$^1$ is selected from hydrogen or methyl;
R$^2$ is —CN;
R$^3$ is selected from the group consisting of: phenyl, 2-methylphenyl, 3-methylphenyl, 4-methylphenyl, 2-ethylphenyl, 3-ethylphenyl, 4-ethylphenyl, 2-chlorophenyl, 3-chlorophenyl, 4-chlorophenyl, 2,6-dichlorophenyl, 2-fluorophenyl, 3-fluorophenyl, 4-fluorophenyl, 2,4-difluorophenyl, 2,6-difluorophenyl, 2-methoxyphenyl, 3-methoxyphenyl, 4-methoxyphenyl, 2-trifluoromethylphenyl, 3-trifluoromethylphenyl, 4-trifluoromethylphenyl, 3-trifluoromethoxyphenyl, 4-trifluoromethoxyphenyl, 2-cyanophenyl 3-cyanophenyl, 4-cyanophenyl, 4-methane sulfonylphenyl, pyridine-2-yl, 6-bromopyridin-2-yl, pyridin-3-yl, pyridin-4-yl, pyrimidin-2-yl, pyrazine-3-yl, 6-chloropyrazin-3-yl, benzyl, 4-methoxybenzyl, cyclopentyl, cyclohexyl, 4,4'-difluorocyclohexyl, tert-butyl or isopropyl;
each of R$^4$, R$^6$ and R$^7$ is independently selected from the group consisting of hydrogen, F, Cl, methyl, ethyl, trifluoromethyl, hydroxymethyl, 2-hydroxyethyl, 2-hydroxyethyloxy, methoxy, ethoxy, —CONH$_2$, —NHCOCH$_3$, or CN;
R$^5$ is selected from: CH$_2$OH, —CH(CH$_3$)OH, —C(CH$_3$)$_2$OH, —CH$_2$CH$_2$OH, —CH$_2$CH$_2$CH$_2$OH,

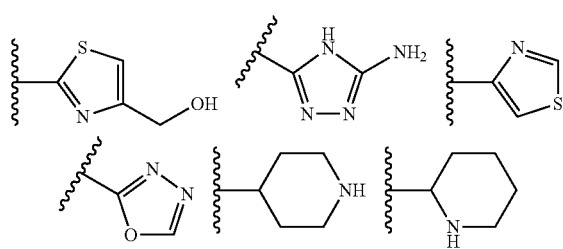

or
R$^6$ and R$^7$, taken together with the aromatic ring to which they are bound, form a group:

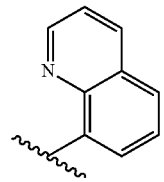 [SMILES: *c1cccc2cccnc12]

with the proviso that the compound of formula (I) is not:
5-[(4-cyanophenoxy)methyl]-3-methyl-1-phenyl-pyrazole-4-carbonitrile,
5-[[2-chloro-4-(hydroxymethyl)phenoxy]methyl]3-methyl-1-phenyl-pyrazole-4-carbonitrile;
5-[(2-chloro-4-cyano-phenoxy)methyl]-3-methyl-1-phenyl-pyrazole-4-carbonitrile; and
3-methyl-5-(phenoxymethyl)-1-phenyl-pyrazole-4-carbonitrile.

5. The compound of formula (I) according to claim 1 selected from the group consisting of:
5-[[4-(hydroxymethyl)phenoxy]methyl]-3-methyl-1-phenyl-pyrazole-4-carbonitrile
5-[[4-(2-hydroxyethyl)phenoxy]methyl]-3-methyl-1-phenyl-pyrazole-4-carbonitrile
5-[[2,3-difluoro-4-(hydroxymethyl)phenoxy]methyl]-3-methyl-1-phenyl-pyrazole-4-carbonitrile
5-[[4-(hydroxymethyl)-2-methyl-phenoxy]methyl]-3-methyl-1-phenyl-pyrazole-4-carbonitrile
5-[[4-(hydroxymethyl)-2,6-dimethyl-phenoxy]methyl]3-methyl-1-phenyl-pyrazole-4-carbonitrile
5-[[2-fluoro-4-(hydroxymethyl)phenoxy]methyl]-3-methyl-1-phenyl-pyrazole-4-carbonitrile
5-[[2,6-difluoro-4-(hydroxymethyl)phenoxy]methyl]-3-methyl-1-phenyl-pyrazole-4-carbonitrile
5-[[2,6-difluoro-4-(3-hydroxypropyl)phenoxy]methyl]3-methyl-1-phenyl-pyrazole-4-carbonitrile
5-[[2-fluoro-4-(2-hydroxyethyl)phenoxy]methyl]-3-methyl-1-phenyl-pyrazole-4-carbonitrile
5-[[4-(3-hydroxypropyl)phenoxy]methyl]-3-methyl-1-phenyl-pyrazole-4-carbonitrile
5-[[2-fluoro-4-(3-hydroxypropyl)phenoxy]methyl]-3-methyl-1-phenyl-pyrazole-4-carbonitrile
5-[[4-(1-hydroxypropyl)phenoxy]methyl]-3-methyl-1-phenyl-pyrazole-4-carbonitrile
5-[[4-(1-hydroxy-1-methyl-ethyl)phenoxy]methyl]-3-methyl-1-phenyl-pyrazole-4-carbonitrile
5-[[4-(3-hydroxypropyl)-2-methoxy-phenoxy]methyl]-3-methyl-1-phenyl-pyrazole-4-carbonitrile
5-[[4-(1-hydroxyethyl)phenoxy]methyl]-3-methyl-1-phenyl-pyrazole-4-carbonitrile
5-[[4-(2-hydroxyethyl)anilino]methyl]-3-methyl-1-phenyl-pyrazole-4-carbonitrile
5-[[4-(2-hydroxyethyl)-~{N}-methyl-anilino]methyl]-3-methyl-1-phenyl-pyrazole-4-carbonitrile
5-[[4-(2-hydroxyethyl)phenyl]sulfanylmethyl]-3-methyl-1-phenyl-pyrazole-4-carbonitrile
5-[[4-(2-hydroxyethyl)phenoxy]methyl]-3-methyl-1-(o-tolyl)pyrazole-4-carbonitrile
5-[[4-(2-hydroxyethyl)phenoxy]methyl]-3-methyl-1-(m-tolyl)pyrazole-4-carbonitrile
5-[[4-(2-hydroxyethyl)phenoxy]methyl]-3-methyl-1-(p-tolyl)pyrazole-4-carbonitrile 1-(3-chlorophenyl)-5-[[4-(2-hydroxyethyl)phenoxy] methyl]-3-methyl-pyrazole-4-carbonitrile
1-(4-chlorophenyl)-5-[[4-(2-hydroxyethyl)phenoxy] methyl]-3-methyl-pyrazole-4-carbonitrile
5-[[4-(2-hydroxyethyl)phenoxy]methyl]-3-methyl-1-[3-(trifluoromethyl)phenyl]pyrazole-4-carbonitrile
1-(4-ethylphenyl)-5-[[4-(2-hydroxyethyl)phenoxy] methyl]3-methyl-pyrazole-4-carbonitrile
5-[[4-(2-hydroxyethyl)phenoxy]methyl]-1-(3-methoxyphenyl)-3-methyl-pyrazole-4-carbonitrile
5-[[4-(2-hydroxyethyl)phenoxy]methyl]-1-(4-methoxyphenyl)-3-methyl-pyrazole-4-carbonitrile
5-[[4-(2-hydroxyethyl)phenoxy]methyl]-3-methyl-1-[3-(trifluoromethoxy)phenyl]pyrazole-4-carbonitrile
1-(2-fluorophenyl)-5-[[4-(2-hydroxyethyl)phenoxy] methyl]-3-methyl-pyrazole-4-carbonitrile
1-(4-fluorophenyl)-5-[[4-(2-hydroxyethyl)phenoxy] methyl]-3-methyl-pyrazole-4-carbonitrile
1-(4-fluorophenyl)-5-[[4-(3-hydroxypropyl)phenoxy] methyl]-3-methyl-pyrazole-4-carbonitrile
1-benzyl-5-[[4-(2-hydroxyethyl)phenoxy]methyl]-3-methyl-pyrazole-4-carbonitrile
1-benzyl-5-[[4-(3-hydroxypropyl)phenoxy]methyl]-3-methyl-pyrazole-4-carbonitrile
1-benzyl-5-[[2,6-difluoro-4-(3-hydroxypropyl)phenoxy] methyl]-3-methyl-pyrazole-4-carbonitrile
5-[[4-(2-hydroxyethyl)phenoxy]methyl]-1-[(4-methoxyphenyl)methyl]-3-methyl-pyrazole-4-carbonitrile
5-[1-[4-(2-hydroxyethyl)phenoxy]ethyl]-3-methyl-1-phenyl-pyrazole-4-carbonitrile
5-[1-[2,6-difluoro-4-(3-hydroxypropyl)phenoxy]ethyl]-3-methyl-1-phenyl-pyrazole-4-carbonitrile
5-[difluoro-[4-(2-hydroxyethyl)phenoxy]methyl]-3-methyl-1-phenyl-pyrazole-4-carbonitrile
5-[difluoro-[4-(3-hydroxypropyl)phenoxy]methyl]-3-methyl-1-phenyl-pyrazole-4-carbonitrile
5-[[2,6-difluoro-4-(3-hydroxypropyl)phenoxy]-difluoromethyl]-3-methyl-1-phenyl-pyrazole-4-carbonitrile
1-(2-ethylphenyl)-5-[[4-(2-hydroxyethyl)phenoxy] methyl]3-methyl-pyrazole-4-carbonitrile
5-[[4-(2-hydroxyethyl)phenoxy]methyl]-3-methyl-1-(4-methylsulfonylphenyl)pyrazole-4-carbonitrile
1-(3-fluorophenyl)-5-[[4-(2-hydroxyethyl)phenoxy] methyl]-3-methyl-pyrazole-4-carbonitrile
5-[[4-(2-hydroxyethyl)phenoxy]methyl]-3-methyl-1-(2-pyridyl) pyrazole-4-carbonitrile
5-[[4-(2-hydroxyethyl)phenoxy]methyl]-3-methyl-1-(3-pyridyl) pyrazole-4-carbonitrile
5-[[4-(2-hydroxyethyl)phenoxy]methyl]-3-methyl-1-(4-pyridyl) pyrazole-4-carbonitrile
5-[[4-(2-hydroxyethyl)phenoxy]methyl]-3-methyl-1-pyrimidin-2-yl-pyrazole-4-carbonitrile
5-[[4-(2-hydroxyethyl)phenoxy]methyl]-3-methyl-1-pyridazin-3-yl-pyrazole-4-carbonitrile
1-(4-cyanophenyl)-5-[[4-(2-hydroxyethyl)phenoxy] methyl]-3-methyl-pyrazole-4-carbonitrile
1-(3-cyanophenyl)-5-[[4-(2-hydroxyethyl)phenoxy] methyl]-3-methyl-pyrazole-4-carbonitrile
5-[[4-(2-hydroxyethyl)phenoxy]methyl]-3-methyl-1-[4-(trifluoromethyl)phenyl]pyrazole-4-carbonitrile
1-(3-bromo-2-pyridyl)-5-[[4-(2-hydroxyethyl)phenoxy] methyl]-3-methyl-pyrazole-4-carbonitrile
1-(2,6-dichlorophenyl)-5-[[4-(2-hydroxyethyl)phenoxy] methyl]3-methyl-pyrazole-4-carbonitrile
1-(2,6-difluorophenyl)-5-[[4-(2-hydroxyethyl)phenoxy] methyl]3-methyl-pyrazole-4-carbonitrile
1-(2-chlorophenyl)-5-[[4-(2-hydroxyethyl)phenoxy] methyl]-3-methyl-pyrazole-4-carbonitrile
1-(2,4-difluorophenyl)-5-[[4-(2-hydroxyethyl)phenoxy] methyl]3-methyl-pyrazole-4-carbonitrile
5-[[4-(2-hydroxyethyl)phenoxy]methyl]3-methyl-1-[4-(trifluoromethoxy)phenyl]-pyrazole-4-carbonitrile
1-(6-chloropyridazin-3-yl)-5-[[4-(2-hydroxyethyl)phenoxy]methyl]3-methyl-pyrazole-4-carbonitrile
1-cyclopentyl-5-[[4-(2-hydroxyethyl)phenoxy]methyl]3-methyl-pyrazole-4-carbonitrile
1-cyclohexyl-5-[[4-(2-hydroxyethyl)phenoxy]methyl]3-methyl-pyrazole-4-carbonitrile
1-(4,4-difluorocyclohexyl)-5-[[4-(2-hydroxyethyl)phenoxy]methyl]3-methyl-pyrazole-4-carbonitrile
5-[[4-(2-hydroxyethyl)phenoxy]methyl]-1-phenyl-pyrazole-4-carbonitrile
5-[[4-(3-hydroxypropyl)phenoxy]methyl]1-phenyl-pyrazole-4-carbonitrile
5-[[4-(2-hydroxyethyl)phenyl]sulfinylmethyl]-3-methyl-1-phenyl-pyrazole-4-carbonitrile
5-[[4-(2-hydroxyethyl)phenyl]sulfonylmethyl]-3-methyl-1-phenyl-pyrazole-4-carbonitrile
5-[[4-(hydroxymethyl)-2-(trifluoromethyl)phenoxy] methyl]3-methyl-1-phenyl-pyrazole-4-carbonitrile
5-[[4-(3-hydroxypropyl)phenoxy]methyl]3-methyl-1-(2-pyridyl)pyrazole-4-carbonitrile
5-[[4-(3-hydroxypropyl)phenoxy]methyl]3-methyl-1-(p-tolyl)pyrazole-4-carbonitrile
1-(4-ethylphenyl)-5-[[4-(3-hydroxypropyl)phenoxy] methyl]3-methyl-pyrazole-4-carbonitrile
1-(4-chlorophenyl)-5-[[4-(3-hydroxypropyl)phenoxy] methyl]3-methyl-pyrazole-4-carbonitrile
1-cyclopentyl-5-[[4-(3-hydroxypropyl)phenoxy]methyl] 3-methyl-pyrazole-4-carbonitrile
1-(5-fluoro-2-pyridyl)-5-[[4-(3-hydroxypropyl)phenoxy] methyl]-3-methyl-pyrazole-4-carbonitrile
1-(5-chloro-2-pyridyl)-5-[[4-(3-hydroxypropyl)phenoxy] methyl]-3-methyl-pyrazole-4-carbonitrile
5-[[4-(3-hydroxypropyl)phenoxy]methyl]3-methyl-1-(5-methyl-2-pyridyl)pyrazole-4-carbonitrile
5-[[4-(3-hydroxypropyl)phenoxy]methyl]1-(5-methoxy-2-pyridyl)-3-methyl-pyrazole-4-carbonitrile
5-[[2,6-difluoro-4-(3-hydroxypropyl)phenoxy]methyl]-3-methyl-1-(2-pyridyl)pyrazole-4-carbonitrile
5-[[2,6-difluoro-4-(3-hydroxypropyl)phenoxy]methyl]-3-methyl-1-(p-tolyl)pyrazole-4-carbonitrile
5-[[2,6-difluoro-4-(3-hydroxypropyl)phenoxy]methyl]-1-(4-ethylphenyl)-3-methyl-pyrazole-4-carbonitrile
5-[[2,6-difluoro-4-(3-hydroxypropyl)phenoxy]methyl]-1-(4-methoxyphenyl)-3-methyl-pyrazole-4-carbonitrile
1-(4-chlorophenyl)-5-[[2,6-difluoro-4-(3-hydroxypropyl) phenoxy]methyl]-3-methyl-pyrazole-4-carbonitrile
1-cyclopentyl-5-[[2,6-difluoro-4-(3-hydroxypropyl)phenoxy]methyl]-3-methyl-pyrazole-4-carbonitrile
5-[[2,6-difluoro-4-(3-hydroxypropyl)phenoxy]methyl]-1-(5-fluoro-2-pyridyl)-3-methyl-pyrazole-4-carbonitrile
5-[[2,6-difluoro-4-(3-hydroxypropyl)phenoxy]methyl]-3-methyl-1-(5-methyl-2-pyridyl)pyrazole-4-carbonitrile
1-(5-chloro-2-pyridyl)-5-[[2,6-difluoro-4-(3-hydroxypropyl)phenoxy]methyl]-3-methyl-pyrazole-4-carbonitrile
5-[[2,6-difluoro-4-(3-hydroxypropyl)phenoxy]methyl]-1-(5-methoxy-2-pyridyl)-3-methyl-pyrazole-4-carbonitrile.

6. A process for preparing a compound of formula (I) according to claim 1 or a salt thereof comprising the step of:

a) reacting a compound of formula (II):

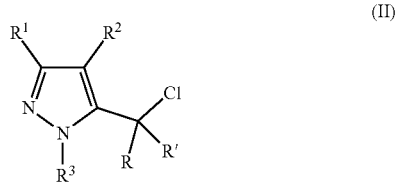
(II)

wherein the meanings of R1, R2 and R3 are as defined in claim 1, R and R' are independently selected from hydrogen, methyl or F, with a compound of formula (III):

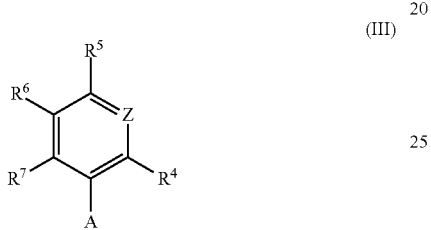
(III)

wherein R4, R5, R6, R7 and Z are as defined in claim 1, and A is an hydroxyl, thiol, amino, methylamino, or hydroxymethylene group;

and converting the obtained compound of formula (I) into a pharmaceutically acceptable salt thereof.

7. A medicament comprising the compound of Formula (I) according to claim 1 or a salt thereof.

8. A pharmaceutical formulation comprising a compound of Formula (I) according to claim 1 or a salt thereof as active ingredient a pharmaceutically acceptable excipient and/or carrier.

9. A process for preparing a compound of formula (I) according to claim 1 or a salt thereof comprising the step of:

a) reacting a compound of formula (II):

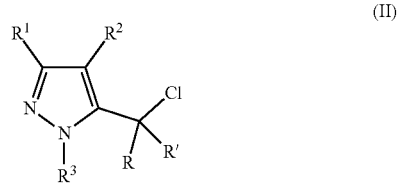
(II)

wherein the meanings of R1, R2 and R3 are as defined in claim 1, R and R' are independently selected from hydrogen, methyl or F, with a compound of formula (III):

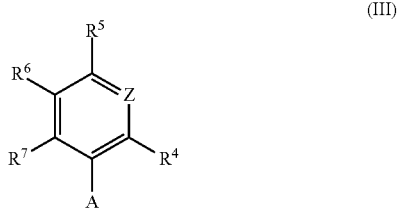
(III)

wherein R4, R5, R6, R7 and Z are as defined in claim 1, and A is an hydroxyl, thiol, amino, methylamino, or hydroxymethylene group.

* * * * *